(12) United States Patent
Bhatia et al.

(10) Patent No.: US 9,029,361 B2
(45) Date of Patent: May 12, 2015

(54) AGENTS FOR TREATING PAIN AND USES THEREOF

(71) Applicant: AbbVie Inc., North Chicago, IL (US)

(72) Inventors: Pramila A. Bhatia, Libertyville, IL (US); John T. Randolph, Libertyville, IL (US); Michael R. Schrimpf, Grayslake, IL (US); Qingwei I. Zhang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/101,912

(22) Filed: Dec. 10, 2013

(65) Prior Publication Data

US 2014/0171423 A1 Jun. 19, 2014

Related U.S. Application Data

(60) Provisional application No. 61/736,262, filed on Dec. 12, 2012, provisional application No. 61/760,984, filed on Feb. 5, 2013.

(51) Int. Cl.
*A61K 31/551* (2006.01)
*C07D 487/04* (2006.01)

(52) U.S. Cl.
CPC .................... *C07D 487/04* (2013.01)

(58) Field of Classification Search
CPC .................................................. C07D 487/04
USPC ........................................ 514/221; 540/567
See application file for complete search history.

(56) References Cited

U.S. PATENT DOCUMENTS

| | | | |
|---|---|---|---|
| 6,316,626 | B1 | 11/2001 | Swayze et al. |
| 8,044,069 | B2 | 10/2011 | Bhatia et al. |
| 8,101,614 | B2 | 1/2012 | Zhang et al. |
| 8,129,417 | B2 | 3/2012 | Stewart et al. |
| 2004/0147559 | A1 | 7/2004 | Taveras et al. |
| 2005/0148587 | A1 | 7/2005 | Fraser et al. |
| 2011/0230459 | A1 | 9/2011 | Drizin et al. |
| 2011/0281870 | A1 | 11/2011 | Searle et al. |
| 2011/0294854 | A1 | 12/2011 | Searle et al. |
| 2013/0085141 | A1 | 4/2013 | Li et al. |
| 2013/0085142 | A1 | 4/2013 | Li et al. |
| 2013/0178477 | A1 | 7/2013 | Zhang et al. |

FOREIGN PATENT DOCUMENTS

| | | |
|---|---|---|
| EP | 2098526 A1 | 9/2009 |
| WO | 9912034 A1 | 3/1999 |
| WO | 0059882 A1 | 10/2000 |
| WO | 02055518 A1 | 7/2002 |
| WO | 03084955 A1 | 10/2003 |
| WO | 2005079574 A1 | 9/2005 |
| WO | 2007028654 A1 | 3/2007 |
| WO | 2007084394 A2 | 7/2007 |
| WO | 2010083264 A1 | 7/2010 |

OTHER PUBLICATIONS

Allen, Loyd V. et al., Editors "Ansel's Pharmaceutical Dosage Forms and Drug Delivery Systems," Lippincott Williams & Wilkins, 2011 (Table of Contents).
Banfi, Luca et al., "A convergent synthesis of enantiopure bicyclic scaffolds through multicomponent Ugi reaction," Tetrahedron 64(6): 1114-1134 (2008), Available online Oct. 22, 2007.
Bennett G., et al. "A peripheral mononeuropathy in rat that produces disorders of pain sensation like those seen in man," Pain, 33: 87-107 (1988).
Black, T. et al., "Silver(I) Trifluoromethanesulfonate", e-EROS Encyclopedia of Reagents for Organic Synthesis (2001), No pp. given. John Wiley & Sons, Ltd., Chichester, UK.
Brennan, Timothy J. et al., "Characterization of a rat model of incisional pain." Pain 64(3): 493-502 (1996).
CAS RN 1000577-71-8, Octahydropyrrolo[1,2-a][1,4]diazepin-5-one; Entered Jan. 23, 2008, by Supplier Activate Scientific GmbH.
CAS RN 1027062-21-0, Butanediamide, 2-(2-methylpropyl)-N1-[(4R,9aS)-octahydro-1,5-dioxo-1H-pyrrolo[1,2-a][1,4]diazepin-4-yl]-3-(2-propen-1-yl)-, (2S,3R)-; Entered Jun. 10, 2008, by Supplier ChemSpider (ChemZoo, Inc.).
CAS RN 1314389-74-6, 1H-Pyrrolo[1,2-a][1,4]diazepine-2(3H)-carboxylic acid, 9a-(aminomethyl)-hexahydro-5-oxo-, 1,1-dimethylethyl ester, (9aR)-; Entered Aug. 2, 2011, by Supplier WuXi AppTec Co., Ltd.
CAS RN 1314394-87-0, Index Name Not Assigned; Entered Aug. 2, 2011, by Supplier WuXi AppTec Co., Ltd.
CAS RN 1314399-12-6, 1H-Pyrrolo[1,2-a][1,4]diazepine-2(3H)-carboxylic acid, 8-aminohexahydro-5-oxo-, 1,1-dimethylethyl ester, (8R,9aS)-rel-; Entered Aug. 2, 2011, by Supplier WuXi AppTec Co., Ltd.
CAS RN 1314400-07-1, 1H-Pyrrolo[1,2-a][1,4]diazepine-2(3H)-carboxylic acid, 8-aminohexahydro-5-oxo-, 1,1-dimethylethyl ester, (8R,9aR)-rel-; Entered Aug. 2, 2011, by Supplier WuXi AppTec Co., Ltd.
CAS RN 1314402-25-9, Index Name Not Assigned; Entered Aug. 2, 2011, by Supplier, WuXi AppTec Co., Ltd.
Chaplan S.R., et al. "Quantitative assessment of tactile allodynia in the rat paw," J Neuroscience Methods 53(1): 55-63 (1994).
Chung, Sung-Kee et al., "Novel asymmetric phenylselenium-induced lactamizations of olefinic amides: stereoselective routes to alpha- and beta-amino acids," J Chem. Soc., Perkin Trans. 1, Issue 5: 969-976 (1998).
Chung, Sung-Kee et al., "A diastereoselective phenylselenium-induced lactamization of olefinic amides. A possible route to alpha-and beta-amino acid derivatives," Tetrahedron: Asymmetry, 8(1): 5-9 (1997).

(Continued)

*Primary Examiner* — Taofiq A Solola

(57) ABSTRACT

This invention relates to: (a) compounds and salts thereof that, inter alia, treat pain; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

22 Claims, No Drawings

(56) References Cited

OTHER PUBLICATIONS

Curran, Timothy P. et al., "A short synthesis of bicyclic dipeptides corresponding to Xxx-L-Pro and Xxx-D-Pro having constrained cis-proline amides," Tetrahedron Letters, 36(2):191-194 (1995).

Curran, Timothy P. et al., "A short synthesis of bicyclic dipeptides corresponding to Xxx-L-Pro Xxx-D-Pro having constrained trans-proline amides," Organic Letters, 1(8): 1225-1228 (1999).

Dixon, W. J. "Efficient Analysis of Experimental Observations," Ann. Rev. Pharmacol. Toxicol. 20: 441-462 (1980).

Fobian, Yevette M. et al., "New routes to conformationally restricted peptide building blocks: a convenient preparation of bicyclic piperazinone derivatives," Bioorganic & Medicinal Chemistry Letters, 6(3): 315-318 (1996).

Gennaro, Alfonso R., Editor "Remington's Pharmaceutical Sciences," Mack Publishing Co., 1980 (Table of Contents).

Greene, Theodora W. et al., "Protective Groups in Organic Synthesis" (3rd ed.), John Wiley & Sons, NY (1999) (Table of Contents).

Gudasheva, T. A. et al., "Synthesis and Nootropic activity of pyrrolidino[1,2-a]diazacycloalkanes," Pharmaceutical Chemistry Journal, 30(9): 562-567 (1996).

Huang, Ri-Ming et al., "A new 1,4-diazepine from South China Sea Marine Sponge *Callyspongia* Species," Molecules, 15: 871-877 (2010).

International Search Report and Written Opinion for PCT/US2013/074119 dated Feb. 5, 2014, 8 pages.

IUPAC Handbook of Pharmaceutical Salts: Properties, Selection, and Use Edited by P. Heinrich Stahl and G. Wermuth, Wiley-VCH, Weinheim, Germany, 2002, (Table of Contents).

Iwaoka, M. et al., "Benzeneselenenyl Trifluoromethanesulfonate," e-EROS Encyclopedia of Reagents for Organic Synthesis, (2001), No pp. given. John Wiley & Sons, Ltd. Chichester, UK.

Jew, Sang-Sup et al., "Enantioselective synthesis of beta-amino acid via asymmetric bromolactamization," Heterocycles, 50(2): 677-680 (1999).

Liu, Yugang et al., "Practical synthesis of a peptide deformylase (PDF) inhibitor," Organic Process Research & Development, 12(2): 183-191 (2008).

Mogil, Jeffrey S. et al., "Heritability of nociception I: Responses of 11 inbred mouse strains on 12 measures of nociception," Pain, 80(1): 67-82 (1999).

Muller-Hartwieg, J. Constanze D. et al., "Synthesis and conformational investigation of cyclic dipeptides: 7-membered rings containing alpha- and beta-amino acids," J. Peptide Sci. 9(3), 187-199 (2003).

Nozaki-Taguchi, Natsuko et al., "Vincristine-induced allodynia in the rat," Pain 93:69-76 (2001).

Painter, Thomas O. et al., "In Situ Generation and Intramolecular Schmidt Reaction of Keto Azides in a Microwave-Assisted Flow Format", Chemistry—A Europen Journal, 17(35): 9595-9598, S9595/1-S9595/54 (2011).

Pikul, Stanislaw et al. "Heterocycle-based MMP Inhibitors with P2' Substituents," Bioorganic & Medicinal Chemistry Letters 11(8): 1009-1013 (2001).

Pinnen, Francesco et al., "Cyclol formation from tripeptides containing beta-alanine," J. Chem. Soc. Perkin Trans. I, Issue 6: 1311-16 (1982).

Stoeckel-Maschek, Angela et al., "Novel 3-amino-2-hydroxy acids containing protease inhibitors. Synthesis and kinetic characterization as aminopeptidase P inhibitors," Bioorganic & Medicinal Chemistry 13(16): 4806-4820 (2005).

Vasudevan, Anil et al., "Synthesis of Diazepinones via Intramolecular Transamidation," Organic Letters 6(19): 3361-3364 (2004).

AGENTS FOR TREATING PAIN AND USES THEREOF

CROSS REFERENCE TO RELATED APPLICATIONS

This application claims priority to U.S. Provisional Application No. 61/736,262 filed Dec. 12, 2012, and U.S. Provisional Application No. 61/760,984 filed Feb. 5, 2013, which are incorporated herein by reference in their entirety.

FIELD OF THE INVENTION

This invention is directed to: (a) compounds and salts thereof that, inter alia, are useful to treat pain; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND OF THE INVENTION

Voltage-gated calcium channels have been implicated in regulation of membrane ion conductance, neurotransmitter release, and cellular excitability, and can generally be classified into low-voltage activated and high-voltage activated channels based on differences in structure and function. The N-type calcium channel in particular has been generally implicated in regulation of pain.

Inadequate pain management is a major public health problem. There is a continuing need for the development of new therapeutic agents to treat pain including calcium channel blocker therapeutics with improved safety, potency, and/or other desirable pharmacological properties relative to currently available therapeutic agents for the treatment of pain. This invention provides compounds (including salts thereof), compositions, and methods of treatment that generally address such a need.

BRIEF DESCRIPTION OF THE INVENTION

In one aspect, the invention is directed to compounds that correspond in structure to Formula (I):

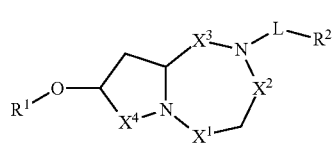

wherein:

$R^1$ is selected from the group consisting of pyridinyl, pyrimidinyl, pyrazinyl, and pyridazinyl, wherein each such substituent is optionally substituted with one, two, or three substituents independently selected from the group consisting of halogen, $C_1$-$C_6$-alkyl, halo-$C_1$-$C_6$-alkyl, and $C_3$-$C_6$-cycloalkyl;

$R^2$ is selected from the group consisting of phenyl, pyridinyl, pyrimidinyl, pyrazinyl, and pyridazinyl, wherein each such substituent is optionally substituted with one, two, or three substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl;

as to $X^1$, $X^2$, $X^3$, $X^4$, and L:

$X^1$ is —$CH_2$—; $X^2$ is —$CH_2$—; $X^3$ is —$CH_2$—; $X^4$ is —$CH_2$—; and L is selected from the group consisting of a bond, —$CH_2$—, —C(O)—, —C(O)C($R^3$)(H)—, and —S(O)$_2$—; or $X^1$ is —$CH_2$—; one of $X^2$ and $X^3$ is —C(O)— and the other one of $X^2$ and $X^3$ is —$CH_2$—; $X^4$ is —$CH_2$—; and L is selected from the group consisting of a bond, —$CH_2$—, —C(O)—, and —C(O)C($R^4$)(H)—; or one of $X^1$ and $X^4$ is —C(O)— and the other one of $X^1$ and $X^4$ is —$CH_2$—; $X^2$ is —$CH_2$—; $X^3$ is —$CH_2$—; and L is selected from the group consisting of a bond, —$CH_2$—, —C(O)—, —C(O)C($R^5$)(H)—, and —S(O)$_2$—; and $R^3$, $R^4$, and $R^5$ are independently selected from the group consisting of hydrogen, hydroxy, $C_1$-$C_6$-alkyl, $C_1$-$C_6$-alkoxy, and amino, wherein such amino is optionally substituted with one or two independently selected $C_1$-$C_6$-alkyl.

In another aspect, the invention is directed to the salts (including pharmaceutically acceptable salts) of the compounds of the invention.

In another aspect, the invention is directed to compositions (including pharmaceutical compositions) that comprise one or more compounds and/or salts of the invention, and, optionally, one or more additional therapeutic agents.

In another aspect, the invention is directed to kits that comprise one or more compounds and/or salts of the invention, and, optionally, one or more additional therapeutic agents.

In another aspect, the invention is directed to methods of using the compounds, salts, compositions, and/or kits of the invention to treat, for example, an N-type calcium channel-mediated condition, such as pain.

In another aspect, the invention is directed to one or more compounds and/or salts of the invention for use in the treatment of an N-type calcium channel-mediated condition, such as pain.

In another aspect, the invention is directed to a use of one or more compounds and/or salts of the invention to prepare a medicament. The medicament optionally can comprise one or more additional therapeutic agents. In some embodiments, the medicament is useful for treating pain.

In another aspect, the invention is directed to methods for synthesizing a compound of Formula (I), or a salt thereof, and intermediates that are useful in the synthesis of the compound.

Further benefits of Applicants' invention will be apparent to one skilled in the art from reading this patent application. The embodiments of the invention described in the following paragraphs are intended to illustrate the invention and should not be deemed to narrow the scope of the invention.

DETAILED DESCRIPTION OF THE INVENTION

A. Definitions

With respect to the inventions disclosed in this application, the following terms have the meanings set forth below:

The term "hydrogen" (alone or in combination with another term(s)) means a hydrogen radical, and may be depicted as —H.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

The term "hydroxy" (alone or in combination with another term(s)) means —OH.

The term "amino" (alone or in combination with another term(s)) means —NH$_2$.

The term "cyano" (alone or in combination with another term(s)) means —CN, which also may be depicted as —C≡N.

The term "alkyl" (alone or in combination with another term(s)) means a straight-or branched-chain saturated hydrocarbyl substituent, typically a straight-or branched-chain saturated hydrocarbyl substituent containing from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "cycloalkyl" (alone or in combination with another term(s)) means a saturated cyclic hydrocarbyl substituent, typically a single carbon ring containing from 3 to 6 carbon ring atoms. Examples of single-ring cycloalkyls include cyclopropyl, cyclobutyl, cyclopentyl, and cyclohexyl.

The term "alkoxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

A substituent is "substitutable" if it comprises at least one carbon or nitrogen atom that is bonded to one or more hydrogen atoms. Thus, for example, hydrogen, halogen, hydroxy, and oxo do not fall within this definition.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X"-L-R$^2$ and L is described as —C(O)C(R$^3$)(H)—, then the chemical structure would be X"—C(O)C(R$^3$)(H)—R$^2$.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

As used herein, reference to "a" or "an" means "one or more." Throughout, the plural and singular should be treated as interchangeable, other than the indication of number. For example, reference to "a compound" includes a single compound as well as one or more additional compounds, reference to "a pharmaceutically acceptable carrier" includes a single pharmaceutically acceptable carrier as well as one or more additional pharmaceutically acceptable carriers, and the like.

Advanced Chemistry Development Name software has been used to generate the compound names in this patent application.

B. Compounds

This invention is directed, in part, to compounds that correspond in structure to Formula (I):

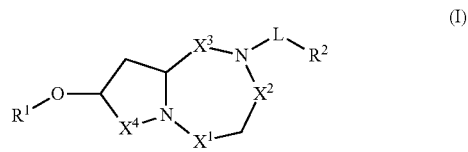

wherein:
R$^1$ is selected from the group consisting of pyridinyl, pyrimidinyl, pyrazinyl, and pyridazinyl, wherein each such substituent is optionally substituted with one, two, or three substituents independently selected from the group consisting of halogen, $C_1$-$C_6$-alkyl, halo-$C_1$-$C_6$-alkyl, and $C_3$-$C_6$-cycloalkyl;

R$^2$ is selected from the group consisting of phenyl, pyridinyl, pyrimidinyl, pyrazinyl, and pyridazinyl, wherein each such substituent is optionally substituted with one, two, or three substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl;

as to $X^1$, $X^2$, $X^3$, $X^4$, and L:

$X^1$ is —$CH_2$—; $X^2$ is —$CH_2$—; $X^3$ is —$CH_2$—; $X^4$ is —$CH_2$—; and L is selected from the group consisting of a bond, —$CH_2$—, —C(O)—, —C(O)C($R^3$)(H)—, and —S(O)$_2$—; or $X^1$ is —$CH_2$—; one of $X^2$ and $X^3$ is —C(O)— and the other one of $X^2$ and $X^3$ is —$CH_2$—; $X^4$ is —$CH_2$—; and L is selected from the group consisting of a bond, —$CH_2$—, —C(O)—, and —C(O)C($R^4$)(H)—; or one of $X^1$ and $X^4$ is —C(O)— and the other one of $X^1$ and $X^4$ is —$CH_2$—; $X^2$ is —$CH_2$—; $X^3$ is —$CH_2$—; and L is selected from the group consisting of a bond, —$CH_2$—, —C(O)—, —C(O)C($R^5$)(H)—, and —S(O)$_2$—; and $R^3$, $R^4$, and $R^5$ are independently selected from the group consisting of hydrogen, hydroxy, $C_1$-$C_6$-alkyl, $C_1$-$C_6$-alkoxy, and amino, wherein such amino is optionally substituted with one or two independently selected $C_1$-$C_6$-alkyl.

B-1: Compound Stereochemistry

The compounds of Formula (I) can have the configuration of Formula (I-i), (I-ii), (I-iii), or (I-iv) as further discussed below.

In one embodiment, the compounds of Formula (I) correspond in structure to Formula (I-i):

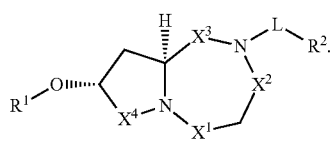

(I-i)

In another embodiment, the compounds of Formula (I) correspond in structure to Formula (I-ii):

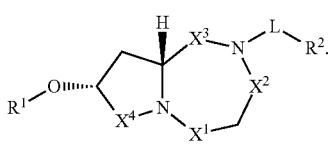

(I-ii)

In another embodiment, the compounds of Formula (I) correspond in structure to Formula (I-iii):

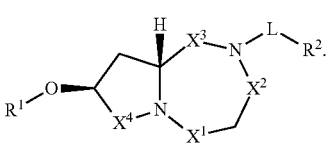

(I-iii)

In another embodiment, the compounds of Formula (I) correspond in structure to Formula (I-iv):

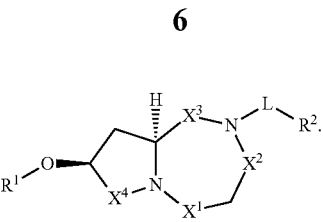

(I-iv)

B-2: Pyrrolo[1,2-a][1,4]-Diazepine Ring

In one embodiment of the compounds of Formula (I), $X^1$ is —$CH_2$—; $X^2$ is —$CH_2$—; $X^3$ is —$CH_2$—; $X^4$ is —$CH_2$—; and L is selected from the group consisting of a bond, —$CH_2$—, —C(O)—, —C(O)C($R^3$)(H)—, and —S(O)$_2$—. Such compounds correspond in structure to Formula (I-A):

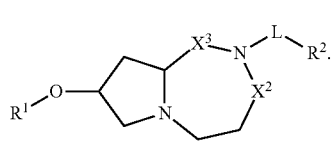

(I-A)

In another embodiment, $X^1$ is —$CH_2$—; one of $X^2$ and $X^3$ is —C(O)— and the other one of $X^2$ and $X^3$ is —$CH_2$—; $X^4$ is —$CH_2$—; and L is selected from the group consisting of a bond, —$CH_2$—, —C(O)—, and —C(O)C($R^4$)(H)—. Such compounds correspond in structure to Formula (I-B):

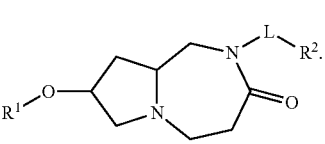

(I-B)

In another embodiment, $X^1$ is —$CH_2$—; $X^2$ is —C(O)—; $X^3$ is —$CH_2$—; $X^4$ is —$CH_2$—; and L is selected from the group consisting of a bond, —$CH_2$—, —C(O)—, and —C(O)C($R^4$)(H)—. Such compounds correspond in structure to Formula (I-B-1):

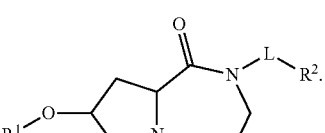

(I-B-1)

In another embodiment, $X^1$ is —$CH_2$—; $X^2$ is —$CH_2$—; $X^3$ is —C(O)—; $X^4$ is —$CH_2$—; and L is selected from the group consisting of a bond, —$CH_2$—, —C(O)—, and —C(O)C($R^4$)(H)—. Such compounds correspond in structure to Formula (I-B-2):

(I-B-2)

In another embodiment, one of $X^1$ and $X^4$ is —C(O)— and the other one of $X^1$ and $X^4$ is —CH$_2$—; $X^2$ is —CH$_2$—; $X^3$ is —CH$_2$—; and L is selected from the group consisting of a bond, —CH$_2$—, —C(O)—, —C(O)C(R$^5$)(H)—, and —S(O)$_2$—. Such compounds correspond in structure to Formula I-C:

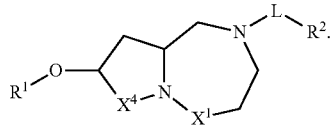
(I-C)

In another embodiment, $X^1$—C(O)—; $X^2$ is —CH$_2$—; $X^3$ is —CH$_2$—; $X^4$ is —CH$_2$—; and L is selected from the group consisting of a bond, —CH$_2$—, —C(O)—, —C(O)C(R$^5$)(H)—, and —S(O)$_2$—. Such compounds correspond in structure to Formula I-C-1:

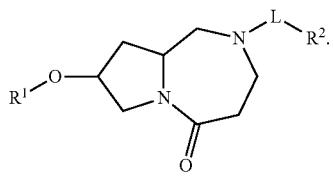
(I-C-1)

In another embodiment, $X^1$ is —CH$_2$—; $X^2$ is —CH$_2$—; $X^3$ is —CH$_2$—; $X^4$ is —C(O)—; and L is selected from the group consisting of a bond, —CH$_2$—, —C(O)—, —C(O)C(R$^5$)(H)—, and —S(O)$_2$—. Such compounds correspond in structure to Formula I-C-2:

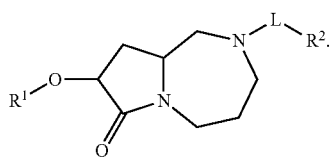
(I-C-2)

The compounds of Formulae (I-A), (I-B), (I-B-1), (I-B-2), (I-C), (I-C-1), and (I-C-2) can have configurations that correspond to any of Formula (I-i), (I-ii), (I-iii), or (I-iv) discussed above. For example, the compounds of Formula (I-C-1) can correspond in structure to any of Formulae (I-C-1-i), (I-C-1-ii), (I-C-1-iii), and (I-C-1-iv):

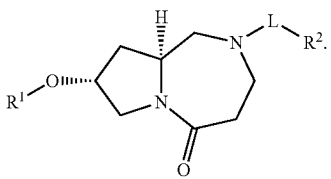
(I-C-1-i)

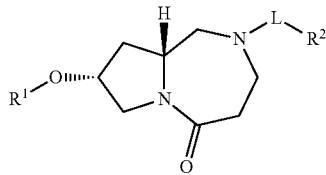
(I-C-1-ii)

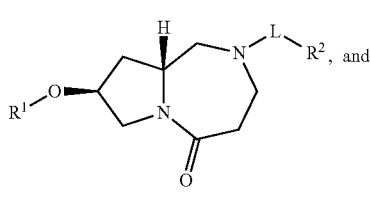
(I-C-1-iii)

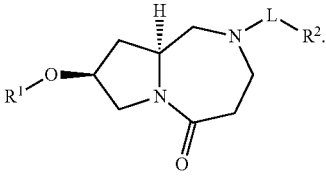
(I-C-1-iv)

B-3: L Substituent

In one embodiment of the compounds of Formula (I), L is selected from the group consisting of a bond, —CH$_2$—, —C(O)—, and —S(O)$_2$—.

In another embodiment, L is selected from the group consisting of a bond, —CH$_2$—, and —C(O)—.

In another embodiment, L is selected from the group consisting of a bond, —CH$_2$—, and —S(O)$_2$—.

In another embodiment, L is selected from the group consisting of a bond, —C(O)—, and —S(O)$_2$—.

In another embodiment, L is selected from the group consisting of —CH$_2$—, —C(O)—, and —S(O)$_2$—.

In another embodiment, L is selected from the group consisting of a bond and —CH$_2$.

In another embodiment, L is selected from the group consisting of a bond and —C(O)—.

In another embodiment, L is selected from the group consisting of a bond and —S(O)$_2$—.

In another embodiment, L is selected from the group consisting of —CH$_2$— and —C(O)—.

In another embodiment, L is selected from the group consisting of —CH$_2$— and —S(O)$_2$—.

In another embodiment, L is selected from the group consisting of —C(O)— and —S(O)$_2$—.

In another embodiment, L is a bond.
In another embodiment, L is —CH$_2$—.
In another embodiment, L is —C(O)—.
In another embodiment, L is —S(O)$_2$—.
In another embodiment, L is —C(O)C(R$^3$)(H)—.
In another embodiment, L is —C(O)C(R$^4$)(H)—.
In another embodiment, L is —C(O)C(R$^5$)(H)—.

B-4: $R^3$, $R^4$, and $R^5$ Substituents

In one embodiment of the compounds of Formula (I), $R^3$, $R^4$, and $R^5$ are independently selected from the group consisting of hydrogen, hydroxy, $C_1$-$C_3$-alkyl, $C_1$-$C_3$-alkoxy, and amino, wherein such amino is optionally substituted with one or two independently selected $C_1$-$C_3$-alkyl.

In another embodiment, $R^3$, $R^4$, and $R^5$ are independently selected from the group consisting of hydrogen, hydroxy, $C_1$-$C_3$-alkyl, and amino, wherein such amino is optionally substituted with one or two independently selected $C_1$-$C_3$-alkyl.

In another embodiment, $R^3$, $R^4$, and $R^5$ are independently selected from the group consisting of hydrogen, hydroxy, and amino In another embodiment, $R^3$ is selected from the group consisting of hydrogen, hydroxy, $C_1$-$C_3$-alkyl, $C_1$-$C_3$-alkoxy, and amino, wherein such amino is optionally substituted with one or two independently selected $C_1$-$C_3$-alkyl.

In another embodiment, $R^3$ is independently selected from the group consisting of hydrogen, hydroxy, $C_1$-$C_3$-alkyl, and amino, wherein such amino is optionally substituted with one or two independently selected $C_1$-$C_3$-alkyl.

In another embodiment, $R^3$ is selected from the group consisting of hydrogen, hydroxy, and amino In another embodiment, $R^3$ is hydrogen.

In another embodiment, $R^3$ is hydroxy.

In another embodiment, $R^3$ is $C_1$-$C_3$-alkyl.

In another embodiment, $R^3$ is amino, wherein such amino is optionally substituted with one or two independently selected $C_1$-$C_3$-alkyl.

In another embodiment, $R^3$ is selected from the group consisting of amino, methylamino, and dimethylamino.

In another embodiment, $R^3$ is amino

In another embodiment, $R^3$ is methylamino.

In another embodiment, $R^3$ is dimethylamino

In another embodiment, $R^4$ is selected from the group consisting of hydrogen, hydroxy, $C_1$-$C_3$-alkyl, $C_1$-$C_3$-alkoxy, and amino, wherein such amino is optionally substituted with one or two independently selected $C_1$-$C_3$-alkyl.

In another embodiment, $R^4$ is independently selected from the group consisting of hydrogen, hydroxy, $C_1$-$C_3$-alkyl, and amino, wherein such amino is optionally substituted with one or two independently selected $C_1$-$C_3$-alkyl.

In another embodiment, $R^4$ is selected from the group consisting of hydrogen, hydroxy, and amino In another embodiment, $R^4$ is hydrogen.

In another embodiment, $R^4$ is hydroxy.

In another embodiment, $R^4$ is $C_1$-$C_3$-alkyl.

In another embodiment, $R^4$ is amino, wherein such amino is optionally substituted with one or two independently selected $C_1$-$C_3$-alkyl.

In another embodiment, $R^4$ is selected from the group consisting of amino, methylamino, and dimethylamino.

In another embodiment, $R^4$ is amino.

In another embodiment, $R^4$ is methylamino.

In another embodiment, $R^4$ is dimethylamino.

In another embodiment, $R^5$ is selected from the group consisting of hydrogen, hydroxy, $C_1$-$C_3$-alkyl, $C_1$-$C_3$-alkoxy, and amino, wherein such amino is optionally substituted with one or two independently selected $C_1$-$C_3$-alkyl.

In another embodiment, $R^5$ is independently selected from the group consisting of hydrogen, hydroxy, $C_1$-$C_3$-alkyl, and amino, wherein such amino is optionally substituted with one or two independently selected $C_1$-$C_3$-alkyl.

In another embodiment, $R^5$ is selected from the group consisting of hydrogen, hydroxy, and amino In another embodiment, $R^5$ is hydrogen.

In another embodiment, $R^5$ is hydroxy.

In another embodiment, $R^5$ is $C_1$-$C_3$-alkyl.

In another embodiment, $R^5$ is amino, wherein such amino is optionally substituted with one or two independently selected $C_1$-$C_3$-alkyl.

In another embodiment, $R^5$ is selected from the group consisting of amino, methylamino, and dimethylamino.

In another embodiment, $R^5$ is amino

In another embodiment, $R^5$ is methylamino.

In another embodiment, $R^5$ is dimethylamino

B-5: $R^1$ Substituent

In one embodiment of the compounds of Formula (I), $R^1$ is selected from the group consisting of pyridinyl, pyrimidinyl, pyrazinyl, and pyridazinyl, wherein each such substituent is optionally substituted with one, two, or three substituents independently selected from the group consisting of halogen, $C_1$-$C_4$-alkyl, halo-$C_1$-$C_4$-alkyl, and $C_3$-$C_4$-cycloalkyl.

In another embodiment, $R^1$ is selected from the group consisting of pyridinyl, pyrimidinyl, pyrazinyl, and pyridazinyl, wherein each such substituent is optionally substituted with one or two substituents independently selected from the group consisting of halogen, $C_1$-$C_4$-alkyl, halo-$C_1$-$C_4$-alkyl, and $C_3$-$C_4$-cycloalkyl.

In another embodiment, $R^1$ is selected from the group consisting of pyridinyl, pyrimidinyl, pyrazinyl, and pyridazinyl, wherein each such substituent is optionally substituted with one substituent selected from the group consisting of halogen, $C_1$-$C_4$-alkyl, halo-$C_1$-$C_4$-alkyl, and $C_3$-$C_4$-cycloalkyl.

In another embodiment, $R^1$ is selected from the group consisting of pyridinyl, pyrimidinyl, pyrazinyl, and pyridazinyl, wherein each such substituent is optionally substituted with one, two, or three substituents independently selected from the group consisting of halo-$C_1$-$C_6$-alkyl and $C_3$-$C_6$-cycloalkyl.

In another embodiment, $R^1$ is selected from the group consisting of pyridinyl, pyrimidinyl, pyrazinyl, and pyridazinyl, wherein each such substituent is optionally substituted with one or two substituents independently selected from the group consisting of halo-$C_1$-$C_6$-alkyl and $C_3$-$C_6$-cycloalkyl.

In another embodiment, $R^1$ is selected from the group consisting of pyridinyl, pyrimidinyl, pyrazinyl, and pyridazinyl, wherein each such substituent is optionally substituted with one or two substituents independently selected from the group consisting of halo-$C_1$-$C_4$-alkyl and $C_3$-$C_4$-cycloalkyl. In one embodiment, the optional substituent is halo-$C_1$-$C_4$-alkyl. In one embodiment, the optional substituent is $C_3$-$C_4$-cycloalkyl.

In another embodiment, $R^1$ is selected from the group consisting of pyridinyl, pyrimidinyl, pyrazinyl, and pyridazinyl, wherein each such substituent is optionally substituted with one substituent selected from the group consisting of halomethyl and cyclopropyl. In one embodiment, the optional substituent is halomethyl. In one embodiment, the optional substituent is trifluoromethyl. In one embodiment, the optional substituent is cyclopropyl.

B-5(a): $R^1$ Pyridinyl or Pyrazinyl Substituent

In one embodiment of the compounds of Formula (I), $R^1$ is selected from the group consisting of pyridinyl and pyrazinyl, wherein each such substituent is optionally substituted with one, two, or three substituents independently selected from the group consisting of halogen, $C_1$-$C_6$-alkyl, halo-$C_1$-$C_6$-alkyl, and $C_3$-$C_6$-cycloalkyl.

In another embodiment, $R^1$ is selected from the group consisting of pyridinyl and pyrazinyl, wherein each such substituent is optionally substituted with one or two substituents independently selected from the group consisting of halogen, $C_1$-$C_4$-alkyl, halo-$C_1$-$C_4$-alkyl, and $C_3$-$C_4$-cycloalkyl.

In another embodiment, $R^1$ is selected from the group consisting of pyridinyl and pyrazinyl, wherein each such substituent is optionally substituted with one substituent selected from the group consisting of halogen, $C_1$-$C_4$-alkyl, halo-$C_1$-$C_4$-alkyl, and $C_3$-$C_4$-cycloalkyl.

In another embodiment, $R^1$ is selected from the group consisting of pyridinyl and pyrazinyl, wherein each such substituent is optionally substituted with one, two, or three substituents independently selected from the group consisting of halo-$C_1$-$C_6$-alkyl and $C_3$-$C_6$-cycloalkyl.

In another embodiment, $R^1$ is selected from the group consisting of pyridinyl and pyrazinyl, wherein each such substituent is optionally substituted with one or two substituents independently selected from the group consisting of halo-$C_1$-$C_4$-alkyl and $C_3$-$C_4$-cycloalkyl. In one embodiment, the optional substituent is halo-$C_1$-$C_4$-alkyl. In one embodiment, the optional substituent is $C_3$-$C_4$-cycloalkyl.

In another embodiment, $R^1$ is selected from the group consisting of pyridinyl and pyrazinyl, wherein each such substituent is optionally substituted with one substituent selected from the group consisting of halomethyl and cyclopropyl. In one embodiment, the optional substituent is halomethyl. In one embodiment, the optional substituent is trifluoromethyl. In one embodiment, the optional substituent is cyclopropyl.

In another embodiment, $R^1$ is selected from the group consisting of the substituents listed in Table 1.

TABLE 1

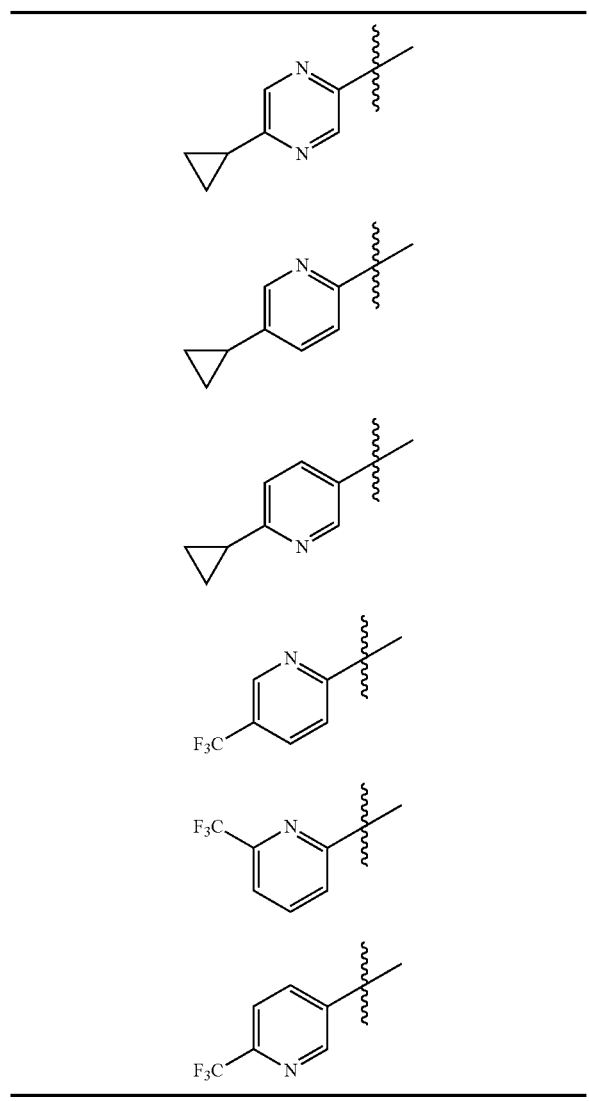

In another embodiment, the compounds correspond to a structure of Formula (I-i), (I-ii), (I-iii), or (I-iv), and $R^1$ is selected from the group consisting of the substituents listed in Table 1.

In another embodiment, the compounds correspond to a structure of Formula (I-A), (I-B), (I-B-1), (I-B-2), (I-C), (I-C-1), or (I-C-2), and $R^1$ is selected from the group consisting of the substituents listed in Table 1.

In another embodiment, $R^1$ is selected from the group consisting of 5-cyclopropyl-pyrazin-2-yl and 5-trifluoromethylpyridin-2-yl, i.e., the compounds of Formula (I) correspond to one of the structures shown in Table 1A.

TABLE 1A

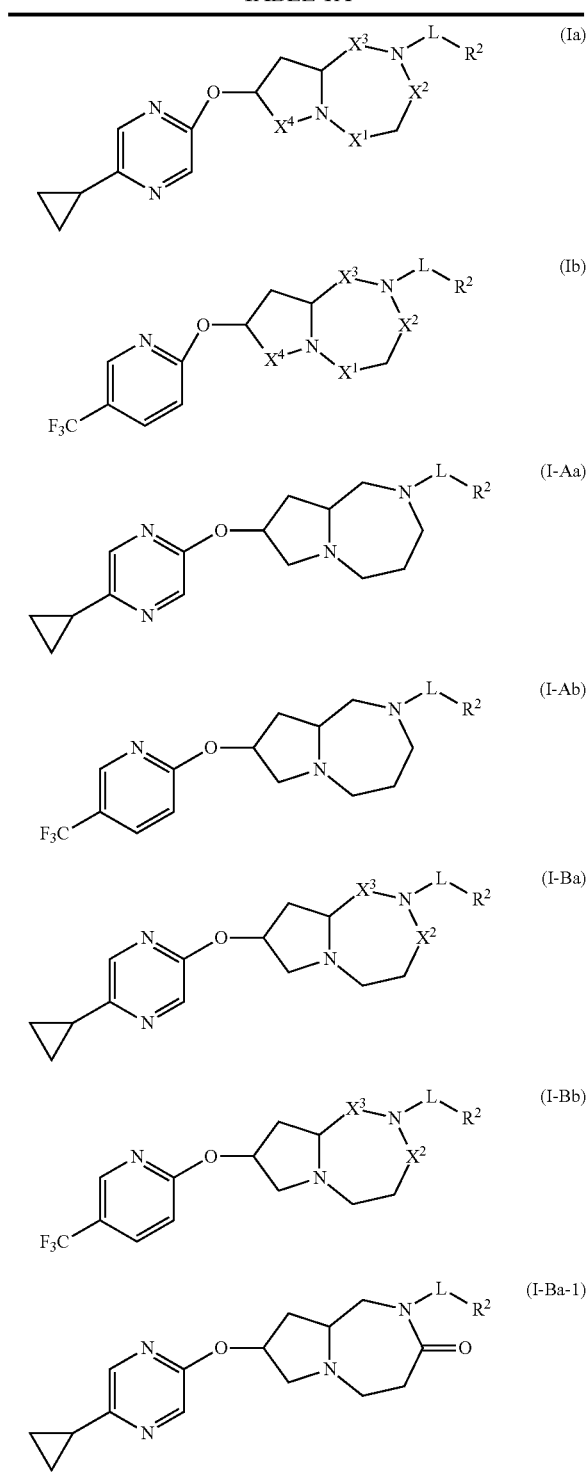

TABLE 1A-continued

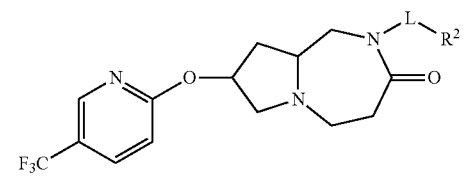
(I-Bb-1)

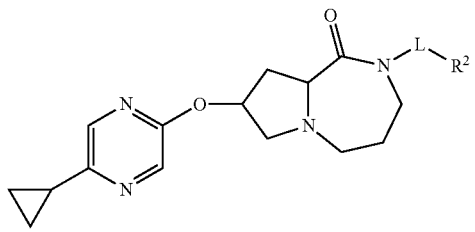
(I-Ba-2)

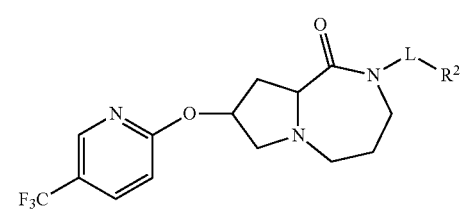
(I-Bb-2)

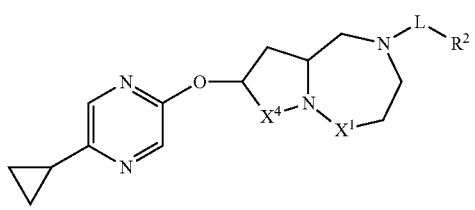
(I-Ca)

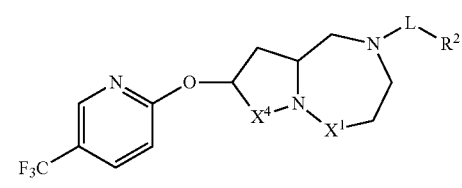
(I-Cb)

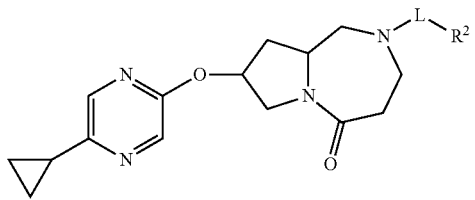
(I-Ca-1)

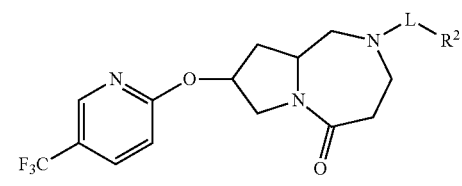
(I-Cb-1)

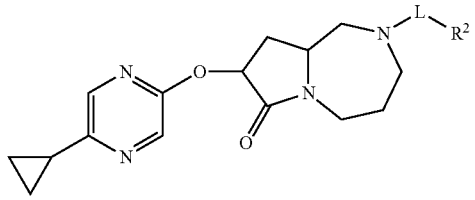
(I-Ca-2)

TABLE 1A-continued

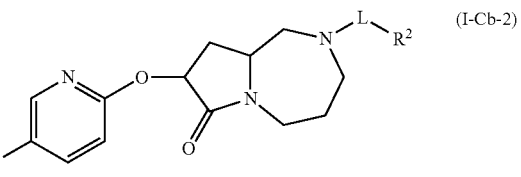
(I-Cb-2)

B-5(b): $R^1$ Pyrazinyl Substituent

In one embodiment of the compounds of Formula (I), $R^1$ is pyrazinyl, wherein such pyrazinyl is optionally substituted with one or two substituents independently selected from the group consisting of halogen, $C_1$-$C_6$-alkyl, halo-$C_1$-$C_6$-alkyl, and $C_3$-$C_6$-cycloalkyl. In one embodiment, $R^1$ is optionally substituted pyrazin-2-yl.

In another embodiment, $R^1$ is pyrazinyl, wherein such pyrazinyl is optionally substituted with one substituent selected from the group consisting of halogen, $C_1$-$C_4$-alkyl, halo-$C_1$-$C_4$-alkyl, and $C_3$-$C_4$-cycloalkyl. In one embodiment, $R^1$ is optionally substituted pyrazin-2-yl. In one embodiment, the optional substituent is halogen. In one embodiment, the optional substituent is $C_1$-$C_4$-alkyl. In one embodiment, the optional substituent is halo-$C_1$-$C_4$-alkyl. In one embodiment, the optional substituent is $C_3$-$C_4$-cycloalkyl.

In another embodiment, $R^1$ is pyrazinyl, wherein such pyrazinyl is optionally substituted with one, two, or three substituents independently selected from the group consisting of halo-$C_1$-$C_6$-alkyl and $C_3$-$C_6$-cycloalkyl. In one embodiment, $R^1$ optionally substituted pyrazin-2-yl.

In another embodiment, $R^1$ is pyrazinyl, wherein such pyrazinyl is optionally substituted with one or two substituents independently selected from the group consisting of halo-$C_1$-$C_4$-alkyl and $C_3$-$C_4$-cycloalkyl. In one embodiment, $R^1$ is optionally substituted pyrazin-2-yl.

In another embodiment, $R^1$ is pyrazinyl, wherein such pyrazinyl is optionally substituted with one substituent selected from the group consisting of halo-$C_1$-$C_4$-alkyl and $C_3$-$C_4$-cycloalkyl. In one embodiment, $R^1$ is optionally substituted pyrazin-2-yl. In one embodiment, the optional substituent is halo-$C_1$-$C_4$-alkyl. In one embodiment, the optional substituent is $C_3$-$C_4$-cycloalkyl.

In another embodiment, $R^1$ is pyrazinyl, wherein such pyrazinyl is optionally substituted with one substituent selected from the group consisting of halomethyl and cyclopropyl.

In another embodiment, the compounds correspond to a structure of Formula (I-i), (I-ii), (I-iii), or (I-iv), and $R^1$ is pyrazinyl, wherein such pyrazinyl is optionally substituted with one substituent selected from the group consisting of halomethyl and cyclopropyl.

In another embodiment, the compounds correspond to a structure of Formula (I-A), (I-B), (I-B-1), (I-B-2), (I-C), (I-C-1), or (I-C-2), and $R^1$ is pyrazinyl, wherein such pyrazinyl is optionally substituted with one substituent selected from the group consisting of halomethyl and cyclopropyl.

In another embodiment, $R^1$ is pyrazinyl that is substituted with trifluoromethyl. In one embodiment, $R^1$ is pyrazin-2-yl that is substituted with trifluoromethyl. In one embodiment, $R^1$ is 5-trifluoromethylpyrazin-2-yl.

In another embodiment, $R^1$ is pyrazinyl that is substituted with cyclopropyl. In one embodiment, $R^1$ is pyrazin-2-yl that is substituted with cyclopropyl. In one embodiment, $R^1$ is 5-cyclopropylpyrazin-2-yl.

B-5(c): R¹ Pyridinyl Substituent

In one embodiment of the compounds of Formula (I), R¹ is pyridinyl, wherein such pyridinyl is optionally substituted with one or two substituents independently selected from the group consisting of halogen, $C_1$-$C_6$-alkyl, halo-$C_1$-$C_6$-alkyl, and $C_3$-$C_6$-cycloalkyl. In one embodiment, R¹ is optionally substituted pyridin-2-yl. In one embodiment, R¹ is optionally substituted pyridin-3-yl. In one embodiment, R¹ is optionally substituted pyridin-4-yl.

In another embodiment, R¹ is pyridinyl, wherein such pyridinyl is optionally substituted with one substituent selected from the group consisting of halogen, $C_1$-$C_4$-alkyl, halo-$C_1$-$C_4$-alkyl, and $C_3$-$C_4$-cycloalkyl. In one embodiment, R¹ is optionally substituted pyridin-2-yl. In one embodiment, R¹ is optionally substituted pyridin-3-yl. In one embodiment, R¹ is optionally substituted pyridin-4-yl. In one embodiment, the optional substituent is halogen. In one embodiment, the optional substituent is $C_1$-$C_4$-alkyl. In one embodiment, the optional substituent is halo-$C_1$-$C_4$-alkyl. In one embodiment, the optional substituent is $C_3$-$C_4$-cycloalkyl.

In another embodiment, R¹ is pyridinyl, wherein such pyridinyl is optionally substituted with one, two, or three substituents independently selected from the group consisting of halo-$C_1$-$C_6$-alkyl and $C_3$-$C_6$-cycloalkyl. In one embodiment, R¹ is optionally substituted pyridin-2-yl. In one embodiment, R¹ is optionally substituted pyridin-3-yl. In one embodiment, R¹ is optionally substituted pyridin-4-yl.

In another embodiment, R¹ is pyridinyl, wherein such pyridinyl is optionally substituted with one or two substituents independently selected from the group consisting of halo-$C_1$-$C_4$-alkyl and $C_3$-$C_4$-cycloalkyl. In one embodiment, R¹ is optionally substituted pyridin-2-yl. In one embodiment, R¹ is optionally substituted pyridin-3-yl. In one embodiment, R¹ is optionally substituted pyridin-4-yl.

In another embodiment, R¹ is pyridinyl, wherein such pyridinyl is optionally substituted with one substituent selected from the group consisting of halo-$C_1$-$C_4$-alkyl and $C_3$-$C_4$-cycloalkyl. In one embodiment, R¹ is optionally substituted pyridin-2-yl. In one embodiment, R¹ is optionally substituted pyridin-3-yl. In one embodiment, R¹ is optionally substituted pyridin-4-yl. In one embodiment, the optional substituent is halo-$C_1$-$C_4$-alkyl. In one embodiment, the optional substituent is $C_3$-$C_4$-cycloalkyl.

In another embodiment, R¹ is pyridinyl, wherein such pyridinyl is optionally substituted with one substituent selected from the group consisting of halomethyl and cyclopropyl. In one embodiment, R¹ is optionally substituted pyridin-2-yl. In one embodiment, R¹ is optionally substituted pyridin-3-yl. In one embodiment, R¹ is optionally substituted pyridin-4-yl.

In another embodiment, the compounds correspond to a structure of Formula (I-i), (I-ii), (I-iii), or (I-iv), and R¹ is pyridinyl, wherein such pyridinyl is optionally substituted with one substituent selected from the group consisting of halomethyl and cyclopropyl.

In another embodiment, the compounds correspond to a structure of Formula (I-A), (I-B), (I-B-1), (I-B-2), (I-C), (I-C-1), or (I-C-2), and R¹ is pyridinyl, wherein such pyridinyl is optionally substituted with one substituent selected from the group consisting of halomethyl and cyclopropyl.

In another embodiment, R¹ is pyridinyl that is substituted with trifluoromethyl. In one embodiment, R¹ is pyridin-2-yl that is substituted with trifluoromethyl. In one embodiment, R¹ is 5-trifluoromethylpyridin-2-yl. In one embodiment, R¹ is pyridin-3-yl that is substituted with trifluoromethyl. In one embodiment, R¹ is 6-trifluoromethylpyridin-3-yl.

In another embodiment, R¹ is pyridinyl that is substituted with cyclopropyl. In one embodiment, R¹ is pyridin-2-yl that is substituted with cyclopropyl. In one embodiment, R¹ is 5-cyclopropylpyridin-2-yl. In one embodiment, R¹ is pyridin-3-yl that is substituted with cyclopropyl. In one embodiment, R¹ is 6-cyclopropylpyridin-3-yl.

In another embodiment, R¹ is selected from the group consisting of the substituents listed in Table 1B:

TABLE 1B

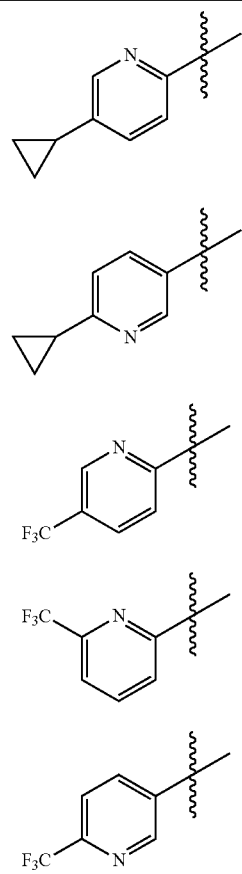

In another embodiment, the compounds correspond to a structure of Formula (I-i), (I-ii), (I-iii), or (I-iv), and R¹ is pyridinyl, wherein such pyridinyl is optionally substituted with one substituent selected from the group consisting the substituents listed in Table 1B.

In another embodiment, the compounds correspond to a structure of Formula (I-A), (I-B), (I-B-1), (I-B-2), (I-C), (I-C-1), or (I-C-2), and R¹ is pyridinyl, wherein such pyridinyl is optionally substituted with one substituent selected from the group consisting of the substituents listed in Table 1B.

B-5(d): R¹ Pyrimidinyl Substituent

In one embodiment of the compounds of Formula (I), R¹ is pyrimidinyl, wherein such pyrimidinyl is optionally substituted with one or two substituents independently selected from the group consisting of halogen, $C_1$-$C_6$-alkyl, halo-$C_1$-$C_6$-alkyl, and $C_3$-$C_6$-cycloalkyl. In one embodiment, R¹ is optionally substituted pyrimidin-2-yl. In one embodiment, R¹ is pyrimidin-3-yl.

In another embodiment, R¹ is pyrimidinyl, wherein such pyrimidinyl is optionally substituted with one substituent selected from the group consisting of halogen, $C_1$-$C_4$-alkyl, halo-$C_1$-$C_4$-alkyl, and $C_3$-$C_4$-cycloalkyl. In one embodiment, $R^1$ is optionally substituted pyrimidin-2-yl. In one embodiment, $R^1$ is pyrimidin-3-yl. In one embodiment, the optional substituent is halogen. In one embodiment, the optional substituent is $C_1$-$C_4$-alkyl. In one embodiment, the optional substituent is halo-$C_1$-$C_4$-alkyl. In one embodiment, the optional substituent is $C_3$-$C_4$-cycloalkyl.

In another embodiment, $R^1$ is pyrimidinyl, wherein such pyrimidinyl is optionally substituted with one, two, or three substituents independently selected from the group consisting of halo-$C_1$-$C_6$-alkyl and $C_3$-$C_6$-cycloalkyl. In one embodiment, $R^1$ is optionally substituted pyrimidin-2-yl. In one embodiment, $R^1$ is pyrimidin-3-yl.

In another embodiment, $R^1$ is pyrimidinyl, wherein such pyrimidinyl is optionally substituted with one or two substituents independently selected from the group consisting of halo-$C_1$-$C_4$-alkyl and $C_3$-$C_4$-cycloalkyl. In one embodiment, $R^1$ is optionally substituted pyrimidin-2-yl. In one embodiment, $R^1$ is pyrimidin-3-yl.

In another embodiment, $R^1$ is pyrimidinyl, wherein such pyrimidinyl is optionally substituted with one substituent selected from the group consisting of halo-$C_1$-$C_4$-alkyl and $C_3$-$C_4$-cycloalkyl. In one embodiment, In one embodiment, $R^1$ is optionally substituted pyrimidin-2-yl. In one embodiment, $R^1$ is pyrimidin-3-yl. In one embodiment, the optional substituent is halo-$C_1$-$C_4$-alkyl. In one embodiment, the optional substituent is $C_3$-$C_4$-cycloalkyl.

In another embodiment, $R^1$ is pyrimidinyl, wherein such pyrimidinyl is optionally substituted with one substituent selected from the group consisting of halomethyl and cyclopropyl. In one embodiment, $R^1$ is optionally substituted pyrimidin-2-yl. In one embodiment, $R^1$ is pyrimidin-3-yl.

In another embodiment, $R^1$ is pyrimidinyl that is substituted with trifluoromethyl. In one embodiment, $R^1$ is pyrimidin-2-yl that is substituted with trifluoromethyl. In one embodiment, $R^1$ is 5-trifluoromethylpyrimidin-2-yl. In one embodiment, $R^1$ is pyrimidin-3-yl that is substituted with trifluoromethyl. In one embodiment, $R^1$ is 6-trifluoromethylpyrimidin-3-yl.

In another embodiment, $R^1$ is pyrimidinyl that is substituted with cyclopropyl. In one embodiment, $R^1$ is pyrimidin-2-yl that is substituted with cyclopropyl. In one embodiment, $R^1$ is 5-cyclopropylpyrimidin-2-yl. In one embodiment, $R^1$ is pyrimidin-3-yl that is substituted with cyclopropyl. In one embodiment, $R^1$ is 6-cyclopropylpyrimidin-3-yl.

B-6: $R^2$ Substituent

In one embodiment of the compounds of Formula (I), $R^2$ is selected from the group consisting of phenyl, pyridinyl, pyrimidinyl, pyrazinyl, and pyridazinyl, wherein each such substituent is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is selected from the group consisting of phenyl, pyridinyl, pyrimidinyl, pyrazinyl, and pyridazinyl, wherein each such substituent is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl. In one embodiment, the optional substituent is halogen. In one embodiment, the optional substituent is cyano. In one embodiment, the optional substituent is $C_1$-$C_6$-alkyl. In one embodiment, the optional substituent is halo-$C_1$-$C_6$-alkyl. In one embodiment, the optional substituent is $C_1$-$C_6$-alkoxy. In one embodiment, the optional substituent is halo-$C_1$-$C_6$-alkoxy. In one embodiment, the optional substituent is $C_3$-$C_6$-cycloalkyl.

In another embodiment, $R^2$ is selected from the group consisting of phenyl, pyridinyl, pyrimidinyl, pyrazinyl, and pyridazinyl, wherein each such substituent is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is selected from the group consisting of phenyl, pyridinyl, pyrimidinyl, pyrazinyl, and pyridazinyl, wherein each such substituent is optionally substituted with one or two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy.

In another embodiment, $R^2$ is selected from the group consisting of phenyl, pyridinyl, pyrimidinyl, pyrazinyl, and pyridazinyl, wherein each such substituent is optionally substituted with one substituent selected from the group consisting of halogen, halo-$C_1$-$C_3$-alkyl, and halo-$C_1$-$C_3$-alkoxy. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is selected from the group consisting of phenyl, pyridinyl, pyrimidinyl, pyrazinyl, and pyridazinyl, wherein each such substituent is optionally substituted with two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

In another embodiment, $R^2$ is selected from the group consisting of the substituents listed in Table 2.

TABLE 2

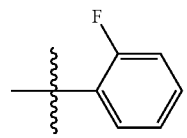

TABLE 2-continued

TABLE 2-continued

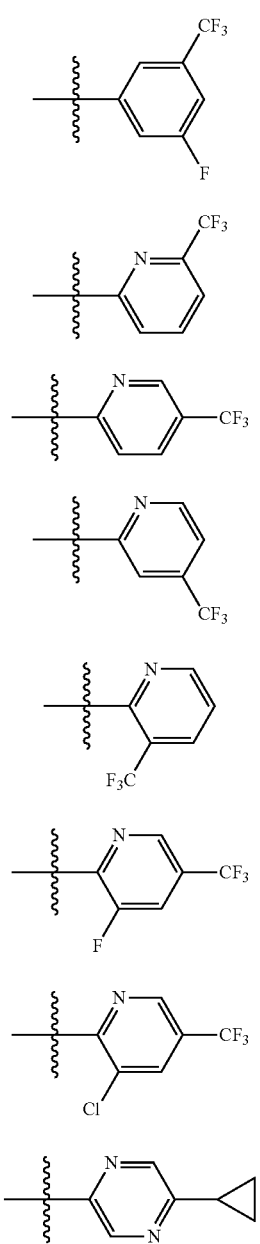

TABLE 2A

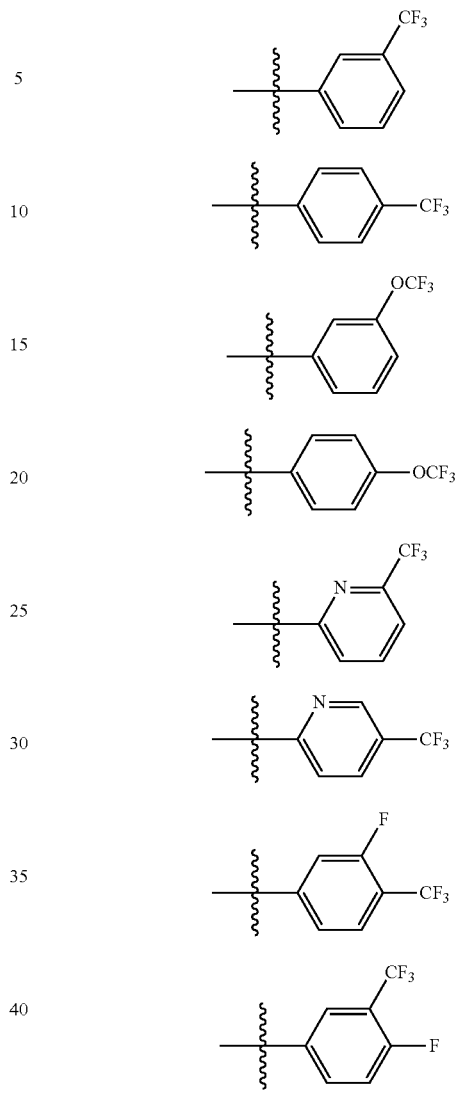

In another embodiment, the compounds correspond to a structure of Formula (I-i), (I-ii), (I-iii), or (I-iv), and $R^2$ is selected from the group consisting of the substituents listed in Table 2.

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2.

In another embodiment, the compounds of Formula (I) correspond to a structure shown in Table 1A, and $R^2$ is selected from the group consisting of the substituents listed in Table 2.

In another embodiment, $R^2$ is selected from the group consisting of the substituents listed in Table 2A.

In another embodiment, the compounds correspond to a structure of Formula (I-i), (I-ii), (I-iii), or (I-iv), and $R^2$ is selected from the group consisting of the substituents listed in Table 2A.

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2A.

In another embodiment, the compounds of Formula (I) correspond to a structure shown in Table 1A, and $R^2$ is selected from the group consisting of the substituents listed in Table 2A.

B-6(a): $R^2$ Phenyl or Pyridinyl Substituent

In one embodiment of the compounds of Formula (I), $R^2$ is selected from the group consisting of phenyl and pyridinyl, wherein each such substituent is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is selected from the group consisting of phenyl and pyridinyl, wherein each such substituent is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl. In one embodiment, the optional substituent is halogen. In one embodiment, the optional substituent is cyano. In one embodiment, the optional substituent is $C_1$-$C_6$-alkyl. In one embodiment, the optional substituent is halo-$C_1$-$C_6$-alkyl. In one embodiment, the optional substituent is $C_1$-$C_6$-alkoxy. In one embodiment, the optional substituent is halo-$C_1$-$C_6$-alkoxy. In one embodiment, the optional substituent is $C_3$-$C_6$-cycloalkyl.

In another embodiment, $R^2$ is selected from the group consisting of phenyl and pyridinyl, wherein each such substituent is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy.

In another embodiment, $R^2$ is selected from the group consisting of phenyl and pyridinyl, wherein each such substituent is optionally substituted with one substituent selected from the group consisting of halogen, halo-$C_1$-$C_3$-alkyl, and halo-$C_1$-$C_3$-alkoxy. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is selected from the group consisting of phenyl and pyridinyl, wherein each such substituent is optionally substituted with two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy. In one embodiment, the optional substituents are fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

B-6(b): $R^2$ Phenyl Substituent

In one embodiment of the compounds of Formula (I), $R^2$ is phenyl, wherein each such phenyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is phenyl, wherein each such phenyl is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is phenyl, wherein each such phenyl is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is phenyl, wherein each such phenyl is optionally substituted with one or two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy.

In another embodiment, the compounds correspond to a structure of Formula (I-i), (I-ii), (I-iii), or (I-iv), and $R^2$ is phenyl substituted with one or two substituents independently selected from the group consisting of fluoro, trifluoromethyl, and trifluoromethoxy.

In another embodiment, the compounds correspond to a structure of Formula (I-A), (I-B), (I-B-1), (I-B-2), (I-C), (I-C-1), or (I-C-2), and $R^2$ is phenyl substituted with one or two substituents independently selected from the group consisting of fluoro, trifluoromethyl, and trifluoromethoxy.

In another embodiment, $R^2$ is phenyl, wherein each such phenyl is optionally substituted with one substituent selected from the group consisting of halogen, halo-$C_1$-$C_3$-alkyl, and halo-$C_1$-$C_3$-alkoxy. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is phenyl, wherein each such phenyl is optionally substituted with two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

In another embodiment, $R^2$ is phenyl substituted with one substituent selected from the group consisting of fluoro, trifluoromethyl, and trifluoromethoxy. In one embodiment, $R^2$ is phenyl substituted with fluoro (e.g., 2-fluorophenyl, 3-fluorophenyl, or 4-fluorophenyl). In one embodiment, $R^2$ is phenyl substituted with trifluoromethyl (e.g., 2-trifluoromethylphenyl, 3-trifluoromethylphenyl, or 4-trifluoromethylphenyl). In one embodiment, $R^2$ is phenyl substituted with trifluoromethoxy (e.g., 2-trifluoromethoxyphenyl, 3-trifluoromethoxyphenyl, or 4-trifluoromethoxyphenyl).

In another embodiment, $R^2$ is phenyl substituted with two substituents independently selected from the group consisting of fluoro, trifluoromethyl, and trifluoromethoxy. In one embodiment, $R^2$ is phenyl substituted with one fluoro substituent and one trifluoromethyl substituent (e.g., 2-fluoro-3-trifluoro-phenyl, 3-fluoro-4-trifluoro-phenyl, 2-trifluoro-3-fluoro-phenyl, 3-trifluoro-4-fluoro-phenyl).

In another embodiment, $R^2$ is selected from the group consisting of the substituents listed in Table 2B.

TABLE 2B

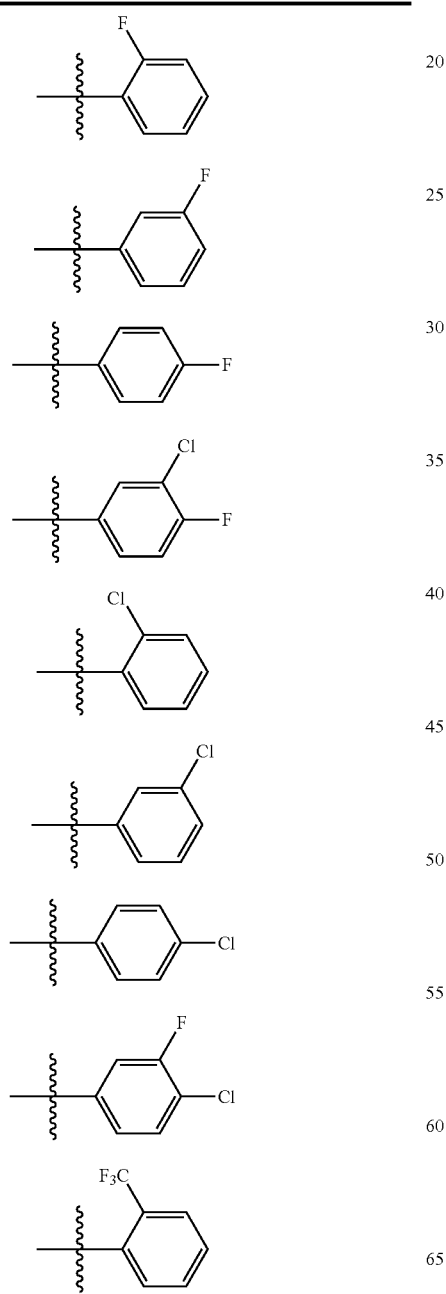

TABLE 2B-continued

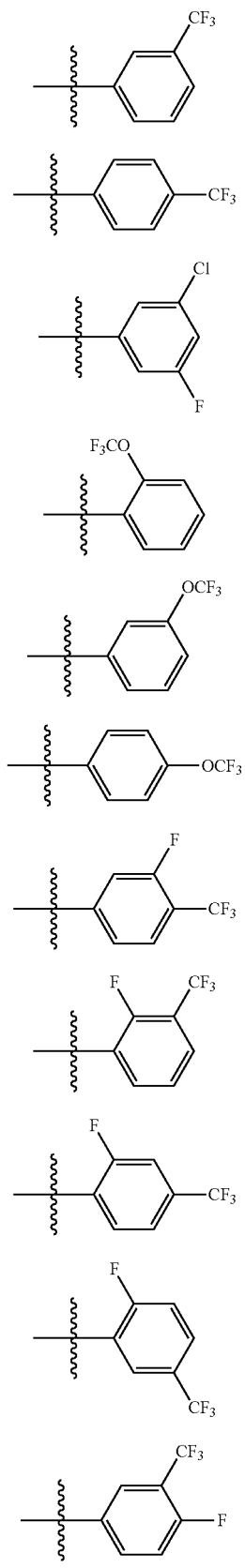

TABLE 2B-continued

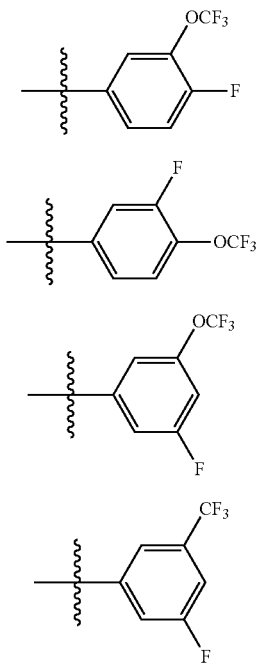

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2B.

In another embodiment, the compounds of Formula (I) correspond to a structure shown in Table 1A, and $R^2$ is selected from the group consisting of the substituents listed in Table 2B.

In another embodiment, $R^2$ is selected from the group consisting of the substituents listed in Table 2C.

TABLE 2C

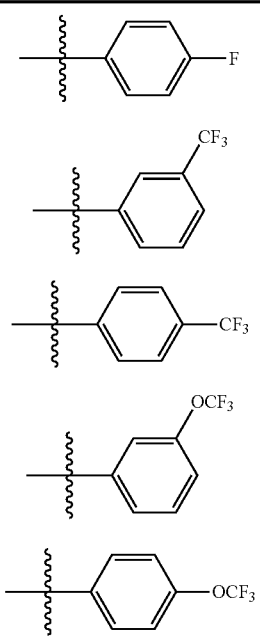

TABLE 2C-continued

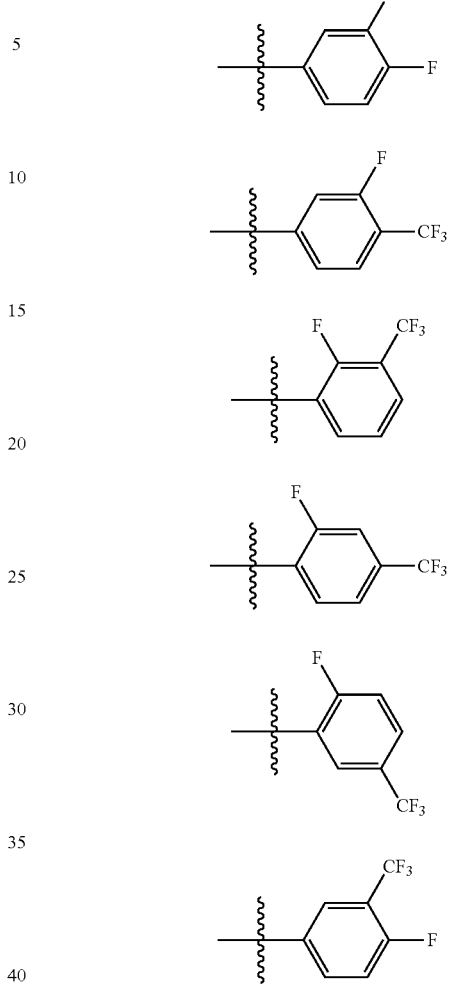

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2C.

In another embodiment, the compounds of Formula (I) correspond to a structure shown in Table 1A, and $R^2$ is selected from the group consisting of the substituents listed in Table 2C.

In another embodiment, $R^2$ is selected from the group consisting of the substituents listed in Table 2D.

TABLE 2D

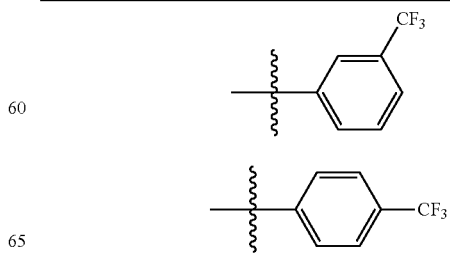

TABLE 2D-continued

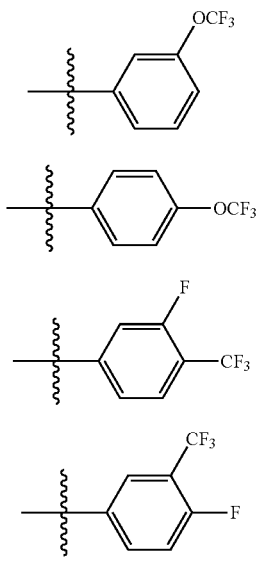

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2D.

In another embodiment, the compounds of Formula (I) correspond to a structure shown in Table 1A, and $R^2$ is selected from the group consisting of the substituents listed in Table 2D.

B-6(c): $R^2$ Pyridinyl Substituent

In one embodiment of the compounds of Formula (I), $R^2$ is pyridinyl, wherein each such pyridinyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl. In one embodiment, $R^2$ is optionally substituted pyridin-2-yl.

In another embodiment, $R^2$ is pyridinyl, wherein each such pyridinyl is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl. In one embodiment, $R^2$ is optionally substituted pyridin-2-yl.

In another embodiment, $R^2$ is pyridinyl, wherein each such pyridinyl is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl. In one embodiment, $R^2$ is optionally substituted pyridin-2-yl.

In another embodiment, $R^2$ is pyridinyl, wherein each such pyridinyl is optionally substituted with one or two substituents independently selected from the group consisting of halogen, halo-$C_1$-$C_3$-alkyl, and halo-$C_1$-$C_3$-alkoxy. In one embodiment, $R^2$ is optionally substituted pyridin-2-yl. In one embodiment, the optional substituents are independently selected from the group consisting of fluoro, trifluoromethyl, and trifluoromethoxy.

In another embodiment, the compounds correspond to a structure of Formula (I-i), (I-ii), (I-iii), or (I-iv), and $R^2$ is pyridinyl substituted with one or two substituents independently selected from the group consisting of fluoro, trifluoromethyl, and trifluoromethoxy.

In another embodiment, the compounds correspond to a structure of Formula (I-A), (I-B), (I-B-1), (I-B-2), (I-C), (I-C-1), or (I-C-2), and $R^2$ is pyridinyl substituted with one or two substituents independently selected from the group consisting of fluoro, trifluoromethyl, and trifluoromethoxy.

In another embodiment, $R^2$ is pyridinyl, wherein each such pyridinyl is optionally substituted with one substituent selected from the group consisting of halogen, halo-$C_1$-$C_3$-alkyl, and halo-$C_1$-$C_3$-alkoxy. In one embodiment, $R^2$ is optionally substituted pyridin-2-yl. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is pyridinyl, wherein each such pyridinyl is optionally substituted with two substituents independently selected from the group consisting of halogen, halo-$C_1$-$C_3$-alkyl, and halo-$C_1$-$C_3$-alkoxy. In one embodiment, $R^2$ is optionally substituted pyridin-2-yl. In one embodiment, the optional substituents are independently selected from the group consisting of fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

In another embodiment, $R^2$ is pyridin-2-yl substituted with one substituent selected from the group consisting of fluoro, trifluoromethyl, and trifluoromethoxy. In one embodiment, $R^2$ is pyridin-2-yl substituted with fluoro (e.g., 3-fluoropyridin-2-yl, 4-fluoropyridin-2-yl, 5-fluoropyridin-2-yl, or 6-fluoropyridin-2-yl). In one embodiment, $R^2$ is pyridin-2-yl substituted with trifluoromethyl (e.g., 3-trifluoromethylpyridin-2-yl, 4-trifluoromethylpyridin-2-yl, 5-trifluoromethylpyridin-2-yl, or 6-trifluoromethylpyridin-2-yl). In one embodiment, $R^2$ is pyridin-2-yl substituted with trifluoromethoxy (e.g., 3-trifluoromethoxypyridin-2-yl, 4-trifluoromethoxypyridin-2-yl, 5-trifluoromethoxypyridin-2-yl, or 6-trifluoromethoxypyridin-2-yl).

In another embodiment, $R^2$ is pyridinyl substituted with two substituents independently selected from the group consisting of fluoro, trifluoromethyl, and trifluoromethoxy. In one embodiment, $R^2$ is substituted pyridin-2-yl.

In another embodiment, $R^2$ is selected from the group consisting of the substituents listed in Table 2E.

TABLE 2E

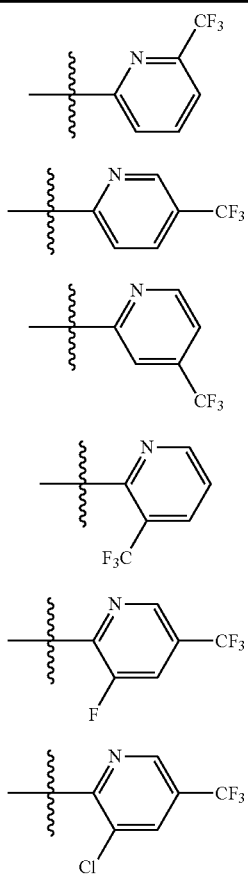

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2E.

In another embodiment, the compounds of Formula (I) correspond to a structure shown in Table 1A, and $R^2$ is selected from the group consisting of the substituents listed in Table 2E.

In another embodiment, $R^2$ is selected from the group consisting of the substituents listed in Table 2F.

TABLE 2F

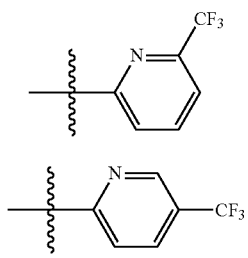

In another embodiment, the compounds correspond to a structure of Formula (I-A), (I-B), (I-B-1), (I-B-2), (I-C), (I-C-1), or (I-C-2), and $R^2$ is selected from the group consisting of the substituents listed in Table 2F.

In another embodiment, the compounds of Formula (I) correspond to a structure shown in Table 1A, and $R^2$ is selected from the group consisting of the substituents listed in Table 2F.

B-6(d): $R^2$ Pyrimidinyl Substituent

In one embodiment of the compounds of Formula (I), $R^2$ is pyrimidinyl, wherein each such pyrimidinyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrimidinyl, wherein each such pyrimidinyl is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrimidinyl, wherein each such pyrimidinyl is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrimidinyl, wherein each such pyrimidinyl is optionally substituted with one or two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy.

In another embodiment, the compounds correspond to a structure of Formula (I-i), (I-ii), (I-iii), or (I-iv), and $R^2$ is pyrimidinyl substituted with one or two substituents independently selected from the group consisting of fluoro, trifluoromethyl, and trifluoromethoxy.

In another embodiment, the compounds correspond to a structure of Formula (I-A), (I-B), (I-B-1), (I-B-2), (I-C), (I-C-1), or (I-C-2), and $R^2$ is pyrimidinyl substituted with one or two substituents independently selected from the group consisting of fluoro, trifluoromethyl, and trifluoromethoxy.

In another embodiment, $R^2$ is pyrimidinyl, wherein each such pyrimidinyl is optionally substituted with one substituent selected from the group consisting of halogen, halo-$C_1$-$C_3$-alkyl, and halo-$C_1$-$C_3$-alkoxy. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is pyrimidinyl, wherein each such pyrimidinyl is optionally substituted with two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

B-6(e): $R^2$ Pyrazinyl Substituent

In one embodiment of the compounds of Formula (I), $R^2$ is pyrazinyl, wherein each such pyrazinyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrazinyl, wherein each such pyrazinyl is optionally substituted with one substituent selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrazinyl, wherein each such pyrazinyl is optionally substituted with two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment, $R^2$ is pyrazinyl, wherein each such pyrazinyl is optionally substituted with one or two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy.

In another embodiment, the compounds correspond to a structure of Formula (I-i), (I-ii), (I-iii), or (I-iv), and $R^2$ is pyrazinyl substituted with one or two substituents independently selected from the group consisting of fluoro, trifluoromethyl, and trifluoromethoxy.

In another embodiment, the compounds correspond to a structure of Formula (I-A), (I-B), (I-B-1), (I-B-2), (I-C), (I-C-1), or (I-C-2), and $R^2$ is pyrazinyl substituted with one or two substituents independently selected from the group consisting of fluoro, trifluoromethyl, and trifluoromethoxy.

In another embodiment, $R^2$ is pyrazinyl, wherein each such pyrazinyl is optionally substituted with one substituent selected from the group consisting of halogen, halo-$C_1$-$C_3$-alkyl, and halo-$C_1$-$C_3$-alkoxy. In one embodiment, the optional substituent is selected from the group consisting of fluoro, trifluoromethyl, and trifluoromethoxy. In one embodiment, the optional substituent is halogen. In one embodiment, the optional substituent is halo-$C_1$-$C_3$-alkyl. In one embodiment, the optional substituent is halo-$C_1$-$C_3$-alkoxy. In one embodiment, the optional substituent is fluoro. In one embodiment, the optional substituent is trifluoromethyl. In one embodiment, the optional substituent is trifluoromethoxy.

In another embodiment, $R^2$ is pyrazinyl, wherein each such pyrazinyl is optionally substituted with two substituents independently selected from the group consisting of halogen, halo-$C_1$-$C_3$-alkyl, and halo-$C_1$-$C_3$-alkoxy. In one embodiment, the optional substituents are independently selected from the group consisting of fluoro, trifluoromethyl, and trifluoromethoxy. In one embodiment, the optional substituents are independently halogen. In one embodiment, the optional substituents are chloro and fluoro. In one embodiment, one optional substituent is halogen and the other optional substituent is trifluoromethyl. In one embodiment, one optional substituent is chloro and the other optional substituent is trifluoromethyl. In one embodiment, one optional substituent is fluoro and the other optional substituent is trifluoromethyl. In one embodiment, one optional substituent is halogen and the other optional substituent is trifluoromethoxy. In one embodiment, one optional substituent is chloro and the other optional substituent is trifluoromethoxy. In one embodiment, one optional substituent is fluoro and the other optional substituent is trifluoromethoxy.

In another embodiment, the compounds of Formula (I) correspond to a structure shown in Table 1A, and $R^2$ is pyrazinyl substituted with one substituent selected from the group consisting of fluoro, trifluoromethyl, and trifluoromethoxy.

In another embodiment, $R^2$ is 5-cyclopropylpyridazin-2-yl.

* * *

Various embodiments of the pyrrolo[1,2-a][1,4]diazepine ring of the present invention and substituents $R^1$, $R^2$, $R^3$, $R^4$, $R^5$, and L have been discussed above. These individual embodiments can be combined to form various additional embodiments of the compounds of Formula (I), (I-i), (I-ii), (I-iii), (I-iv), (I-A), (I-B), (I-B-1), (I-B-2), (I-C), (I-C-1), or (I-C-2). All embodiments of the compounds of Formula (I), (I-i), (I-ii), (I-iii), (I-iv), (I-A), (I-B), (I-B-1), (I-B-2), (I-C), (I-C-1), or (I-C-2) formed by combining the substituent embodiments discussed above are within the scope of applicant's invention, and several representative embodiments of these compounds are provided below.

B-7: $R^1$/$R^2$ Substituents

In one embodiment of the compounds of Formula (I):
$R^1$ is selected from the group consisting of pyridinyl and pyrazinyl, wherein each such substituent is optionally substituted with one or two substituents independently selected from the group consisting of halogen, $C_1$-$C_6$-alkyl, halo-$C_1$-$C_6$-alkyl, and $C_3$-$C_6$-cycloalkyl; and
$R^2$ is selected from the group consisting of phenyl and pyridinyl, wherein each such substituent is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment:
$R^2$ is selected from the group consisting of pyridinyl and pyrazinyl, wherein each such substituent is optionally substituted with one or two substituents independently selected from the group consisting of halogen, $C_1$-$C_4$-alkyl, halo-$C_1$-$C_4$-alkyl, and $C_3$-$C_4$-cycloalkyl; and
$R^2$ is selected from the group consisting of phenyl and pyridinyl, wherein each such substituent is optionally substituted with one or two substituents independently selected from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, and $C_3$-$C_4$-cycloalkyl.

In another embodiment:
$R^1$ is selected from the group consisting of pyridinyl and pyrazinyl, wherein each such substituent is optionally substituted with one or two substituents independently selected from the group consisting of halo-$C_1$-$C_4$-alkyl and $C_3$-$C_4$-cycloalkyl; and
$R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy.

In another embodiment:
$R^1$ is selected from the group consisting of pyridinyl and pyrazinyl, wherein each such substituent is optionally substituted with one substituent selected from the group consisting of halomethyl and cyclopropyl; and
$R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment:
$R^1$ is selected from the group consisting of pyridinyl and pyrazinyl, wherein each such substituent is optionally substituted with one substituent selected from the group consisting of trifluoromethyl and cyclopropyl; and
$R^2$ is selected from the group consisting of phenyl and pyridinyl, wherein each such substituent is optionally substituted with one or two substituents independently selected from the group consisting of fluoro, trifluoromethyl, and trifluoromethoxy.

In additional embodiments, the compounds correspond to a structure of Formula (I-i), (I-ii), (I-iii), or (I-iv), and $R^1$ and $R^2$ are as defined in the various substituent embodiments discussed above.

In additional embodiments, the compounds correspond to a structure of Formula (I-A), (I-B), (I-B-1), (I-B-2), (I-C), (I-C-1), or (I-C-2), and $R^1$ and $R^2$ are as defined in the various substituent embodiments discussed above.

B-7(a): $R^1$ Pyrazinyl/$R^2$ Phenyl Substituents

In one embodiment of the compounds of Formula (I):
$R^1$ is pyrazinyl, wherein such pyrazinyl is optionally substituted with one or two substituents independently selected from the group consisting of halogen, $C_1$-$C_6$-alkyl, halo-$C_1$-$C_6$-alkyl, and $C_3$-$C_6$-cycloalkyl; and
$R^2$ is phenyl, wherein such phenyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment:
$R^1$ is pyrazinyl, wherein such pyrazinyl is optionally substituted with one or two substituents independently selected from the group consisting of halogen, $C_1$-$C_4$-alkyl, halo-$C_1$-$C_4$-alkyl, and $C_3$-$C_4$-cycloalkyl; and
$R^2$ is phenyl, wherein such phenyl is optionally substituted with one or two substituents independently selected from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, and $C_3$-$C_4$-cycloalkyl.

In another embodiment:
$R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and
$R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment:
$R^1$ is pyrazinyl, wherein such pyrazinyl is optionally substituted with one substituent selected from the group consisting of halomethyl and cyclopropyl; and
$R^2$ is phenyl, wherein such phenyl is optionally substituted with one or two substituents independently selected from the group consisting of fluoro, trifluoromethyl, and trifluoromethoxy.

In another embodiment:
$R^1$ is pyrazinyl, wherein such pyrazinyl is optionally substituted with one substituent selected from the group consisting of trifluoromethyl and cyclopropyl; and
$R^2$ is phenyl, wherein such phenyl is optionally substituted with one or two substituents independently selected from the group consisting of fluoro, trifluoromethyl, and trifluoromethoxy.

In another embodiment:
$R^1$ is pyrazinyl, wherein such pyrazinyl is substituted with one substituent selected from the group consisting of trifluoromethyl and cyclopropyl; and
$R^2$ is phenyl, wherein such phenyl is substituted with one substituent selected from the group consisting of fluoro, trifluoromethyl, and trifluoromethoxy.

In another embodiment:
$R^1$ is pyrazinyl, wherein such pyrazinyl is substituted with one substituent selected from the group consisting of trifluoromethyl and cyclopropyl; and
$R^2$ is phenyl, wherein such phenyl is substituted with two substituents independently selected from the group consisting of fluoro, trifluoromethyl, and trifluoromethoxy.

In additional embodiments, the compounds correspond to a structure of Formula (I-i), (I-ii), (I-iii), or (I-iv), and $R^1$ and $R^2$ are as defined in the various substituent embodiments discussed above.

In additional embodiments, the compounds correspond to a structure of Formula (I-A), (I-B), (I-B-1), (I-B-2), (I-C), (I-C-1), or (I-C-2), and $R^1$ and $R^2$ are as defined in the various substituent embodiments discussed above.

B-7(b): $R^1$ Pyrazinyl/$R^2$ Pyridinyl Substituents

In one embodiment of the compounds of Formula (I):
$R^1$ is pyrazinyl, wherein such pyrazinyl is optionally substituted with one or two substituents independently selected from the group consisting of halogen, $C_1$-$C_6$-alkyl, halo-$C_1$-$C_6$-alkyl, and $C_3$-$C_6$-cycloalkyl; and
$R^2$ is pyridinyl, wherein such pyridinyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment:
$R^1$ is pyrazinyl, wherein such pyrazinyl is optionally substituted with one or two substituents independently selected from the group consisting of halogen, $C_1$-$C_4$-alkyl, halo-$C_1$-$C_4$-alkyl, and $C_3$-$C_4$-cycloalkyl; and
$R^2$ is pyridinyl, wherein such pyridinyl is optionally substituted with one or two substituents independently selected from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, and $C_3$-$C_4$-cycloalkyl.

In another embodiment:
$R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and
$R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment:
$R^1$ is pyrazinyl, wherein such pyrazinyl is optionally substituted with one substituent selected from the group consisting of halomethyl and cyclopropyl; and
$R^2$ is pyridinyl, wherein such pyridinyl is optionally substituted with one or two substituents independently selected from the group consisting of fluoro, trifluoromethyl, and trifluoromethoxy.

In another embodiment:
$R^1$ is pyrazinyl, wherein such pyrazinyl is optionally substituted with one substituent selected from the group consisting of trifluoromethyl and cyclopropyl; and
$R^2$ is pyridinyl, wherein such pyridinyl is optionally substituted with one or two substituents independently selected from the group consisting of fluoro, trifluoromethyl, and trifluoromethoxy.

In another embodiment:
- $R^1$ is pyrazinyl, wherein such pyrazinyl is substituted with one substituent selected from the group consisting of trifluoromethyl and cyclopropyl; and
- $R^2$ is pyridinyl, wherein such pyridinyl is substituted with one substituent selected from the group consisting of fluoro, trifluoromethyl, and trifluoromethoxy.

In another embodiment:
- $R^1$ is pyrazinyl, wherein such pyrazinyl is substituted with one substituent selected from the group consisting of trifluoromethyl and cyclopropyl; and
- $R^2$ is pyridinyl, wherein such pyridinyl is substituted with two substituents independently selected from the group consisting of fluoro, trifluoromethyl, and trifluoromethoxy.

In additional embodiments, the compounds correspond to a structure of Formula (I-i), (I-ii), (I-iii), or (I-iv), and $R^1$ and $R^2$ are as defined in the various substituent embodiments discussed above.

In additional embodiments, the compounds correspond to a structure of Formula (I-A), (I-B), (I-B-1), (I-B-2), (I-C), (I-C-1), or (I-C-2), and $R^1$ and $R^2$ are as defined in the various substituent embodiments discussed above.

B-7(c): $R^1$ Pyridinyl/$R^2$ Phenyl Substituents

In one embodiment of the compounds of Formula (I):
- $R^1$ is pyridinyl, wherein such pyridinyl is optionally substituted with one or two substituents independently selected from the group consisting of halogen, $C_1$-$C_6$-alkyl, halo-$C_1$-$C_6$-alkyl, and $C_3$-$C_6$-cycloalkyl; and
- $R^2$ is phenyl, wherein such phenyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment:
- $R^1$ is pyridinyl, wherein such pyridinyl is optionally substituted with one or two substituents independently selected from the group consisting of halogen, $C_1$-$C_4$-alkyl, halo-$C_1$-$C_4$-alkyl, and $C_3$-$C_4$-cycloalkyl; and
- $R^2$ is phenyl, wherein such phenyl is optionally substituted with one or two substituents independently selected from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, and $C_3$-$C_4$-cycloalkyl.

In another embodiment:
- $R^1$ is pyridinyl, wherein such pyridinyl is optionally substituted with one or two substituents independently selected from the group consisting of halo-$C_1$-$C_4$-alkyl and $C_3$-$C_4$-cycloalkyl; and
- $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment:
- $R^1$ is pyridinyl, wherein such pyridinyl is optionally substituted with one substituent selected from the group consisting of halomethyl and cyclopropyl; and
- $R^2$ is phenyl, wherein such phenyl is optionally substituted with one or two substituents independently selected from the group consisting of fluoro, trifluoromethyl, and trifluoromethoxy.

In another embodiment:
- $R^1$ is pyridinyl, wherein such pyrazinyl is optionally substituted with one substituent selected from the group consisting of trifluoromethyl and cyclopropyl; and
- $R^2$ is phenyl, wherein such phenyl is optionally substituted with one or two substituents independently selected from the group consisting of fluoro, trifluoromethyl, and trifluoromethoxy.

In another embodiment:
- $R^1$ is pyridinyl, wherein such pyridinyl is substituted with one substituent selected from the group consisting of trifluoromethyl and cyclopropyl; and
- $R^2$ is phenyl, wherein such phenyl is substituted with one substituent selected from the group consisting of fluoro, trifluoromethyl, and trifluoromethoxy.

In another embodiment:
- $R^1$ is pyridinyl, wherein such pyridinyl is substituted with one substituent selected from the group consisting of trifluoromethyl and cyclopropyl; and
- $R^2$ is phenyl, wherein such phenyl is substituted with two substituents independently selected from the group consisting of fluoro, trifluoromethyl, and trifluoromethoxy.

In additional embodiments, the compounds correspond to a structure of Formula (I-i), (I-ii), (I-iii), or (I-iv), and $R^1$ and $R^2$ are as defined in the various substituent embodiments discussed above.

In additional embodiments, the compounds correspond to a structure of Formula (I-A), (I-B), (I-B-1), (I-B-2), (I-C), (I-C-1), or (I-C-2), and $R^1$ and $R^2$ are as defined in the various substituent embodiments discussed above.

B-7(d): $R^1$ Pyridinyl/$R^2$ Pyridinyl Substituents

In one embodiment of the compounds of Formula (I):
- $R^1$ is pyridinyl, wherein such pyridinyl is optionally substituted with one or two substituents independently selected from the group consisting of halogen, $C_1$-$C_6$-alkyl, halo-$C_1$-$C_6$-alkyl, and $C_3$-$C_6$-cycloalkyl; and
- $R^2$ is pyridinyl, wherein such pyridinyl is optionally substituted with one or two substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl.

In another embodiment:
- $R^1$ is pyridinyl, wherein such pyridinyl is optionally substituted with one or two substituents independently selected from the group consisting of halogen, $C_1$-$C_4$-alkyl, halo-$C_1$-$C_4$-alkyl, and $C_3$-$C_4$-cycloalkyl; and
- $R^2$ is pyridinyl, wherein such pyridinyl is optionally substituted with one or two substituents independently selected from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, and $C_3$-$C_4$-cycloalkyl.

In another embodiment:
- $R^1$ is pyridinyl, wherein such pyridinyl is optionally substituted with one or two substituents independently selected from the group consisting of halo-$C_1$-$C_4$-alkyl and $C_3$-$C_4$-cycloalkyl; and
- $R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment:
- $R^1$ is pyridinyl, wherein such pyridinyl is optionally substituted with one substituent selected from the group consisting of halomethyl and cyclopropyl; and
- $R^2$ is pyridinyl, wherein such pyridinyl is optionally substituted with one or two substituents independently selected from the group consisting of fluoro, trifluoromethyl, and trifluoromethoxy.

In another embodiment:
R¹ is pyridinyl, wherein such pyridinyl is optionally substituted with one substituent selected from the group consisting of trifluoromethyl and cyclopropyl; and
R² is pyridinyl, wherein such pyridinyl is optionally substituted with one or two substituents independently selected from the group consisting of fluoro, trifluoromethyl, and trifluoromethoxy.

In another embodiment:
R¹ is pyridinyl, wherein such pyridinyl is substituted with one substituent selected from the group consisting of trifluoromethyl and cyclopropyl; and
R² is pyridinyl, wherein such pyridinyl is substituted with one substituent selected from the group consisting of fluoro, trifluoromethyl, and trifluoromethoxy.

In another embodiment:
R¹ is pyridinyl, wherein such pyridinyl is substituted with one substituent selected from the group consisting of trifluoromethyl and cyclopropyl; and
R² is pyridinyl, wherein such pyridinyl is substituted with two substituents independently selected from the group consisting of fluoro, trifluoromethyl, and trifluoromethoxy.

In additional embodiments, the compounds correspond to a structure of Formula (I-i), (I-ii), (I-iii), or (I-iv), and R¹ and R² are as defined in the various substituent embodiments discussed above.

In additional embodiments, the compounds correspond to a structure of Formula (I-A), (I-B), (I-B-1), (I-B-2), (I-C), (I-C-1), or (I-C-2), and R¹ and R² are as defined in the various substituent embodiments discussed above.

B-7(e): Representative R¹/R² Substituents

In one embodiment of the compounds of Formula (I):
R¹ is selected from the group consisting of:

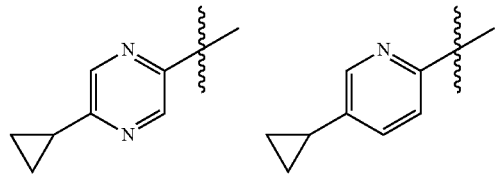

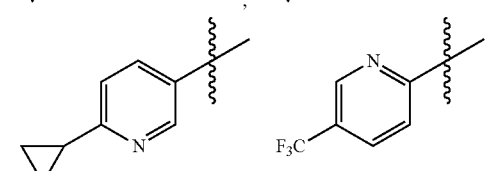

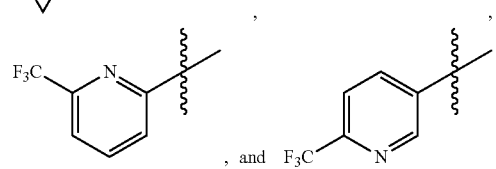

and
R² is selected from the group consisting of phenyl and pyridinyl, wherein each such substituent is substituted with one or two substituents independently selected from the group consisting of fluoro, trifluoromethyl, and trifluoromethoxy.

In one embodiment, R² is phenyl that is substituted with one substituent independently selected from the group consisting of fluoro, trifluoromethyl, and trifluoromethoxy. In one embodiment, R² is phenyl that is substituted with two substituents independently selected from the group consisting of fluoro, trifluoromethyl, and trifluoromethoxy. In one embodiment, R² is pyridinyl that is substituted with one substituent independently selected from the group consisting of fluoro, trifluoromethyl, and trifluoromethoxy. In one embodiment, R² is pyridinyl that is substituted with two substituents independently selected from the group consisting of fluoro, trifluoromethyl, and trifluoromethoxy.

In another embodiment:
R¹ is selected from the group consisting of pyridinyl and pyrazinyl, wherein each such substituent is substituted with one substituent selected from the group consisting of halomethyl and cyclopropyl; and
R² is selected from the group consisting of:

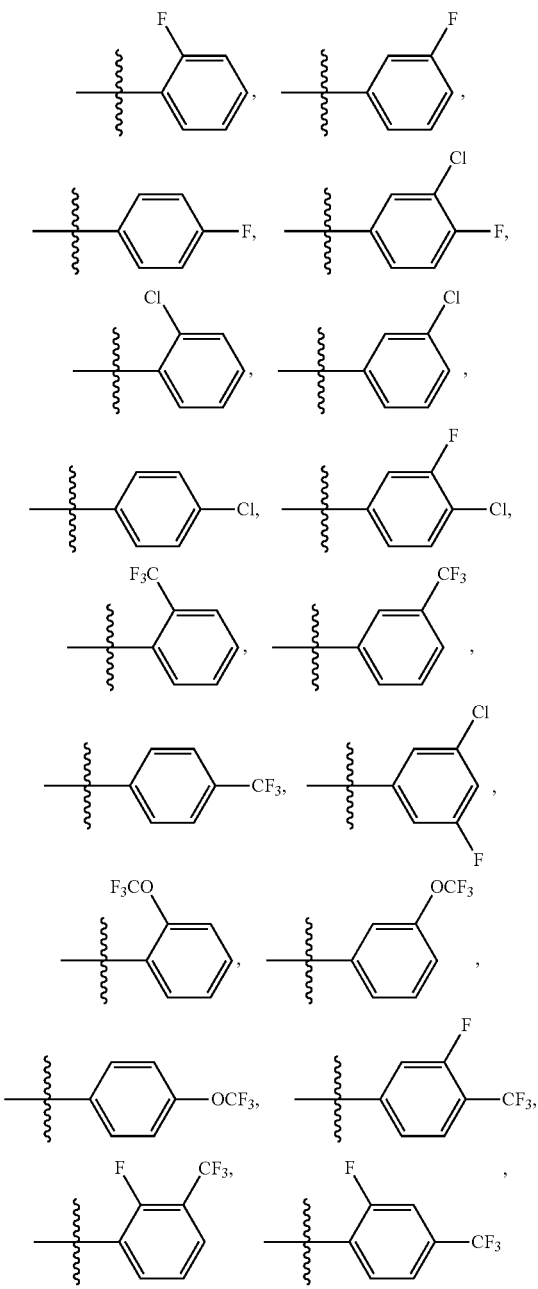

-continued

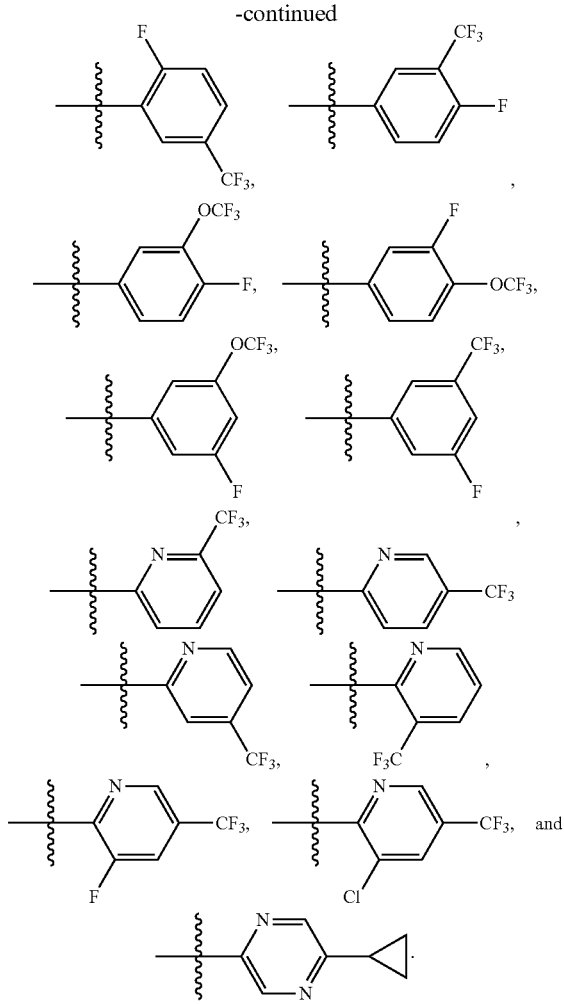

In one embodiment, $R^1$ is pyridinyl that is substituted with one substituent selected from the group consisting of halomethyl and cyclopropyl. In one embodiment, $R^1$ is pyridinyl that is substituted with one halomethyl substituent. In one embodiment, $R^1$ is pyridinyl that is substituted with one trifluoromethyl substituent. In one embodiment, $R^1$ is pyridinyl that is substituted with one cyclopropyl substituent. In one embodiment, $R^1$ is pyrazinyl that is substituted with one substituent selected from the group consisting of halomethyl and cyclopropyl. In one embodiment, $R^1$ is pyrazinyl that is substituted with one halomethyl substituent. In one embodiment, $R^1$ is pyrazinyl that is substituted with one trifluoromethyl substituent. In one embodiment, $R^1$ is pyrazinyl that is substituted with one cyclopropyl substituent.

In another embodiment:

$R^1$ is selected from the group consisting of:

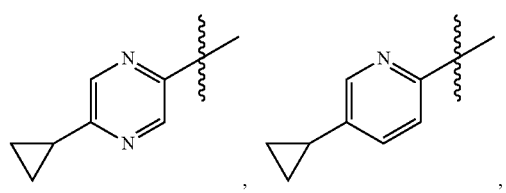

-continued

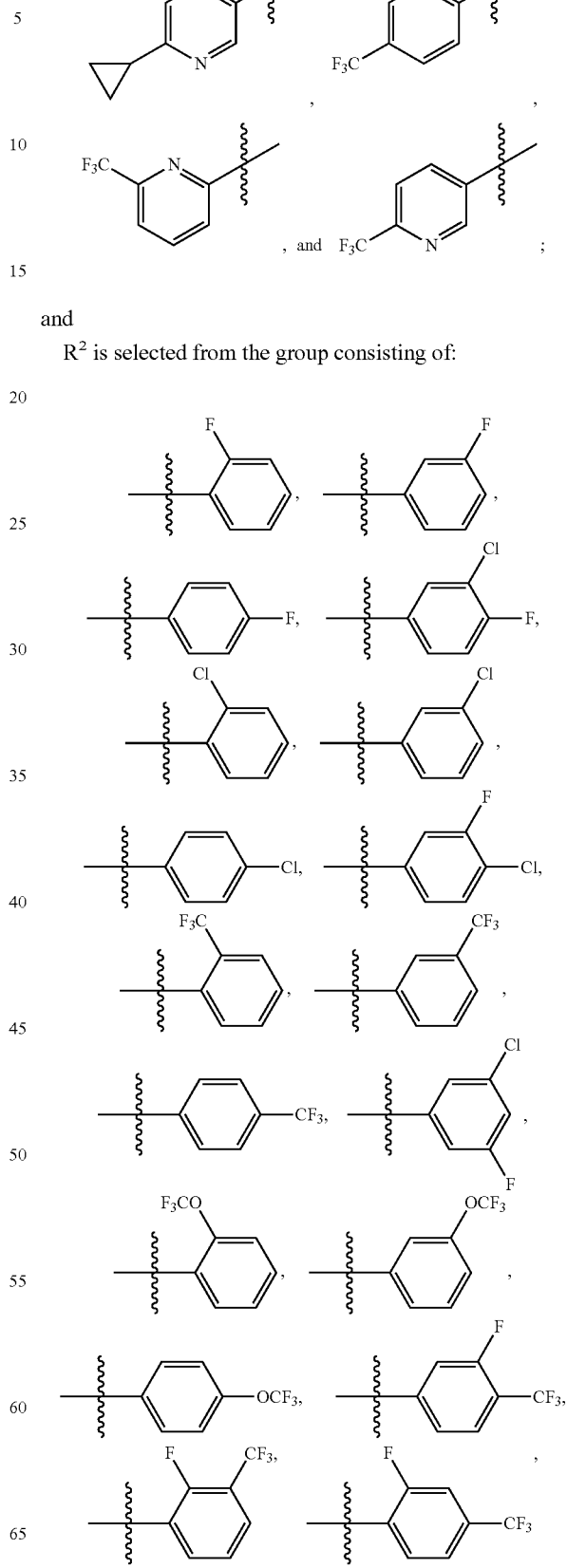

and $R^2$ is selected from the group consisting of:

-continued

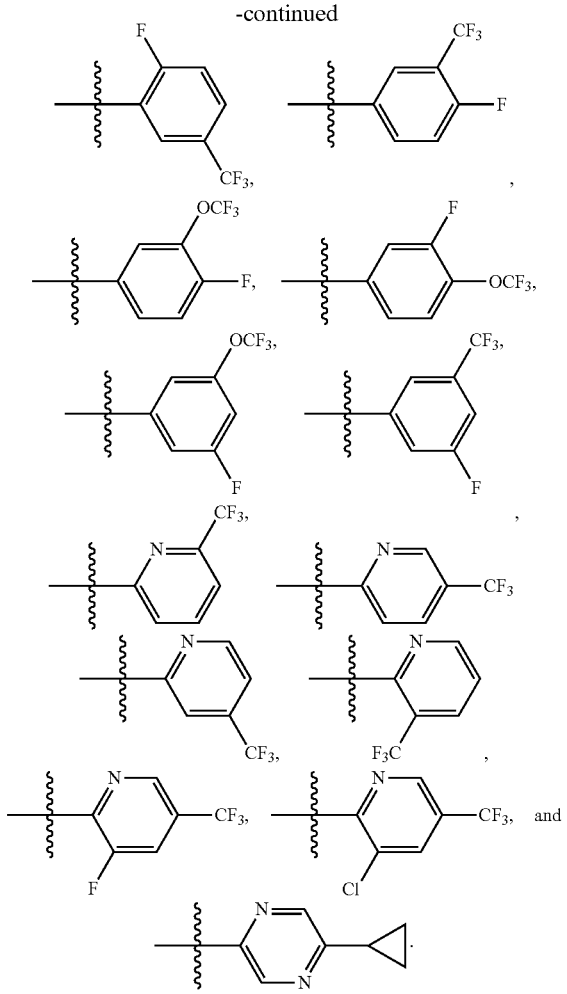

In another embodiment:
R[1] is

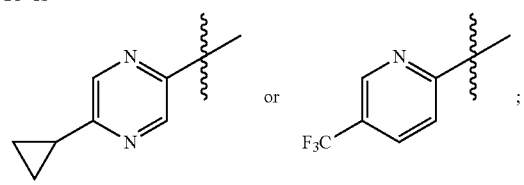

and

R[2] is selected from the group consisting of phenyl and pyridinyl, wherein each such substituent is substituted with one or two substituents independently selected from the group consisting of fluoro, trifluoromethyl, and trifluoromethoxy.

In one embodiment, R[2] is phenyl that is substituted with one substituent independently selected from the group consisting of fluoro, trifluoromethyl, and trifluoromethoxy. In one embodiment, R[2] is phenyl that is substituted with two substituents independently selected from the group consisting of fluoro, trifluoromethyl, and trifluoromethoxy. In one embodiment, R[2] is pyridinyl that is substituted with one substituent independently selected from the group consisting of fluoro, trifluoromethyl, and trifluoromethoxy. In one embodiment, R[2] is pyridinyl that is substituted with two substituents independently selected from the group consisting of fluoro, trifluoromethyl, and trifluoromethoxy.

In another embodiment:
R[1] is selected from the group consisting of pyridinyl and pyrazinyl, wherein each such substituent is substituted with one substituent selected from the group consisting of halomethyl and cyclopropyl; and
R[2] is selected from the group consisting of:

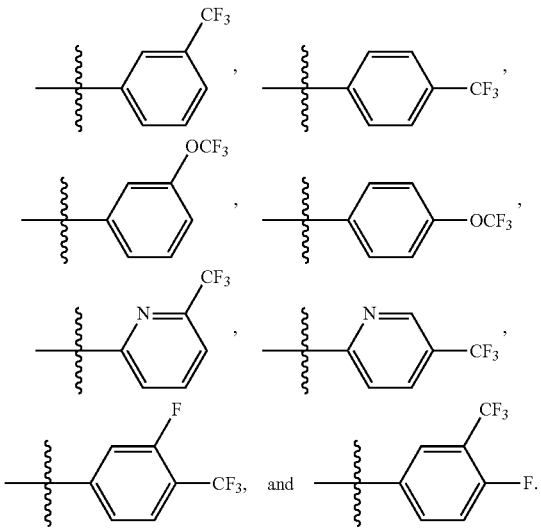

In one embodiment, R[1] is pyridinyl that is substituted with one substituent selected from the group consisting of halomethyl and cyclopropyl. In one embodiment, R[1] is pyridinyl that is substituted with one halomethyl substituent. In one embodiment, R[1] is pyridinyl that is substituted with one trifluoromethyl substituent. In one embodiment, R[1] is pyridinyl that is substituted with one cyclopropyl substituent. In one embodiment, R[1] is pyrazinyl that is substituted with one substituent selected from the group consisting of halomethyl and cyclopropyl. In one embodiment, R[1] is pyrazinyl that is substituted with one halomethyl substituent. In one embodiment, R[1] is pyrazinyl that is substituted with one trifluoromethyl substituent. In one embodiment, R[1] is pyrazinyl that is substituted with one cyclopropyl substituent.

In another embodiment:
R[1] is

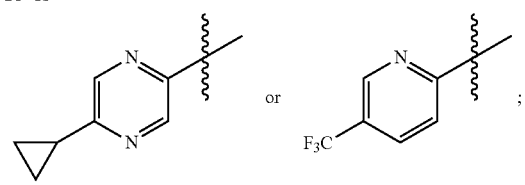

and

R[2] is selected from the group consisting of:

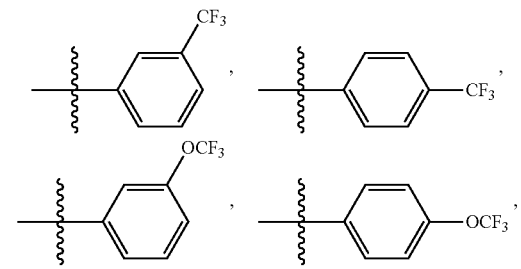

-continued

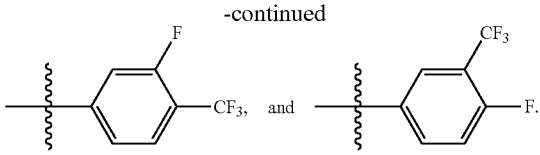 and

B-8: Formula (I-A)

In one embodiment, the compounds of Formula (I) correspond in structure to Formula (I-A):

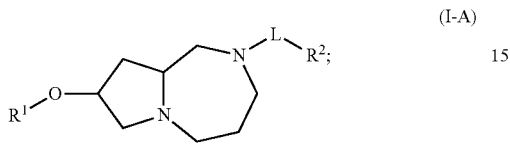

(I-A)

$R^1$ is selected from the group consisting of pyridinyl and pyrazinyl, wherein each such substituent is optionally substituted with one or two substituents independently selected from the group consisting of halo-$C_1$-$C_4$-alkyl and $C_3$-$C_4$-cycloalkyl; and $R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy.

L is selected from the group consisting of a bond, —$CH_2$—, —C(O)—, —C(O)C($R^3$)(H)—, and —S(O)$_2$—; and $R^3$ is selected from the group consisting of hydrogen, hydroxy, amino, methylamino, and dimethylamino.

In another embodiment of the compounds of Formula (I-A):

$R^1$ is selected from the group consisting of pyridinyl and pyrazinyl, wherein each such substituent is optionally substituted with one substituent selected from the group consisting of halomethyl and cyclopropyl; and $R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-A):

$R^1$ is selected from the group consisting of pyridinyl and pyrazinyl, wherein each such substituent is optionally substituted with one substituent selected from the group consisting of trifluoromethyl and cyclopropyl; and $R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-A):

$R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-A):

$R^1$ is pyrazinyl, wherein such pyrazinyl is substituted with one substituent selected from the group consisting of trifluoromethyl and cyclopropyl; and $R^2$ is phenyl, wherein such phenyl is substituted with one substituent selected from the group consisting of fluoro, trifluoromethyl, and trifluoromethoxy.

In another embodiment of the compounds of Formula (I-A):

$R^1$ is pyrazinyl, wherein such pyrazinyl is substituted with one substituent selected from the group consisting of trifluoromethyl and cyclopropyl; and $R^2$ is phenyl, wherein such phenyl is substituted with two substituents independently selected from the group consisting of fluoro, trifluoromethyl, and trifluoromethoxy.

In another embodiment of the compounds of Formula (I-A):

$R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and $R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-A):

$R^1$ is pyrazinyl, wherein such pyrazinyl is substituted with one substituent selected from the group consisting of trifluoromethyl and cyclopropyl; and $R^2$ is pyridinyl, wherein such pyridinyl is substituted with one substituent selected from the group consisting of fluoro, trifluoromethyl, and trifluoromethoxy.

In another embodiment of the compounds of Formula (I-A):

$R^1$ is pyrazinyl, wherein such pyrazinyl is substituted with one substituent selected from the group consisting of trifluoromethyl and cyclopropyl; and $R^2$ is pyridinyl, wherein such pyridinyl is substituted with two substituents independently selected from the group consisting of fluoro, trifluoromethyl, and trifluoromethoxy.

In another embodiment of the compounds of Formula (I-A):

$R^1$ is pyridinyl, wherein such pyridinyl is optionally substituted with one or two substituents independently selected from the group consisting of halo-$C_1$-$C_4$-alkyl and $C_3$-$C_4$-cycloalkyl; and $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-A):

$R^1$ is pyridinyl, wherein such pyridinyl is substituted with one substituent selected from the group consisting of trifluoromethyl and cyclopropyl; and $R^2$ is phenyl, wherein such phenyl is substituted with one substituent selected from the group consisting of fluoro, trifluoromethyl, and trifluoromethoxy.

In another embodiment of the compounds of Formula (I-A):

$R^1$ is pyridinyl, wherein such pyridinyl is substituted with one substituent selected from the group consisting of trifluoromethyl and cyclopropyl; and R² is phenyl, wherein such phenyl is substituted with two substituents independently selected from the group consisting of fluoro, trifluoromethyl, and trifluoromethoxy.

In another embodiment of the compounds of Formula (I-A):
- R¹ is pyridinyl, wherein such pyridinyl is optionally substituted with one or two substituents independently selected from the group consisting of halo-$C_1$-$C_4$-alkyl and $C_3$-$C_4$-cycloalkyl; and
- R² is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-A):
- R¹ is pyridinyl, wherein such pyridinyl is substituted with one substituent selected from the group consisting of trifluoromethyl and cyclopropyl; and
- R² is pyridinyl, wherein such pyridinyl is substituted with one substituent selected from the group consisting of fluoro, trifluoromethyl, and trifluoromethoxy.

In another embodiment of the compounds of Formula (I-A):
- R¹ is pyridinyl, wherein such pyridinyl is substituted with one substituent selected from the group consisting of trifluoromethyl and cyclopropyl; and
- R² is pyridinyl, wherein such pyridinyl is substituted with two substituents independently selected from the group consisting of fluoro, trifluoromethyl, and trifluoromethoxy.

In another embodiment of the compounds of Formula (I-A):
R¹ is selected from the group consisting of:

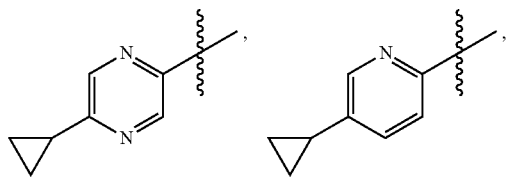

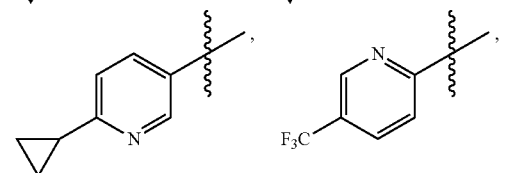

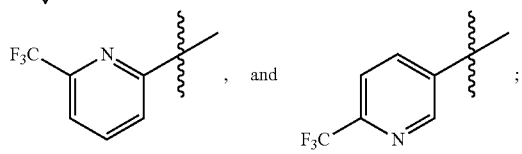

, and and

R² is selected from the group consisting of:

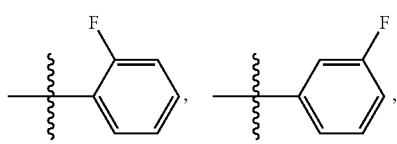

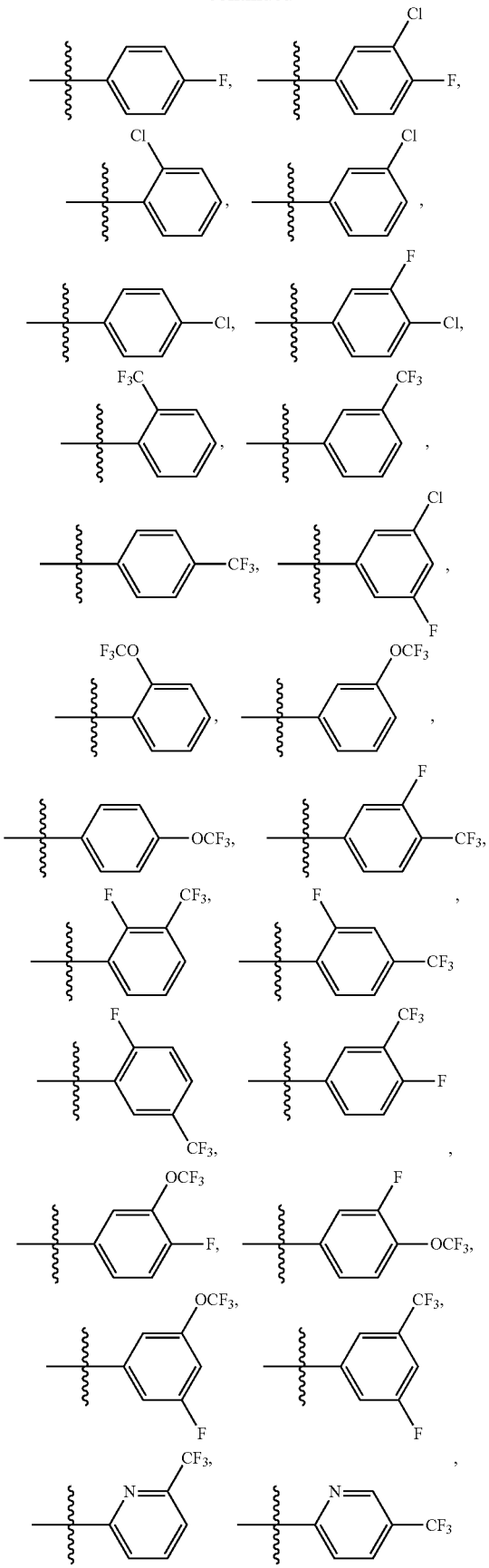

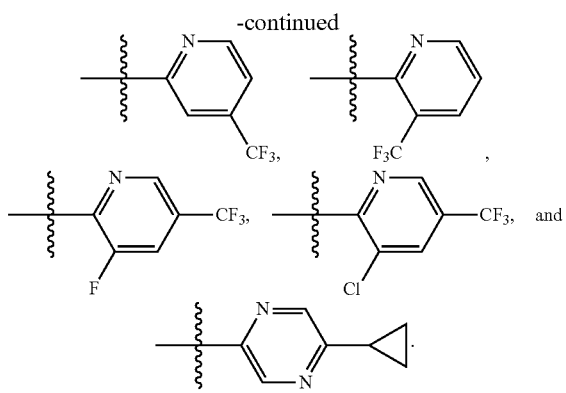

In another embodiment of the compounds of Formula (I-A):

R¹ is

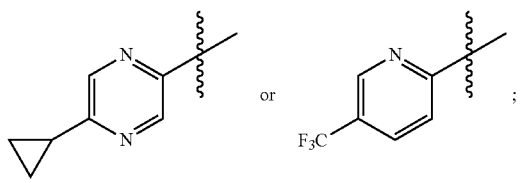

and

R² is selected from the group consisting of:

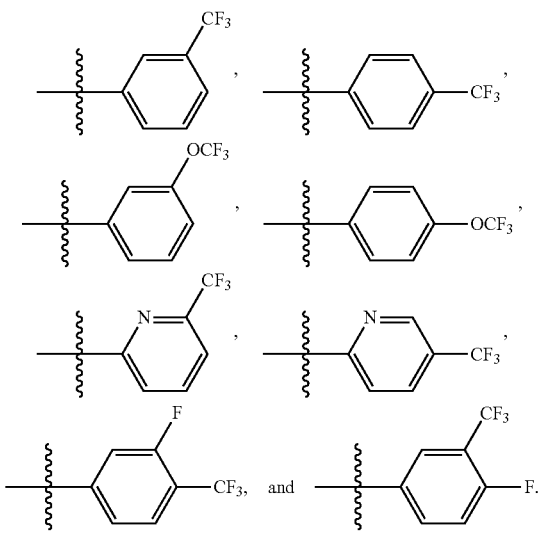

In another embodiment of the compounds of Formula (I-A), L is a bond; and R¹ and R² are as defined in the various substituent embodiments discussed above.

In another embodiment of the compounds of Formula (I-A), L is —CH₂—; and R¹ and R² are as defined in the various substituent embodiments discussed above.

In another embodiment of the compounds of Formula (I-A), L is —C(O)—; and R¹ and R² are as defined in the various substituent embodiments discussed above.

In another embodiment of the compounds of Formula (I-A), L is —S(O)₂—; and R¹ and R² are as defined in the various substituent embodiments discussed above.

In another embodiment of the compounds of Formula (I-A), L is —C(O)C(R³)(H)—; and R¹ and R² are as defined in the various substituent embodiments discussed above.

In another embodiment of the compounds of Formula (I-A), L is —C(O)C(R³)(H)—; R¹ and R² are as defined in the various substituent embodiments discussed above; and R³ is hydrogen.

In another embodiment of the compounds of Formula (I-A), L is —C(O)C(R³)(H)—; R¹ and R² are as defined in the various substituent embodiments discussed above; and R³ is hydroxy.

In another embodiment of the compounds of Formula (I-A), L is —C(O)C(R³)(H)—; R¹ and R² are as defined in the various substituent embodiments discussed above; and R³ is selected from the group consisting of amino, methylamino, and dimethylamino In additional embodiments, the compounds of Formula (I-A) have a configuration that corresponds to a configuration of a compound of Formula (I-i), (I-ii), (I-iii), or (I-iv), and R¹, R², R³, and L are as defined in the various substituent embodiments discussed above.

B-9: Formula (I-B-1)

In one embodiment, the compounds of Formula (I) correspond in structure to Formula (I-B-1):

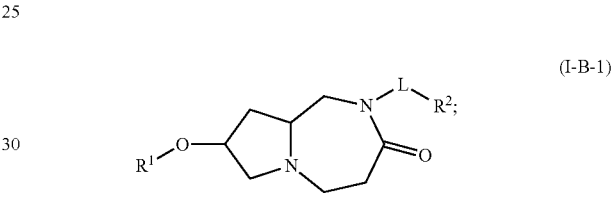

R¹ is selected from the group consisting of pyridinyl and pyrazinyl, wherein each such substituent is optionally substituted with one or two substituents independently selected from the group consisting of halo-C₁-C₄-alkyl and C₃-C₄-cycloalkyl; and R² is selected from the group consisting of phenyl and pyridinyl, wherein each such substituent is optionally substituted with one or two substituents independently selected from the group consisting of halogen, halo-C₁-C₃-alkyl, and halo-C₁-C₃-alkoxy.

L is selected from the group consisting of a bond, —CH₂—, —C(O)—, and —C(O)C(R⁴)(H)—; and R⁴ is selected from the group consisting of hydrogen, hydroxy, amino, methylamino, and dimethylamino In another embodiment of the compounds of Formula (I-B-1):

R¹ is selected from the group consisting of pyridinyl and pyrazinyl, wherein each such substituent is optionally substituted with one substituent selected from the group consisting of halomethyl and cyclopropyl; and R² is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-B-1):

R¹ is selected from the group consisting of pyridinyl and pyrazinyl, wherein each such substituent is optionally substituted with one substituent selected from the group consisting of trifluoromethyl and cyclopropyl; and R² is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-B-1):
- $R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and
- $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-1):
- $R^1$ is pyrazinyl, wherein such pyrazinyl is substituted with one substituent selected from the group consisting of trifluoromethyl and cyclopropyl; and
- $R^2$ is phenyl, wherein such phenyl is substituted with one substituent selected from the group consisting of fluoro, trifluoromethyl, and trifluoromethoxy.

In another embodiment of the compounds of Formula (I-B-1):
- $R^1$ is pyrazinyl, wherein such pyrazinyl is substituted with one substituent selected from the group consisting of trifluoromethyl and cyclopropyl; and
- $R^2$ is phenyl, wherein such phenyl is substituted with two substituents independently selected from the group consisting of fluoro, trifluoromethyl, and trifluoromethoxy.

In another embodiment of the compounds of Formula (I-B-1):
- $R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and
- $R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-1):
- $R^1$ is pyrazinyl, wherein such pyrazinyl is substituted with one substituent selected from the group consisting of trifluoromethyl and cyclopropyl; and
- $R^2$ is pyridinyl, wherein such pyridinyl is substituted with one substituent selected from the group consisting of fluoro, trifluoromethyl, and trifluoromethoxy.

In another embodiment of the compounds of Formula (I-B-1):
- $R^1$ is pyrazinyl, wherein such pyrazinyl is substituted with one substituent selected from the group consisting of trifluoromethyl and cyclopropyl; and
- $R^2$ is pyridinyl, wherein such pyridinyl is substituted with two substituents independently selected from the group consisting of fluoro, trifluoromethyl, and trifluoromethoxy.

In another embodiment of the compounds of Formula (I-B-1):
- $R^1$ is pyridinyl, wherein such pyridinyl is optionally substituted with one or two substituents independently selected from the group consisting of halo-$C_1$-$C_4$-alkyl and $C_3$-$C_4$-cycloalkyl; and
- $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-1):
- $R^1$ is pyridinyl, wherein such pyridinyl is substituted with one substituent selected from the group consisting of trifluoromethyl and cyclopropyl; and
- $R^2$ is phenyl, wherein such phenyl is substituted with one substituent selected from the group consisting of fluoro, trifluoromethyl, and trifluoromethoxy.

In another embodiment of the compounds of Formula (I-B-1):
- $R^1$ is pyridinyl, wherein such pyridinyl is substituted with one substituent selected from the group consisting of trifluoromethyl and cyclopropyl; and
- $R^2$ is phenyl, wherein such phenyl is substituted with two substituents independently selected from the group consisting of fluoro, trifluoromethyl, and trifluoromethoxy.

In another embodiment of the compounds of Formula (I-B-1):
- $R^1$ is pyridinyl, wherein such pyridinyl is optionally substituted with one or two substituents independently selected from the group consisting of halo-$C_1$-$C_4$-alkyl and $C_3$-$C_4$-cycloalkyl; and
- $R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-1):
- $R^1$ is pyridinyl, wherein such pyridinyl is substituted with one substituent selected from the group consisting of trifluoromethyl and cyclopropyl; and
- $R^2$ is pyridinyl, wherein such pyridinyl is substituted with one substituent selected from the group consisting of fluoro, trifluoromethyl, and trifluoromethoxy.

In another embodiment of the compounds of Formula (I-B-1):
- $R^1$ is pyridinyl, wherein such pyridinyl is substituted with one substituent selected from the group consisting of trifluoromethyl and cyclopropyl; and
- $R^2$ is pyridinyl, wherein such pyridinyl is substituted with two substituents independently selected from the group consisting of fluoro, trifluoromethyl, and trifluoromethoxy.

In another embodiment of the compounds of Formula (I-B-1):
- $R^1$ is selected from the group consisting of:

and
R² is selected from the group consisting of:
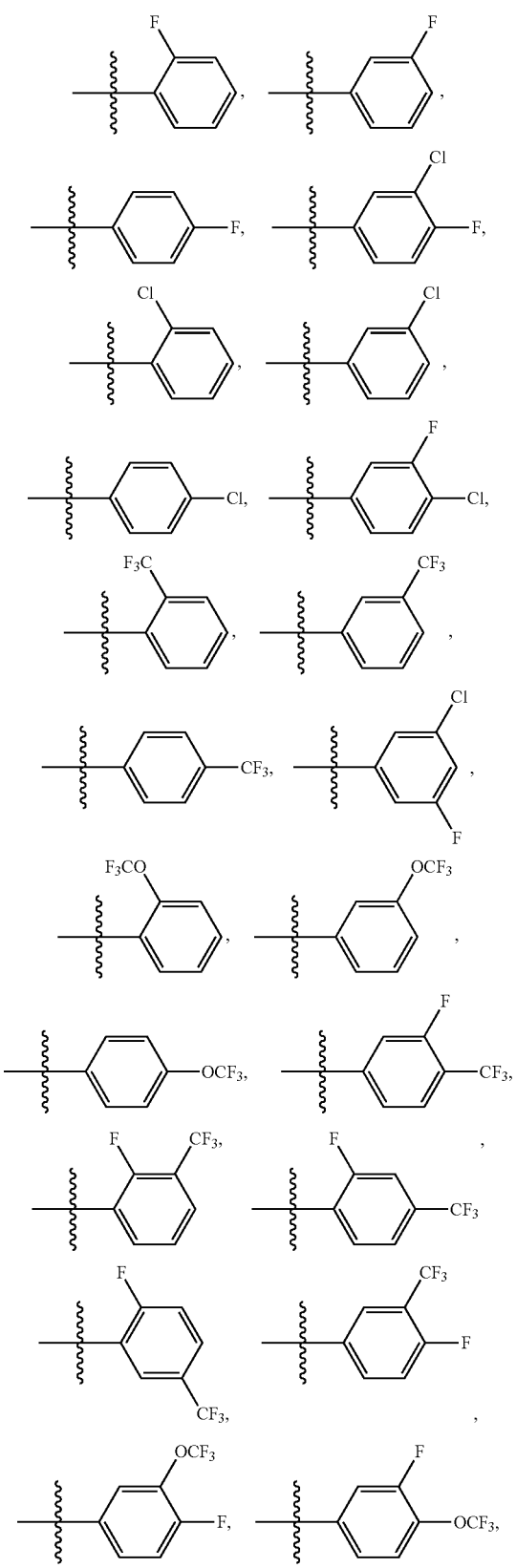
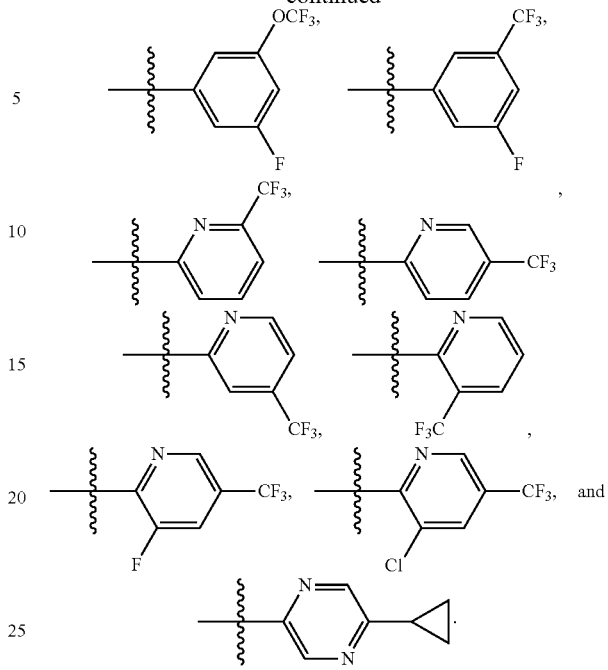
In another embodiment of the compounds of Formula (I-B-1):
R¹ is
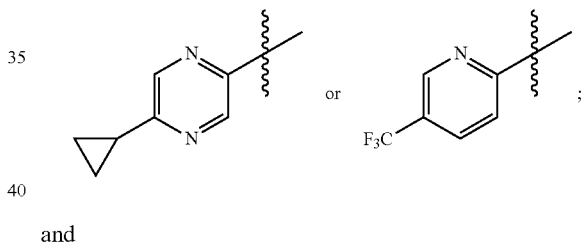
and
R² is selected from the group consisting of:
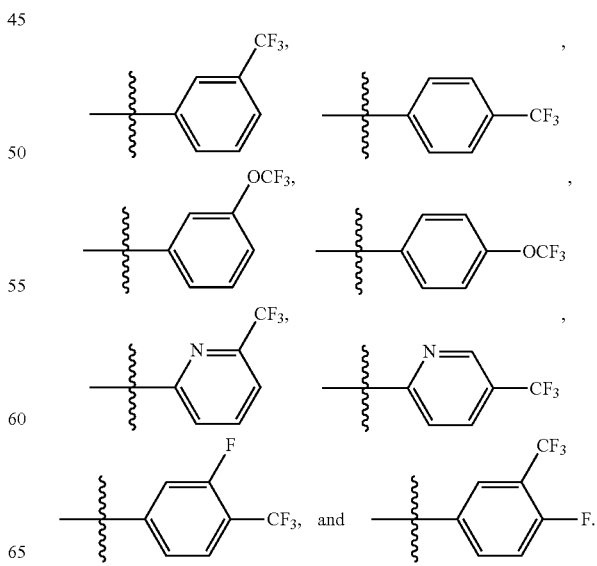

In another embodiment of the compounds of Formula (I-B-1), L is a bond; and R¹ and R² are as defined in the various substituent embodiments discussed above.

In another embodiment of the compounds of Formula (I-B-1), L is —CH₂—; and R¹ and R² are as defined in the various substituent embodiments discussed above.

In another embodiment of the compounds of Formula (I-B-1), L is —C(O)—; and R¹ and R² are as defined in the various substituent embodiments discussed above.

In another embodiment of the compounds of Formula (I-B-1), L is —C(O)C(R⁴)(H)—; and R¹ and R² are as defined in the various substituent embodiments discussed above.

In another embodiment of the compounds of Formula (I-B-1), L is —C(O)C(R⁴)(H)—; R¹ and R² are as defined in the various substituent embodiments discussed above; and R⁴ is hydrogen.

In another embodiment of the compounds of Formula (I-B-1), L is —C(O)C(R⁴)(H)—; R¹ and R² are as defined in the various substituent embodiments discussed above; and R⁴ is hydroxy.

In another embodiment of the compounds of Formula (I-B-1), L is —C(O)C(R⁴)(H)—; R¹ and R² are as defined in the various substituent embodiments discussed above; and R⁴ is selected from the group consisting of amino, methylamino, and dimethylamino In additional embodiments, the compounds of Formula (I-B-1) have a configuration that corresponds to a configuration of a compound of Formula (I-i), (I-ii), (I-iii), or (I-iv), and R¹, R², R⁴, and L are as defined in the various substituent embodiments discussed above.

B-10: Formula (I-B-2)

In one embodiment, the compounds of Formula (I) correspond in structure to Formula (I-B-2):

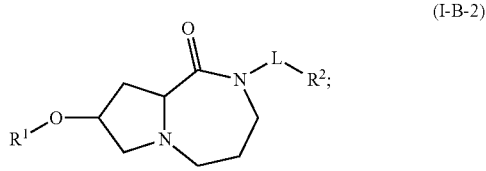

(I-B-2)

R¹ is selected from the group consisting of pyridinyl and pyrazinyl, wherein each such substituent is optionally substituted with one or two substituents independently selected from the group consisting of halo-C₁-C₄-alkyl and C₃-C₄-cycloalkyl; and R² is selected from the group consisting of phenyl and pyridinyl, wherein each such substituent is optionally substituted with one or two substituents independently selected from the group consisting of halogen, halo-C₁-C₃-alkyl, and halo-C₁-C₃-alkoxy.

L is selected from the group consisting of a bond, —CH₂—, —C(O)—, and —C(O)C(R⁴)(H)—; and R⁴ is selected from the group consisting of hydrogen, hydroxy, amino, methylamino, and dimethylamino In another embodiment of the compounds of Formula (I-B-2):
R¹ is selected from the group consisting of pyridinyl and pyrazinyl, wherein each such substituent is optionally substituted with one substituent selected from the group consisting of halomethyl and cyclopropyl; and
R² is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-B-2):
R¹ is selected from the group consisting of pyridinyl and pyrazinyl, wherein each such substituent is optionally substituted with one substituent selected from the group consisting of trifluoromethyl and cyclopropyl; and
R² is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-B-2):
R¹ is pyrazinyl, wherein such pyrazinyl is optionally substituted with one or two substituents independently selected from the group consisting of halo-C₁-C₄-alkyl and C₃-C₄-cycloalkyl; and
R² is phenyl, wherein such phenyl is optionally substituted with one or two substituents independently selected from the group consisting of halogen, halo-C₁-C₃-alkyl, and halo-C₁-C₃-alkoxy.

In another embodiment of the compounds of Formula (I-B-2):
R¹ is pyrazinyl, wherein such pyrazinyl is substituted with one substituent selected from the group consisting of trifluoromethyl and cyclopropyl; and
R² is phenyl, wherein such phenyl is substituted with one substituent selected from the group consisting of fluoro, trifluoromethyl, and trifluoromethoxy.

In another embodiment of the compounds of Formula (I-B-2):
R¹ is pyrazinyl, wherein such pyrazinyl is substituted with one substituent selected from the group consisting of trifluoromethyl and cyclopropyl; and
R² is phenyl, wherein such phenyl is substituted with two substituents independently selected from the group consisting of fluoro, trifluoromethyl, and trifluoromethoxy.

In another embodiment of the compounds of Formula (I-B-2):
R¹ is pyrazinyl, wherein such pyrazinyl is optionally substituted with one or two substituents independently selected from the group consisting of halo-C₁-C₄-alkyl and C₃-C₄-cycloalkyl; and
R² is pyridinyl, wherein such pyridinyl is optionally substituted with one or two substituents independently selected from the group consisting of halogen, halo-C₁-C₃-alkyl, and halo-C₁-C₃-alkoxy.

In another embodiment of the compounds of Formula (I-B-2):
R¹ is pyrazinyl, wherein such pyrazinyl is substituted with one substituent selected from the group consisting of trifluoromethyl and cyclopropyl; and
R² is pyridinyl, wherein such pyridinyl is substituted with one substituent selected from the group consisting of fluoro, trifluoromethyl, and trifluoromethoxy.

In another embodiment of the compounds of Formula (I-B-2):
R¹ is pyrazinyl, wherein such pyrazinyl is substituted with one substituent selected from the group consisting of trifluoromethyl and cyclopropyl; and
R² is pyridinyl, wherein such pyridinyl is substituted with two substituents independently selected from the group consisting of fluoro, trifluoromethyl, and trifluoromethoxy.

In another embodiment of the compounds of Formula (I-B-2):
- R¹ is pyridinyl, wherein such pyridinyl is optionally substituted with one or two substituents independently selected from the group consisting of halo-$C_1$-$C_4$-alkyl and $C_3$-$C_4$-cycloalkyl; and
- R² is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-2):
- R¹ is pyridinyl, wherein such pyridinyl is substituted with one substituent selected from the group consisting of trifluoromethyl and cyclopropyl; and
- R² is phenyl, wherein such phenyl is substituted with one substituent selected from the group consisting of fluoro, trifluoromethyl, and trifluoromethoxy.

In another embodiment of the compounds of Formula (I-B-2):
- R¹ is pyridinyl, wherein such pyridinyl is substituted with one substituent selected from the group consisting of trifluoromethyl and cyclopropyl; and
- R² is phenyl, wherein such phenyl is substituted with two substituents independently selected from the group consisting of fluoro, trifluoromethyl, and trifluoromethoxy.

In another embodiment of the compounds of Formula (I-B-2):
- R¹ is pyridinyl, wherein such pyridinyl is optionally substituted with one or two substituents independently selected from the group consisting of halo-$C_1$-$C_4$-alkyl and $C_3$-$C_4$-cycloalkyl; and
- R² is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-B-2):
- R¹ is pyridinyl, wherein such pyridinyl is substituted with one substituent selected from the group consisting of trifluoromethyl and cyclopropyl; and
- R² is pyridinyl, wherein such pyridinyl is substituted with one substituent selected from the group consisting of fluoro, trifluoromethyl, and trifluoromethoxy.

In another embodiment of the compounds of Formula (I-B-2):
- R¹ is pyridinyl, wherein such pyridinyl is substituted with one substituent selected from the group consisting of trifluoromethyl and cyclopropyl; and
- R² is pyridinyl, wherein such pyridinyl is substituted with two substituents independently selected from the group consisting of fluoro, trifluoromethyl, and trifluoromethoxy.

In another embodiment of the compounds of Formula (I-B-2):
- R¹ is selected from the group consisting of:

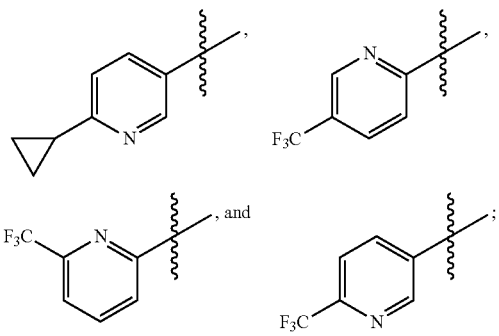

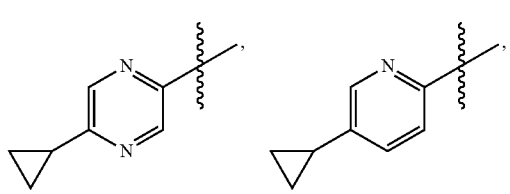

and

R² is selected from the group consisting of:

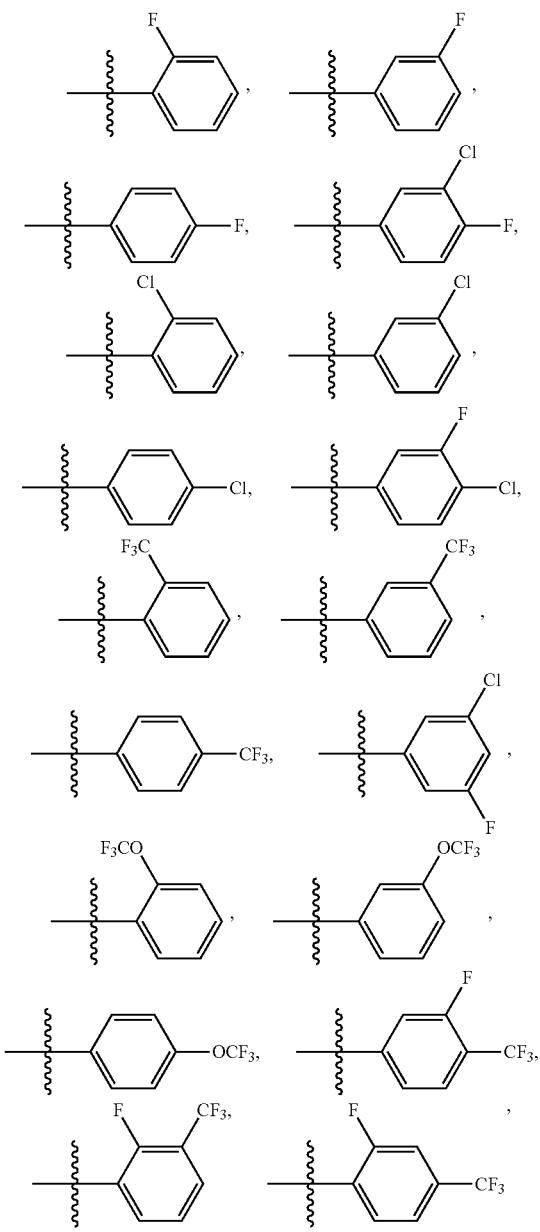

-continued

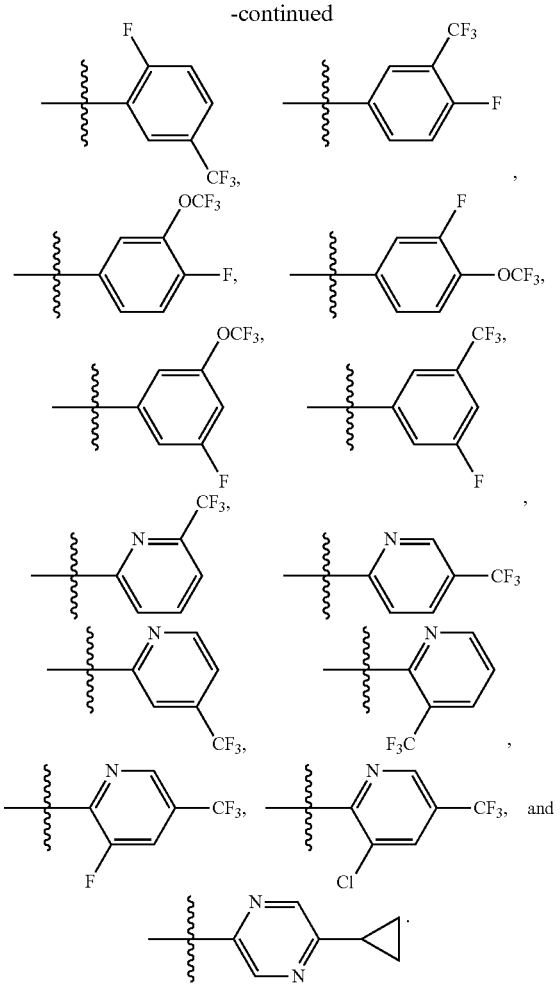

In another embodiment of the compounds of Formula (I-B-2):
R¹ is

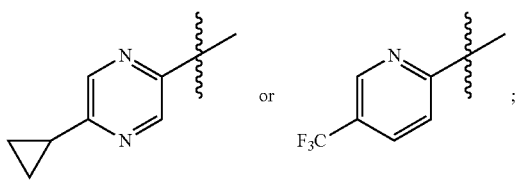 [SMILES: *c1cnc(C2CC2)cn1 ; *c1ccc(C(F)(F)F)cn1]

and
R² is selected from the group consisting of:

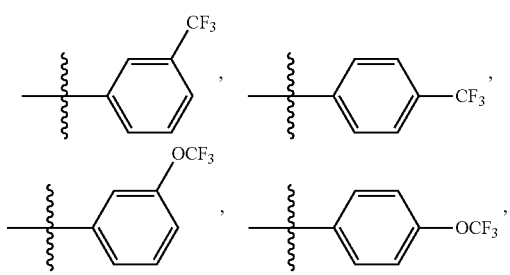

-continued

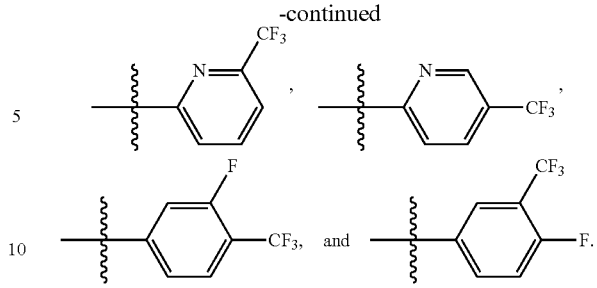

In another embodiment of the compounds of Formula (I-B-2), L is a bond; and R¹ and R² are as defined in the various substituent embodiments discussed above.

In another embodiment of the compounds of Formula (I-B-2), L is —CH₂—; and R¹ and R² are as defined in the various substituent embodiments discussed above.

In another embodiment of the compounds of Formula (I-B-2), L is —C(O)—; and R¹ and R² are as defined in the various substituent embodiments discussed above.

In another embodiment of the compounds of Formula (I-B-2), L is —C(O)C(R⁴)(H)—; and R¹ and R² are as defined in the various substituent embodiments discussed above.

In another embodiment of the compounds of Formula (I-B-2), L is —C(O)C(R⁴)(H)—; R¹ and R² are as defined in the various substituent embodiments discussed above; and R⁴ is hydrogen.

In another embodiment of the compounds of Formula (I-B-2), L is —C(O)C(R⁴)(H)—; R¹ and R² are as defined in the various substituent embodiments discussed above; and R⁴ is hydroxy.

In another embodiment of the compounds of Formula (I-B-2), L is —C(O)C(R⁴)(H)—; R¹ and R² are as defined in the various substituent embodiments discussed above; and R⁴ is selected from the group consisting of amino, methylamino, and dimethylamino In additional embodiments, the compounds of Formula (I-B-2) have a configuration that corresponds to a configuration of a compound of Formula (I-i), (I-ii), (I-iii), or (I-iv), and R¹, R², R⁴, and L are as defined in the various substituent embodiments discussed above.

B-11: Formula (I-C-1)

In one embodiment, the compounds of Formula (I) correspond in structure to Formula (I-C-1):

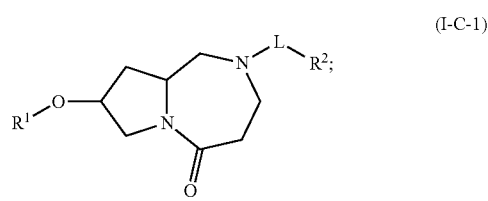

(I-C-1)

R¹ is selected from the group consisting of pyridinyl and pyrazinyl, wherein each such substituent is optionally substituted with one or two substituents independently selected from the group consisting of halo-C₁-C₄-alkyl and C₃-C₄-cycloalkyl; and R² is selected from the group consisting of phenyl and pyridinyl, wherein each such substituent is optionally substituted with one or two substituents independently selected from the group consisting of halogen, halo-C₁-C₃-alkyl, and halo-C₁-C₃-alkoxy.

L is selected from the group consisting of a bond, —CH$_2$—, —C(O)—, —C(O)C(R$^5$)(H)—, and —S(O)$_2$—; and R$^5$ is selected from the group consisting of hydrogen, hydroxy, amino, methylamino, and dimethylamino.

In another embodiment of the compounds of Formula (I-C-1):

R$^1$ is selected from the group consisting of pyridinyl and pyrazinyl, wherein each such substituent is optionally substituted with one substituent selected from the group consisting of halomethyl and cyclopropyl; and R$^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-C-1):

R$^1$ is selected from the group consisting of pyridinyl and pyrazinyl, wherein each such substituent is optionally substituted with one substituent selected from the group consisting of trifluoromethyl and cyclopropyl; and R$^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-C-1):

R$^1$ is pyrazinyl, wherein such pyrazinyl is optionally substituted with one or two substituents independently selected from the group consisting of halo-C$_1$-C$_4$-alkyl and C$_3$-C$_4$-cycloalkyl; and R$^2$ is phenyl, wherein such phenyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (I-C-1):

R$^1$ is pyrazinyl, wherein such pyrazinyl is substituted with one substituent selected from the group consisting of trifluoromethyl and cyclopropyl; and R$^2$ is phenyl, wherein such phenyl is substituted with one substituent selected from the group consisting of fluoro, trifluoromethyl, and trifluoromethoxy.

In another embodiment of the compounds of Formula (I-C-1):

R$^1$ is pyrazinyl, wherein such pyrazinyl is substituted with one substituent selected from the group consisting of trifluoromethyl and cyclopropyl; and R$^2$ is phenyl, wherein such phenyl is substituted with two substituents independently selected from the group consisting of fluoro, trifluoromethyl, and trifluoromethoxy.

In another embodiment of the compounds of Formula (I-C-1):

R$^1$ is pyrazinyl, wherein such pyrazinyl is optionally substituted with one or two substituents independently selected from the group consisting of halo-C$_1$-C$_4$-alkyl and C$_3$-C$_4$-cycloalkyl; and R$^2$ is pyridinyl, wherein such pyridinyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (I-C-1):

R$^1$ is pyrazinyl, wherein such pyrazinyl is substituted with one substituent selected from the group consisting of trifluoromethyl and cyclopropyl; and R$^2$ is pyridinyl, wherein such pyridinyl is substituted with one substituent selected from the group consisting of fluoro, trifluoromethyl, and trifluoromethoxy.

In another embodiment of the compounds of Formula (I-C-1):

R$^1$ is pyrazinyl, wherein such pyrazinyl is substituted with one substituent selected from the group consisting of trifluoromethyl and cyclopropyl; and R$^2$ is pyridinyl, wherein such pyridinyl is substituted with two substituents independently selected from the group consisting of fluoro, trifluoromethyl, and trifluoromethoxy.

In another embodiment of the compounds of Formula (I-C-1):

R$^1$ is pyridinyl, wherein such pyridinyl is optionally substituted with one or two substituents independently selected from the group consisting of halo-C$_1$-C$_4$-alkyl and C$_3$-C$_4$-cycloalkyl; and R$^2$ is phenyl, wherein such phenyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (I-C-1):

R$^1$ is pyridinyl, wherein such pyridinyl is substituted with one substituent selected from the group consisting of trifluoromethyl and cyclopropyl; and R$^2$ is phenyl, wherein such phenyl is substituted with one substituent selected from the group consisting of fluoro, trifluoromethyl, and trifluoromethoxy.

In another embodiment of the compounds of Formula (I-C-1):

R$^1$ is pyridinyl, wherein such pyridinyl is substituted with one substituent selected from the group consisting of trifluoromethyl and cyclopropyl; and R$^2$ is phenyl, wherein such phenyl is substituted with two substituents independently selected from the group consisting of fluoro, trifluoromethyl, and trifluoromethoxy.

In another embodiment of the compounds of Formula (I-C-1):

R$^1$ is pyridinyl, wherein such pyridinyl is optionally substituted with one or two substituents independently selected from the group consisting of halo-C$_1$-C$_4$-alkyl and C$_3$-C$_4$-cycloalkyl; and R$^2$ is pyridinyl, wherein such pyridinyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (I-C-1):

R$^1$ is pyridinyl, wherein such pyridinyl is substituted with one substituent selected from the group consisting of trifluoromethyl and cyclopropyl; and R$^2$ is pyridinyl, wherein such pyridinyl is substituted with one substituent selected from the group consisting of fluoro, trifluoromethyl, and trifluoromethoxy.

In another embodiment of the compounds of Formula (I-C-1):

R$^1$ is pyridinyl, wherein such pyridinyl is substituted with one substituent selected from the group consisting of trifluoromethyl and cyclopropyl; and R² is pyridinyl, wherein such pyridinyl is substituted with two substituents independently selected from the group consisting of fluoro, trifluoromethyl, and trifluoromethoxy.

In another embodiment of the compounds of Formula (I-C-1):

R¹ is selected from the group consisting of:

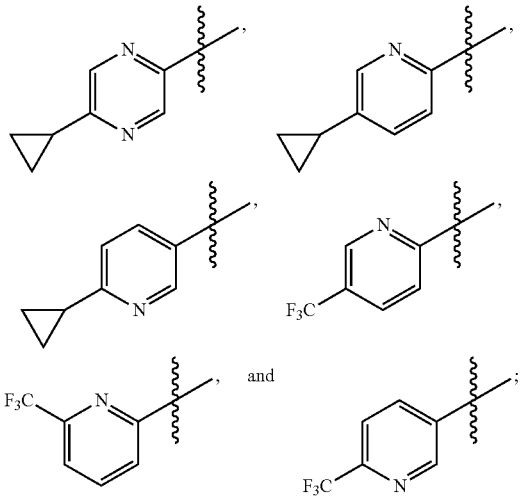

and

R² is selected from the group consisting of:

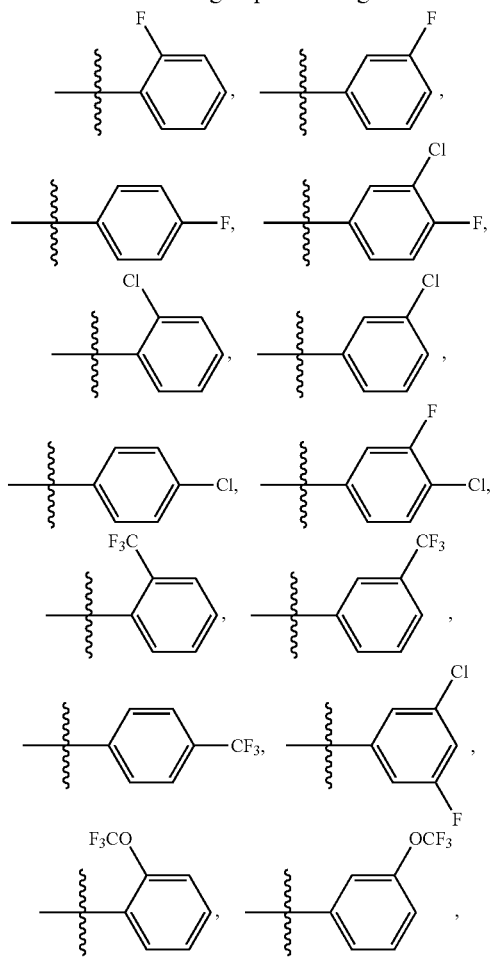

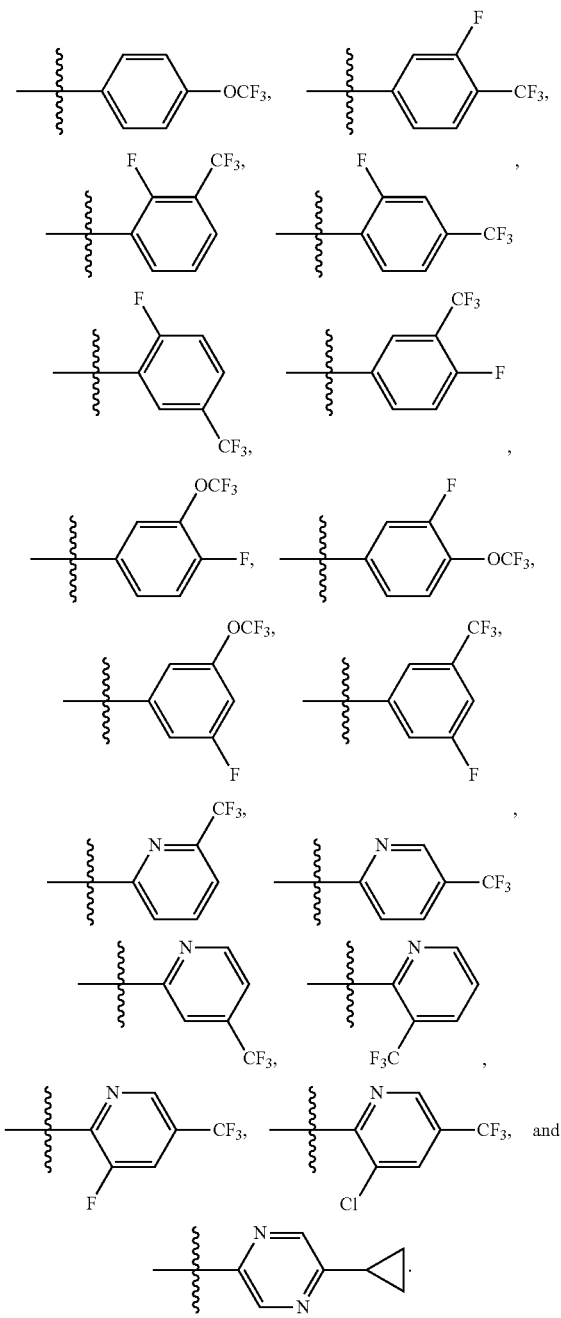

In another embodiment of the compounds of Formula (I-C-1):

R¹ is

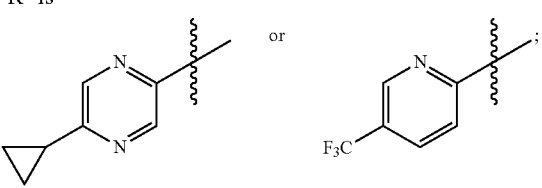

and $R^2$ is selected from the group consisting of:

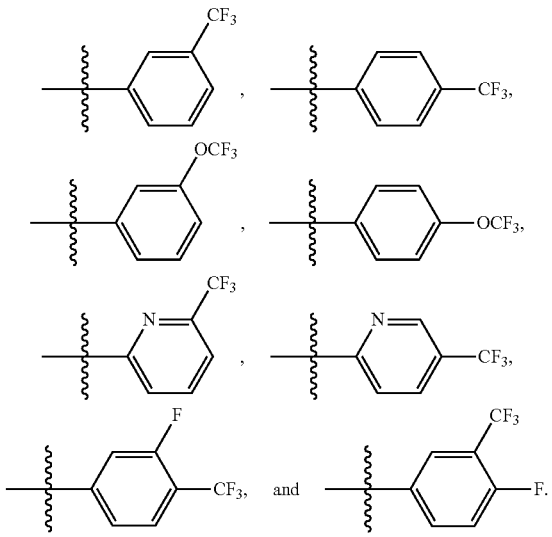

In another embodiment of the compounds of Formula (I-C-1), L is a bond; and $R^1$ and $R^2$ are as defined in the various substituent embodiments discussed above.

In another embodiment of the compounds of Formula (I-C-1), L is —CH$_2$—; and $R^1$ and $R^2$ are as defined in the various substituent embodiments discussed above.

In another embodiment of the compounds of Formula (I-C-1), L is —C(O)—; and $R^1$ and $R^2$ are as defined in the various substituent embodiments discussed above.

In another embodiment of the compounds of Formula (I-C-1), L is —S(O)$_2$—; and $R^1$ and $R^2$ are as defined in the various substituent embodiments discussed above.

In another embodiment of the compounds of Formula (I-C-1), L is —C(O)C(R$^5$)(H)—; and $R^1$ and $R^2$ are as defined in the various substituent embodiments discussed above.

In another embodiment of the compounds of Formula (I-C-1), L is —C(O)C(R$^5$)(H)—; $R^1$ and $R^2$ are as defined in the various substituent embodiments discussed above; and $R^5$ is hydrogen.

In another embodiment of the compounds of Formula (I-C-1), L is —C(O)C(R$^5$)(H)—; $R^1$ and $R^2$ are as defined in the various substituent embodiments discussed above; and $R^5$ is hydroxy.

In another embodiment of the compounds of Formula (I-C-1), L is —C(O)C(R$^5$)(H)—; $R^1$ and $R^2$ are as defined in the various substituent embodiments discussed above; and $R^5$ is selected from the group consisting of amino, methylamino, and dimethylamino In additional embodiments, the compounds of Formula (I-C-1) have a configuration that corresponds to a configuration of a compound of Formula (I-i), (I-ii), (I-iii), or (I-iv), and $R^1$, $R^2$, $R^5$, and L are as defined in the various substituent embodiments discussed above.

B-12: Formula (I-C-2)

In one embodiment, the compounds of Formula (I) correspond in structure to Formula (I-C-2):

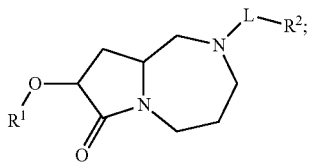

$R^1$ is selected from the group consisting of pyridinyl and pyrazinyl, wherein each such substituent is optionally substituted with one or two substituents independently selected from the group consisting of halo-$C_1$-$C_4$-alkyl and $C_3$-$C_4$-cycloalkyl; and $R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy;

L is selected from the group consisting of a bond, —CH$_2$—, —C(O)—, —C(O)C(R$^5$)(H)—, and —S(O)$_2$—; and $R^5$ is selected from the group consisting of hydrogen, hydroxy, amino, methylamino, and dimethylamino In another embodiment of the compounds of Formula (I-C-2):

$R^1$ is selected from the group consisting of pyridinyl and pyrazinyl, wherein each such substituent is optionally substituted with one substituent selected from the group consisting of halomethyl and cyclopropyl; and $R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-C-2):

$R^1$ is selected from the group consisting of pyridinyl and pyrazinyl, wherein each such substituent is optionally substituted with one substituent selected from the group consisting of trifluoromethyl and cyclopropyl; and $R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (I-C-2):

$R^1$ is pyrazinyl, wherein such pyrazinyl is optionally substituted with one or two substituents independently selected from the group consisting of halo-$C_1$-$C_4$-alkyl and $C_3$-$C_4$-cycloalkyl; and $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-C-2):

$R^1$ is pyrazinyl, wherein such pyrazinyl is substituted with one substituent selected from the group consisting of trifluoromethyl and cyclopropyl; and $R^2$ is phenyl, wherein such phenyl is substituted with one substituent selected from the group consisting of fluoro, trifluoromethyl, and trifluoromethoxy.

In another embodiment of the compounds of Formula (I-C-2):

R¹ is pyrazinyl, wherein such pyrazinyl is substituted with one substituent selected from the group consisting of trifluoromethyl and cyclopropyl; and R² is phenyl, wherein such phenyl is substituted with two substituents independently selected from the group consisting of fluoro, trifluoromethyl, and trifluoromethoxy.

In another embodiment of the compounds of Formula (I-C-2):

R¹ is pyrazinyl, wherein such pyrazinyl is optionally substituted with one or two substituents independently selected from the group consisting of halo-$C_1$-$C_4$-alkyl and $C_3$-$C_4$-cycloalkyl; and R² is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-C-2):

R¹ is pyrazinyl, wherein such pyrazinyl is substituted with one substituent selected from the group consisting of trifluoromethyl and cyclopropyl; and R² is pyridinyl, wherein such pyridinyl is substituted with one substituent selected from the group consisting of fluoro, trifluoromethyl, and trifluoromethoxy.

In another embodiment of the compounds of Formula (I-C-2):

R¹ is pyrazinyl, wherein such pyrazinyl is substituted with one substituent selected from the group consisting of trifluoromethyl and cyclopropyl; and R² is pyridinyl, wherein such pyridinyl is substituted with two substituents independently selected from the group consisting of fluoro, trifluoromethyl, and trifluoromethoxy.

In another embodiment of the compounds of Formula (I-C-2):

R¹ is pyridinyl, wherein such pyridinyl is optionally substituted with one or two substituents independently selected from the group consisting of halo-$C_1$-$C_4$-alkyl and $C_3$-$C_4$-cycloalkyl; and R² is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-C-2):

R¹ is pyridinyl, wherein such pyridinyl is substituted with one substituent selected from the group consisting of trifluoromethyl and cyclopropyl; and R² is phenyl, wherein such phenyl is substituted with one substituent selected from the group consisting of fluoro, trifluoromethyl, and trifluoromethoxy.

In another embodiment of the compounds of Formula (I-C-2):

R¹ is pyridinyl, wherein such pyridinyl is substituted with one substituent selected from the group consisting of trifluoromethyl and cyclopropyl; and R² is phenyl, wherein such phenyl is substituted with two substituents independently selected from the group consisting of fluoro, trifluoromethyl, and trifluoromethoxy.

In another embodiment of the compounds of Formula (I-C-2):

R¹ is pyridinyl, wherein such pyridinyl is optionally substituted with one or two substituents independently selected from the group consisting of halo-$C_1$-$C_4$-alkyl and $C_3$-$C_4$-cycloalkyl; and R² is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (I-C-2):

R¹ is pyridinyl, wherein such pyridinyl is substituted with one substituent selected from the group consisting of trifluoromethyl and cyclopropyl; and R² is pyridinyl, wherein such pyridinyl is substituted with one substituent selected from the group consisting of fluoro, trifluoromethyl, and trifluoromethoxy.

In another embodiment of the compounds of Formula (I-C-2):

R¹ is pyridinyl, wherein such pyridinyl is substituted with one substituent selected from the group consisting of trifluoromethyl and cyclopropyl; and R² is pyridinyl, wherein such pyridinyl is substituted with two substituents independently selected from the group consisting of fluoro, trifluoromethyl, and trifluoromethoxy.

In another embodiment of the compounds of Formula (I-C-2):

R¹ is selected from the group consisting of:

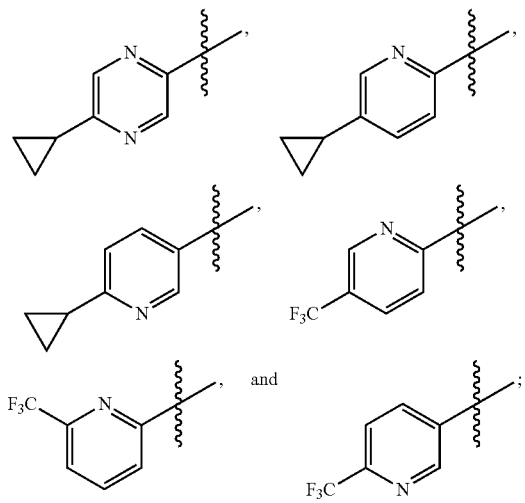

and

R² is selected from the group consisting of:

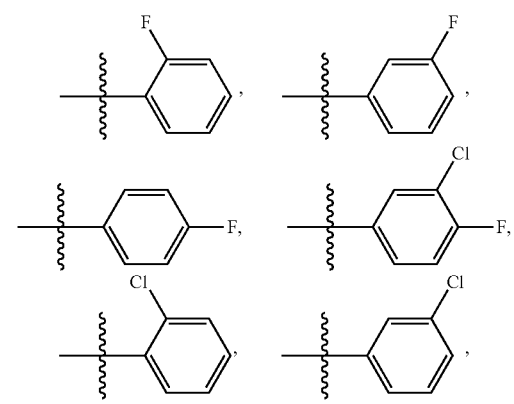

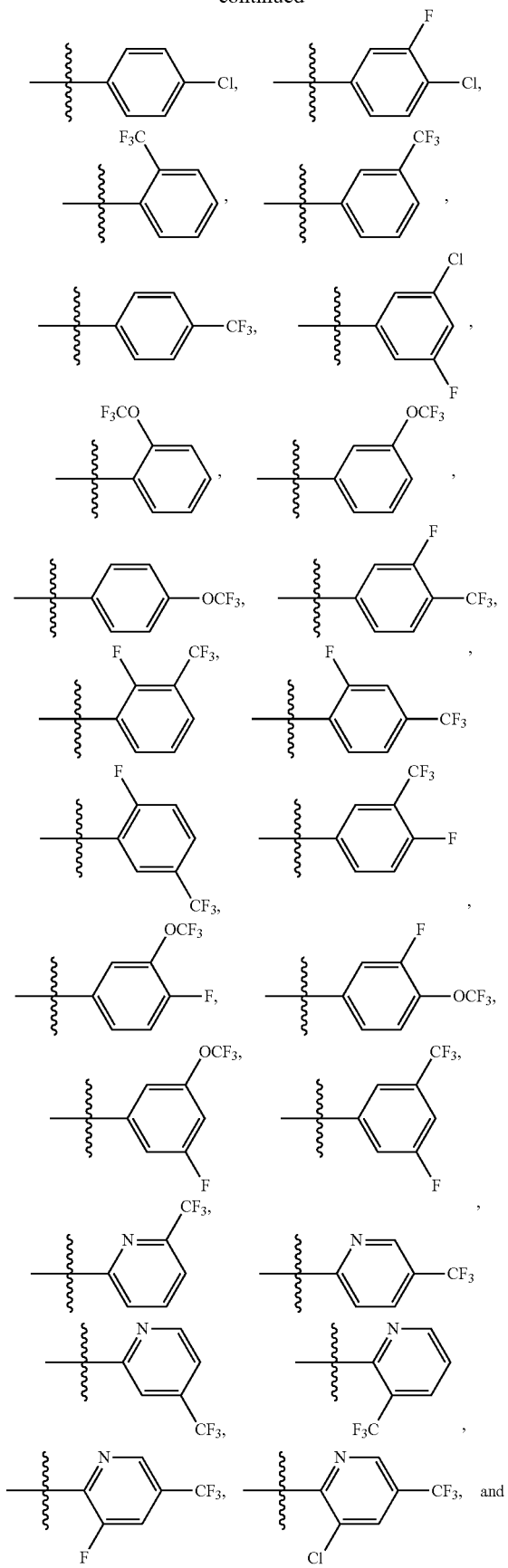

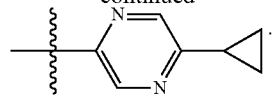

In another embodiment of the compounds of Formula (I-C-2):
R¹ is

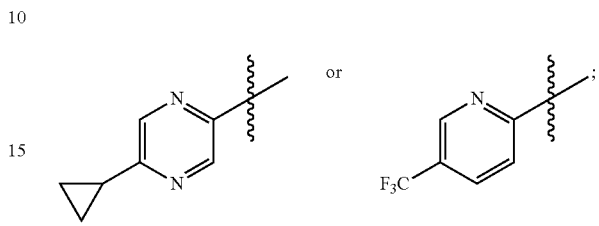

and
R² is selected from the group consisting of:

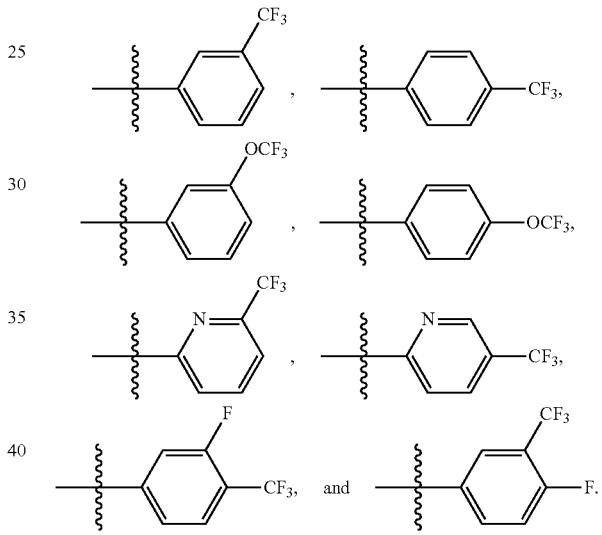

In another embodiment of the compounds of Formula (I-C-2), L is a bond; and R¹ and R² are as defined in the various substituent embodiments discussed above.

In another embodiment of the compounds of Formula (I-C-2), L is —CH₂—; and R¹ and R² are as defined in the various substituent embodiments discussed above.

In another embodiment of the compounds of Formula (I-C-2), L is —C(O)—; and R¹ and R² are as defined in the various substituent embodiments discussed above.

In another embodiment of the compounds of Formula (I-C-2), L is —S(O)₂—; and R¹ and R² are as defined in the various substituent embodiments discussed above.

In another embodiment of the compounds of Formula (I-C-2), L is —C(O)C(R⁵)(H)—; and R¹ and R² are as defined in the various substituent embodiments discussed above.

In another embodiment of the compounds of Formula (I-C-2), L is —C(O)C(R⁵)(H)—; R¹ and R² are as defined in the various substituent embodiments discussed above; and R⁵ is hydrogen.

In another embodiment of the compounds of Formula (I-C-2), L is —C(O)C(R⁵)(H)—; R¹ and R² are as defined in the various substituent embodiments discussed above; and R⁵ is hydroxy.

In another embodiment of the compounds of Formula (I-C-2), L is —C(O)C($R^5$)(H)—; $R^1$ and $R^2$ are as defined in the various substituent embodiments discussed above; and $R^5$ is selected from the group consisting of amino, methylamino, and dimethylamino.

In additional embodiments, the compounds of Formula (I-C-2) have a configuration that corresponds to a configuration of a compound of Formula (I-i), (I-ii), (I-iii), or (I-iv), and $R^1$, $R^2$, $R^4$, and L are as defined in the various substituent embodiments discussed above.

B-13: Formula (Ia)

In one embodiment, the compounds of Formula (I) correspond in structure to Formula (Ia):

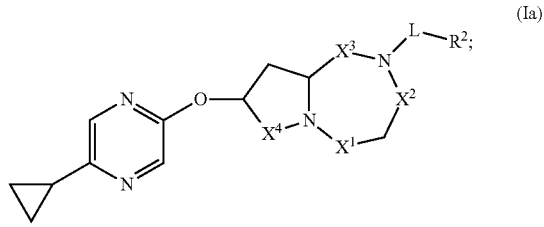

(Ia)

$R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy;

as to $X^1$, $X^2$, $X^3$, $X^4$, and L:

$X^1$ is —$CH_2$—; $X^2$ is —$CH_2$—; $X^3$ is —$CH_2$—; $X^4$ is —$CH_2$—; and L is selected from the group consisting of a bond, —$CH_2$—, —C(O)—, —C(O)C($R^3$)(H)—, and —S(O)$_2$—; or $X^1$ is —$CH_2$—; one of $X^2$ and $X^3$ is —C(O)— and the other one of $X^2$ and $X^3$ is —$CH_2$—; $X^4$ is —$CH_2$—; and L is selected from the group consisting of a bond, —$CH_2$—, —C(O)—, and —C(O)C($R^4$)(H)—; or one of $X^1$ and $X^4$ is —C(O)— and the other one of $X^1$ and $X^4$ is —$CH_2$—; $X^2$ is —$CH_2$—; $X^3$ is —$CH_2$—; and L is selected from the group consisting of a bond, —$CH_2$—, —C(O)—, —C(O)C($R^5$)(H)—, and —S(O)$_2$—; and $R^3$, $R^4$, and $R^5$ are independently selected from the group consisting of hydrogen, hydroxy, amino, methylamino, and dimethylamino In another embodiment of the compounds of Formula (Ia), $R^2$ is selected from the group consisting of phenyl and pyridinyl, wherein each such substituent is optionally substituted with one or two substituents independently selected from the group consisting of halogen, halo-$C_1$-$C_3$-alkyl, and halo-$C_1$-$C_3$-alkoxy.

In another embodiment of the compounds of Formula (Ia), $R^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (Ia), $R^2$ is phenyl, wherein such phenyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (Ia), $R^2$ is phenyl, wherein such phenyl is optionally substituted with one or two substituents independently selected from the group consisting of fluoro, trifluoromethyl, and trifluoromethoxy.

In another embodiment of the compounds of Formula (Ia), $R^2$ is phenyl, wherein such phenyl is substituted with one substituent selected from the group consisting of fluoro, trifluoromethyl, and trifluoromethoxy.

In another embodiment of the compounds of Formula (Ia), $R^2$ is phenyl, wherein such phenyl is substituted with two substituents independently selected from the group consisting of fluoro, trifluoromethyl, and trifluoromethoxy.

In another embodiment of the compounds of Formula (Ia), $R^2$ is pyridinyl, wherein such pyridinyl is optionally substituted with one or two substituents independently selected from the group consisting of halogen, halo-$C_1$-$C_3$-alkyl, and halo-$C_1$-$C_3$-alkoxy.

In another embodiment of the compounds of Formula (Ia), $R^2$ is pyridinyl, wherein such pyridinyl is optionally substituted with one or two substituents independently selected from the group consisting of fluoro, trifluoromethyl, and trifluoromethoxy.

In another embodiment of the compounds of Formula (Ia), $R^2$ is pyridinyl, wherein such pyridinyl is substituted with one substituent selected from the group consisting of fluoro, trifluoromethyl, and trifluoromethoxy.

In another embodiment of the compounds of Formula (Ia), $R^2$ is pyridinyl, wherein such pyridinyl is substituted with two substituents independently selected from the group consisting of fluoro, trifluoromethyl, and trifluoromethoxy.

In another embodiment of the compounds of Formula (Ia), $R^2$ is selected from the group consisting of:

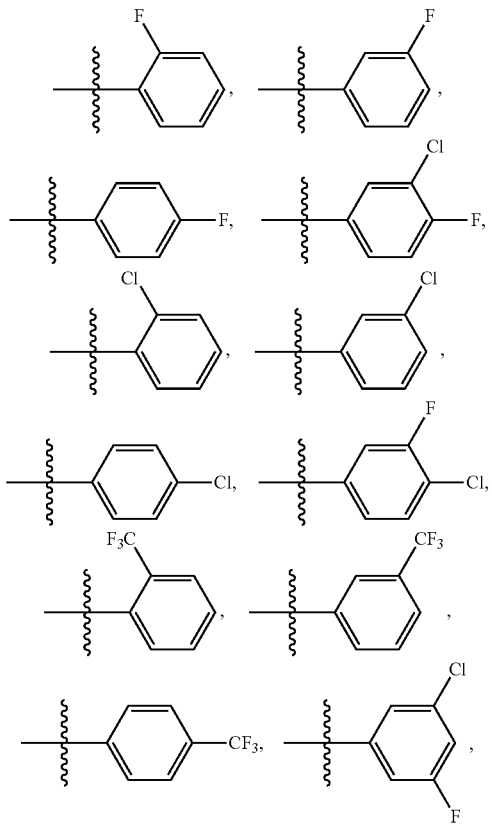

-continued
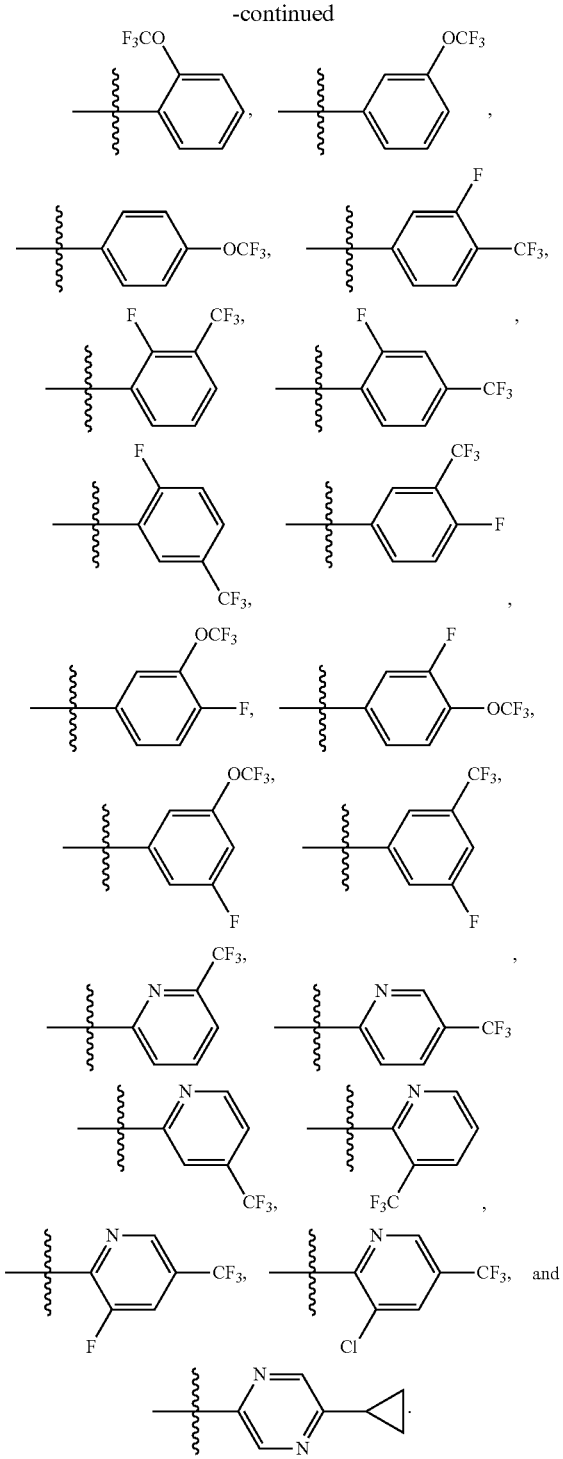
In another embodiment of the compounds of Formula (Ia), R² is selected from the group consisting of:
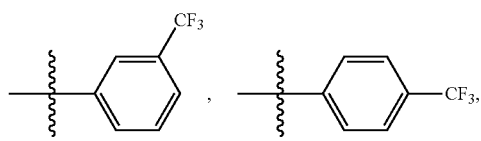
-continued
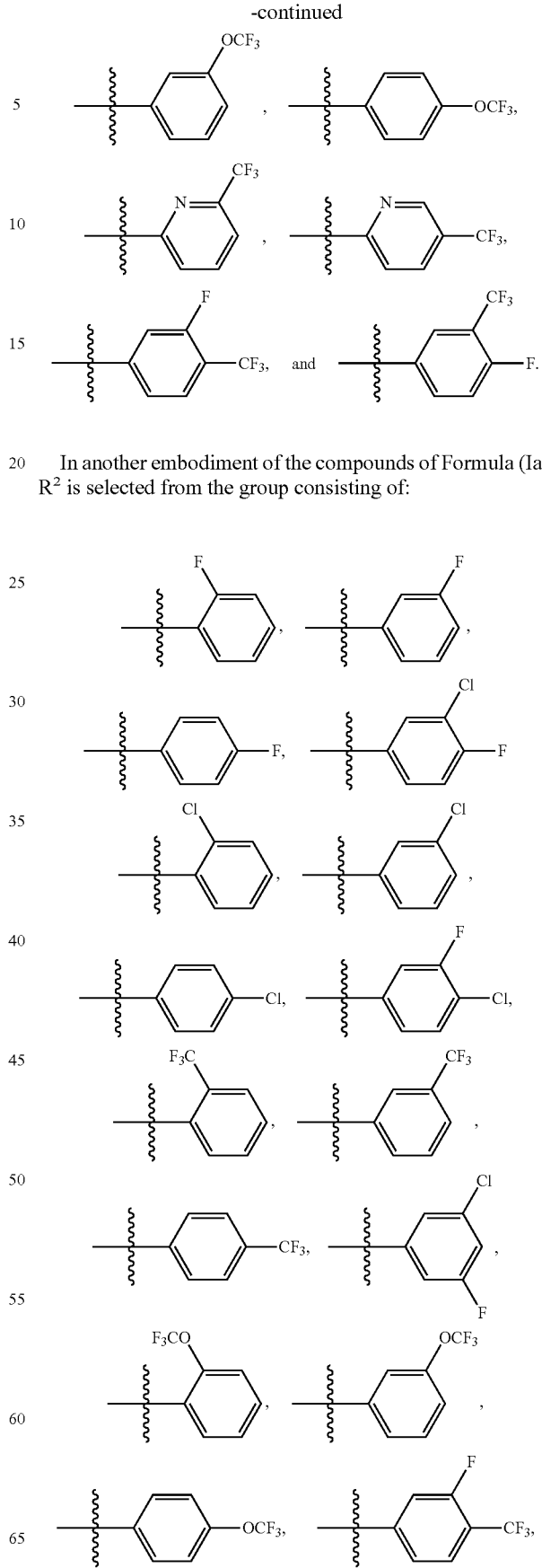
In another embodiment of the compounds of Formula (Ia), R² is selected from the group consisting of:

-continued

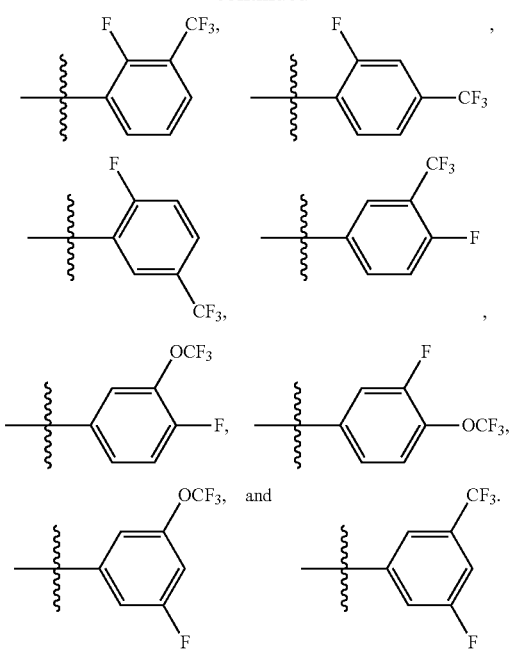

In another embodiment of the compounds of Formula (Ia), $R^2$ is selected from the group consisting of:

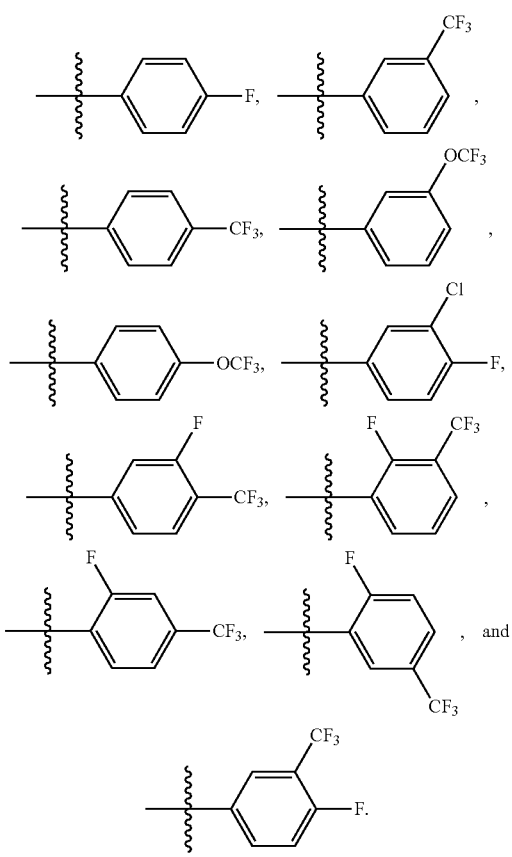

In another embodiment of the compounds of Formula (Ia), $R^2$ is selected from the group consisting of:

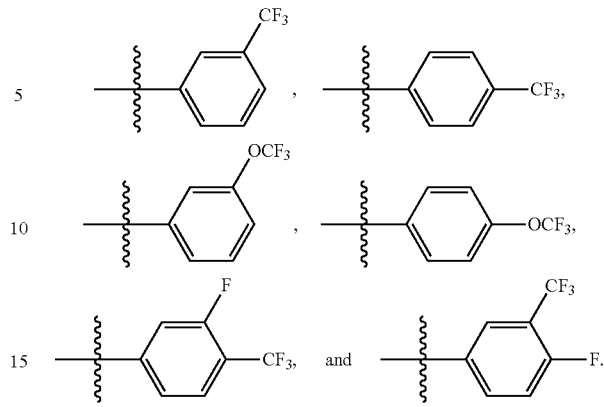

In another embodiment of the compounds of Formula (Ia), $R^2$ is selected from the group consisting of:

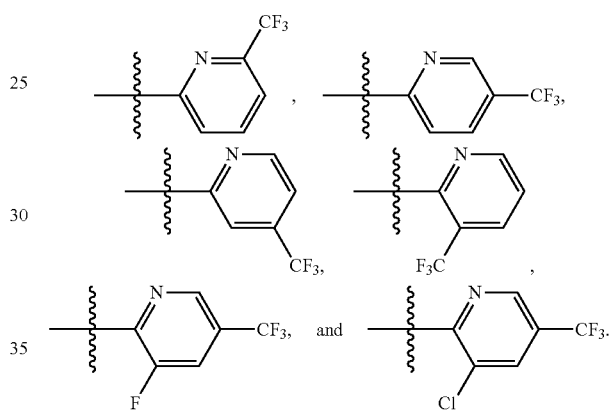

In another embodiment of the compounds of Formula (Ia), $X^1$ is —CH$_2$—; $X^2$ is —CH$_2$—; $X^3$ is —CH$_2$—; $X^4$ is —CH$_2$—; and $R^1$ and $R^2$ are as defined in the various substituent embodiments discussed above. In one embodiment, L is a bond. In one embodiment, L is —CH$_2$—. In one embodiment, L is —C(O)—. In one embodiment, L is —S(O)$_2$—. In one embodiment, L is —C(O)C(R$^3$)(H)—. In one embodiment, L is —C(O)C(R$^3$)(H)—; and R$^3$ is hydrogen. In one embodiment, L is —C(O)C(R$^3$)(H)—; and R$^3$ is hydroxy. In one embodiment, L is —C(O)C(R$^3$)(H)—; and R$^3$ is selected from the group consisting of amino, methylamino, and dimethylamine In another embodiment of the compounds of Formula (Ia), $X^1$ is —CH$_2$—; one of $X^2$ and $X^3$ is —C(O)— and the other one of $X^2$ and $X^3$ is —CH$^2$—; $X^4$ is —CH$_2$—; and $R^1$ and $R^2$ are as defined in the various substituent embodiments discussed above. In one embodiment, L is a bond. In one embodiment, L is —CH$_2$—. In one embodiment, L is —C(O)—. In one embodiment, L is —C(O)C(R$^4$)(H)—. In one embodiment, L is —C(O)C(R$^4$)(H)—; and R$^4$ is hydrogen. In one embodiment, L is —C(O)C(R$^4$)(H)—; and R$^4$ is hydroxy. In one embodiment, L is —C(O)C(R$^4$)(H)—; and R$^4$ is selected from the group consisting of amino, methylamino, and dimethylamine.

In another embodiment of the compounds of Formula (Ia), $X^1$ is —CH$_2$—; $X^2$ is —C(O)—; $X^3$ is —CH$_2$—; $X^4$ is —CH$_2$—; and $R^1$ and $R^2$ are as defined in the various substituent embodiments discussed above. In one embodiment, L is a bond. In one embodiment, L is —CH$_2$—. In one embodiment, L is —C(O)—. In one embodiment, L is —C(O)C(R$^4$)(H)—. In one embodiment, L is —C(O)C(R$^4$)(H)—; and R$^4$ is hydrogen. In one embodiment, L is —C(O)C(R$^4$)(H)—; and R$^4$ is hydroxy. In one embodiment, L is —C(O)C(R$^4$)(H)—; and R$^4$ is selected from the group consisting of amino, methylamino, and dimethylamine.

In another embodiment of the compounds of Formula (Ia), X$^1$ is —CH$_2$—; X$^2$ is —CH$_2$—; X$^3$ is —C(O)—; X$^4$ is —CH$_2$—; and R$^1$ and R$^2$ are as defined in the various substituent embodiments discussed above. In one embodiment, L is a bond. In one embodiment, L is —CH$_2$—. In one embodiment, L is —C(O)—. In one embodiment, L is —C(O)C(R$^4$)(H)—. In one embodiment, L is —C(O)C(R$^4$)(H)—; and R$^4$ is hydrogen. In one embodiment, L is —C(O)C(R$^4$)(H)—; and R$^4$ is hydroxy. In one embodiment, L is —C(O)C(R$^4$)(H)—; and R$^4$ is selected from the group consisting of amino, methylamino, and dimethylamine.

In another embodiment of the compounds of Formula (Ia), one of X$^1$ and X$^4$ is —C(O)— and the other one of X$^1$ and X$^4$ is —CH$_2$—; X$^2$ is —CH$_2$—; X$^3$ is —CH$_2$—; and R$^1$ and R$^2$ are as defined in the various substituent embodiments discussed above. In one embodiment, L is a bond. In one embodiment, L is —CH$_2$—. In one embodiment, L is —C(O)—. In one embodiment, L is —S(O)$_2$—. In one embodiment, L is —C(O)C(R$^5$)(H)—. In one embodiment, L is —C(O)C(R$^5$)(H)—; and R$^5$ is hydrogen. In one embodiment, L is —C(O)C(R$^5$)(H)—; and R$^5$ is hydroxy. In one embodiment, L is —C(O)C(R$^5$)(H)—; and R$^5$ is selected from the group consisting of amino, methylamino, and dimethylamine.

In another embodiment of the compounds of Formula (Ia), X$^1$—C(O)—; X$^2$ is —CH$_2$—; X$^3$ is —CH$_2$—; X$^4$ is —CH$_2$—; and R$^1$ and R$^2$ are as defined in the various substituent embodiments discussed above. In one embodiment, L is a bond. In one embodiment, L is —CH$_2$—. In one embodiment, L is —C(O)—. In one embodiment, L is —S(O)$_2$—. In one embodiment, L is —C(O)C(R$^5$)(H)—. In one embodiment, L is —C(O)C(R$^5$)(H)—; and R$^5$ is hydrogen. In one embodiment, L is —C(O)C(R$^5$)(H)—; and R$^5$ is hydroxy. In one embodiment, L is —C(O)C(R$^5$)(H)—; and R$^5$ is selected from the group consisting of amino, methylamino, and dimethylamine.

In another embodiment of the compounds of Formula (Ia), X$^1$ is —CH$_2$—; X$^2$ is —CH$_2$—; X$^3$ is —CH$_2$—; X$^4$ is —C(O)—; and R$^1$ and R$^2$ are as defined in the various substituent embodiments discussed above. In one embodiment, L is a bond. In one embodiment, L is —CH$_2$—. In one embodiment, L is —C(O)—. In one embodiment, L is —S(O)$_2$—. In one embodiment, L is —C(O)C(R$^5$)(H)—. In one embodiment, L is —C(O)C(R$^5$)(H)—; and R$^5$ is hydrogen. In one embodiment, L is —C(O)C(R$^5$)(H)—; and R$^5$ is hydroxy. In one embodiment, L is —C(O)C(R$^5$)(H)—; and R$^5$ is selected from the group consisting of amino, methylamino, and dimethylamine.

In additional embodiments, the compounds of Formula (Ia) have a configuration that corresponds to a configuration of a compound of Formula (I-i), (I-ii), (I-iii), or (I-iv), and R$^1$, R$^2$, R$^3$, R$^4$, R$^5$, and L are as defined in the various substituent embodiments discussed above.

B-14: Formula (Ib)

In one embodiment, the compounds of Formula (I) correspond in structure to Formula (Ib):

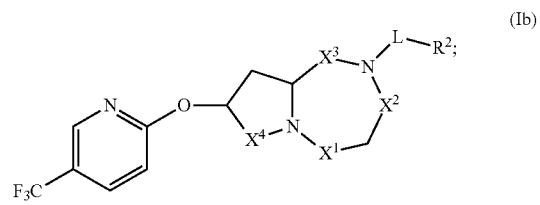

R$^2$ is selected from the group consisting of phenyl and pyridinyl, wherein each such substituent is optionally substituted with one or two substituents independently selected from the group consisting of halogen, halo-C$_1$-C$_3$-alkyl, and halo-C$_1$-C$_3$-alkoxy;

as to X$^1$, X$^2$, X$^3$, X$^4$, and L:

X$^1$ is —CH$_2$—; X$^2$ is —CH$_2$—; X$^3$ is —CH$_2$—; X$^4$ is —CH$_2$—; and L is selected from the group consisting of a bond, —CH$_2$—, —C(O)—, —C(O)C(R$^3$)(H)—, and —S(O)$_2$—; or X$^1$ is —CH$_2$—; one of X$^2$ and X$^3$ is —C(O)— and the other one of X$^2$ and X$^3$ is —CH$_2$—; X$^4$ is —CH$_2$—; and L is selected from the group consisting of a bond, —CH$_2$—, —C(O)—, and —C(O)C(R$^4$)(H)—; or one of X$^1$ and X$^4$ is —C(O)— and the other one of X$^1$ and X$^4$ is —CH$_2$—; X$^2$ is —CH$_2$—; X$^3$ is —CH$_2$—; and L is selected from the group consisting of a bond, —CH$_2$—, —C(O)—, —C(O)C(R$^5$)(H)—, and —S(O)$_2$—; and R$^3$, R$^4$, and R$^5$ are independently selected from the group consisting of hydrogen, hydroxy, amino, methylamino, and dimethylamino In another embodiment of the compounds of Formula (Ib), R$^2$ is selected from the group consisting of phenyl and pyridinyl, wherein each such substituent is optionally substituted with one or two substituents independently selected from the group consisting of halogen, halo-C$_1$-C$_3$-alkyl, and halo-C$_1$-C$_3$-alkoxy.

In another embodiment of the compounds of Formula (Ib), R$^2$ is selected from the group consisting of phenyl and pyridinyl, wherein each such substituent is optionally substituted with one or two substituents independently selected from the group consisting of fluoro, trifluoromethyl, and trifluoromethoxy.

In another embodiment of the compounds of Formula (Ib), R$^2$ is phenyl, wherein such phenyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (Ib), R$^2$ is phenyl, wherein such phenyl is optionally substituted with one or two substituents independently selected from the group consisting of fluoro, trifluoromethyl, and trifluoromethoxy.

In another embodiment of the compounds of Formula (Ib), R$^2$ is phenyl, wherein such phenyl is substituted with one substituent selected from the group consisting of fluoro, trifluoromethyl, and trifluoromethoxy.

In another embodiment of the compounds of Formula (Ib), R$^2$ is phenyl, wherein such phenyl is substituted with two substituents independently selected from the group consisting of fluoro, trifluoromethyl, and trifluoromethoxy.

In another embodiment of the compounds of Formula (Ib), R$^2$ is pyridinyl, wherein such pyridinyl is optionally substituted with one or two substituents independently selected from the group consisting of halogen, halo-C$_1$-C$_3$-alkyl, and halo-C$_1$-C$_3$-alkoxy.

In another embodiment of the compounds of Formula (Ib), $R^2$ is pyridinyl, wherein such pyridinyl is optionally substituted with one or two substituents independently selected from the group consisting of fluoro, trifluoromethyl, and trifluoromethoxy.

In another embodiment of the compounds of Formula (Ib), $R^2$ is pyridinyl, wherein such pyridinyl is substituted with one substituent selected from the group consisting of fluoro, trifluoromethyl, and trifluoromethoxy.

In another embodiment of the compounds of Formula (Ib), $R^2$ is pyridinyl, wherein such pyridinyl is substituted with two substituents independently selected from the group consisting of fluoro, trifluoromethyl, and trifluoromethoxy.

In another embodiment of the compounds of Formula (Ib), $R^2$ is selected from the group consisting of:

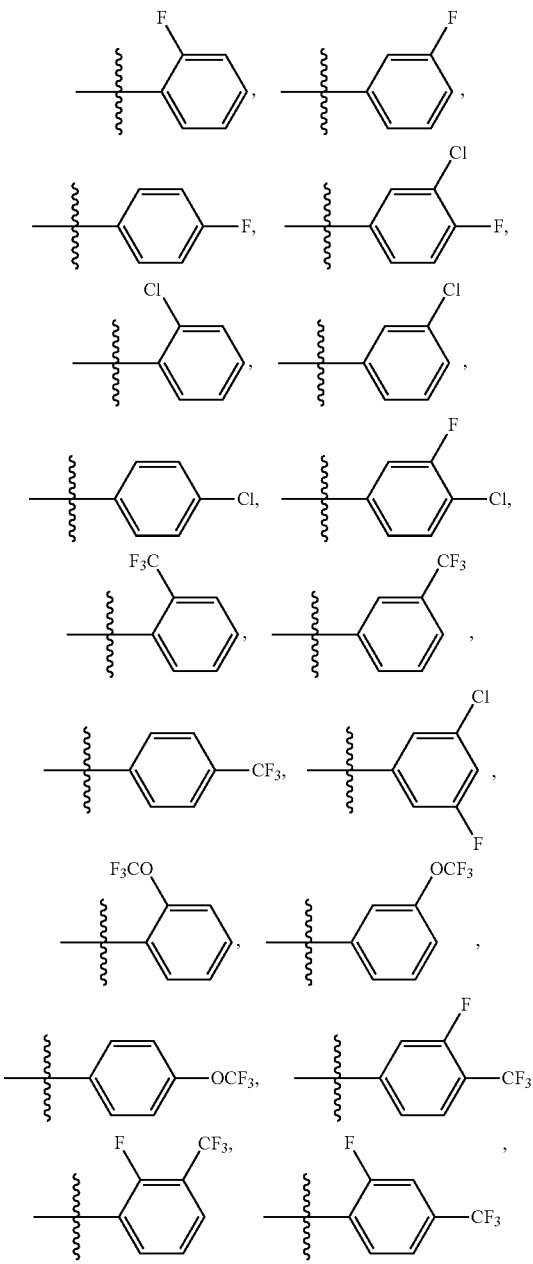

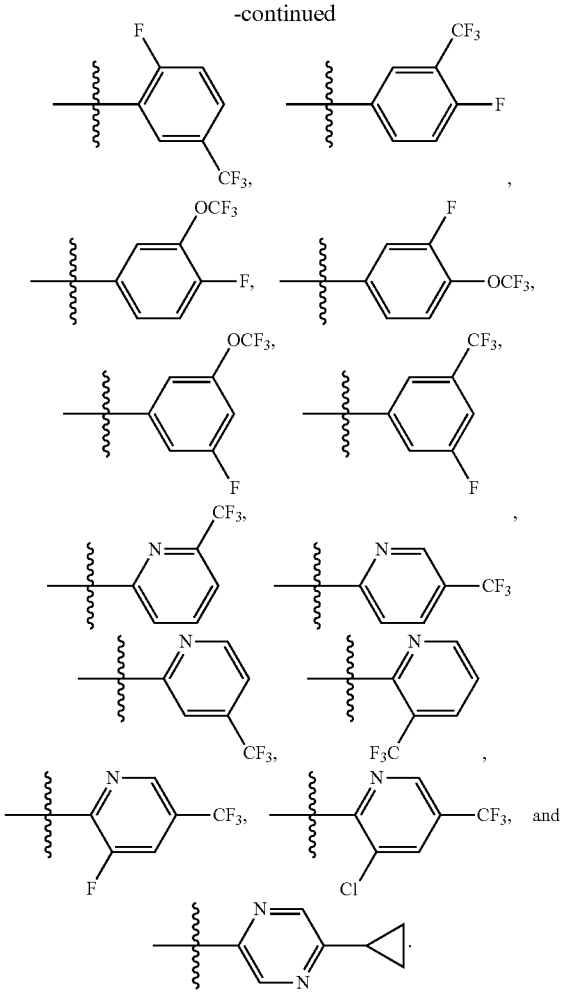

In another embodiment of the compounds of Formula (Ib), $R^2$ is selected from the group consisting of:

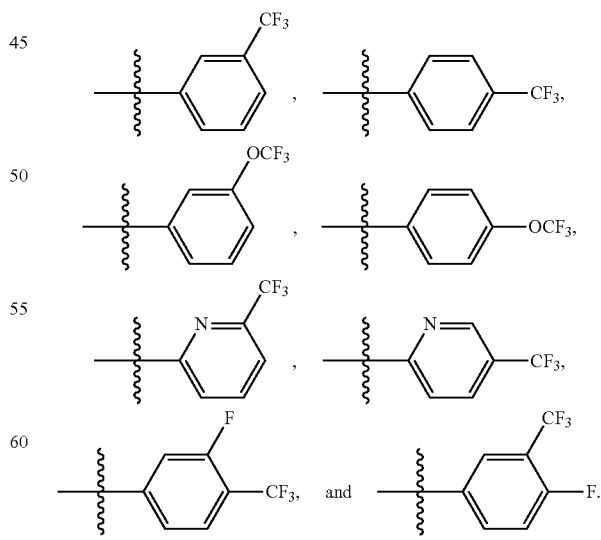

In another embodiment of the compounds of Formula (Ib), $R^2$ is selected from the group consisting of:

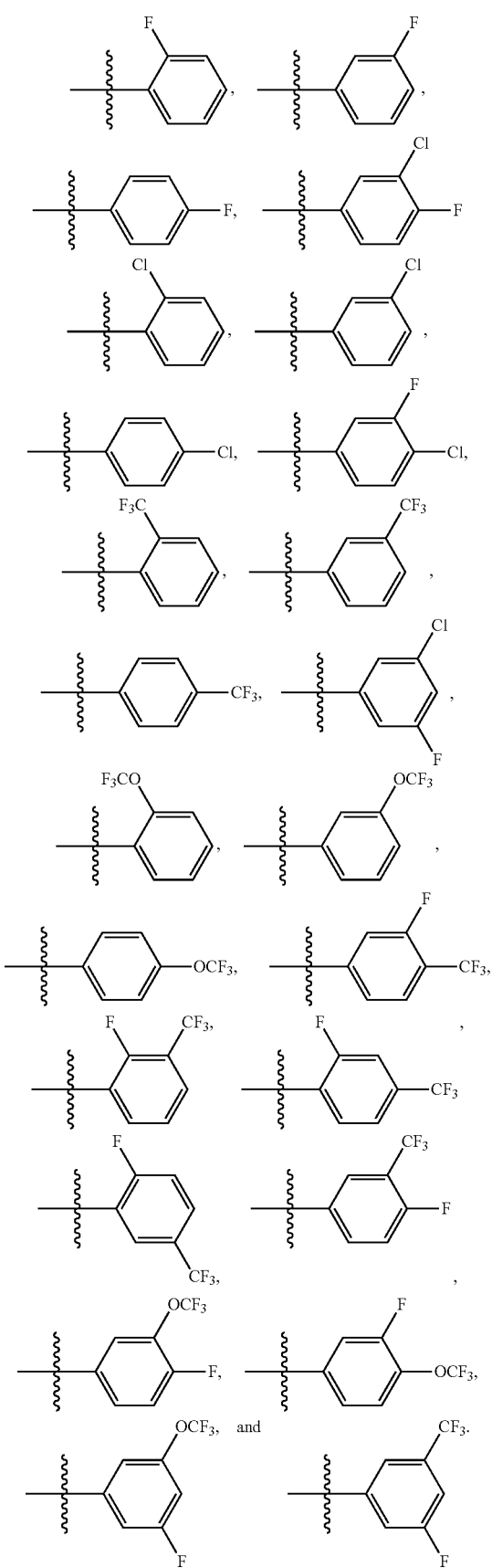
In another embodiment of the compounds of Formula (Ib), $R^2$ is selected from the group consisting of:
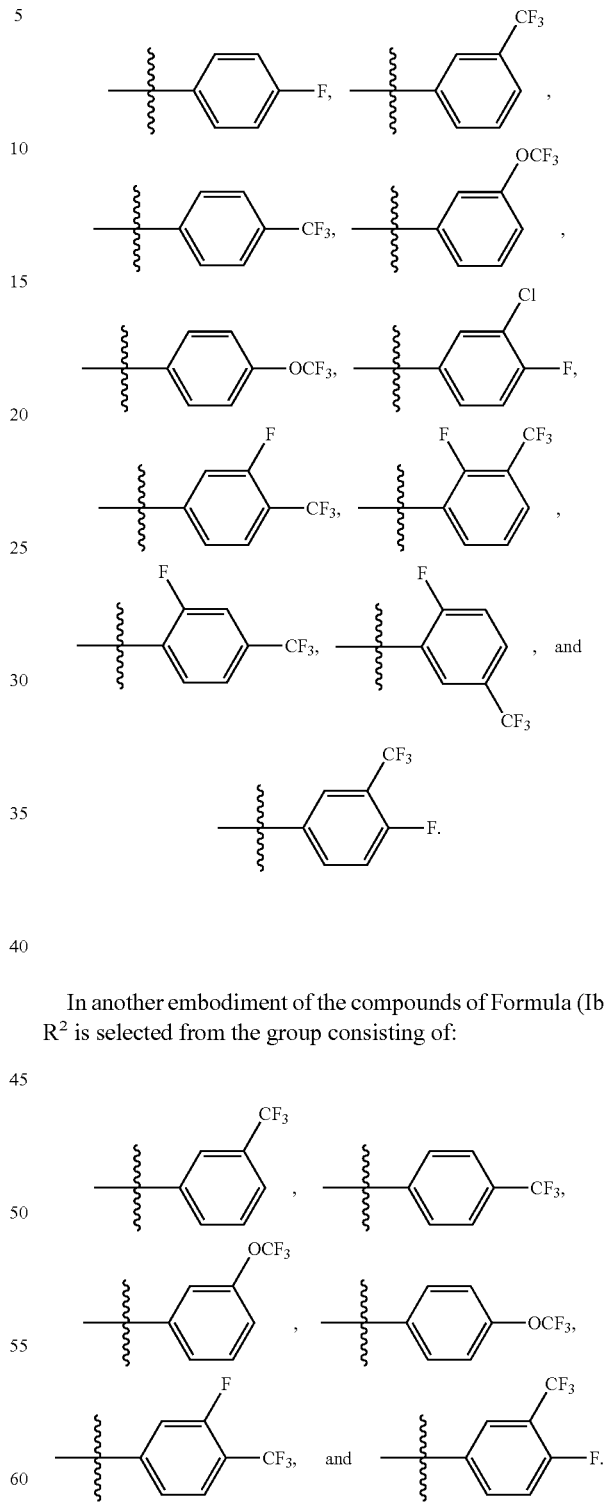
In another embodiment of the compounds of Formula (Ib), $R^2$ is selected from the group consisting of:

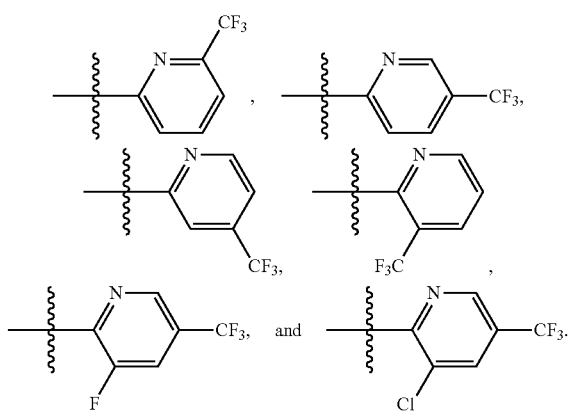

In another embodiment of the compounds of Formula (Ib), $X^1$ is —$CH_2$—; $X^2$ is —$CH_2$—; $X^3$ is —$CH_2$—; $X^4$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —S(O)$_2$—. In one embodiment, L is —C(O)C($R^3$)(H)—. In one embodiment, L is —C(O)C($R^3$)(H)—; and $R^3$ is hydrogen. In one embodiment, L is —C(O)C($R^3$)(H)—; and $R^3$ is hydroxy. In one embodiment, L is —C(O)C($R^3$)(H)—; and $R^3$ is selected from the group consisting of amino, methylamino, and dimethylamine.

In another embodiment of the compounds of Formula (Ib), $X^1$ is —$CH_2$—; one of $X^2$ and $X^3$ is —C(O)— and the other one of $X^2$ and $X^3$ is —$CH_2$—; $X^4$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —C(O)C($R^4$)(H)—. In one embodiment, L is —C(O)C($R^4$)(H)—; and $R^4$ is hydrogen. In one embodiment, L is —C(O)C($R^4$)(H)—; and $R^4$ is hydroxy. In one embodiment, L is —C(O)C($R^4$)(H)—; and $R^4$ is selected from the group consisting of amino, methylamino, and dimethylamine.

In another embodiment of the compounds of Formula (Ib), $X^1$ is —$CH_2$—; $X^2$ is —C(O)—; $X^3$ is —$CH_2$—; $X^4$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —C(O)C($R^4$)(H)—. In one embodiment, L is —C(O)C($R^4$)(H)—; and $R^4$ is hydrogen. In one embodiment, L is —C(O)C($R^4$)(H)—; and $R^4$ is hydroxy. In one embodiment, L is —C(O)C($R^4$)(H)—; and $R^4$ is selected from the group consisting of amino, methylamino, and dimethylamine.

In another embodiment of the compounds of Formula (Ib), $X^1$ is —$CH_2$—; $X^2$ is —$CH_2$—; $X^3$ is —C(O)—; $X^4$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —C(O)C($R^4$) (H)—. In one embodiment, L is —C(O)C($R^4$)(H)—; and $R^4$ is hydrogen. In one embodiment, L is —C(O)C($R^4$)(H)—; and $R^4$ is hydroxy. In one embodiment, L is —C(O)C($R^4$) (H)—; and $R^4$ is selected from the group consisting of amino, methylamino, and dimethylamine.

In another embodiment of the compounds of Formula (Ib), one of $X^1$ and $X^4$ is —C(O)— and the other one of $X^1$ and $X^4$ is —$CH_2$—; $X^2$ is —$CH_2$—; $X^3$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —S(O)$_2$—. In one embodiment, L is —C(O)C($R^5$)(H)—. In one embodiment, L is —C(O)C($R^5$)(H)—; and $R^5$ is hydrogen. In one embodiment, L is —C(O)C($R^5$)(H)—; and $R^5$ is hydroxy. In one embodiment, L is —C(O)C($R^5$)(H)—; and $R^5$ is selected from the group consisting of amino, methylamino, and dimethylamine.

In another embodiment of the compounds of Formula (Ib), $X^1$—C(O)—; $X^2$ is —$CH_2$—; $X^3$ is —$CH_2$—; $X^4$ is —$CH_2$—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —S(O)$_2$—. In one embodiment, L is —C(O)C($R^5$)(H)—. In one embodiment, L is —C(O)C($R^5$)(H)—; and $R^5$ is hydrogen. In one embodiment, L is —C(O)C($R^5$)(H)—; and $R^5$ is hydroxy. In one embodiment, L is —C(O)C($R^5$)(H)—; and $R^5$ is selected from the group consisting of amino, methylamino, and dimethylamine.

In another embodiment of the compounds of Formula (Ib), $X^1$ is —$CH_2$—; $X^2$ is —$CH_2$—; $X^3$ is —$CH_2$—; $X^4$ is —C(O)—; and $R^1$ and $R^2$ are as defined in the various substituent embodiments discussed above. In one embodiment, L is a bond. In one embodiment, L is —$CH_2$—. In one embodiment, L is —C(O)—. In one embodiment, L is —S(O)$_2$—. In one embodiment, L is —C(O)C($R^5$)(H)—. In one embodiment, L is —C(O)C($R^5$)(H)—; and $R^5$ is hydrogen. In one embodiment, L is —C(O)C($R^5$)(H)—; and $R^5$ is hydroxy. In one embodiment, L is —C(O)C($R^5$)(H)—; and $R^5$ is selected from the group consisting of amino, methylamino, and dimethylamine.

In additional embodiments, the compounds of Formula (Ib) have a configuration that corresponds to a configuration of a compound of Formula (I-i), (I-ii), (I-iii), or (I-iv), and $R^1$, $R^2$, $R^3$, $R^4$, $R^5$, and L are as defined in the various substituent embodiments discussed above.

Specific compounds of Formula (I) include the compounds of Examples 1 through 208 discussed below.

In one embodiment, the compounds are selected from the group consisting of the compounds of Examples 1 through 55.

In one embodiment, the compounds are selected from the group consisting of the compounds of Examples 1 through 21.

In another embodiment, the compounds are selected from the group consisting of consisting of the compounds of Examples 22 through 27.

In another embodiment, the compounds are selected from the group consisting of the compounds of Examples 28 through 55.

(i) Isomers

This invention also is directed, in part, to all isomers of the compounds of Formula (I) and salts thereof (e.g., structural and stereoisomers). Structural isomers include chain and position isomers. Stereoisomers include E/Z isomers (i.e., isomers with regard to one or more double bonds), enantiomers (i.e., stereoisomers that have opposite configurations at all stereogenic centers), and diastereoisomers (i.e., stereoisomers that have the same configuration at one or more stereogenic centers, but differ at other stereogenic centers).

As previously discussed, the stereoisomers of the compounds of Formula (I) include those depicted below as Formulae (I-i), (I-ii), (I-iii), and (I-iv):

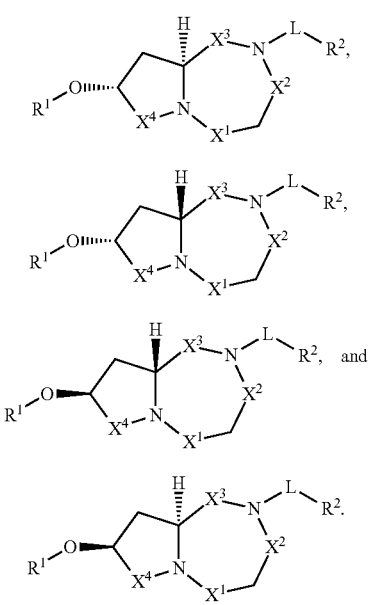

Further, as previously discussed, the stereoisomers of the compounds of Formulae (I-A), (I-B), (I-B-1), (I-B-2), (I-C), (I-C-1), or (I-C-2) can be depicted in a similar manner. For example, the stereoisomers of the compounds of Formula (I-A) include those depicted below as Formulae (I-C-1-i), (I-C-1-ii), (I-C-1-iii), and (I-C-1-iv):

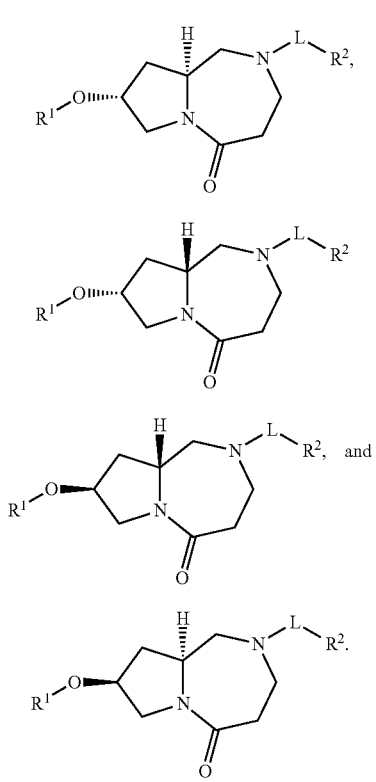

Stereoisomeric mixtures, e.g., mixtures of diastereomers, can be separated into their isomers using conventional separation methods. For example, diastereomeric mixtures can be separated into their individual diastereomers by means of fractional crystallization, chromatography, solvent distribution, and similar procedures. This separation can take place at any appropriate step of the compound synthesis or purification, e.g., through use of a chiral starting compound or chiral intermediate compound, or purification of the final compound itself. Enantiomers can be separated, for example, through the formation of diastereomeric salts (e.g., by salt formation with an enantiomerically pure chiral acid), or by means of chromatography (e.g., high performance liquid chromatography) using chiral chromatographic media.

In one embodiment, the compound is present as a substantially pure single isomer. In another embodiment, the compound is present as a mixture of two or more isomers. Mixtures of the compounds within this embodiment include racemic or equimolar mixtures as well as mixtures of the compounds where one isomeric form is enriched relative to the other isomeric forms of the compound. In additional embodiments, any form of the compound, such as an isomeric form of a compound disclosed in one of the Examples of this application, can make up about 60, 70, 80, 85, 90, 95, 97, 99, 99.5, 99.7, 99.9 percent or more of the mixture of the isomeric forms of that compound on a molar or weight basis. In one illustrative embodiment, a specific isomeric form of the compound can make up about 90 percent or more of the mixture of the isomeric forms of that compound on a molar or weight basis. In another illustrative embodiment, a specific form of the compound can make up about 95 percent or more of the mixture of the isomeric forms of that compound on a molar or weight basis. In yet another illustrative embodiment, a specific form of the compound can make up about 99 percent or more of the mixture of the isomeric forms of that compound on a molar or weight basis.

(ii) Salts

Those skilled in the art will recognize that the compounds described in this application, including those set forth in the Examples, can occur in the free form (i.e., non-salt form) or in the salt form. In addition to encompassing the free form of the compounds of Formula (I), this invention is directed, in part, to all salts of the compounds of Formula (I). Depending upon the specific compound, a salt form may be advantageous relative to the non-salt form due to one or more physical properties of the salt, such as stability, solubility, or ease of isolation, purification, and/or resolution of the compound. Where a salt is intended to be administered to a patient (as opposed to, for example, being in use in an in vitro context), the salt preferably is pharmaceutically acceptable and/or physiologically compatible. Salts can be prepared in situ during the final isolation and purification of the compounds of the invention or separately, e.g., by reacting a free base function with a suitable organic acid.

The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of Formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of Formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Additional examples of pharmaceutically acceptable salts are described in "Handbook of Pharmaceutical Salts: Properties, Selection, and Use" by Stahl and Wermuth (Wiley-VCH, Weinheim, Germany, 2002).

(iii) Additional Forms

The compounds of the invention also can exist in unsolvated or solvated form. Solvents can include, for example, pharmaceutically acceptable solvents such as water (resulting in hydrates of the compound), ethanol, and the like. For the purposes of the present invention, solvated forms of the compounds are considered equivalent to unsolvated forms of the compounds and both are included within the scope of the compounds of the invention.

C. Compositions

This invention also is directed, in part, to compositions comprising one or more compounds and/or salts of the invention. Although the compound may be administered alone or in the form of a pharmaceutical composition, administration generally will be in the form of a pharmaceutical composition. In some embodiments, the composition comprises a compound of Formula (I), or a pharmaceutically acceptable salt thereof, in association with a pharmaceutically acceptable carrier. The preferred composition depends on the method of administration, and typically comprises one or more conventional pharmaceutically acceptable carriers, adjuvants, and/or vehicles (together referred to as "excipients"). Such compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

The compounds of the present invention can be formulated for administration topically to the skin or mucosa, i.e., dermally or transdermally. Such administration can include the use, e.g., of transdermal patches or iontophoresis devices.

In some embodiments, the compositions further comprise one or more additional therapeutic agents. Such therapeutic agents can, but need not be, additional therapeutic agents for treating pain. In one embodiment, the additional therapeutic agent is selected from the group consisting of acetaminophen, NSAIDs (such aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

Besides those representative dosage forms described above, pharmaceutically acceptable excipients and carriers are generally known to those skilled in the art and are thus included in the instant invention. Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

The therapeutically effective dose level for any particular patient will depend upon the specific situation and can depend upon a variety of factors including the type, age, weight, sex, diet, and condition of the patient being treated; the severity of the pathological condition; activity of the specific compound employed; the specific composition employed; the age, body weight, general health, sex and diet of the patient; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The preferred total daily dose of the compound or salt (administered in single or divided doses) typically is from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Depending upon the route and frequency of administration, the pharmaceutical compositions of the present invention can contain, for example, from about 0.1 percent by weight to about 99 percent or more by weight of the active ingredient. Depending upon the compound administered, the amount of active ingredient contained in the dosage unit composition employed for adult human treatment generally can range, for example, from about 0.01 mg to about 3000 mg. For the therapeutic uses described in this application, the amount of active ingredient contained in the dosage unit composition generally will be in the range, for example, from about 0.1 mg to about 1000 mg. In one embodiment, the amount of active ingredient contained in the dosage unit composition is in a range from about 1 mg to about 500 mg. In another embodiment, the amount of active ingredient contained in the dosage unit composition is in a range from about 1 mg to about 250 mg. In another embodiment, the amount of active ingredient contained in the dosage unit composition is in a range from about 1 mg to about 25 mg. In another embodiment, the amount of active ingredient contained in the dosage unit composition is in a range from about 25 mg to about 50 mg. In another embodiment, the amount of active ingredient contained in the dosage unit composition is in a range from about 50 mg to about 100 mg. In another embodiment, the amount of active ingredient contained in the dosage unit composition is in a range from about 100 mg to about 150 mg. In another embodiment, the amount of active ingredient contained in the dosage unit composition is in a range from about 150 mg to about 200 mg. In another embodiment, the amount of active ingredient contained in the dosage unit composition is in a range from about 200 mg to about 250 mg.

D. Kits

This invention also is directed, in part, to a kit comprising one or more compounds and/or salts of the invention. The kit can optionally contain one or more additional therapeutic agents and/or instructions for, for example, using the kit. In one embodiment, the kit includes a unit dosage form comprising a compound of Formula (I), or a pharmaceutically acceptable salt thereof, contained within a packaging material and a label or package insert which indicates that the unit dosage form can be used for treating pain. In another embodiment, the kit includes a unit dosage form comprising a compound of Formula (I), or a pharmaceutically acceptable salt thereof contained within a packaging material; a second therapeutic agent; and a label or package insert which indicates that the unit dosage form and second therapeutic agent can be used for treating pain.

E. Methods of Use

This invention also is directed, in part, to a method for blocking calcium channel activation, particularly N-type calcium channel activation. In one embodiment, the invention is directed, in part, to a method for blocking calcium channel activation in vitro. In another embodiment, the invention is directed, in part, to a method for blocking calcium channel activation in vivo.

In one embodiment, the invention is directed to methods for treating a condition in a subject that can be treated by blocking N-Type calcium channel activation in the subject. These methods comprise administering to the subject one or more compounds and/or salts of the invention, and, optionally, one or more additional therapeutic agents. In some embodiments, a therapeutically effective amount of the compound(s) and/or salt(s) is administered to the subject.

The terms "treat," "treating," and "treatment" are readily understood by a physician of ordinary skill and, with respect to treatment of a particular condition, can include ameliorating, suppressing, eradicating, preventing, reducing the risk of, and/or delaying the onset of the disease being treated.

A "therapeutically-effective amount" or "effective amount" is an amount that will achieve the goal of treating the targeted condition. Where the compound or composition is being administered to treat pain, for example, a therapeutically effective amount of the compound or composition is an amount that is sufficient, either alone or in combination with additional therapies, to provide an anti-pain effect in a subject as compared to the response obtained without administration of the compound or composition.

The term "subject" includes animals such as mammals, including primates (e.g., humans), cows, sheep, goats, horses, dogs, cats, rabbits, rats, mice and the like. The methods of treatment are particularly suitable for use with a human subject, but may be used with other animal subjects, particularly mammals.

One embodiment of the present invention provides a method of treating pain in a subject in need thereof. The method comprises administering to the subject, including a mammal, such as a human, a therapeutically effective amount of a compound of Formula (I), or a pharmaceutically acceptable salt thereof. Conditions related to pain include, for example, acute pain, chronic pain, neuropathic pain, nociceptive pain, allodynia, inflammatory pain, inflammatory hyperalgesia, post herpetic neuralgia, post-operative pain, post-stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, menstrual pain.

Pain generally can be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain include neuropathic pain (e.g., painful diabetic neuropathy, postherpetic neuralgia), carpal tunnel syndrome, back pain, headache, cancer pain, arthritic pain and chronic post-surgical pain. In one embodiment, the condition related to pain is chronic pain. In another embodiment, the condition related to pain is acute pain.

Pain also can be divided into a number of different subtypes according to differing pathophysiology, including neuropathic, nociceptive, and inflammatory pain. Some types of pain have multiple etiologies and can be classified in more than one area, e.g., back pain and cancer pain have both nociceptive and neuropathic components.

In one embodiment, the condition related to pain is selected from the group consisting of neuropathic pain, nociceptive pain, and inflammatory pain.

In another embodiment, the condition related to pain is neuropathic pain. Neuropathic pain generally is defined as pain initiated or caused by a primary lesion or dysfunction in the nervous system and can result, for example, from trauma or disease. The term neuropathic pain encompasses many conditions with diverse etiologies including peripheral neuropathy, diabetic neuropathy, post-herpetic neuralgia, trigeminal neuralgia, back pain, cancer neuropathy, HIV-neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency.

In another embodiment, the condition related to pain is nociceptive pain. Nociceptive pain is induced by tissue injury or by intense stimuli with the potential to cause injury. When a substantial injury occurs to body tissue through trauma or disease, the characteristics of nociceptor activation are altered and there is sensitization in the periphery leading to a heightened sensation of pain in the subject. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e.g., bone pain, headache, facial pain or visceral pain) or pain associated with cancer therapy (e.g., post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament.

In another embodiment, the condition related to pain is inflammatory pain. A common type of inflammatory pain is arthritic pain arising from rheumatoid disease (such as ankylosing spondylitis) or symptomatic osteoarthritis or degenerative joint disease. Another type of inflammatory pain is visceral pain. Visceral pain is pain associated with the viscera, which encompass the organs of the abdominal cavity including the sex organs, spleen and part of the digestive system. Pain associated with the viscera can be divided into digestive visceral pain and non-digestive visceral pain. Commonly encountered gastrointestinal disorders that cause pain include functional bowel disorder and inflammatory bowel disease. These gastrointestinal disorders include a wide range of disease states that are currently only moderately controlled, including, with respect to functional bowel disorder, gastro-esophageal reflux, dyspepsia, irritable bowel syndrome, and functional abdominal pain syndrome, and, in respect of inflammatory bowel disease, Crohn's disease, ileitis and ulcerative colitis, all of which regularly produce visceral pain. Other types of visceral pain include the pain associated with dysmenorrhea, cystitis and pancreatitis and pelvic pain.

In another embodiment, the condition related to pain results from a musculo-skeletal condition such as myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In some embodiments, the methods comprise combination therapy, wherein the compound(s) and/or salt(s) of the invention is/are co-administered with a second (or even a third, fourth, etc.) compound, such as, for example, another therapeutic agent used to treat pain. The compound(s) and/or salt(s) of this invention can also be co-administered with therapeutic agents other than therapeutic agents used to treat pain. In these co-administration embodiments, the compound(s) and/or salt(s) of the invention and the second, etc. therapeutic agent(s) may be administered in a substantially simultaneous manner (e.g., or within about five minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

In certain embodiments, the method comprises co-administering to the subject the compound(s) and/or salt(s) of the invention with one or more compounds selected from the group consisting of nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-$HT_{2A}$ receptor antagonists, cholinergic analgesics, $α_2δ$ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-$HT_3$ antagonists, N-methyl-D-aspartic acid receptor antagonists, and phosphodiesterase V inhibitors.

In one embodiment, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In one embodiment, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

The present invention also is directed, in part, to one or more compounds and/or salts of the invention for use in the treatment of an N-type calcium channel-mediated condition, such as pain.

The present invention also is directed, in part, to one or more compounds and/or salts of the invention, and, optionally one or more additional therapeutic agents, for use as a medicament. In some embodiments, the medicament is for treating pain. In another embodiment, the medicament is for treating neuropathic pain. In another embodiment, the medicament is for treating nociceptive pain. In another embodiment, the medicament is for treating inflammatory pain.

The present invention is further directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating pain. In some embodiments, the medicament is for treating neuropathic pain. In some embodiments, the medicament is for treating nociceptive pain. In some embodiments, the medicament is for treating inflammatory pain.

F. Intermediate Compounds

This invention also is directed, in part, to novel intermediates that can be used to prepare the compounds of Formula (I), and their corresponding salts, as shown in Schemes 1-13 and as described in the Examples below.

G. Methods for Preparation

This invention also is directed, in part, to a process for preparing a compound of Formula (I), or a pharmaceutically acceptable salt thereof, e.g., as described in any one of the reaction schemes or Examples of the present application. This invention also encompasses compounds of the invention when prepared by metabolic processes. Preparation of the compounds by metabolic processes includes those occurring in the human or animal body (in vivo) or processes occurring in vitro.

Unless otherwise noted, the compounds of the invention wherein the groups $R^1$, $R^2$, and L have the meanings as set forth in the Brief Description of the Invention and Detailed Description of the Invention sections can be synthesized as shown in Schemes 1-13. One of skill in the art will appreciate that the compounds of the invention can be prepared by a variety of processes known for the preparation of compounds of this class and that the methods below are representative and not inclusive of all possible methods for preparing compounds of the present invention.

Abbreviations which have been used in the descriptions of the Schemes and the Examples that follow are: APCI for atmospheric pressure chemical ionization; Bn for benzyl; Boc for tert-butoxycarbonyl; Bu for butyl; i-Bu for isobutyl; DIAD for diisopropyl azodicarboxylate; DMSO for dimethyl sulfoxide; ESI for electrospray ionization; Et for ethyl; LCMS for liquid chromatography-mass spectrometry; HPLC for high performance liquid chromatography; Me for methyl; MeOH for methanol; Ms for methanesulfonyl; Ph for phenyl; $PPh_3$ for triphenylphosphine; and psi for pounds per square inch.

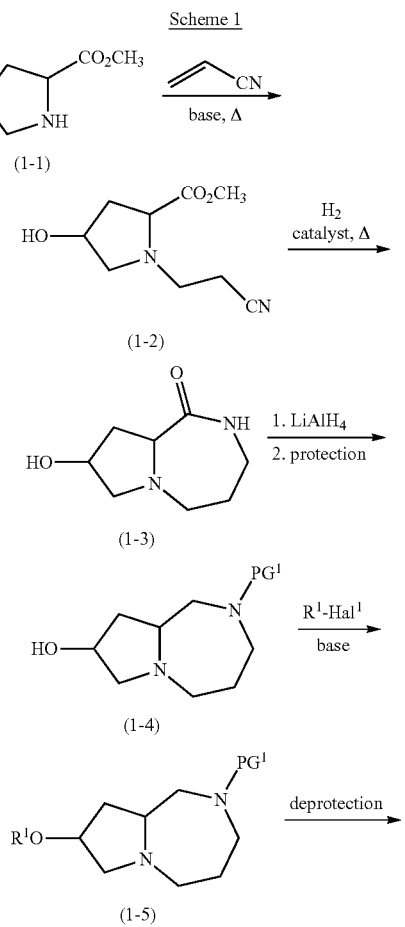

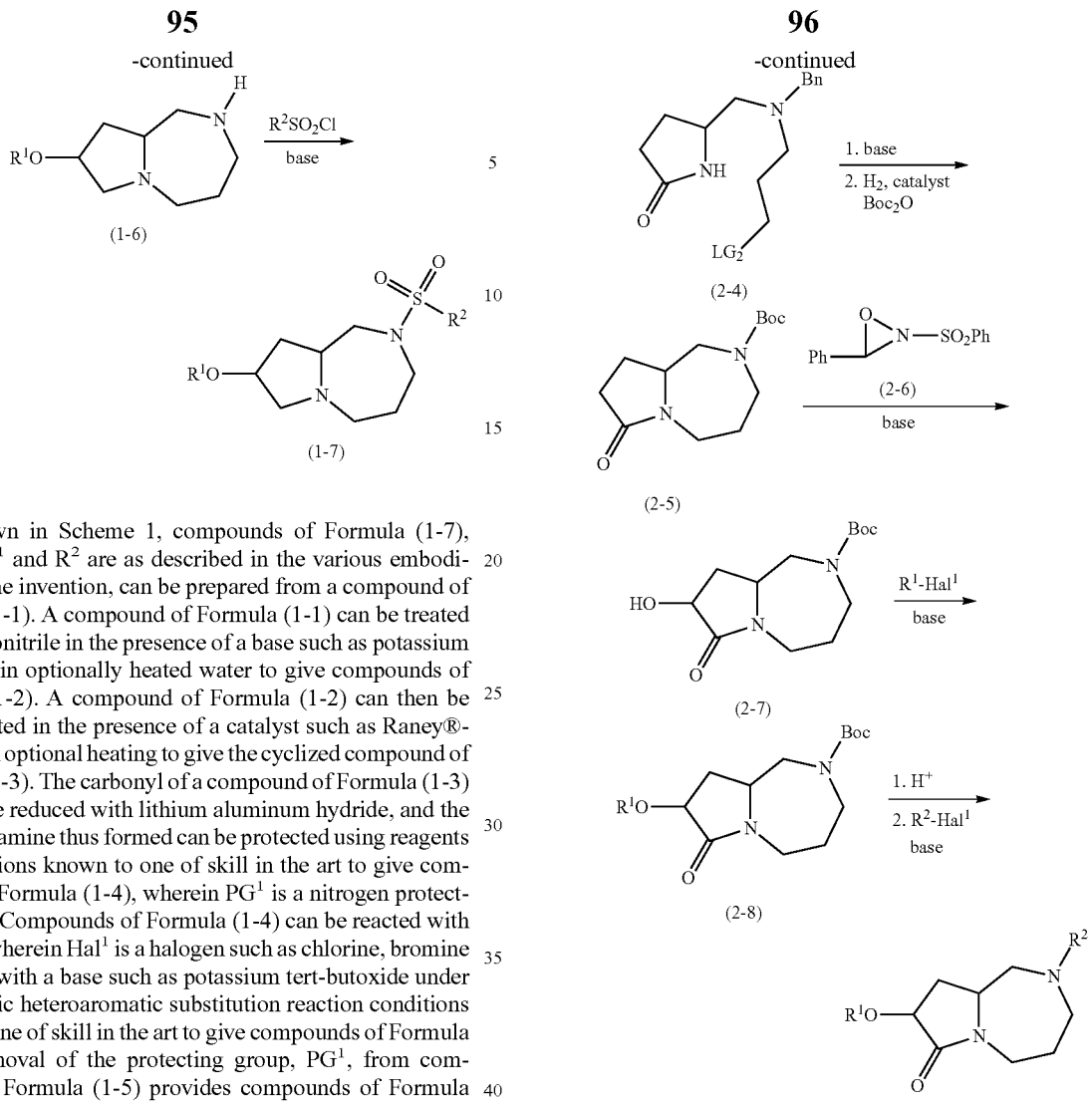

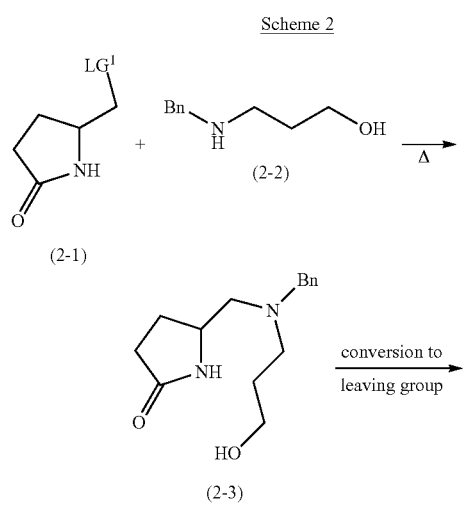

As shown in Scheme 1, compounds of Formula (1-7), wherein $R^1$ and $R^2$ are as described in the various embodiments of the invention, can be prepared from a compound of Formula (1-1). A compound of Formula (1-1) can be treated with acrylonitrile in the presence of a base such as potassium hydroxide in optionally heated water to give compounds of Formula (1-2). A compound of Formula (1-2) can then be hydrogenated in the presence of a catalyst such as Raney®-nickel with optional heating to give the cyclized compound of Formula (1-3). The carbonyl of a compound of Formula (1-3) can then be reduced with lithium aluminum hydride, and the secondary amine thus formed can be protected using reagents and conditions known to one of skill in the art to give compounds of Formula (1-4), wherein $PG^1$ is a nitrogen protecting group. Compounds of Formula (1-4) can be reacted with $R^1$-$Hal^1$ (wherein $Hal^1$ is a halogen such as chlorine, bromine or iodine) with a base such as potassium tert-butoxide under nucleophilic heteroaromatic substitution reaction conditions known to one of skill in the art to give compounds of Formula (1-5). Removal of the protecting group, $PG^1$, from compounds of Formula (1-5) provides compounds of Formula (1-6). Reaction of compounds of Formula (1-6) with a sulfonyl chloride, $R^2SO_2Cl$, in the presence of a base such as a tertiary amine gives compounds of Formula (1-7). Compounds of Formula (1-7) are representative of compounds of Formula (I), including compounds of Formula (I-A).

As shown in Scheme 2, compounds of Formula (2-9), wherein $R^1$ and $R^2$ are as described in the various embodiments of the invention, can be prepared from a compound of Formula (2-1). A compound of Formula (2-1) wherein $LG^1$ is a leaving group (such as a sulfonate, chlorine, bromine or iodine) can be treated with a compound of Formula (2-2) with optional heating to give a compound of Formula (2-3). The primary hydroxy moiety in compounds of Formula (2-3) can be converted to a leaving group, $LG^2$ (wherein $LG^2$ is a leaving group such as a sulfonate, chlorine, bromine or iodine), using conditions known to one of skill in the art to provide a compound of Formula (2-4). A compound of Formula (2-4) can be treated with a base such as sodium hydride to form a seven-membered ring compound. Subsequent hydrogenation of the seven-membered ring compound in the presence of di-tert-butyl dicarbonate removes the benzyl group and introduces the tert-butoxycarbonyl moiety to give a compound of Formula (2-5). Treatment of a compound of Formula (2-5) with a base such as a lithium amide base and a compound of Formula (2-6) results in hydroxylation adjacent to the lactam carbonyl giving a compound of Formula (2-7). A compound of Formula (2-7) can be reacted with $R^1$-$Hal^1$ (wherein $Hal^1$ is a halogen such as chlorine, bromine or iodine) with a base such as sodium hydride under nucleophilic heteroaromatic substitution reaction conditions known to one of skill in the art to give compounds of Formula (2-8). The tert-butoxycarbonyl moiety of compounds of Formula (2-8) can be removed under acidic conditions and the exposed secondary amine can be reacted with $R^2$-$Hal^1$ in the presence of base such as a tertiary amine base and optional heating to give compounds of Formula (2-9). Compounds of Formula (2-9) are representative of compounds of Formula (I), including compounds of Formula (I-C-2).

As shown in Scheme 3, compounds of Formula (3-7) wherein $R^1$ and $R^2$ are as described in the various embodiments of the invention, can be prepared from a compound of Formula (3-1). A compound of Formula (3-1) can be converted to a compound of Formula (3-2) in a three-step process. The first step is conversion of the carboxylic acid to an anhydride by treatment with a chloroformate in the presence of a base. The mixed anhydride is then reduced to the corresponding primary alcohol with a reductant such as sodium borohydride. The sequence is completed with oxidation of the primary alcohol with such reagents as sulfur trioxide pyridine complex or under Swern oxidation conditions to give a compound of Formula (3-2). A compound of Formula (3-2) can then be reductively aminated with ethyl 3-(benzylamino)propanoate to give a compound of Formula (3-3). The reductive amination can be achieved in the presence of acetic acid and sodium cyanoborohydride or resin-bound cyanoborohydride. Alternatively, sodium triacetoxyborohydride can be used as the reductant. Removal of the tert-butoxycarbonyl moiety in a compound of Formula (3-3) followed by treatment with a base, such as a tertiary amine base, and optional heating results in cyclization to a compound of Formula (3-4). Alternatively, after tert-butoxycarbonyl moiety removal, the intermediate acid salt can be free based with a base such as sodium carbonate, and then the free base can be heated in a solvent such as toluene to give the cyclized compound of Formula (3-4). Hydrogenation of a compound of Formula (3-4) in the presence of di-tert-butyl dicarbonate removes both benzyl groups and introduces the tert-butoxycarbonyl moiety selectively to give a compound of Formula (3-5). Introduction of $R^1$ under the heteroaromatic nucleophilic substitution reaction conditions described in Schemes 1 and 2 followed by acid removal of the tert-butoxycarbonyl protecting group gives compounds of Formula (3-6). Reaction of compounds of Formula (3-6) with a sulfonyl chloride, $R^2SO_2Cl$, in the presence of a base such as a tertiary amine gives compounds of Formula (3-7). Compounds of Formula (3-7) are representative of compounds of Formula (I), including compounds of Formula (I-C-1).

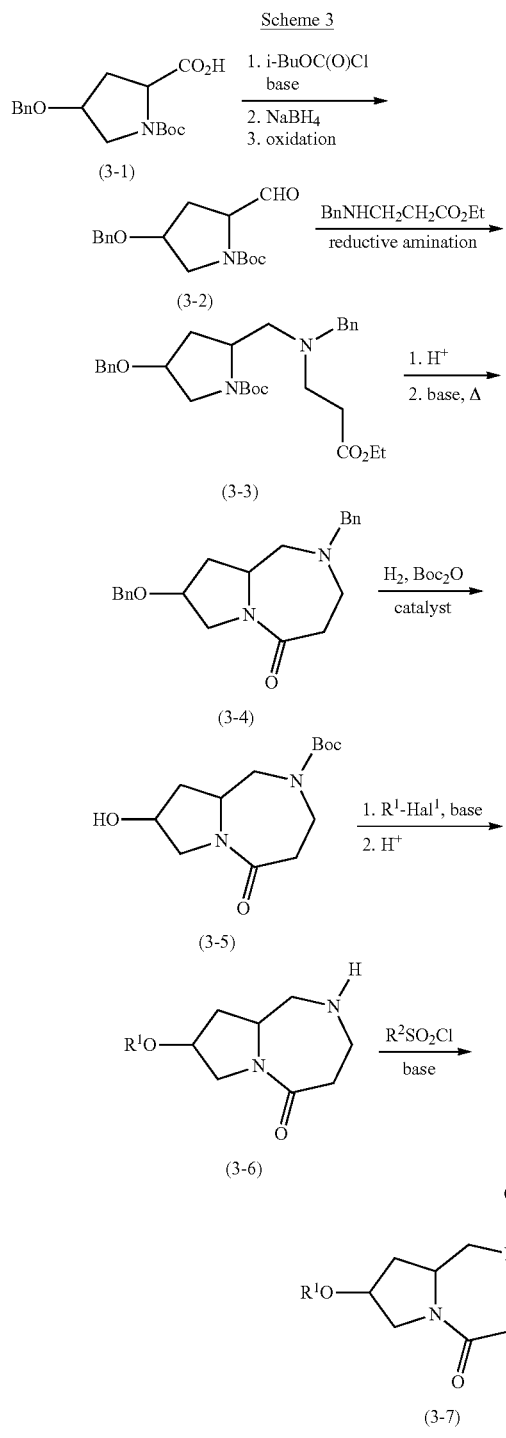

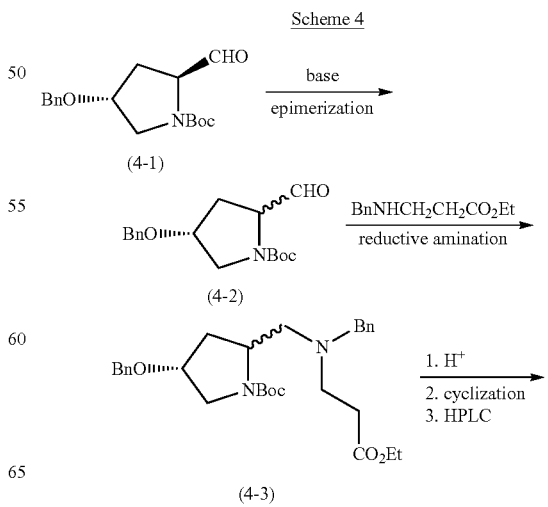

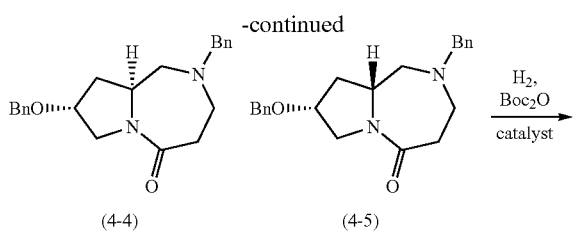

(4-4)    (4-5)

H₂, Boc₂O
catalyst

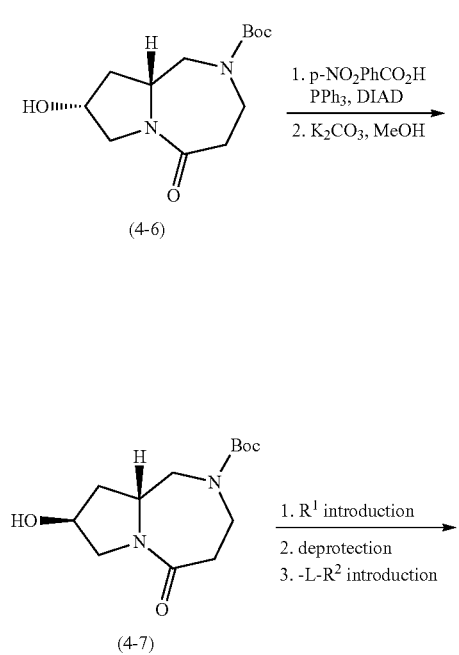

(4-6)

1. p-NO₂PhCO₂H PPh₃, DIAD
2. K₂CO₃, MeOH (4-7)

1. R¹ introduction
2. deprotection
3. -L-R² introduction (4-8)

As shown in Scheme 4, the stereochemistry of many intermediates can be manipulated to give diastereomers. For example, the chiral compound of Formula (4-1) (which can be prepared as described in Scheme 3 for the preparation of a compound of Formula (3-2) starting from (2S,4R)-4-(benzyloxy)-1-(tert-butoxycarbonyl)pyrrolidine-2-carboxylic acid) can be epimerized with a base such as 1,8-diazabicyclo[5.4.0]undec-7-ene in tetrahydrofuran to the diastereomeric mixture of compounds of Formula (4-2). Using the methods previously described in Scheme 3, the mixture of compounds of Formula (4-2) can be converted to the compounds of Formula (4-3) and then to compounds of Formula (4-4) and Formula (4-5). Diastereomeric compounds of Formula (4-4) and Formula (4-5) can be chromatographically separated. Each diastereomer can then be carried forward independently. For example, a compound of Formula (4-5) can be transformed by hydrogenation in the presence of di-tert-butyl dicarbonate to remove both benzyl groups and introduce the tert-butoxycarbonyl moiety selectively to give a compound of Formula (4-6). The stereochemistry of the hydroxy group can be inverted in a two-step process. Introduction of a 4-nitrobenzoyl group under Mitsunobu conditions results in inversion of the hydroxy group stereocenter. Subsequent hydrolysis of the intermediate 4-nitrobenzoyl group provides a compound of Formula (4-7). A compound of Formula (4-7) can be converted to compounds of Formula (4-8) using methodologies described in the above and below Schemes.

Scheme 5

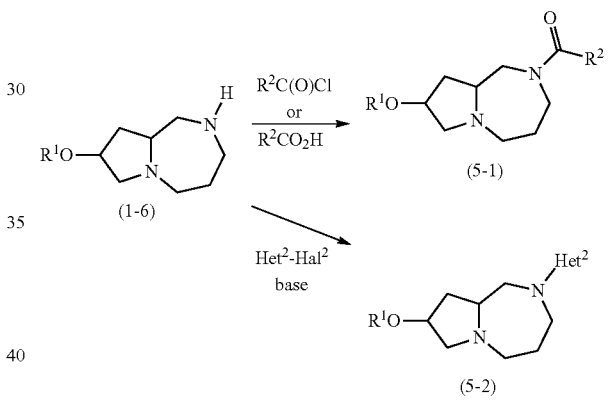

As shown in Scheme 5, compounds of Formula (5-1) and Formula (5-2) wherein $R^1$ and $R^2$ are as described in the various embodiments of the invention can be prepared from a compound of Formula (1-6). Compounds of Formula (1-6) can be reacted with a carboxylic acid chloride, $R^2C(O)Cl$, in the presence of a base (such as a tertiary amine) to give compounds of Formula (5-1). Compounds of Formula (1-6) can also be transformed to compounds of Formula (5-1) by coupling with a carboxylic acid, $R^2CO_2H$. Examples of conditions known to generate amides from a mixture of a carboxylic acid and an amine include but are not limited to adding a coupling reagent such as but not limited to N-(3-dimethylaminopropyl)-N'-ethylcarbodiimide (EDC, EDAC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures. Compounds of Formula (5-1) are representative of compounds of Formula (I).

Compounds of Formula (1-6) can be reacted with a Het²-Hal² (wherein Het² is pyridinyl, pyrimidinyl, pyrazinyl, or pyridazinyl optionally substituted as described for R²; and Hal² is halogen selected from fluorine, chlorine, bromine or iodine) to give compounds of Formula (5-2). The reaction is performed in the presence of a base, such as sodium carbonate, in an optionally heated solvent, such as dimethyl sulfoxide. Compounds of Formula (5-2) are representative of compounds of Formula (I), including compounds of Formula (I-A).

Scheme 6

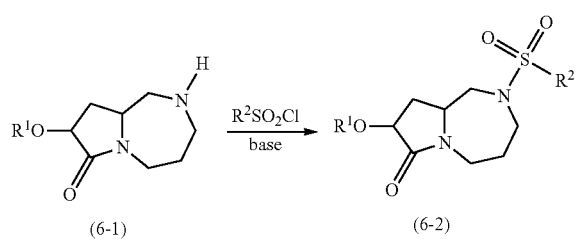

(2-8)

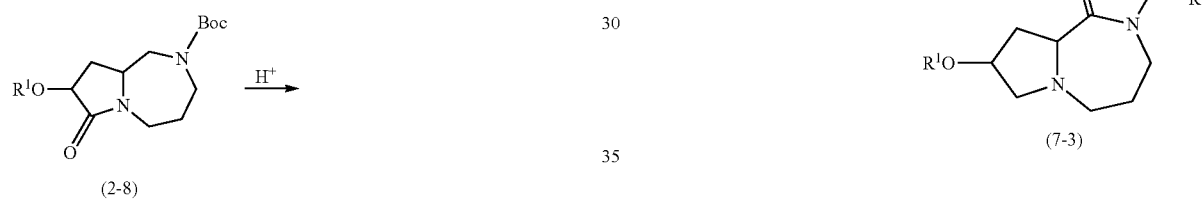

As shown in Scheme 6, compounds of Formula (6-2) wherein $R^1$ and $R^2$ are as described in the various embodiments of the invention can be prepared from compounds of Formula (2-8). Compounds of Formula (2-8) can be deprotected to give compounds of Formula (6-1) upon treatment with acid. For example, treatment with trifluoroacetic acid in dichloromethane, hydrochloric acid in dioxane, or acetyl chloride in methanol will convert compounds of Formula (2-8) to compounds of Formula (6-1). Reaction of compounds of Formula (6-1) with a sulfonyl chloride, $R^2SO_2Cl$, in the presence of a base such as a tertiary amine gives compounds of Formula (6-2). Compounds of Formula (6-2) are representative of compounds of Formula (I), including compounds of Formula (I-C-2).

Scheme 7

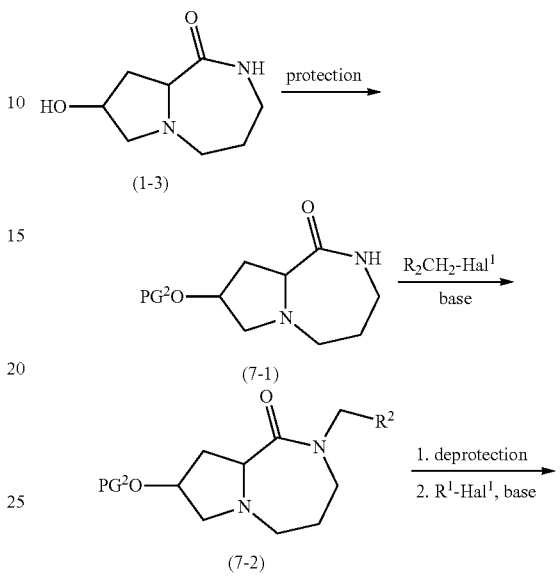

As shown in Scheme 7, compounds of Formula (7-3) wherein $R^1$ and $R^2$ are as described in the various embodiments of the invention can be prepared from compounds of Formula (1-3). The hydroxy moiety of compounds of Formula (1-3) can be protected to give compounds of Formula (7-1), wherein $PG^2$ is a hydroxy protecting group such as triethylsilyl or t-butyldimethylsilyl. To install the triethyl silyl protecting group, for examples, compounds of Formula (1-3) can be treated with triethylsilyl chloride in the presence of imidazole in N,N-dimethylformamide. Compounds of Formula (7-1) can be reacted with $R^2CH_2$-$Hal^1$ (wherein $Hal^1$ is a halogen such as chlorine, bromine or iodine) and a base (such as sodium hydride) in a solvent (such as N,N-dimethylformamide) to give compounds of Formula (7-2). Compounds of Formula (7-2) can be converted to compounds of Formula (7-3) in a two-step process. In the first step, the protecting group, $PG^2$, can be removed under conditions known to one of skill in the art. In the case where $PG^2$ is triethylsilyl, treatment with acetic acid in water removes the protecting group. In the second step, reaction with $R^1$-$Hal^1$ (wherein $Hal^1$ is a halogen such as chlorine, bromine or iodine) and a base (such as potassium tert-butoxide) under nucleophilic heteroaromatic substitution reaction conditions known to one of skill in the art gives compounds of Formula (7-3). Compounds of Formula (7-3) are representative of compounds of Formula (I), including compounds of Formula (I-B-2).

Scheme 8

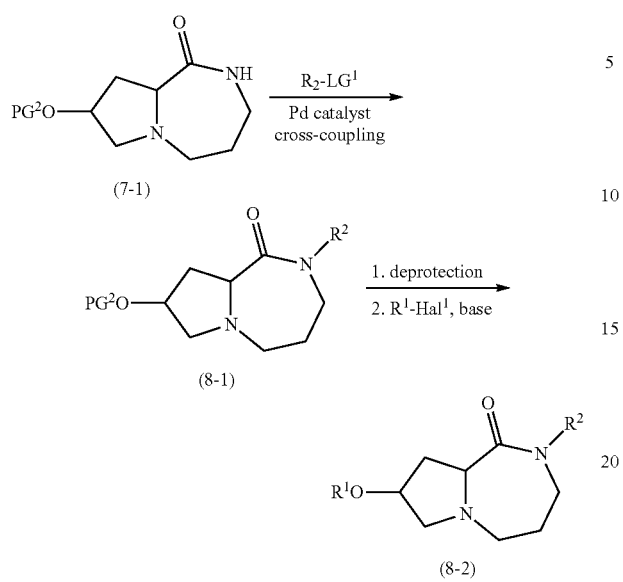

As shown in Scheme 8, compounds of Formula (8-2) wherein $R^1$ and $R^2$ are as described in the various embodiments of the invention can be prepared from compounds of Formula (7-1). Compounds of Formula (7-1) can be cross-coupled with $R^2$-$LG^1$ (wherein $LG^1$ is a leaving group such as a sulfonate, chlorine, bromine or iodine) to give compounds of Formula (8-1). One set of cross-coupling conditions is treatment with tris(dibenzylideneacetone)dipalladium(0), 4,5-bis(diphenylphosphino)-9,9-dimethylxanthene (XANT-PHOS), and cesium carbonate in deoxygenated and heated dioxane. Compounds of Formula (8-1) can be converted to compounds of Formula (8-2) in a two-step process. In the first step, the protecting group, $PG^2$, can be removed under conditions known to one of skill in the art. In the case where $PG^2$ is triethylsilyl, treatment with acetic acid in water removes the protecting group. In the second step, reaction with $R^1$-$Hal^1$ (wherein $Hal^1$ is a halogen such as chlorine, bromine or iodine) and a base (such as potassium tert-butoxide) under nucleophilic heteroaromatic substitution reaction conditions known to one of skill in the art gives compounds of Formula (8-2). Compounds of Formula (8-2) are representative of compounds of Formula (I), including compounds of Formula (I-B-2).

Scheme 9

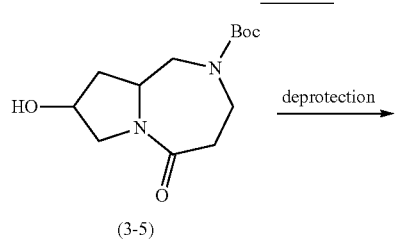

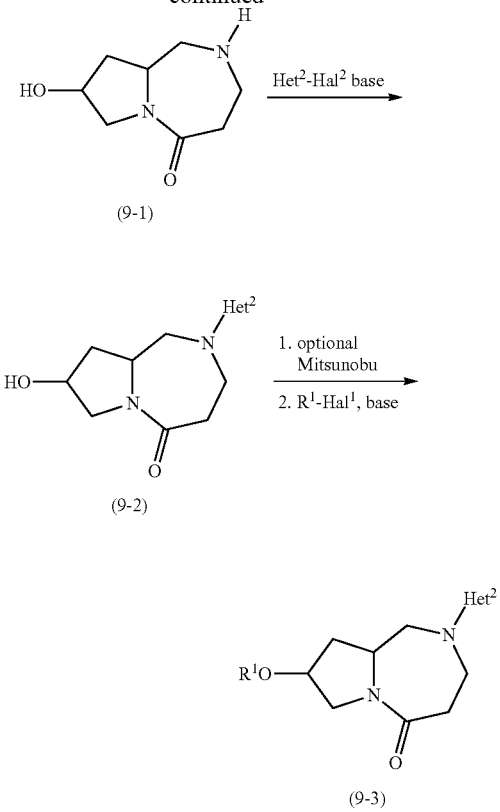

As shown in Scheme 9, compounds of Formula (9-3) wherein $R^1$ and $R^2$ are as described in the various embodiments of the invention can be prepared from compounds of Formula (3-5). Compounds of Formula (3-5) can be deprotected to give compounds of Formula (9-1) upon treatment with acid. For example, treatment with trifluoroacetic acid in dichloromethane, hydrochloric acid in dioxane, or acetyl chloride in methanol will convert compounds of Formula (3-5) to compounds of Formula (9-1). Compounds of Formula (9-1) can be reacted with a $Het^2$-$Hal^2$ (wherein $Het^2$ is pyridinyl, pyrimidinyl, pyrazinyl, or pyridazinyl optionally substituted as described for $R^2$; and $Hal^2$ is halogen selected from fluorine, chlorine, bromine or iodine) to give compounds of Formula (9-2). The reaction is performed in the presence of a base, such as sodium carbonate, in an optionally heated solvent, such as dimethyl sulfoxide. The stereochemistry of the hydroxy group of compounds of Formula (9-2) can optionally be inverted using the Mitsunobu reaction sequence described in Scheme 4 to convert compounds of Formula (4-6) to compound of Formula (4-7). Reaction of compounds of Formula (9-2) with $R^1$-$Hal^1$ (wherein $Hal^1$ is a halogen such as chlorine, bromine or iodine) with a base (such as potassium tert-butoxide) under nucleophilic heteroaromatic substitution reaction conditions known to one of skill in the art gives compounds of Formula (9-3). Compounds of Formula (9-3) are representative of compounds of Formula (I), including compounds of Formula (I-C-1).

Scheme 10
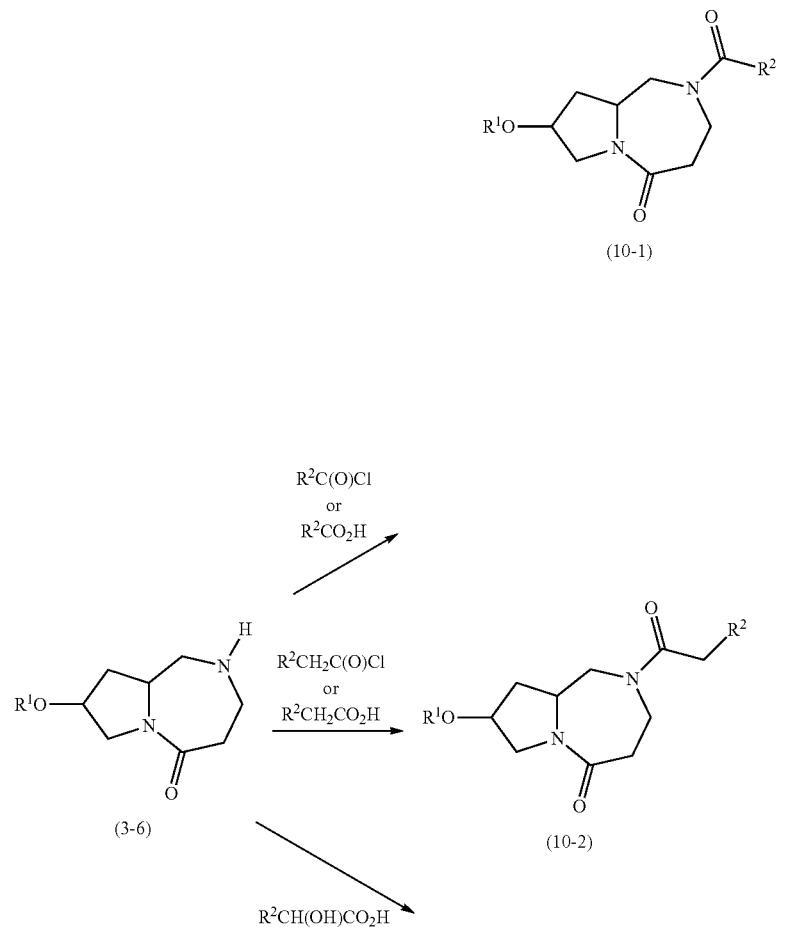
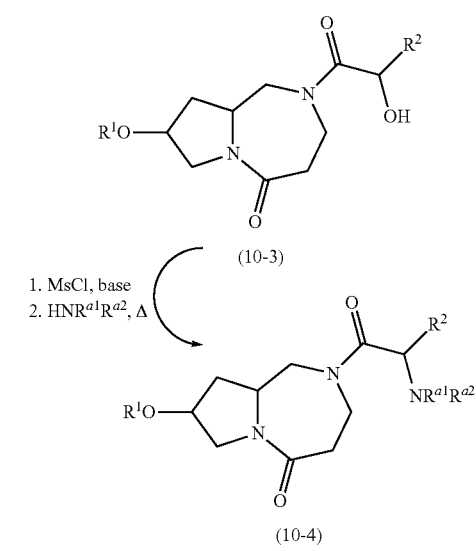

As illustrated in Scheme 10, compounds of Formula (3-6) can be converted to compounds of Formulas (10-1), (10-2), (10-3) and (10-4), wherein $R^1$ and $R^2$ are as described in the various embodiments of the invention. Compounds of Formula (3-6) can be reacted with a carboxylic acid chloride ($R^2C(O)Cl$) in the presence of a base (such as a tertiary amine) to give compounds of Formula (10-1). Compounds of Formula (3-6) also can be transformed to compounds of Formula (10-1) by coupling with a carboxylic acid ($R^2CO_2H$). Examples of conditions known to generate amides from a mixture of a carboxylic acid and an amine include but are not limited to adding a coupling reagent such as but not limited to N-(3-dimethylaminopropyl)-N-ethylcarbodiimide (EDC, EDAC or EDCI), 1,3-dicyclohexylcarbodiimide (DCC), bis (2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N', N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures. Compounds of Formula (10-1) are representative of compounds of Formula (I), including compounds of Formula (I-C-1).

Compounds of Formula (3-6) can be reacted with $R^2CH_2C(O)Cl$ or $R^2CH_2CO_2H$ using the methodology described above to give compounds of Formula (10-2). Compounds of Formula (10-2) are representative of compounds of Formula (I).

Compounds of Formula (3-6) can be reacted with $R^2CH(OH)CO_2H$ using the coupling methodology described above for joining a carboxylic acid and amine to give compounds of Formula (10-3). Compounds of Formula (10-3) are representative of compounds of Formula (I), including compounds of Formula (I-C-1).

Compounds of Formula (10-3) can be converted to compounds of Formula (10-4) in a two-step process. In the first step, the hydroxy moiety can be converted to the corresponding sulfonate by treatment with methanesulfonyl chloride in the presence of a tertiary amine. In the second step, treatment of the intermediate sulfonate with $HNR^{a1}R^{a2}$, wherein $R^{a1}$ and $R^{a2}$ are each independently either hydrogen or independently selected $C_1$-$C_6$-alkyl, with optional heating gives compounds of Formula (10-4). Compounds of Formula (10-4) are representative of compounds of Formula (I), including compounds of Formula (I-C-1).

Scheme 11

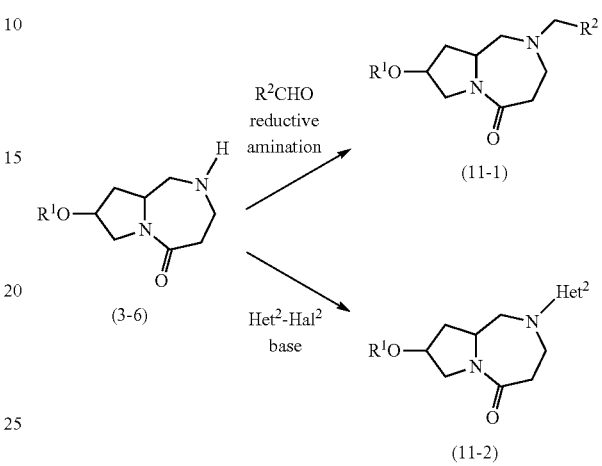

As shown in Scheme 11, compounds of Formula (3-6) can be converted to compounds of Formulas (11-1) and (11-2), wherein $R^1$ and $R^2$ are as described in the various embodiments of the invention. Compounds of Formula (3-6) can be reductively aminated with aldehydes, $R^2CHO$, to give compounds of Formula (11-1). The reductive amination can be achieved in the presence of acetic acid and sodium cyanoborohydride or resin-bound cyanoborohydride. Alternatively, sodium triacetoxyborohydride can be used as the reductant. Compounds of Formula (11-1) are representative of compounds of Formula (I), including compounds of Formula (I-C-1).

Compounds of Formula (3-6) can also be reacted with a $Het^2$-$Hal^2$ (wherein $Het^2$ is pyridinyl, pyrimidinyl, pyrazinyl, or pyridazinyl optionally substituted as described for $R^2$; and $Hal^2$ is halogen selected from fluorine, chlorine, bromine or iodine) to give compounds of Formula (11-2). The reaction is performed in the presence of a base (such as sodium carbonate) in an optionally heated solvent (such as dimethyl sulfoxide). Compounds of Formula (11-2) are representative of compounds of Formula (I), including compounds of Formula (I-C-1).

Scheme 12

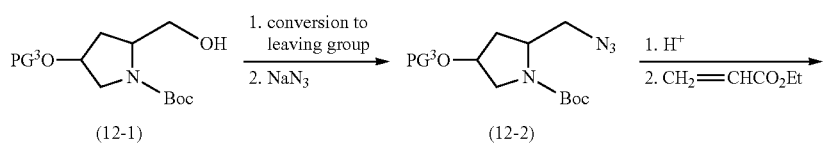

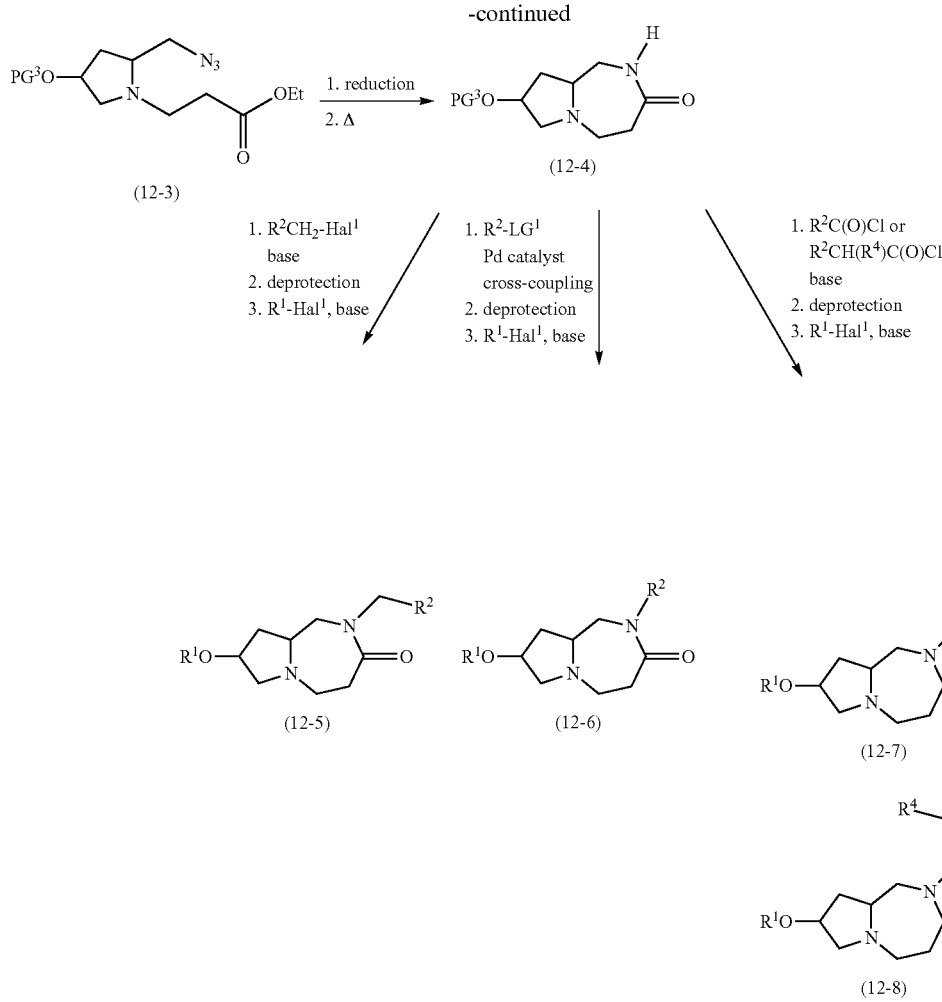

As shown in Scheme 12, compounds of Formula (12-5), Formula (12-6), Formula (12-7), and Formula (12-8) wherein $R^1$ and $R^2$ are as described in the various embodiments of the invention can be prepared from a compound of Formula (12-1). Compounds of Formula (12-1) wherein $PG^3$ is a suitable hydroxy protecting group can be converted to compounds of Formula (12-2) in a two-step process. Initially, the primary hydroxy group can be converted to a leaving group such as a sulfonate, chlorine, bromine or iodine using methodology known to one of skill in the art. For example, treatment with methanesulfonyl chloride in the presence of a tertiary amine yields the corresponding sulfonate. Then, displacement of the leaving group upon treatment with sodium azide gives compounds of Formula (12-2). The tert-butoxycarbonyl moiety can be removed by treatment with an acid, and then reaction with ethyl acrylate gives compounds of Formula (12-3). Reduction of the azide of compounds of Formula (12-3) gives the corresponding amines that cyclize upon warming to give compounds of Formula (12-4). Compounds of Formula (12-4) can be reacted using the methodology described in Scheme 7 to convert compounds of Formula (7-1) to compounds of Formula (7-3) to give compounds of Formula (12-5). The conditions for the removal of $PG^3$ are dependent upon the particular protecting group employed and are known to one of skill in the art. Compounds of Formula (12-5) are representative of compounds of Formula (I), including compounds of Formula (I-B-1).

Compounds of Formula (12-4) can also be transformed to compounds of Formula (12-6). This transformation is accomplished using the methodology described in Scheme 8 for the conversion of compounds of Formula (7-1) to compounds of Formula (8-2). Compounds of Formula (12-6) are representative of compounds of Formula (I), including compounds of Formula (I-B-1).

Compounds of Formula (12-7) and Formula (12-8) can also be obtained from compounds of Formula (12-4). Compounds of Formula (12-4) can be acylated with $R^2C(O)Cl$ or $R^2CH(R^4)C(O)Cl$ in the presence of a base. Subsequent removal of $PG^3$ and introduction of $R^1$ with a nucleophilic heteroaromatic substitution reaction give compounds of Formula (12-7) and Formula (12-8). A protecting group may be required for the acylation step when $R^4$ is hydroxy or amino, wherein amino is optionally substituted with one $C_1$-$C_6$-alkyl. The protecting group can be removed after the introduction of $R^1$ to give compounds of Formula (12-7) and Formula (12-8). Alternatively, $R^4$ can be converted from a hydroxy group to an amino moiety, —$NR^{a1}R^{a2}$, using the methodology described in the conversion of compounds of Formula (10-3) to compounds of Formula (10-4). Compounds of Formula (12-7) and Formula (12-8) are representative of compounds of Formula (I), including compounds of Formula (I-B-1).

Scheme 13

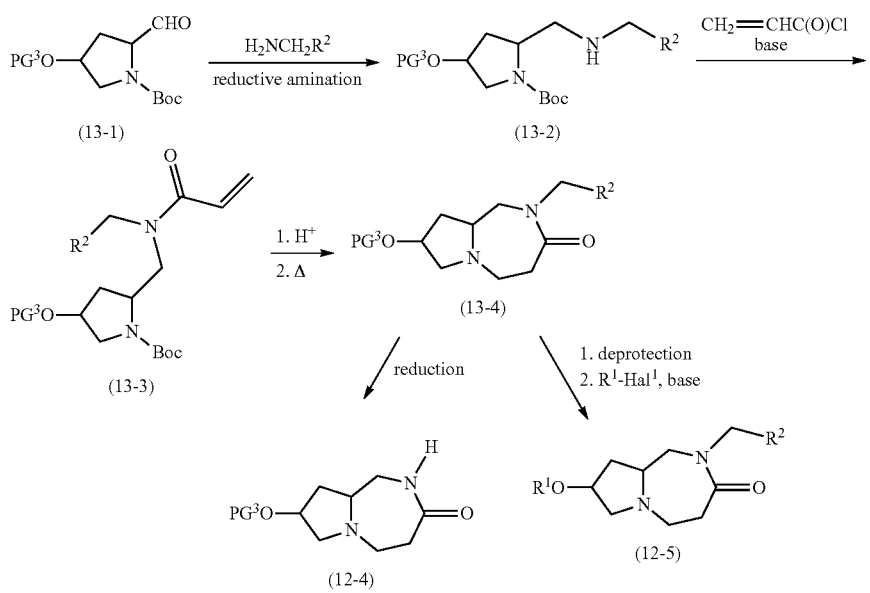

As shown in Scheme 13, compounds of Formula (12-4) and Formula (12-5) wherein $R^1$ and $R^2$ are as described in the various embodiments of the invention can be prepared from a compound of Formula (13-1). Compounds of Formula (13-1), wherein $PG^3$ is a suitable hydroxy protecting group can be converted to compounds of Formula (13-2) by reductive amination with $H_2NCH_2R^2$. Compounds of Formula (13-2) can be reacted with acryloyl chloride to give compounds of Formula (13-3). Upon acidic treatment to remove the ten-butoxycarbonyl moiety and subsequent heating, compounds of Formula 13-3 are transformed to compounds of Formula (13-4). Removal of the protecting group, $PG^3$, of Formula (13-4) followed by reaction with $R^1$-$Hal^1$ in the presence of base delivers compounds of Formula (12-5). The conditions for the removal of $PG^3$ are dependent upon the particular protecting group employed and are known to one of skill in the art. $Hal^1$ is a halogen such as chlorine, bromine or iodine. Compounds of Formula (12-5) are representative of compounds of Formula (I), including compounds of Formula (I-B-1).

When $R^2$ is phenyl in compounds of Formula (13-4), catalytic reduction or reaction with sodium in ammonia converts compounds of Formula (13-4) to compounds of Formula (12-4). Compounds of Formula (12-4) can be further reacted as described in Scheme 12.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protective Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

H. EXAMPLES

The following examples are merely illustrative, and not limiting to this disclosure in any way.

Example 1

Preparation of (8R,9aS)-8-[(5-cyclopropylpyrazin-2-yl)oxy]-2-{[3-(trifluoromethyl)phenyl]sulfonyl}octahydro-1H-pyrrolo[1,2-a][1,4]diazepane

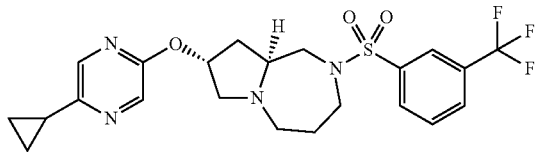 [SMILES: O=S(=O)(c1cccc(C(F)(F)F)c1)N1CCCN2C[C@H](Oc3cnc(C4CC4)cn3)C[C@H]2C1]

Part A. Preparation of methyl (4R)-1-(2-cyanoethyl)-4-hydroxy-L-prolinate

To a solution of methyl (4R)-4-hydroxy-L-prolinate hydrochloride (4.53 g, 25 mmol) in water (10 mL) was added acrylonitrile (6.63 g, 125 mmol). The mixture was stirred while heating at 50° C., and a solution of potassium hydroxide (1.403 g, 25 mmol) in water (15 mL) was added dropwise. The resulting mixture was heated to 70° C. and stirred for two hours. The cooled mixture was extracted with diethyl ether (4×25 mL). The combined ether extracts were dried with MgSO4, filtered, and concentrated in vacuo. The residue was purified by column chromatography on silica gel using a solvent gradient of 2-5% methanol in dichloromethane to obtain desired the title compound as colorless oil (2.3 g, 46%). $^1$H NMR (400 MHz, DMSO-d6) δ ppm 4.95-4.87 (m, 1H), 4.26-4.17 (m, 1H), 3.62 (s, 3H), 3.50 (t, J=7.6, 1H), 3.27-3.15 (m, 1H), 2.98-2.87 (m, 1H), 2.76-2.66 (m, 1H), 2.67-2.56 (m, 2H), 2.41-2.33 (m, 1H), 1.99 (ddd, J=12.8, 7.4, 6.4, 1H), 1.93-1.83 (m, 1H); MS (ESI) m/z 199 (M+H)+.

Part B. Preparation of (8R,9aS)-8-hydroxyoctahydro-1H-pyrrolo[1,2-a][1,4]diazepin-1-one A mixture of the product from Part A (1.3 g, 6.56 mmol), methanol (40 mL), and Raney®-nickel 2800, water slurry (1.30 g, 22.2 mmol) in a 250 mL stainless steel pressure bottle was stirred for six hours under hydrogen (60 psi) at 80° C. The mixture was filtered through a nylon membrane and concentrated in vacuo to give the title compound as a waxy solid (1.05 g, 94%). $^1$H NMR (400 MHz, DMSO-$d_6$) δ ppm 7.48 (bs, 1H), 4.79 (bs, 1H), 4.03 (p, J=6.3, 1H), 3.29-3.10 (m, 3H), 3.12-2.84 (m, 2H), 2.43 (dd, J=12.0, 3.0, 1H), 2.24 (dd, J=9.1, 6.6, 1H), 1.69-1.42 (m, 3H); MS (ESI) m/z 171 (M+H)+.

Part C. Preparation of tert-butyl (8R,9aS)-8-hydroxyhexahydro-1H-pyrrolo[1,2-a][1,4]diazepine-2(3H)-carboxylate To a stirred solution of the product from Part B (0.60 g, 3.53 mmol) in tetrahydrofuran (15 mL) at 10° C., was slowly added a 2.0 M solution of lithium aluminum hydride in tetrahydrofuran (5.29 mL, 10.58 mmol). The resulting mixture was stirred at 65° C. for 48 hours. The mixture was cooled to 0-5° C., and quenched by the dropwise addition of ethyl acetate (5 mL), water (1 mL), 10% aqueous NaOH solution (1 mL), and water (1 mL). The resulting mixture was stirred at room temperature for 30 minutes and filtered through diatomaceous earth. The filtrate was concentrated in vacuo, and the crude oily product was dissolved in a 1:1 mixture of acetonitrile:water (30 mL). Triethylamine (0.606 g, 0.835 mL, 5.99 mmol) was added, followed by di-tert-butyl dicarbonate (0.923 g, 4.23 mmol). The resulting mixture was stirred at room temperature for 16 hours, and then it was concentrated in vacuo to remove acetonitrile. The resulting aqueous mixture was extracted with ethyl acetate, and the organic extract was dried over MgSO4, filtered, and concentrated in vacuo. The residue was purified by column chromatography on silica gel using a solvent gradient of 2-15% methanol in dichloromethane to give the title compound as color less oil (0.235 g, 26%). $^1$H NMR (400 MHz, pyridine-$d_5$) δ ppm 4.56-4.46 (m, 1H), 3.64-3.53 (m, 1H), 3.53-3.40 (m, 3H), 3.00-2.83 (m, 3H), 2.58 (dd, J=9.3, 5.6, 1H), 2.41-2.30 (m, 1H), 2.16-1.95 (m, 1H), 1.84-1.68 (m, 3H), 1.50 (s, 9H); MS (ESI) m/z 257 (M+H)+.

Part D. Preparation of tert-butyl (8R,9aS)-8-[(5-cyclopropylpyrazin-2-yl)oxy]hexahydro-1H-pyrrolo[1,2-a][1,4]diazepine-2(3H)-carboxylate To a solution of the product from Part C (180 mg, 0.702 mmol) in tetrahydrofuran (4 mL), was added a 1.0 M solution of potassium tert-butoxide (0.983 mL, 0.983 mmol), followed by a solution of 2-bromo-5-cyclopropylpyrazine (168 mg, 0.843 mmol) in tetrahydrofuran (2 mL). The mixture was stirred at room temperature for 48 hours, and then it was concentrated in vacuo. The residue was dissolved in ethyl acetate (20 mL), washed successively with water and brine, and dried over MgSO4. The solution was filtered and concentrated in vacuo, and the crude product was purified by column chromatography on silica gel using 30% hexanes in ethyl acetate. The title compound was obtained as a waxy solid (0.120 g, 45.6%). $^1$H NMR (400 MHz, pyridine-$d_5$, 90° C.) δ ppm 8.11 (d, J=1.5 Hz, 1 H), 8.01 (d, J=1.5 Hz, 1 H), 5.32-5.43 (m, 1 H), 3.56-3.69 (m, 1 H), 3.40-3.51 (m, 1 H), 2.76-2.99 (m, 3 H), 2.56 (dd, J=10.1, 5.5 Hz, 1 H), 2.29-2.38 (m, 1 H), 1.86-2.08 (m, 3 H), 1.72-1.83 (m, 2 H), 1.51 (s, 9 H), 0.97-1.03 (m, 2 H), 0.84-0.90 (m, 2 H); MS (ESI) m/z 375 (M+H)+.

Part E. Preparation of (8R,9aS)-8-[(5-cyclopropylpyrazin-2-yl)oxy]-2-{[3-(trifluoromethyl)phenyl]sulfonyl}octahydro-1H-pyrrolo[1,2-a][1,4]diazepane To a solution of the product from Part D (0.050 g, 0.134 mmol) in anhydrous methanol (2 mL) was added 4 M HCl in 1,4-dioxane (0.167 mL, 0.668 mmol). The resulting mixture was stirred at room temperature for 18 hours, and then it was concentrated in vacuo. To the residue was added dichloromethane (2 mL), 3-(trifluoromethyl)benzene-1-sulfonyl chloride (0.033 g, 0.134 mmol), and triethylamine (0.093 mL, 0.668 mmol). The resulting mixture was stirred at room temperature for 16 hours, and then it was partitioned between water and ethyl acetate. The organic extract was washed successively with water and brine, dried with MgSO4, filtered, and concentrated in vacuo. The crude product was purified by column chromatography on silica gel using a solvent gradient of 0-4% methanol in dichloromethane to give the title compound as a colorless solid (0.039 g, 60% yield). $^1$H NMR (400 MHz, pyridine-$d_5$, 90° C.) δ ppm 8.46 (bs, 1H), 8.30-8.24 (m, 1H), 8.22 (d, J=1.4, 1H), 8.11 (d, J=1.4, 1H), 7.93-7.87 (m, 1H), 7.72 (t, J=7.9, 1H), 5.37-5.29 (m, 1H), 4.06 (d, J=11.8, 1H), 3.69-3.55 (m, 2H), 3.45 (dt, J=13.4, 5.7, 1H), 2.98-2.82 (m, 3H), 2.53 (dd, J=10.2, 5.1, 1H), 2.42-2.33 (m, 1H), 2.08-1.96 (m, 2H), 1.95-1.85 (m, 1H), 1.83-1.72 (m, 2H), 1.12-1.02 (m, 2H), 0.98-0.87 (m, 2H); MS (ESI) m/z 483 (M+H)$^+$.

Example 2

Preparation of (8R,9aS)-8-[(5-cyclopropylpyrazin-2-yl)oxy]-2-{[4-(trifluoromethyl)phenyl]sulfonyl}octahydro-1H-pyrrolo[1,2-a][1,4]diazepane

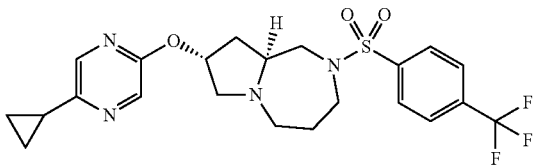 [SMILES: O=S(=O)(c1ccc(C(F)(F)F)cc1)N1CCCN2C[C@H](Oc3cnc(C4CC4)cn3)C[C@H]2C1]

The title compound was prepared according to the procedure described in Example 1, Part E, substituting 4-(trifluoromethyl) benzene-1-sulfonyl chloride for 3-(trifluoromethyl)benzene-1-sulfonyl chloride. $^1$H NMR (400 MHz, pyridine-$d_5$, 90° C.) δ ppm 8.23 (d, J=1.2, 2H), 8.21 (s, 1H), 8.11 (d, J=1.4, 1H), 7.91 (s, 1H), 7.90 (s, 1H), 5.38-5.30 (m, 1H), 4.10-3.98 (m, 1H), 3.67-3.58 (m, 2H), 3.47-3.39 (m, 1H), 2.97-2.87 (m, 3H), 2.54 (dd, J=10.2, 5.1, 1H), 2.41 (dd, J=13.1, 6.5, 1H), 2.10-1.97 (m, 2H), 1.99-1.88 (m, 1H), 1.78 (p, J=5.8, 2H), 1.14-1.02 (m, 2H), 1.02-0.85 (m, 2H); MS (ESI) m/z 483 (M+H)$^+$.

Example 3

Preparation of (8S,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

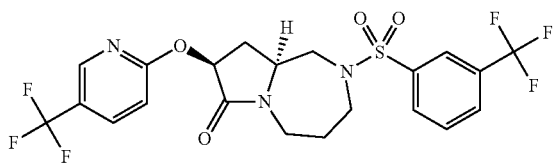 [SMILES: O=C1[C@@H](Oc2ccc(C(F)(F)F)cn2)C[C@H]2CN(S(=O)(=O)c3cccc(C(F)(F)F)c3)CCCN12]

Part A. Preparation of tert-butyl (9aS)-7-oxo-8-{[5-(trifluoromethyl)pyridin-2-yl]oxy}hexahydro-1H-pyrrolo[1,2-a][1,4]diazepine-2(3H)-carboxylate To a solution of the product from Example 21, Part G (0.10 g, 0.370 mmol) in anhydrous N,N-dimethylformamide (4 mL) at 0° C. under $N_2$ was added sodium hydride (60% suspension in mineral oil) (0.016 g, 0.407 mmol), followed by 2-bromo-5-(trifluoromethyl)pyridine (0.125 g, 0.555 mmol). The resulting mixture was stirred at room temperature for four hours, and then it was partitioned between water and ethyl acetate. The organic extract were dried over $Na_2SO_4$, the drying agent was removed by filtration, and the solution was concentrated in vacuo to give a crude product that was purified by column chromatography on silica gel using a solvent gradient of 0-5% methanol in dichloromethane. The title compound was obtained as a colorless solid (0.113 g, 74%).

Part B. Preparation of (9aS)-8-{[5-(trifluoromethyl)pyridin-2-yl]oxy}octahydro-7H-pyrrolo[1,2-a][1,4]diazepin-7-one hydrochloride A solution of the product from Part A (0.109 g, 0.262 mmol) in 1,4-dioxane (1.3 mL) was treated with hydrogen chloride (4 N in 1,4-dioxane, 0.066 mL, 0.262 mmol). The resulting mixture was stirred at room temperature for 90 minutes, and then it was concentrated and dried in vacuo to give the title compound.

Part C. Preparation of (8S,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one To a solution of the product from Part B (46.1 mg, 0.131 mmol) and triethylamine (0.055 mL, 0.393 mmol) in dichloromethane (1.5 mL) was added 3-(trifluoromethyl)benzene-1-sulfonyl chloride (0.025 mL, 0.157 mmol). The resulting mixture was stirred at room temperature for two hours, and then it was partitioned between water and dichloromethane (3×). The organic extracts were combined and dried over $Na_2SO_4$, the drying agent was removed by filtration, and the solution was concentrated in vacuo to give a crude product that was purified by column chromatography on silica gel using a solvent gradient of 0-5% methanol in dichloromethane. The title compound was the first of two stereoisomers to elute, and it was obtained as a colorless solid (6.5 mg, 9%). $^1$H NMR (400 MHz, CDCl$_3$) δ ppm 1.88-2.07 (m, 3 H) 2.83-2.95 (m, 1 H) 2.97-3.11 (m, 1 H) 3.22-3.34 (m, 2 H) 3.35-3.46 (m, 1 H) 3.53 (dd, J=14.80, 3.20 Hz, 1 H) 3.82-3.92 (m, 1 H) 4.12-4.23 (m, 1 H) 5.73 (t, J=8.39 Hz, 1 H) 6.95 (d, J=8.85 Hz, 1 H) 7.71 (t, J=7.78 Hz, 1 H) 7.81 (dd, J=8.70, 2.29 Hz, 1 H) 7.88 (d, J=7.93 Hz, 1 H) 7.99 (d, J=7.93 Hz, 1 H) 8.04 (s, 1 H) 8.41 (s, 1 H); MS (APCI) m/z 524 (M+H)$^+$.

Example 4

Preparation of (8R,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

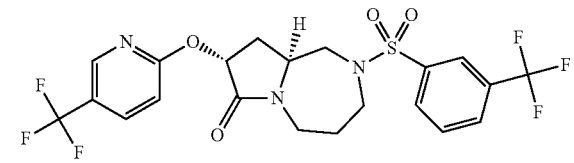 [SMILES: O=C1[C@H](Oc2ccc(C(F)(F)F)cn2)C[C@H]2CN(S(=O)(=O)c3cccc(C(F)(F)F)c3)CCCN12]

The title compound was obtained from the procedure described for Example 3, Part C, and was the second of two stereoisomers to elute during chromatography (40 mg, 58%). $^1$H NMR (400 MHz, CDCl$_3$) δ ppm 1.92-2.11 (m, 2 H) 2.23-2.36 (m, 1 H) 2.37-2.48 (m, 1 H) 3.01 (dd, J=14.19, 8.09 Hz, 1 H) 3.08-3.20 (m, 2 H) 3.51-3.64 (m, 1 H) 3.77 (dd, J=14.34, 3.36 Hz, 1 H) 3.98-4.08 (m, 1 H) 4.13-4.24 (m, 1 H) 5.69 (dd, J=7.93, 5.19 Hz, 1 H) 6.91 (d, J=8.85 Hz, 1 H) 7.71 (t, J=7.93 Hz, 1 H) 7.81 (dd, J=8.54, 2.44 Hz, 1 H) 7.88 (d, J=7.93 Hz, 1 H) 7.99 (d, J=7.93 Hz, 1 H) 8.06 (s, 1 H) 8.41 (s, 1 H); MS (APCI) m/z 524 (M+H)$^+$.

Example 5

Preparation of (8S,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

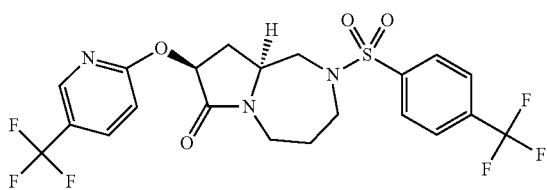 [SMILES: O=C1[C@@H](Oc2ccc(C(F)(F)F)cn2)C[C@H]2CN(S(=O)(=O)c3ccc(C(F)(F)F)cc3)CCCN12]

The title compound was obtained according to the procedures described in Example 3, Part C, substituting 4-(trifluoromethyl)benzene-1-sulfonyl chloride for 3-(trifluoromethyl)benzene-1-sulfonyl chloride, and it was the first of two stereoisomers to elute during chromatography. $^1$H NMR (400 MHz, CDCl$_3$) δ ppm 1.86-2.07 (m, 3 H) 2.82-2.95 (m, 1 H) 2.96-3.08 (m, 1 H) 3.22-3.34 (m, 2 H) 3.35-3.45 (m, 1H) 3.52 (dd, J=14.80, 3.20 Hz, 1 H) 3.81-3.92 (m, 1 H) 4.11-4.22 (m, 1 H) 5.73 (t, J=8.39 Hz, 1 H) 6.95 (d, J=8.85 Hz, 1 H) 7.81 (d, J=8.24 Hz, 3 H) 7.92 (d, J=8.24 Hz, 2 H) 8.41 (s, 1 H); MS (APCI) m/z 524 (M+H)$^+$.

Example 6

Preparation of (8R,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

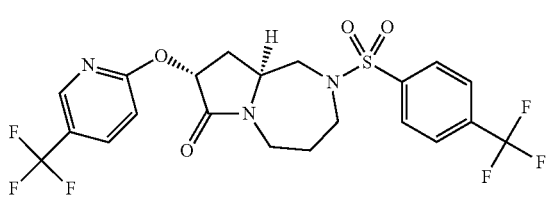 [SMILES: O=C1[C@H](Oc2ccc(C(F)(F)F)cn2)C[C@H]2CN(S(=O)(=O)c3ccc(C(F)(F)F)cc3)CCCN12]

The title compound was obtained according to the procedures described in Example 3, Part C, substituting 4-(trifluoromethyl)benzene-1-sulfonyl chloride for 3-(trifluoromethyl)benzene-1-sulfonyl chloride, and was the second of two stereoisomers to elute during chromatography. $^1$H NMR (400 MHz, CDCl$_3$) δ ppm 1.92-2.12 (m, 2 H) 2.23-2.34 (m, 1 H) 2.36-2.47 (m, 1 H) 3.00 (dd, J=14.19, 8.09 Hz, 1 H) 3.07-3.20 (m, 2 H) 3.51-3.63 (m, 1 H) 3.76 (dd, J=14.19, 3.20 Hz, 1 H) 3.97-4.09 (m, 1 H) 4.12-4.24 (m, 1 H) 5.69 (dd, J=8.09, 5.34 Hz, 1 H) 6.91 (d, J=8.54 Hz, 1 H) 7.76-7.86 (m, 3 H) 7.93 (d, J=8.24 Hz, 2 H) 8.41 (s, 1 H); MS (APCI) m/z 524 (M+H)$^+$.

Example 7

Preparation of [(8R,9aS)-8-[(5-cyclopropylpyrazin-2-yl)oxy]hexahydro-1H-pyrrolo[1,2-a][1,4]diazepin-2(3H)-yl][3-(trifluoromethyl)phenyl]methanone

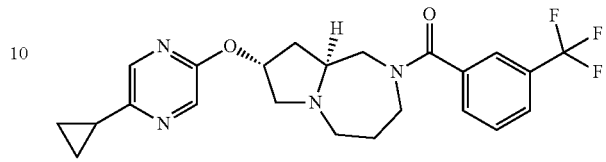

The title compound was prepared according to the procedure described in Example 1, Part E, substituting 3-(trifluoromethyl)benzoyl chloride for 3-(trifluoromethyl)benzene-1-sulfonyl chloride. $^1$H NMR (400 MHz, pyridine-d$_5$, 90° C.) δ ppm 8.12 (d, J=1.4, 1H), 8.00 (d, J=1.4, 1H), 7.90 (bs, 1H), 7.74-7.67 (m, 1H), 7.68-7.61 (m, 1H), 7.47 (t, J=1.4, 1H), 5.41-5.34 (m, 1H), 3.75-3.43 (m, 4H), 3.12 (dd, J=13.7, 9.7, 1H), 3.07-2.84 (m, 3H), 2.60 (dd, J=10.2, 5.1, 1H), 2.46-2.35 (m, 1H), 2.29-1.18 (m, 4H), 1.14-0.93 (m, 2H), 0.95-0.74 (m, 2H); MS (ESI) m/z 447 (M+H)$^+$.

Example 8

Preparation of [(8R,9aS)-8-[(5-cyclopropylpyrazin-2-yl)oxy]hexahydro-1H-pyrrolo[1,2-a][1,4]diazepin-2(3H)-yl](4-fluorophenyl)methanone

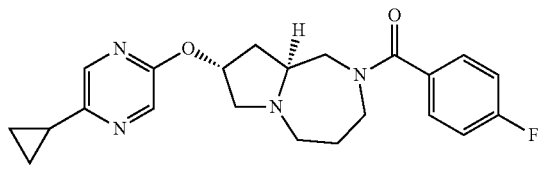 [SMILES: O=C(c1ccc(F)cc1)N1CCCN2C[C@H](Oc3cnc(C4CC4)cn3)C[C@H]2C1]

The title compound was prepared according to the procedure described in Example 1, Part E, substituting 4-fluorobenzoyl chloride for 3-(trifluoromethyl)benzene-1-sulfonyl chloride. $^1$H NMR (400 MHz, pyridine-d$_5$, 90° C.) δ ppm 8.23 (d, J=1.2, 2H), 8.21 (s, 1H), 8.11 (d, J=1.4, 1H), 7.91 (s, 1H), 7.90 (s, 1H), 5.38-5.30 (m, 1H), 4.10-3.98 (m, 1H), 3.67-3.58 (m, 2H), 3.47-3.39 (m, 1H), 2.97-2.87 (m, 3H), 2.54 (dd, J=10.2, 5.1, 1H), 2.41 (dd, J=13.1, 6.5, 1H), 2.10-1.97 (m, 2H), 1.99-1.88 (m, 1H), 1.78 (p, J=5.8, 2H), 1.14-1.02 (m, 2H), 1.02-0.85 (m, 2H); MS (ESI) m/z 397 (M+H)$^+$.

Example 9

Preparation of [(8R,9aS)-8-[(5-cyclopropylpyrazin-2-yl)oxy]hexahydro-1H-pyrrolo[1,2-a][1,4]diazepin-2(3H)-yl][3-(trifluoromethoxy)phenyl]methanone

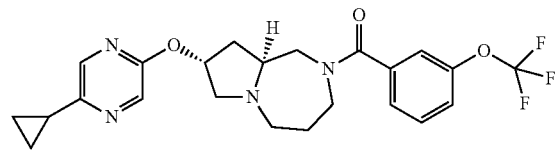 [SMILES: O=C(c1cccc(OC(F)(F)F)c1)N1CCCN2C[C@H](Oc3cnc(C4CC4)cn3)C[C@H]2C1]

The title compound was prepared according to the procedure described in Example 1, Part E, substituting 3-(trifluoromethoxy)benzoyl chloride for 3-(trifluoromethyl)benzene-1-sulfonyl chloride. ¹H NMR (400 MHz, pyridine-d₅) δ ppm 8.27-8.19 (m, 1H), 8.15-8.07 (m, 1H), 7.63-7.54 (m, 2H), 7.49 (dd, J=15.1, 7.5 Hz, 1H), 7.41-7.30 (m, 1H), 5.46-5.29 (m, 1H), 3.99-3.84 (m, 1H), 3.79-3.65 (m, 2H), 3.54-3.34 (m, 1H), 3.16 (dt, J=13.7, 10.1 Hz, 1H), 3.08-2.92 (m, 2H), 2.63-2.52 (m, 1H), 2.45-2.29 (m, 1H), 2.19-1.70 (m, 4H), 1.62-1.21 (m, 1H), 1.12-1.03 (m, 2H), 1.00-0.84 (m, 2H); MS (ESI) m/z 463 (M+H)⁺.

Example 10

Preparation of [(8R,9aS)-8-[(5-cyclopropylpyrazin-2-yl)oxy]hexahydro-1H-pyrrolo[1,2-a][1,4]diazepin-2(3H)-yl][2-fluoro-3-(trifluoromethyl)phenyl]methanone

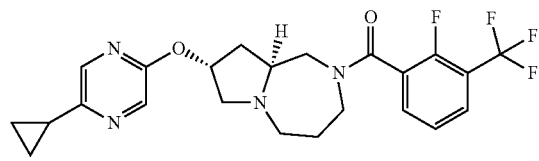 [SMILES: O=C(c1cccc(C(F)(F)F)c1F)N1CCCN2C[C@H](Oc3cnc(C4CC4)cn3)C[C@H]2C1]

The title compound was prepared according to the procedure described in Example 1, Part E, substituting 2-fluoro-3-(trifluoromethyl)benzoyl chloride for 3-(trifluoromethyl)benzene-1-sulfonyl chloride. ¹H NMR (400 MHz, pyridine-d₅) δ ppm 8.22 (dd, J=26.1, 1.4 Hz, 1H), 8.10 (dd, J=22.0, 1.4 Hz, 1H), 7.91-7.79 (m, 1H), 7.68 (dt, J=22.5, 7.0 Hz, 1H), 7.42-7.30 (m, 1H), 5.45-5.29 (m, 1H), 4.57 (dd, J=13.7, 2.0 Hz, 1H), 3.98-3.89 (m, 1H), 3.76-3.59 (m, 2H), 3.54-3.32 (m, 1H), 3.26-3.11 (m, 1H), 3.08-2.77 (m, 2H), 2.63-2.51 (m, 1H), 2.45-2.31 (m, 1H), 2.16-1.75 (m, 4H), 1.13-0.98 (m, 2H), 1.00-0.86 (m, 2H); MS (ESI) m/z 465 (M+H)⁺.

Example 11

Preparation of [(8R,9aS)-8-[(5-cyclopropylpyrazin-2-yl)oxy]hexahydro-1H-pyrrolo[1,2-a][1,4]diazepin-2(3H)-yl][5-(trifluoromethyl)pyridin-2-yl]methanone

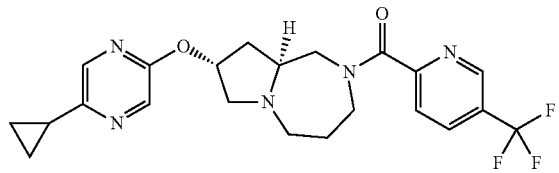 [SMILES: O=C(c1ccc(C(F)(F)F)cn1)N1CCCN2C[C@H](Oc3cnc(C4CC4)cn3)C[C@H]2C1]

To a solution of the product from Example 1, Part D (50 mg, 0.134 mmol) in anhydrous methanol (2 mL) was added 4 M HCl in 1,4-dioxane (0.334 mL, 1.335 mmol), and the resulting mixture was stirred at room temperature for 18 hours and concentrated in vacuo. The residue was dissolved in a mixture of dichloromethane (8 mL) and triethylamine (0.093 mL, 0.668 mmol), and then 5-(trifluoromethyl)picolinic acid (0.026 g, 0.134 mmol), 1-hydroxybenzotriazole hydrate (0.025 g, 0.160 mmol) and N-(3-dimethylaminopropyl)-N'-ethylcarbodiimide hydrochloride (0.031 g, 0.160 mmol) were added. The resulting mixture was stirred at room temperature for 16 hours, and then it was partitioned between water and ethyl acetate. The organic extract was washed successively with water and brine, dried over MgSO₄, and filtered. The filtrate was concentrated in vacuo. The crude product was purified by column chromatography on silica gel using a solvent gradient of 0-4% methanol in dichloromethane to give the title compound as a waxy solid (0.042 g, 70%). ¹H NMR (400 MHz, pyridine-d₅) δ ppm 9.05-8.97 (m, 1H), 8.28-8.13 (m, 2H), 8.11 (dd, J=19.6, 1.4 Hz, 1H), 8.00 (dd, J=18.4, 8.2 Hz, 1H), 5.45-5.32 (m, 1H), 4.59 (dd, J=13.5, 2.2 Hz, 1H), 4.14-3.95 (m, 1H), 3.85-3.68 (m, 1H), 3.59 (dd, J=12.1, 6.0 Hz, 2H), 3.18 (ddd, J=17.4, 13.7, 9.8 Hz, 1H), 3.10-2.94 (m, 2H), 2.64-2.53 (m, 1H), 2.51-2.38 (m, 1H), 2.16-1.70 (m, 4H), 1.14-0.98 (m, 2H), 0.99-0.84 (m, 2H); MS (ESI) m/z 448 (M+H)⁺.

Example 12

Preparation of [(8R,9aS)-8-[(5-cyclopropylpyrazin-2-yl)oxy]hexahydro-1H-pyrrolo[1,2-a][1,4]diazepin-2(3H)-yl][6-(trifluoromethyl)pyridin-2-yl]methanone

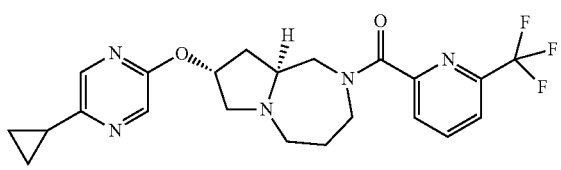 [SMILES: O=C(c1cccc(C(F)(F)F)n1)N1CCCN2C[C@H](Oc3cnc(C4CC4)cn3)C[C@H]2C1]

The title compound was prepared according to the procedure described in Example 11, substituting 6-(trifluoromethyl)picolinic acid for 5-(trifluoromethyl)picolinic acid. ¹H NMR (400 MHz, pyridine-d₅) δ ppm 8.24 (dd, J=6.2, 1.4 Hz, 1H), 8.15-7.97 (m, 3H), 7.83-7.72 (m, 1H), 5.44-5.34 (m, 1H), 4.17-3.95 (m, 1H), 3.77-3.67 (m, 2H), 3.63-3.55 (m, 2H), 3.20-3.08 (m, 1H), 3.05-2.92 (m, 2H), 2.59 (dd, J=10.4, 5.2 Hz, 1H), 2.50-2.35 (m, 1H), 2.16-1.72 (m, 4H), 1.15-0.98 (m, 2H), 1.00-0.81 (m, 2H); MS (ESI) m/z 448 (M+H)⁺.

Example 13

Preparation of [(8R,9aS)-8-[(5-cyclopropylpyrazin-2-yl)oxy]hexahydro-1H-pyrrolo[1,2-a][1,4]diazepin-2(3H)-yl][4-(trifluoromethyl)phenyl]methanone

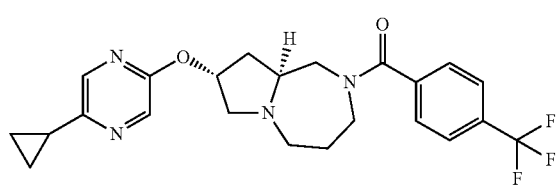 [SMILES: O=C(c1ccc(C(F)(F)F)cc1)N1CCCN2C[C@H](Oc3cnc(C4CC4)cn3)C[C@H]2C1]

The title compound was prepared according to the procedure described in Example 1, Part E, substituting 4-(trifluoromethyl)benzoyl chloride for 3-(trifluoromethyl)benzene-1-sulfonyl chloride. $^1$H NMR (500 MHz, pyridine-$d_5$) δ ppm 8.23 (d, J=24.4 Hz, 1H), 8.11 (dd, J=27.2, 0.8 Hz, 1H), 7.81-7.75 (m, 2H), 7.77-7.71 (m, 2H), 5.46-5.29 (m, 1H), 4.56 (dd, J=13.6, 1.6 Hz, 1H), 4.00-3.85 (m, 1H), 3.78-3.66 (m, 2H), 3.61 (s, 1H), 3.54-3.32 (m, 1H), 3.17 (dt, J=13.6, 10.0 Hz, 1H), 3.02 (ddt, J=26.2, 12.5, 4.3 Hz, 2H), 2.82 (q, J=7.2 Hz, 1H), 2.59 (ddd, J=18.3, 10.2, 5.3 Hz, 1H), 2.44-2.29 (m, 1H), 2.18-1.72 (m, 3H), 1.15-1.01 (m, 2H), 0.98-0.88 (m, 2H); MS (ESI) m/z 447 (M+H)$^+$.

Example 14

Preparation of [(8R,9aS)-8-[(5-cyclopropylpyrazin-2-yl)oxy]hexahydro-1H-pyrrolo[1,2-a][1,4]diazepin-2(3H)-yl][4-fluoro-3-(trifluoromethyl)phenyl]methanone

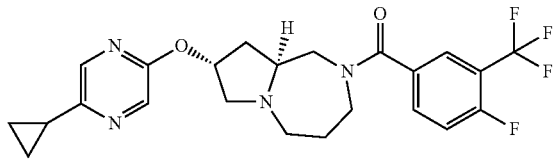 [SMILES: O=C(c1ccc(F)c(C(F)(F)F)c1)N1CCCN2C[C@H](Oc3cnc(C4CC4)cn3)C[C@H]2C1]

The title compound was prepared according to the procedure described in Example 1, Part E, substituting 4-fluoro-3-(trifluoromethyl)benzoyl chloride for 3-(trifluoromethyl)benzene-1-sulfonyl chloride. $^1$H NMR (500 MHz, pyridine-$d_5$) δ ppm 8.28-8.19 (m, 1H), 8.15-8.01 (m, 2H), 7.91-7.80 (m, 1H), 7.46-7.29 (m, 1H), 5.45-5.30 (m, 1H), 4.55 (d, J=13.6 Hz, 1H), 4.00-3.81 (m, 1H), 3.76-3.67 (m, 2H), 3.62 (d, J=5.0 Hz, 1H), 3.58-3.37 (m, 1H), 3.27-3.11 (m, 1H), 3.09-2.88 (m, 1H), 2.63-2.53 (m, 1H), 2.50-2.29 (m, 1H), 2.10-1.76 (m, 3H), 1.12-1.04 (m, 2H), 0.96-0.88 (m, 2H); MS (ESI) m/z 465 (M+H)$^+$.

Example 15

Preparation of [(8R,9aS)-8-[(5-cyclopropylpyrazin-2-yl)oxy]hexahydro-1H-pyrrolo[1,2-a][1,4]diazepin-2(3H)-yl][3-fluoro-4-(trifluoromethyl)phenyl]methanone

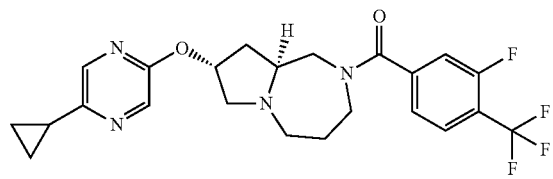 [SMILES: O=C(c1ccc(C(F)(F)F)c(F)c1)N1CCCN2C[C@H](Oc3cnc(C4CC4)cn3)C[C@H]2C1]

The title compound was prepared according to the procedure described in Example 1, Part E, substituting 3-fluoro-4-(trifluoromethyl)benzoyl chloride for 3-(trifluoromethyl)benzene-1-sulfonyl chloride. $^1$H NMR (500 MHz, pyridine-$d_5$) δ ppm 8.28-8.19 (m, 1H), 8.15-8.05 (m, 1H), 7.79-7.60 (m, 2H), 7.52 (dd, J=19.8, 7.9 Hz, 1H), 5.45-5.29 (m, 1H), 4.55 (d, J=13.6 Hz, 1H), 3.89 (t, J=5.9 Hz, 1H), 3.76-3.68 (m, 1H), 3.62 (d, J=5.2 Hz, 1H), 3.55-3.33 (m, 1H), 3.16 (ddd, J=26.6, 13.7, 9.9 Hz, 1H), 3.08-2.92 (m, 2H), 2.63-2.53 (m, 1H), 2.49-2.30 (m, 1H), 2.19-1.74 (m, 4H), 1.14-1.01 (m, 2H), 1.03-0.85 (m, 2H); MS (ESI) m/z 465 (M+H)$^+$.

Example 16

Preparation of (3-chloro-4-fluorophenyl)[(8R,9aS)-8-[(5-cyclopropylpyrazin-2-yl)oxy]hexahydro-1H-pyrrolo[1,2-a][1,4]diazepin-2(3H)-yl]methanone

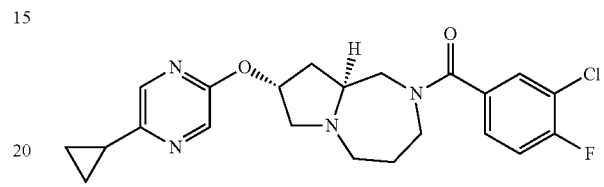

The title compound was prepared according to the procedure described in Example 1, Part E, substituting 3-chloro-4-fluorobenzoyl chloride for 3-(trifluoromethyl)benzene-1-sulfonyl chloride. $^1$H NMR (500 MHz, pyridine-$d_5$) δ ppm 8.22 (dd, J=22.2, 11.5 Hz, 1H), 8.16-8.04 (m, 1H), 7.86-7.70 (m, 1H), 7.56-7.46 (m, 1H), 7.34-7.23 (m, 1H), 5.66 (q, J=5.3 Hz, 0.5H), 5.50-5.29 (m, 1H), 4.60-4.46 (m, 0.5H), 3.96-3.82 (m, 1H), 3.79-3.67 (m, 2H), 3.55-3.33 (m, 1H), 3.25-3.06 (m, 1H), 3.06-2.92 (m, 2H), 2.89-2.75 (m, 1H), 2.66-2.51 (m, 1H), 2.45-2.26 (m, 1H), 2.20-1.76 (m, 3H), 1.17-1.01 (m, 2H), 0.99-0.86 (m, 2H); MS (ESI) m/z 431 (M+H)$^+$.

Example 17

Preparation of [(8R,9aS)-8-[(5-cyclopropylpyrazin-2-yl)oxy]hexahydro-1H-pyrrolo[1,2-a][1,4]diazepin-2(3H)-yl][2-fluoro-5-(trifluoromethyl)phenyl]methanone

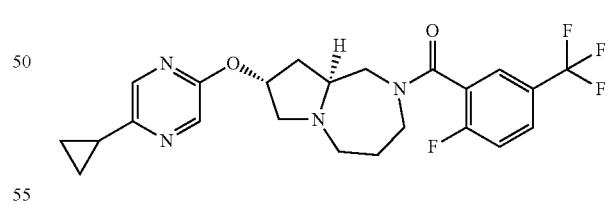

The title compound was prepared according to the procedure described in Example 1, Part E, substituting 2-fluoro-5-(trifluoromethyl)benzoyl chloride for 3-(trifluoromethyl)benzene-1-sulfonyl chloride. $^1$H NMR (500 MHz, pyridine-$d_5$) δ ppm 8.23 (dd, J=28.8, 1.3 Hz, 1H), 8.17-8.00 (m, 2H), 7.78-7.65 (m, 1H), 7.35 (dt, J=28.4, 8.8 Hz, 1H), 5.66 (q, J=5.3 Hz, 0.5H), 5.44-5.27 (m, 1H), 4.59 (dd, J=13.7, 1.9 Hz, 0.5H), 3.95 (t, J=5.9 Hz, 1H), 3.79-3.54 (m, 3H), 3.52-3.32 (m, 1H), 3.25-3.09 (m, 1H), 3.08-2.88 (m, 2H), 2.61-2.51 (m, 1H), 2.44-2.31 (m, 1H), 2.15-1.73 (m, 3H), 1.15-0.98 (m, 2H), 0.99-0.79 (m, 2H); MS (ESI) m/z 465 (M+H)$^+$.

Example 18

Preparation of [(8R,9aS)-8-[(5-cyclopropylpyrazin-2-yl)oxy]hexahydro-1H-pyrrolo[1,2-a][1,4]diazepin-2(3H)-yl][2-fluoro-4-(trifluoromethyl)phenyl]methanone

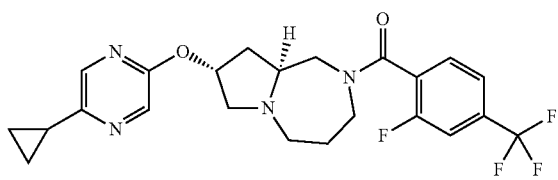 [SMILES: O=C(c1ccc(C(F)(F)F)cc1F)N1CCCN2C[C@H](Oc3cnc(C4CC4)cn3)C[C@H]2C1]

The title compound was prepared according to the procedure described in Example 1, Part E, substituting 2-fluoro-4-(trifluoromethyl)benzoyl chloride for 3-(trifluoromethyl)benzene-1-sulfonyl chloride. $^1$H NMR (500 MHz, pyridine-$d_5$) δ ppm 8.23 (dd, J=30.2, 1.4 Hz, 1H), 8.09 (dd, J=31.0, 1.4 Hz, 1H), 7.81-7.70 (m, 1H), 7.63 (t, J=9.8 Hz, 1H), 7.54 (d, J=7.9 Hz, 1H), 5.67 (d, J=5.2 Hz, 0.5H), 5.44-5.28 (m, 1H), 4.58 (dd, J=13.6, 1.9 Hz, 0.5H), 4.03-3.84 (m, 1H), 3.75-3.67 (m, 1H), 3.69-3.59 (m, 1H), 3.51-3.32 (m, 1H), 3.17 (ddd, J=23.6, 13.8, 9.9 Hz, 1H), 3.07-2.92 (m, 1H), 2.82 (s, 1H), 2.63-2.53 (m, 1H), 2.50-2.33 (m, 1H), 2.18-1.73 (m, 4H), 1.38-0.98 (m, 2H), 1.00-0.83 (m, 2H); MS (ESI) m/z 465 (M+H)$^+$.

Example 19

Preparation of (8R,9aS)-8-[(5-cyclopropylpyrazin-2-yl)oxy]-2-[5-(trifluoromethyl)pyridin-2-yl]octahydro-1H-pyrrolo[1,2-a][1,4]diazepane

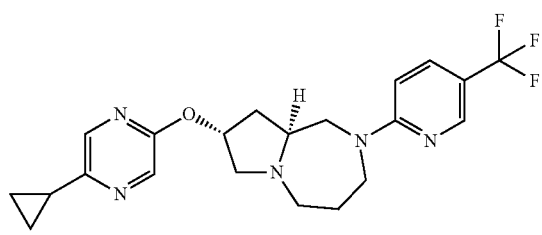 [SMILES: FC(F)(F)c1ccc(N2CCCN3C[C@H](Oc4cnc(C5CC5)cn4)C[C@H]3C2)nc1]

To a solution of the product from Example 1, Part D (60 mg, 0.160 mmol) in anhydrous methanol (2 mL) was added 4 M HCl in 1,4-dioxane (0.40 mL, 1.60 mmol), and the resulting mixture was stirred at room temperature for 18 hours and then concentrated in vacuo. The residue was dissolved in dimethyl sulfoxide (1 mL), and sodium carbonate (0.085 g, 0.801 mmol) and 2-chloro-5-(trifluoromethyl)pyridine (0.038 g, 0.208 mmol) were added. The resulting mixture was stirred at 115° C. for 16 hours. The cooled mixture was partitioned between water and ethyl acetate. The organic extract was washed successively with water and brine, dried over MgSO$_4$, filtered, and concentrated in vacuo. The crude product was purified by column chromatography on silica gel using a solvent gradient of 0-4% methanol in dichloromethane to give the title compound as a waxy solid (0.046 g, 68.4% yield). $^1$H NMR (400 MHz, pyridine-$d_5$) δ ppm 8.69-8.57 (m, 1H), 8.24 (d, J=1.4 Hz, 1H), 8.13 (d, J=1.4 Hz, 1H), 7.76 (dd, J=9.0, 2.6 Hz, 1H), 6.66 (d, J=9.0 Hz, 1H), 5.50-5.33 (m, 1H), 3.80-3.59 (m, 3H), 3.05 (dd, J=13.7, 9.9 Hz, 1H), 2.96 (dt, J=12.8, 4.3 Hz, 1H), 2.91-2.80 (m, 1H), 2.55 (dd, J=10.1, 5.5 Hz, 1H), 2.30-1.96 (m, 5H), 1.98-1.83 (m, 2H), 1.13-1.01 (m, 2H), 1.00-0.82 (m, 2H); MS (ESI) m/z 420 (M+H)$^+$.

Example 20

Preparation of (8R,9aS)-8-[(5-cyclopropylpyrazin-2-yl)oxy]-2-[6-(trifluoromethyl)pyridin-2-yl]octahydro-1H-pyrrolo[1,2-a][1,4]diazepane

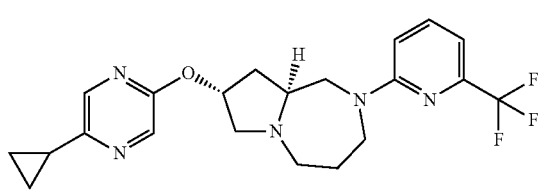 [SMILES: FC(F)(F)c1cccc(N2CCCN3C[C@H](Oc4cnc(C5CC5)cn4)C[C@H]3C2)n1]

The title compound was prepared according to the procedure described in Example 19, substituting 2-chloro-6-(trifluoromethyl)pyridine for 2-chloro-5-(trifluoromethyl)pyridine. $^1$H NMR (400 MHz, pyridine-$d_5$) δ ppm 8.23 (d, J=1.4 Hz, 1H), 8.12 (d, J=1.4 Hz, 1H), 7.65-7.56 (m, 1H), 6.99 (d, J=7.2 Hz, 1H), 6.76 (d, J=8.7 Hz, 1H), 5.45-5.29 (m, 1H), 4.50-4.38 (m, 1H), 3.78-3.59 (m, 4H), 3.05 (dd, J=13.8, 9.9 Hz, 1H), 2.93 (dt, J=12.7, 4.2 Hz, 1H), 2.82 (tdd, J=9.6, 7.0, 2.6 Hz, 1H), 2.52 (dd, J=10.0, 5.6 Hz, 1H), 2.18 (ddd, J=12.8, 9.1, 5.7 Hz, 1H), 2.10-1.99 (m, 1H), 1.97-1.79 (m, 2H), 1.13-1.00 (m, 3H), 1.00-0.85 (m, 2H); MS (ESI) m/z 420 (M+H)$^+$.

Example 21

Preparation of (8R,9aS)-8-[(5-cyclopropylpyrazin-2-yl)oxy]-2-[5-(trifluoromethyl)pyridin-2-yl]octahydro-7H-pyrrolo[1,2-a][1,4]diazepin-7-one

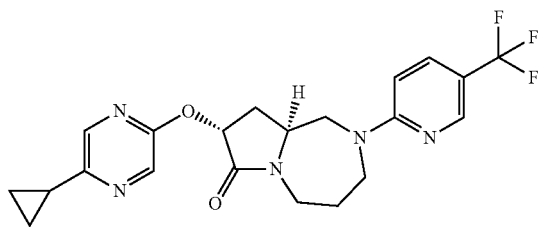 [SMILES: O=C1[C@H](Oc2cnc(C3CC3)cn2)C[C@H]2CN(c3ccc(C(F)(F)F)cn3)CCCN12]

Part A. Preparation of 3-(benzylamino)propan-1-ol

A solution of 3-aminopropan-1-ol (3 g, 39.9 mmol) and benzaldehyde (4.05 mL, 39.9 mmol) in methanol (200 mL) was stirred at room temperature overnight. The solution was cooled to 0° C., and sodium borohydride (1.813 g, 47.9 mmol) was added slowly in several portions. The resulting mixture was stirred at room temperature for three hours, and then it was partitioned between water and dichloromethane (3×). The organic extracts were combined and dried over Na$_2$SO$_4$, the drying agent was removed by filtration, and the solution was concentrated in vacuo to give the title compound as an oil (6.5 g, 98%).

Part B. Preparation of [(2S)-5-oxopyrrolidin-2-yl]methyl methanesulfonate

To a solution of (5S)-5-(hydroxymethyl)pyrrolidin-2-one (1.0 g, 8.69 mmol) in dichloromethane (40 mL) at 0° C. was added triethylamine (1.816 mL, 13.03 mmol) followed by dropwise addition of methanesulfonyl chloride (0.812 mL, 10.42 mmol). The resulting mixture was stirred at room temperature for two hours, and then it was partitioned between water and dichloromethane (3×). The organic extracts were combined and dried over $Na_2SO_4$, the drying agent was removed by filtration, and the solution was concentrated in vacuo to give the title compound as a colorless, waxy solid (1.68 g, quantitative).

Part C. Preparation of (5S)-5-{[benzyl(3-hydroxypropyl)amino]methyl}pyrrolidin-2-one A mixture of the product from Part B (0.5 g, 2.59 mmol) and the product from Part A (1.5 g, 9.08 mmol) was heated at 50° C. for 2 days. The cooled mixture was partitioned between water and ethyl acetate (3×). The organic extracts were combined and dried over $Na_2SO_4$, the drying agent was removed by filtration, and the solution was concentrated in vacuo to give a crude product that was purified by column chromatography on silica gel using a solvent gradient of 0-5% methanol in dichloromethane. The title compound was obtained as a colorless solid (0.468 g, 69%).

Part D. Preparation of 3-(benzyl{[(2S)-5-oxopyrrolidin-2-yl]methyl}amino)propyl methanesulfonate To a solution of the product from Part C (0.45 g, 1.715 mmol) in dichloromethane (17 mL) at 0° C. was added triethylamine (0.359 mL, 2.57 mmol) followed by the dropwise addition of methanesulfonyl chloride (0.160 mL, 2.058 mmol). The resulting mixture was stirred at 0° C. for two hours, and then it was partitioned between water and ethyl acetate (3×). The organic extracts were combined and dried over $Na_2SO_4$, the drying agent was removed by filtration, and the solution was concentrated in vacuo to give the title compound (0.58 g, quantitative).

Part E. Preparation of (9aS)-2-benzyloctahydro-7H-pyrrolo[1,2-a][1,4]diazepin-7-one To a solution of the product from Part D (0.47 g, 1.38 mmol) in anhydrous 1,4-dioxane (47 mL) under $N_2$ was added sodium hydride (60% suspension in mineral oil) (66 mg, 1.65 mmol), and the resulting mixture was stirred at room temperature for three hours. The mixture was poured into water and extracted with ethyl acetate (3×). The organic extracts were combined and dried over $Na_2SO_4$, the drying agent was removed by filtration, and the solution was concentrated in vacuo to give a crude product that was purified by column chromatography on silica gel using a solvent gradient of 0-5% methanol in dichloromethane. The title compound was obtained as a colorless solid (0.223 g, 74%).

Part F. Preparation of tert-butyl (9aS)-7-oxohexahydro-1H-pyrrolo[1,2-a][1,4]diazepine-2(3H)-carboxylate A mixture of the product from Part E (0.219 g, 0.896 mmol), ethanol (3 mL), 20% palladium hydroxide on carbon, wet (22.4 mg, 0.160 mmol), and di-tert-butyl dicarbonate (0.224 g, 1.025 mmol) in a 4 mL pressure bottle was stirred under 60 psi of $H_2$ at 50° C. for 3.5 hours. The cooled mixture was filtered and concentrated in vacuo, and the crude product was purified by column chromatography on silica gel using a solvent gradient of 0-5% methanol in dichloromethane. The title compound was obtained as a colorless solid (0.21 g, 91%).

Part G. Preparation of tert-butyl (8R,9aS)-8-hydroxy-7-oxohexahydro-1H-pyrrolo[1,2-a][1,4]diazepine-2(3H)-carboxylate and tert-butyl (8S,9aS)-8-hydroxy-7-oxohexahydro-1H-pyrrolo[1,2-a][1,4]diazepine-2(3H)-carboxylate To a solution of the product from Part F (0.21 g, 0.826 mmol) in anhydrous tetrahydrofuran (6 mL) under $N_2$ at −78° C. was added lithium bis(trimethylsilyl)amide (1.0 M solution in tetrahydrofuran) (1.239 mL, 1.239 mmol) dropwise over two to three minutes. The resulting mixture was stirred at −78° C. for 15 minutes, and a solution of 3-phenyl-2-(phenylsulfonyl)-1,2-oxaziridine (0.432 g, 1.651 mmol) in anhydrous tetrahydrofuran (3 mL) was added dropwise via canula over five minutes. The resulting mixture was stirred at −40° C. for two hours. A solution of 10% $NH_4Cl$ in water was added, the resulting mixture was allowed to warm to room temperature, and then it was partitioned between water and ethyl acetate (5×). The organic extracts were combined and dried over $Na_2SO_4$, the drying agent was removed by filtration, and the solution was concentrated in vacuo to give a crude product that was purified by column chromatography on silica gel using a solvent gradient of 0-10% methanol in dichloromethane. The title compound was obtained as a colorless solid (0.10 g, 45%), and was approximately a 5:1 mixture of trans:cis isomers according to $^1H$ NMR.

Part H. Preparation of tert-butyl (8R,9aS)-8-[(5-cyclopropylpyrazin-2-yl)oxy]-7-oxohexahydro-1H-pyrrolo[1,2-a][1,4]diazepine-2(3H)-carboxylate To a solution of the product from Part G (98 mg, 0.363 mmol) in anhydrous N,N-dimethylformamide (3.6 mL) under $N_2$ at 0° C. was added sodium hydride (60% dispersion in mineral oil) (16 mg, 0.40 mmol). The resulting mixture was stirred at 0° C. for 20 minutes, and then 2-bromo-5-cyclopropylpyrazine (108 mg, 0.544 mmol) was added. The resulting mixture was allowed to warm to room temperature and stirred under $N_2$ for 16 hours. The mixture was partitioned between water and ethyl acetate, and the organic extract was dried over $Na_2SO_4$. The drying agent was removed by filtration, and the filtrate was concentrated in vacuo to give a crude product that was purified by column chromatography on silica gel using a solvent gradient of 0-5% methanol in dichloromethane. The resulting product was resubjected to silica gel chromatography using a solvent gradient of 0-100% ethyl acetate in hexanes to separate the trans isomer from the cis isomer. The title compound was first to elute, and was obtained as a colorless solid (62 mg, 44%).

Part I. Preparation of (8R,9aS)-8-[(5-cyclopropylpyrazin-2-yl)oxy]octahydro-7H-pyrrolo[1,2-a][1,4]diazepin-7-one hydrochloride To a solution of the product from Part H (60 mg, 0.154 mmol) in 1,4-dioxane (0.2 mL) was added hydrogen chloride solution (4 N solution in dioxane) (0.2 mL, 0.800 mmol), and the resulting mixture was stirred at room temperature for 90 minutes. The mixture was concentrated and dried in vacuo to give the title compound (50 mg, quantitative).

Part J. Preparation of (8R,9aS)-8-[(5-cyclopropylpyrazin-2-yl)oxy]-2-[5-(trifluoromethyl)pyridin-2-yl]octahydro-7H-pyrrolo[1,2-a][1,4]diazepin-7-one To a solution of the product from Part I (83 mg, 0.257 mmol) and 2-bromo-5-(trifluoromethyl)pyridine (87 mg, 0.386 mmol) in anhydrous 1,4-dioxane (3 mL) was added triethylamine (0.107 mL, 0.771 mmol), and the resulting mixture was stirred at 80° C. for 16 hours. The mixture was partitioned between water and ethyl acetate (3×), and the organic extracts were combined and dried over $Na_2SO_4$. The drying agent was removed by filtration, and the solution was concentrated in vacuo to give a crude product that was purified by column chromatography on silica gel using a solvent gradient of 0-5% methanol in dichloromethane. The title compound was obtained as a colorless solid (55 mg, 49%). $^1$H NMR (300 MHz, $CDCl_3$) δ ppm 0.90-1.01 (m, 4 H) 1.94-2.16 (m, 3 H) 2.20-2.32 (m, 1 H) 2.36-2.48 (m, 1 H) 2.69-2.83 (m, 1 H) 3.24 (dd, J=14.24, 9.83 Hz, 1 H) 3.40-3.54 (m, 1 H) 3.85-4.00 (m, 2 H) 4.20-4.32 (m, 1 H) 4.62 (dd, J=14.24, 3.73 Hz, 1 H) 5.64 (dd, J=8.14, 6.44 Hz, 1 H) 6.56 (d, J=9.16 Hz, 1 H) 7.65 (dd, J=8.82, 2.37 Hz, 1 H) 7.95 (d, J=1.36 Hz, 1 H) 8.14 (d, J=1.36 Hz, 1 H) 8.39 (d, J=2.37 Hz, 1 H); MS (APCI) m/z 434 (M+H)$^+$.

Example 22

Preparation of (8R,9aS)-8-[(5-cyclopropylpyrazin-2-yl)oxy]-2-[3-(trifluoromethyl)benzyl]octahydro-1H-pyrrolo[1,2-a][1,4]diazepin-1-one

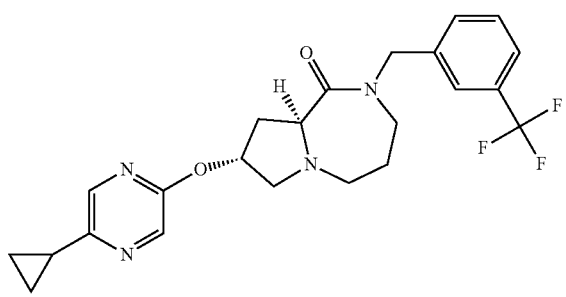 [SMILES: O=C1[C@@H]2C[C@@H](Oc3cnc(C4CC4)cn3)CN2CCCN1Cc1cccc(C(F)(F)F)c1]

Part A. Preparation of (8R,9aS)-8-[(triethylsilyl)oxy]octahydro-1H-pyrrolo[1,2-a][1,4]diazepin-1-one To a solution of the product from Example 1, Part B (0.33 g, 1.94 mmol) in anhydrous N,N-dimethylformamide (10 mL) was added imidazole (0.264 g, 3.88 mmol) and triethylsilyl chloride (0.488 mL, 2.91 mmol). The resulting solution was stirred at room temperature for 16 hours. The mixture was partitioned between ethyl acetate (50 mL) and water (2×50 mL), and the organic extract was dried over $Na_2SO_4$. The drying agent was removed by filtration, and the filtrate was concentrated in vacuo to give a crude product that was purified by column chromatography on silica gel using a solvent gradient of 0-10% methanol in dichloromethane. The title compound was obtained as a colorless solid (0.28 g, 51%).

Part B. Preparation of (8R,9aS)-8-[(triethylsilyl)oxy]-2-[3-(trifluoromethyl)benzyl]octahydro-1H-pyrrolo[1,2-a][1,4]diazepin-1-one To a solution of the product from Part A (50 mg, 0.176 mmol) in anhydrous N,N-dimethylformamide (1.5 mL) under $N_2$ was added sodium hydride (60% weight suspension in mineral oil) (8.4 mg, 0.21 mmol). The resulting mixture was stirred at room temperature for 10 minutes, and 1-(bromomethyl)-3-(trifluoromethyl)benzene (0.032 mL, 0.211 mmol) was added. The resulting mixture was stirred at room temperature for two hours. The mixture was partitioned between water and ethyl acetate (3×), and the organic extracts were combined and dried over $Na_2SO_4$. The drying agent was removed by filtration, and the filtrate was concentrated in vacuo to give a crude product that was purified by column chromatography on silica gel using a solvent gradient of 0-10% methanol in dichloromethane. The title compound was obtained as a colorless solid (35 mg, 45%).

Part C. Preparation of (8R,9aS)-8-[(5-cyclopropylpyrazin-2-yl)oxy]-2-[3-(trifluoromethyl)benzyl]octahydro-1H-pyrrolo[1,2-a][1,4]diazepin-1-one A solution of the product from Part B (33 mg, 0.075 mmol) in acetic acid (0.9 mL) and water (0.3 mL) was stirred at room temperature for 36 hours and concentrated and dried in vacuo. The residue was dissolved in tetrahydrofuran (0.7 mL) and 2-bromo-5-cyclopropylpyrazine (22.4 mg, 0.113 mmol) was added, followed by a 1.0 M solution of potassium tert-butoxide in tetrahydrofuran (0.090 mL, 0.090 mmol). The resulting mixture was stirred at room temperature for two hours. The mixture was partitioned between water and ethyl acetate (3×), and the organic extracts were combined and dried over $Na_2SO_4$. The drying agent was removed by filtration, and the filtrate was concentrated in vacuo to give a crude product that was purified by column chromatography on silica gel using a solvent gradient of 0-5% methanol in dichloromethane. The title compound was obtained as a colorless solid (16 mg, 48%). $^1$H NMR (300 MHz, $CDCl_3$) δ ppm 0.86-1.01 (m, 4 H), 1.65-1.80 (m, 2 H), 1.90-2.06 (m, 1 H), 2.14-2.83 (m, 3 H), 2.93-3.12 (m, 1 H), 3.14-3.91 (m, 5 H), 4.28-4.56 (m, 1 H), 4.81-5.02 (m, 1 H), 5.29-5.47 (m, 1 H), 7.39-7.58 (m, 4 H), 7.90-8.17 (m, 2 H); MS (ESI) m/z 447 (M+H)$^+$.

Example 23

Preparation of (8R,9aS)-8-[(5-cyclopropylpyrazin-2-yl)oxy]-2-[4-(trifluoromethyl)benzyl]octahydro-1H-pyrrolo[1,2-a][1,4]diazepin-1-one

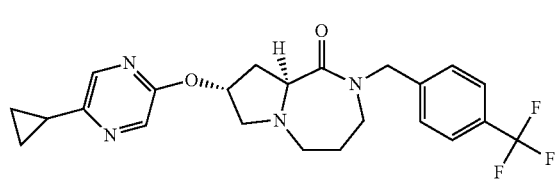 [SMILES: O=C1[C@@H]2C[C@@H](Oc3cnc(C4CC4)cn3)CN2CCCN1Cc1ccc(C(F)(F)F)cc1]

Part A. Preparation of (8R,9aS)-8-[(triethylsilyl)oxy]-2-[4-(trifluoromethyl)benzyl]octahydro-1H-pyrrolo[1,2-a][1,4]diazepin-1-one To a solution of the product from Example 22, Part A (0.10 g, 0.352 mmol) in anhydrous N,N-dimethylformamide (3.0 mL) under $N_2$ was added sodium hydride (60% weight suspension in mineral oil) (17 mg, 0.42 mmol). The resulting mixture was stirred at room temperature for 10 minutes, and 1-(bromomethyl)-4-(trifluoromethyl)benzene (0.065 mL, 0.422 mmol) was added. The resulting mixture was stirred at room temperature for two hours. The mixture was partitioned between water and ethyl acetate (3×), and the organic extracts were combined and dried over Na$_2$SO$_4$. The drying agent was removed by filtration, and the filtrate was concentrated in vacuo to give the title compound as a solid (0.16 g, quantitative).

Part B. Preparation of (8R,9aS)-8-hydroxy-2-[4-(trifluoromethyl)benzyl]octahydro-1H-pyrrolo[1,2-a][1,4]diazepin-1-one A solution of the product from Part A (0.16 g, 0.36 mmol) in acetic acid (1.5 mL) and water (0.5 mL) was stirred at room temperature for 24 hours and concentrated in vacuo. The crude product was purified by column chromatography on silica gel using a solvent gradient of 0-10% methanol in dichloromethane. The title compound eluted at 8-10% methanol (72 mg, 62%).

Part C. Preparation of (8R,9aS)-8-[(5-cyclopropylpyrazin-2-yl)oxy]-2-[4-(trifluoromethyl)benzyl]octahydro-1H-pyrrolo[1,2-a][1,4]diazepin-1-one To a solution of the product from Part B (0.065 g, 0.198 mmol) and 2-bromo-5-cyclopropylpyrazine (0.059 g, 0.297 mmol) in anhydrous tetrahydrofuran (2.0 mL) at 0° C. under N$_2$ was added a 1.0 M solution of potassium tert-butoxide in tetrahydrofuran (0.238 mL, 0.238 mmol). The resulting mixture was stirred at room temperature for 90 minutes. The mixture was partitioned between water and ethyl acetate (3×), and the organic extracts were combined and dried over Na$_2$SO$_4$. The drying agent was removed by filtration, the filtrate was concentrated in vacuo, and the crude product was purified by column chromatography on silica gel using a solvent gradient of 0-5% methanol in dichloromethane. The title compound was the second of two stereoisomers to elute (21 mg, 24%). $^1$H NMR (500 MHz, CDCl$_3$) δ ppm 0.89-1.00 (m, 4 H) 1.66-1.74 (m, 2 H) 1.95-2.04 (m, 1 H) 2.16-2.25 (m, 1 H) 2.58-2.66 (m, 1 H) 2.68 (dd, J=10.99, 3.97 Hz, 1 H) 2.95-3.06 (m, 1 H) 3.16-3.28 (m, 2 H) 3.56-3.66 (m, 1 H) 3.69-3.77 (m, 2 H) 4.55 (d, J=14.95 Hz, 1 H) 4.79 (d, J=14.95 Hz, 1 H) 5.33-5.41 (m, 1 H) 7.39 (d, J=8.24 Hz, 2 H) 7.58 (d, J=7.93 Hz, 2 H) 7.96 (s, 1 H) 8.03 (s, 1 H); MS (APCI) m/z 447 (M+H)$^+$.

Example 24

Preparation of (8R,9aR)-8-[(5-cyclopropylpyrazin-2-yl)oxy]-2-[4-(trifluoromethyl)benzyl]octahydro-1H-pyrrolo[1,2-a][1,4]diazepin-1-one

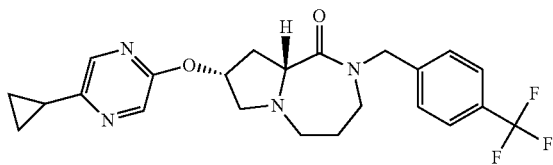 [SMILES: O=C1[C@H]2C[C@@H](Oc3cnc(C4CC4)cn3)CN2CCCN1Cc1ccc(C(F)(F)F)cc1]

The title compound was obtained from the procedure described in Example 23, Part C and was the first of two stereoisomers to elute during chromatography (9 mg, 10%). $^1$H NMR (500 MHz, CDCl$_3$) δ ppm 0.90-0.98 (m, 4 H) 1.68-1.76 (m, 1 H) 1.83-1.94 (m, 1 H) 1.94-2.02 (m, 1 H) 2.35-2.43 (m, 1 H) 2.46-2.55 (m, 1 H) 2.74 (dd, J=10.99, 4.88 Hz, 1 H) 3.05 (dd, J=15.26, 6.10 Hz, 1 H) 3.22-3.35 (m, 2 H) 3.38 (dd, J=10.07, 6.10 Hz, 1 H) 3.43 (d, J=11.29 Hz, 1 H) 3.55 (dd, J=15.11, 11.44 Hz, 1 H) 4.41 (d, J=15.26 Hz, 1 H) 4.90 (d, J=14.95 Hz, 1 H) 5.36 (t, J=5.04 Hz, 1 H) 7.38 (d, J=7.93 Hz, 2 H) 7.56 (d, J=8.24 Hz, 2 H) 7.93 (s, 1 H) 8.15 (s, 1 H); MS (APCI) m/z 447 (M+H)$^+$.

Example 25

Preparation of (8R,9aS)-8-[(5-cyclopropylpyrazin-2-yl)oxy]-2-[3-fluoro-4-(trifluoromethyl)benzyl]octahydro-1H-pyrrolo[1,2-a][1,4]diazepin-1-one

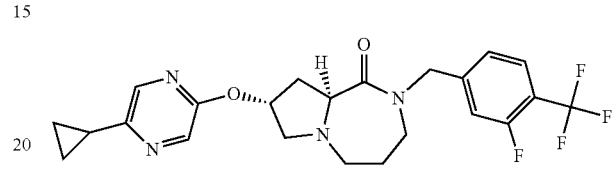

Part A. Preparation of (8R,9aS)-2-[3-fluoro-4-(trifluoromethyl)benzyl]-8-hydroxyoctahydro-1H-pyrrolo[1,2-a][1,4]diazepin-1-one To a solution of the product from Example 22, Part A (75 mg, 0.264 mmol) in tetrahydrofuran (2.0 mL) under N$_2$ was added sodium hydride (60% weight suspension in mineral oil) (11.6 mg, 0.290 mmol). The resulting mixture was stirred at room temperature for five minutes, and 4-(bromomethyl)-2-fluoro-1-(trifluoromethyl)benzene (0.050 mL, 0.290 mmol) was added. The resulting mixture was stirred at room temperature for two hours. The mixture was partitioned between water and ethyl acetate (3×), and the organic extracts were combined and dried over Na$_2$SO$_4$. The drying agent was removed by filtration, and the filtrate was concentrated in vacuo. The residue was stirred in a mixture of acetic acid (1.5 mL) and water (0.500 mL) for 24 hours. The mixture was concentrated in vacuo and purified by column chromatography on silica gel using a solvent gradient of 0-10% methanol in dichloromethane. The title compound eluted at 8-10% methanol (70 mg, 77%).

Part B. Preparation of (8R,9aS)-8-[(5-cyclopropylpyrazin-2-yl)oxy]-2-[3-fluoro-4-(trifluoromethyl)benzyl]octahydro-1H-pyrrolo[1,2-a][1,4]diazepin-1-one To a solution of the product from Part A (66 mg, 0.191 mmol) and 2-bromo-5-cyclopropylpyrazine (57 mg, 0.286 mmol) in anhydrous tetrahydrofuran (2.0 mL) at 0° C. under N$_2$ was added a 1.0 M solution of potassium tert-butoxide in tetrahydrofuran (0.20 mL, 0.200 mmol). The resulting mixture was stirred at room temperature for 90 minutes. The mixture was partitioned between water and ethyl acetate (3×), and the organic extracts were combined and dried over Na$_2$SO$_4$. The drying agent was removed by filtration, the filtrate was concentrated in vacuo, and the crude product was purified by column chromatography on silica gel using a solvent gradient of 0-5% methanol in dichloromethane. The title compound was obtained as a colorless solid (16 mg, 18%). $^1$H NMR (300 MHz, CDCl$_3$) δ ppm 0.89-1.04 (m, 4 H) 1.65-1.84 (m, 2 H) 1.92-2.11 (m, 1 H) 2.14-2.36 (m, 2 H) 2.55-2.82 (m, 2 H) 2.92-3.09 (m, 1 H) 3.14-3.36 (m, 2 H) 3.52-3.87 (m, 2 H) 4.47-4.63 (m, 1 H) 4.82 (d, J=14.24 Hz, 1

H) 5.33-5.51 (m, 1 H) 7.10-7.33 (m, 2 H) 7.53-7.61 (m, 1 H) 7.97 (s, 1 H) 8.04 (s, 1 H); MS (APCI) m/z 465 (M+H)⁺.

Example 26

Preparation of (8R,9aS)-8-[(5-cyclopropylpyrazin-2-yl)oxy]-2-[4-fluoro-3-(trifluoromethyl)benzyl]octahydro-1H-pyrrolo[1,2-a][1,4]diazepin-1-one

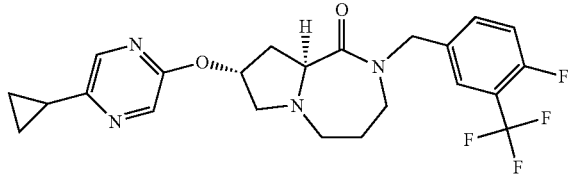 [SMILES: O=C1[C@@H]2C[C@@H](Oc3cnc(C4CC4)cn3)CN2CCCN1Cc1ccc(F)c(C(F)(F)F)c1]

The title compound was obtained according to the procedure described for Example 25, substituting 4-(bromomethyl)-1-fluoro-2-(trifluoromethyl)benzene for 4-(bromomethyl)-2-fluoro-1-(trifluoromethyl)benzene. ¹H NMR (300 MHz, CDCl₃) δ ppm 0.89-1.01 (m, 4 H) 1.64-1.82 (m, 2H) 1.92-2.07 (m, 1 H) 2.14-2.33 (m, 2 H) 2.56-2.80 (m, 2 H) 2.92-3.09 (m, 1 H) 3.14-3.37 (m, 2 H) 3.53-3.86 (m, 2 H) 4.47 (d, J=14.58 Hz, 1 H) 4.78 (d, J=14.92 Hz, 1 H) 5.32-5.44 (m, 1 H) 7.12-7.21 (m, 1 H) 7.45-7.58 (m, 2 H) 7.96 (s, 1 H) 8.03 (s, 1 H); MS (APCI) m/z 465 (M+H)⁺.

Example 27

Preparation of (8R,9aS)-8-[(5-cyclopropylpyrazin-2-yl)oxy]-2-[3-(trifluoromethyl)phenyl]octahydro-1H-pyrrolo[1,2-a][1,4]diazepin-1-one

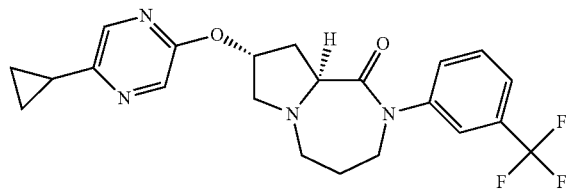 [SMILES: O=C1[C@@H]2C[C@@H](Oc3cnc(C4CC4)cn3)CN2CCCN1c1cccc(C(F)(F)F)c1]

Part A. Preparation of (8R,9aS)-8-[(triethylsilyl)oxy]-2-[3-(trifluoromethyl)phenyl]octahydro-1H-pyrrolo[1,2-a][1,4]diazepin-1-one A mixture of the product from Example 22, Part A (100 mg, 0.352 mmol), 1-iodo-3-(trifluoromethyl)benzene (0.061 mL, 0.422 mmol), 4,5-bis(diphenylphosphino)-9,9-dimethylxanthene (XANTPHOS, 6.10 mg, 10.55 μmol), and cesium carbonate (172 mg, 0.527 mmol) in 1,4-dioxane (2.0 mL) was deoxygenated by bubbling with N₂ for 20 minutes. Tris (dibenzylideneacetone)dipalladium(0) (57.9 mg, 0.063 mmol) was added, and N₂ bubbling was continued for five minutes. The reaction container was sealed, and the stirred mixture was heated at 90° C. for 16 hours. The cooled mixture was partitioned between water and ethyl acetate (3×), and the organic extracts were combined and dried over Na₂SO₄. The drying agent was removed by filtration, the filtrate was concentrated in vacuo, and the crude product was purified by column chromatography on silica gel using a solvent gradient of 0-10% methanol in dichloromethane. The title compound was obtained as a colorless solid (96 mg, 64%).

Part B. Preparation of (8R,9aS)-8-[(5-cyclopropylpyrazin-2-yl)oxy]-2-[3-(trifluoromethyl)phenyl]octahydro-1H-pyrrolo[1,2-a][1,4]diazepin-1-one The title compound was obtained according to the procedure described in Example 22, Part C, substituting the product from Part A for the product from Example 22, Part B. ¹H NMR (300 MHz, CDCl₃) δ ppm 0.88-0.99 (m, 4 H) 1.83-2.30 (m, 4 H) 2.70-2.86 (m, 2 H) 2.91-3.06 (m, 1 H) 3.24-3.38 (m, 1 H) 3.64-3.82 (m, 2 H) 3.81-3.94 (m, 1 H) 4.00-4.14 (m, 1 H) 5.34-5.44 (m, 1 H) 7.42-7.52 (m, 4 H) 7.96 (d, J=1.36 Hz, 1 H) 8.05 (d, J=1.36 Hz, 1 H); MS (APCI) m/z 433 (M+H)⁺.

Example 28

Preparation of (8R,9aS)-8-[(5-cyclopropylpyrazin-2-yl)oxy]-2-{[3-(trifluoromethyl)phenyl]sulfonyl}octahydro-5H-pyrrolo[1,2-a][1,4]diazepin-5-one

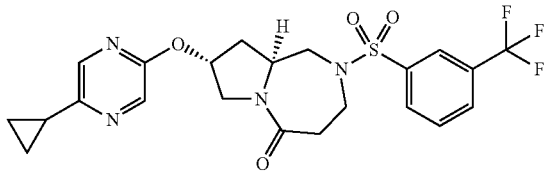 [SMILES: O=C1CCN(S(=O)(=O)c2cccc(C(F)(F)F)c2)C[C@@H]2C[C@@H](Oc3cnc(C4CC4)cn3)CN12]

Part A. Preparation of tert-butyl (2S,4R)-4-(benzyloxy)-2-(hydroxymethyl)pyrrolidine-1-carboxylate To a solution of (2S,4R)-4-(benzyloxy)-1-(tert-butoxycarbonyl)pyrrolidine-2-carboxylic acid (5.00 g, 15.56 mmol) in tetrahydrofuran (50 mL) at −10° C. was added N-methylmorpholine (1.882 mL, 17.11 mmol). To this solution was added slowly isobutyl chloroformate (2.34 g, 2.25 mL, 17.11 mmol). The resulting mixture was stirred for 30 minutes and filtered, and the filtrate was added to a solution of sodium borohydride (1.18 g, 31.1 mmol) in water (1.5 mL) at 0° C. The resulting mixture was stirred at 0° C. for 30 minutes, and the reaction was quenched by the addition of a saturated solution of NH₄Cl. The mixture was extracted with ethyl acetate, and the organic extract was washed with brine, dried with MgSO₄, filtered, and concentrated in vacuo. The crude product was purified by column chromatography on silica gel using a solvent gradient of 0-2% methanol in dichloromethane to give the title compound as a colorless oil (3.93 g, 82%). ¹H NMR (400 MHz, pyridine-d₅, 90° C.) δ ppm 7.36 (d, J=7.4 Hz, 2 H), 7.30 (t, J=7.3 Hz, 2 H), 7.23 (t, J=7.2 Hz, 1 H), 4.50 (s, 2 H), 4.20-4.29 (m, 2 H), 3.92-4.00 (m, 1 H), 3.80-3.87 (m, 2 H), 3.50-3.59 (m, 1 H), 2.16-2.30 (m, 2 H), 1.47 (s, 9 H).

Part B. Preparation of tert-butyl (2S,4R)-4-(benzyloxy)-2-formylpyrrolidine-1-carboxylate To a stirred solution of oxalyl chloride (2.21 mL, 25.4 mmol) in dichloromethane (120 mL) at −78° C. was added dimethyl sulfoxide (3.6 mL, 50.8 mmol) dropwise via syringe. The mixture was stirred at −78° C. for 10 minutes, and a solution of tert-butyl (2S,4R)-4-(benzyloxy)-2-(hydroxymethyl)pyrrolidine-1-carboxylate (3.9 g, 12.69 mmol, Part A) in dichloromethane (30 mL) was added. The mixture was stirred at −78° C. for 15 minutes, and triethylamine (7.07 mL, 50.8 mol) was added. After 15 minutes, the reaction mixture was allowed to warm to 0° C. and stirred at that temperature for 30 minutes. The mixture was washed successively with water and brine, dried with MgSO$_4$, filtered, and concentrated in vacuo. The crude product was purified by column chromatography on silica gel using a solvent gradient of 20-50% ethyl acetate in hexanes to give the title compound as a colorless oil (3.25 g, 84%). $^1$H NMR (400 MHz, pyridine-d$_5$, 90° C.) δ ppm 9.62 (s, 1 H), 7.18-7.41 (m, 5 H), 4.37-4.56 (m, 3 H), 4.08-4.14 (m, 1 H), 3.88-3.74 (m, 1 H), 3.56 (dd, J=11.7, 4.7 Hz, 1 H) 2.19-2.29 (m, 1 H) 1.95-2.05 (m, 1 H) 1.45 (s, 9 H).

To a solution of tert-butyl (2S,4R)-4-(benzyloxy)-2-(hydroxymethyl)pyrrolidine-1-carboxylate (20 g, 0.065 mol, Part A) and triethylamine (27 ml, 0.195 mol) in dichloromethane (200 mL) was added a solution of sulfur trioxide pyridine complex (31 g, 0.195 mol) in dimethyl sulfoxide (200 mL) at −15° C. The reaction mixture was stirred at that temperature for one hour and then another lot of sulfur trioxide pyridine complex (5.1 g, 0.033 mol) in dimethyl sulfoxide (35 mL) was added. The reaction mixture was allowed to stir at 20-25° C. for 18 hours, and then it was poured into cold water (400 mL) and extracted with ten-butyl methyl ether (200 mL×2). The combined organic layers were washed with 10% citric acid solution (200 mL), saturated sodium bicarbonate solution (200 mL), water (100 mL) and brine solution (100 mL). The organic layer was dried over anhydrous sodium sulfate, filtered and concentrated to give tert-butyl (2S,4R)-4-(benzyloxy)-2-formylpyrrolidine-1-carboxylate (17 g, 85%) as pale yellow oil which was used without further purification.

Part C. Preparation of tert-butyl (2S,4R)-2-{[benzyl (3-ethoxy-3-oxopropyl)amino]methyl}-4-(benzyloxy)pyrrolidine-1-carboxylate To a solution of the product from Part B (3.2 g, 10.48 mmol) and ethyl 3-(benzylamino)propanoate (2.17, 10.48 mmol) in dichloromethane (40 mL) was added acetic acid (1.8 mL) and polymer-supported cyanoborohydride (4.57 g, 47.2 mmol). The resulting mixture was stirred at room temperature for 18 hours, filtered and concentrated in vacuo. The crude product was purified by column chromatography on silica gel using a solvent gradient of 20-50% ethyl acetate in hexanes to give the title compound as a colorless oil (4.25 g, 82%). $^1$H NMR (500 MHz, pyridine-d$_5$, 90° C.) δ ppm 7.40 (d, J=7.5 Hz, 2 H), 7.34-7.38 (m, 2 H), 7.28-7.34 (m, 4 H), 7.21-7.27 (m, 2 H), 4.47 (s, 2 H), 4.26-3.70 (m, 5 H), 3.81 (t, J=13.2 Hz, 1 H), 3.52 (d, J=13.8 Hz, 1 H), 3.42 (dd, J=11.6, 5.3 Hz, 1 H), 3.06-3.13 (m, 1 H), 2.82-2.98 (m, 2 H), 2.50-2.62 (m, 2 H), 2.45 (dd, J=12.5, 9.3 Hz, 1 H), 2.05-2.18 (m, 2 H), 1.52 (s, 9 H), 1.14 (t, J=7.1 Hz, 3 H).

Part D. Preparation of (8R,9aS)-2-benzyl-8-(benzyloxy)octahydro-5H-pyrrolo[1,2-a][1,4]diazepin-5-one To a solution of the product from Part C (4.2 g, 8.46 mmol) in anhydrous methanol (15 mL) was added 4 M HCl in 1,4-dioxane (10.57 mL, 42.3 mmol). The resulting mixture was stirred at room temperature for 18 hours and concentrated in vacuo. The residue was suspended in ethanol (75 mL), triethylamine was added (5.8 mL, 41.8 mmol), and the mixture was refluxed for 48 hours. The mixture was concentrated in vacuo. The residue was dissolved in ethyl acetate (100 mL), washed successively with water and brine, dried over MgSO$_4$, filtered, and concentrated in vacuo. The crude product was purified by column chromatography on silica gel using a solvent gradient of 20-70% ethyl acetate in hexanes to give the title compound as a colorless oil (2.25 g, 76% yield).

Part E. Preparation of tert-butyl (8R,9aS)-8-hydroxy-5-oxohexahydro-1H-pyrrolo[1,2-a][1,4]diazepine-2 (3H)-carboxylate A mixture of the product from Part D (2.07 g, 5.91 mmol), ethanol (25 mL), 20% palladium hydroxide on carbon, wet (2.15 g, 15.31 mmol), and di-tert-butyl dicarbonate (1.418 g, 6.50 mmol) was placed in a 250 mL stainless steel pressure bottle. The mixture was shaken under H$_2$ at 30 psi and 50° C. for 15 hours. The mixture was filtered through a nylon membrane, and concentrated in vacuo to give a colorless solid which was slurried in 5% ethyl acetate in hexanes (20 mL) and filtered. The title compound was obtained as a colorless solid (1.4 g, 84%). $^1$H NMR (400 MHz, pyridine-d$_5$, 90° C.) δ ppm 4.40-4.47 (m, 1 H), 4.04-4.31 (m, 3 H), 3.54-3.66 (m, 2 H), 2.97-3.08 (m, 1 H), 2.55-2.81 (m, 3 H), 2.20-2.30 (m, 1 H), 1.67-1.77 (m, 1 H), 1.47 (s, 9 H).

Part F. Preparation of tert-butyl (8R,9aS)-8-[(5-cyclopropylpyrazin-2-yl)oxy]-5-oxohexahydro-1H-pyrrolo[1,2-a][1,4]diazepine-2(3H)-carboxylate To a solution of the product from Part E (1.4 g, 5.18 mmol) in tetrahydrofuran (40 mL) was added a 1.0 M solution of potassium tert-butoxide in tetrahydrofuran (7.25 mL, 7.25 mmol), followed by the dropwise addition of a solution of 2-bromo-5-cyclopropylpyrazine (1.237 g, 6.21 mmol) in tetrahydrofuran (10 mL). The resulting mixture was stirred at room temperature for 48 hours and concentrated in vacuo. The residue was dissolved in ethyl acetate (60 mL), washed successively with water and brine, dried over MgSO$_4$, filtered, and concentrated in vacuo. The crude product was purified by column chromatography on silica gel using a solvent gradient of 0-2% methanol in dichloromethane to give the title compound as a waxy solid (1.62 g, 81%). $^1$H NMR (400 MHz, pyridine-d$_5$, 90° C.) δ ppm 8.05 (d, J=1.2 Hz, 1 H), 7.98 (d, J=1.2 Hz, 1 H), 5.42-5.50 (m, 1 H), 4.30 (d, J=14.3 Hz, 1 H), 4.10-4.24 (m, 3 H), 3.80 (dd, J=13.6, 4.4 Hz, 1 H), 2.98-3.12 (m, 1 H), 2.80 (dd, J=14.3, 9.5 Hz, 1 H), 2.63-2.74 (m, 2 H), 2.41 (dd, J=14.0, 6.7 Hz, 1 H), 1.85-2.03 (m, 2 H), 1.48 (s, 9 H), 0.96-1.02 (m, 2 H), 0.84-0.91 (m, 2 H).

Part G. Preparation of (8R,9aS)-8-[(5-cyclopropylpyrazin-2-yl)oxy]-2-{[3-(trifluoromethyl)phenyl] sulfonyl}octahydro-5H-pyrrolo[1,2-a][1,4]diazepin-5-one The product from Part F (60 mg, 0.134 mmol) in anhydrous methanol (2 mL) was added to 4 M HCl in 1,4-dioxane (0.386 mL, 1.545 mmol). The resulting mixture was stirred at room temperature for 18 hours, and then it was concentrated in vacuo. To the residue was added dichloromethane (4 mL), 3-(trifluoromethyl)benzene-1-sulfonyl chloride (0.042 g, 0.17 mmol), and triethylamine (0.108 mL, 0.772 mmol). The resulting mixture was stirred at room temperature for 16 hours, and then it was partitioned between water and ethyl acetate. The organic extract was washed successively with water and brine, dried with MgSO4, filtered, and concentrated in vacuo. The crude product was purified by column chromatography on silica gel using a solvent gradient of 0-4% methanol in dichloromethane to give the title compound as a colorless solid (51 mg, 66.5%). $^1$H NMR (500 MHz, pyridine-$d_5$, 90° C.) δ ppm 8.42 (bs, 1H), 8.22 (d, J=7.9 Hz, 1H), 8.16 (d, J=1.1 Hz, 1H), 8.06 (d, J=1.4 Hz, 1H), 7.95 (d, J=7.9 Hz, 1H), 7.79-7.64 (m, 1H), 5.43 (t, J=4.1 Hz, 1H), 4.41-4.15 (m, 3H), 4.02-3.69 (m, 1H), 3.64-3.55 (m, 1H), 3.11-2.70 (m, 3H), 2.62 (dd, J=13.2, 9.2 Hz, 1H), 2.54-2.40 (m, 1H), 2.11-1.98 (m, 1H), 1.92 (ddd, J=14.2, 10.0, 4.3 Hz, 1H), 1.14-0.99 (m, 2H), 1.01-0.86 (m, 2H). MS (ESI) m/z 497 (M+H)$^+$.

Example 29

Preparation of (8R,9aS)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one

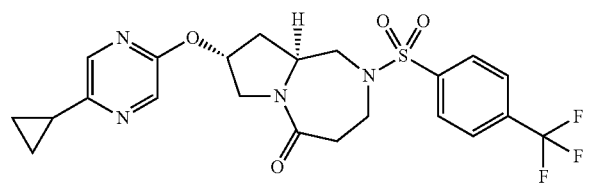 [SMILES: O=C1CCN(S(=O)(=O)c2ccc(C(F)(F)F)cc2)C[C@@H]2C[C@@H](Oc3cnc(C4CC4)cn3)CN12]

The title compound was prepared according to the procedure described in Example 28, Part G, substituting 4-(trifluoromethyl)benzene-1-sulfonyl chloride for 3-(trifluoromethyl)benzene-1-sulfonyl chloride. $^1$H NMR (500 MHz, pyridine-$d_5$, 90° C.) δ ppm 8.19-8.13 (m, 3H), 8.07 (d, J=1.4 Hz, 1H), 7.95-7.90 (m, 2H), 5.45 (t, J=4.1 Hz, 1H), 4.39-4.25 (m, 3H), 4.25-4.15 (m, 1H), 4.06-3.69 (m, 1H), 3.21-2.88 (m, 1H), 2.84 (dd, J=15.0, 6.4 Hz, 1H), 2.76 (d, J=12.4 Hz, 1H), 2.62 (dd, J=13.4, 9.4 Hz, 1H), 2.51-2.42 (m, 1H), 2.27-1.90 (m, 2H), 1.24-1.00 (m, 2H), 1.02-0.82 (m, 2H); MS (ESI) m/z 497 (M+H)$^+$.

Example 30

Preparation of (8S,9aS)-8-[(5-cyclopropylpyrazin-2-yl)oxy]-2-[5-(trifluoromethyl)pyridin-2-yl]octahydro-5H-pyrrolo[1,2-a][1,4]diazepin-5-one

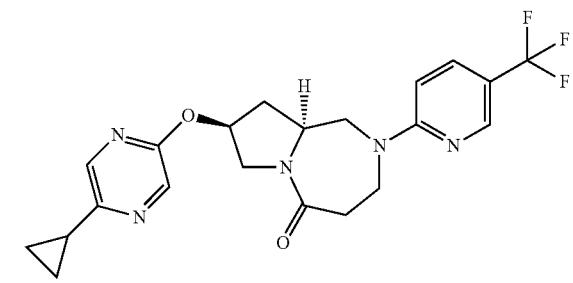 [SMILES: O=C1CCN(c2ccc(C(F)(F)F)cn2)C[C@@H]2C[C@H](Oc3cnc(C4CC4)cn3)CN12]

Part A. Preparation of (8R,9aS)-8-hydroxyoctahydro-5H-pyrrolo[1,2-a][1,4]diazepin-5-one hydrochloride To tert-butyl (8R,9aS)-8-hydroxy-5-oxohexahydro-1H-pyrrolo[1,2-a][1,4]diazepine-2(3H)-carboxylate (122 mg, 0.451 mmol, Example 28, Part E) in methanol (0.2 mL) was added HCl solution (5.42 mmol, 1.35 ml, 4 N in dioxane). The mixture was stirred at room temperature for two hours and then concentrated. The residue was used without purification. MS (APCI) m/z 171 (M+H)$^+$.

Part B. Preparation of (8R,9aS)-8-hydroxy-2-[5-(trifluoromethyl)pyridin-2-yl]octahydro-5H-pyrrolo[1,2-a][1,4]diazepin-5-one A mixture of (8R,9aS)-8-hydroxyoctahydro-5H-pyrrolo[1,2-a][1,4]diazepin-5-one hydrochloride (90 mg, 0.435 mmol, Part A), 2-bromo-5-(trifluoromethyl)pyridine (148 mg, 0.635 mmol) and sodium carbonate (138 mg, 1.306 mmol) in dimethyl sulfoxide (0.4 mL) was stirred at 100° C. overnight. The mixture was purified by chromatography on silica gel (ethyl acetate/methanol=15:1) to give 135 mg (98% yield) of the titled compound. $^1$H NMR (400 MHz, DMSO-$d_6$) δ ppm 1.77 (m, 1H), 2.09 (m, 1 H), 2.50-2.66 (m, 2 H), 3.08 (m, 1 H), 3.35 (m, 2 H), 3.50 (m, 1 H), 3.98 (m, 2 H), 4.20 (m, 1 H), 4.44 (m, 1 H), 4.55 (m, 1H), 4.88 (br s, 1H), 7.01 (d, J=8 Hz, 1H), 7.81 (d, J=8 Hz, 1H), 8.43 (s, 1H); MS (ESI) m/z 316.0 (M+H)$^+$.

Part C. Preparation of (8S,9aS)-5-oxo-2-[5-(trifluoromethyl)pyridin-2-yl]octahydro-1H-pyrrolo[1,2-a][1,4]diazepin-8-yl 4-nitrobenzoate (8R,9aS)-8-Hydroxy-2-[5-(trifluoromethyl)pyridin-2-yl]octahydro-5H-pyrrolo[1,2-a][1,4]diazepin-5-one (100 mg, 0.317 mmol, Part B), triphenylphosphine (104 mg, 0.396 mmol), and 4-nitrobenzoic acid (80 mg, 0.476 mmol) were dissolved in tetrahydrofuran (2 mL), and the resulting solution was cooled to −78° C. Diisopropyl azodicarboxylate (77 mg, 0.381 mmol) in tetrahydrofuran (0.5 mL) was added. The mixture was warmed to room temperature and stirred for two hours. Then 1 drop of water was added. The mixture was purified by chromatography on silica gel (ethyl acetate/heptanes=1:1 then 100% ethyl acetate) to give 138 mg (94% yield) of the titled compound as a solid. $^1$H NMR (400 MHz, CDCl$_3$) δ ppm 2.20 (m, 1H), 2.77 (m, 3 H), 3.33 (m, 1 H), 3.47 (m, 1 H), 3.88 (m, 1 H), 4.00 (m, 1H), 4.12 (m, 1H), 4.37 (m, 1H), 4.77 (dd, J=14, 4 Hz, 1 H), 5.54 (m, 1H), 6.67 (d, J=8 Hz, 1 H), 7.69 (d, J=8 Hz, 1 H), 8.20 (d, J=8 Hz, 2 H), 8.35 (d, J=8 Hz, 2 H), 8.42 (s, 1 H); MS (ESI) m/z 465.0 (M+H)$^+$.

Part D. Preparation of (8S,9aS)-8-hydroxy-2-[5-(trifluoromethyl)pyridin-2-yl]octahydro-5H-pyrrolo[1,2-a][1,4]diazepin-5-one To (8S,9aS)-5-oxo-2-[5-(trifluoromethyl)pyridin-2-yl]octahydro-1H-pyrrolo[1,2-a][1,4]diazepin-8-yl-4-nitrobenzoate (135 mg, 0.291 mmol, Part C) in methanol (2.5 mL) was added potassium carbonate (24 mg, 0.174 mmol). The mixture was stirred at room temperature for 1.5 hours and then concentrated. The residue was purified by chromatography on silica gel (ethyl acetate, then ethyl acetate/methanol=10:1) to give 78 mg (85% yield) of the titled compound as a solid. $^1$H NMR (400 MHz, DMSO-$d_6$) δ ppm 1.72 (m, 1H), 2.28 (m, 1 H), 2.45 (m, 1H), 2.63 (m, 1 H), 3.35 (m, 3 H), 3.44 (m, 1 H), 3.92 (m, 1H), 4.17 (m, 1H), 4.42 (m, 2H), 5.09 (br s, 1H), 7.00 (d, J=8 Hz, 1 H), 7.80 (d, J=8 Hz, 1 H), 8.43 (s, 1 H); MS (ESI) m/z 316.0 (M+H)$^+$.

Part E. Preparation of (8S,9aS)-8-[(5-cyclopropylpyrazin-2-yl)oxy]-2-[5-(trifluoromethyl)pyridin-2-yl]octahydro-5H-pyrrolo[1,2-a][1,4]diazepin-5-one To (8S,9aS)-8-hydroxy-2-[5-(trifluoromethyl)pyridin-2-yl]octahydro-5H-pyrrolo[1,2-a][1,4]diazepin-5-one (74 mg, 0.235 mmol, Part D), 2-bromo-5-cyclopropylpyrazine (79 mg, 0.4 mmol) in tetrahydrofuran (1.2 mL) was added potassium tert-butoxide (0.47 ml, 0.47 mmol, 1 M in tetrahydrofuran). The mixture was stirred at room temperature overnight. The mixture was purified by chromatography on silica gel (ethyl acetate) to give 48 mg (47%) of the titled compound as a solid. $^1$H NMR (400 MHz, CDCl$_3$) δ ppm 0.88-1.04 (m, 4H), 2.00 (m, 1 H), 2.15 (br d, J=14 Hz, 1 H), 2.66 (m, 1 H), 2.72 (m, 2 H), 3.36 (dd, J=14, 10 Hz, 1 H), 3.48 (m, 1 H), 3.83 (dd, J=12, 8 Hz, 1 H), 3.90 (br d, J=12 Hz, 1 H), 4.03 (m, 1H), 4.34 (br d, J=15 Hz, 1 H), 4.63 (d, J=14 Hz, 1 H), 5.44 (m, 1H), 6.65 (d, J=9 Hz, 1 H), 7.66 (dd, J=9, 2 Hz, 1 H), 7.95 (s, 1 H), 8.06 (s, 1 H), 8.41 (s, 1 H); MS (ESI) m/z 434.0 (M+H)$^+$.

Example 31

Preparation of (8R,9aS)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one

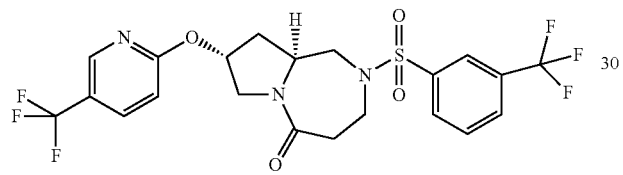

Part A. Preparation of tert-butyl (8R,9aS)-5-oxo-8-{[5-(trifluoromethyl)pyridin-2-yl]oxy}hexahydro-1H-pyrrolo[1,2-a][1,4]diazepine-2(3H)-carboxylate The title compound was prepared according to the procedure described for Example 28, Part F, substituting 2-chloro-5-(trifluoromethyl)pyridine for 2-bromo-5-cyclopropylpyrazine.

Part B. Preparation of (8R,9aS)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one The title compound was prepared according to the procedure described for Example 28, Part G, substituting the product from Part A for the product from Example 28, Part F. $^1$H NMR (400 MHz, pyridine-d$_5$, 90° C.) δ ppm 8.47 (d, J=3.1 Hz, 1H), 8.29 (bs, 1H), 8.16-8.10 (m, 1H), 7.90-7.83 (m, 1H), 7.79 (dd, J=8.7, 2.6 Hz, 1H), 7.66 (t, J=7.8 Hz, 1H), 6.79 (d, J=8.6 Hz, 1H), 5.59-5.53 (m, 1H), 4.31-4.21 (m, 2H), 4.19 (d, J=14.6 Hz, 1H), 4.16-4.05 (m, 1H), 3.73 (dd, J=13.5, 4.3 Hz, 1H), 2.93-2.83 (m, 1H), 2.82 (d, J=12.0 Hz, 1H), 2.80-2.73 (m, 1H), 2.73 (d, J=4.1 Hz, 1H), 2.46 (ddt, J=14.0, 6.8, 1.9 Hz, 1H), 1.94 (ddd, J=14.1, 9.6, 4.6 Hz, 1H); MS (ESI) m/z 524 (M+H)$^+$.

Example 32

Preparation of (8R,9aS)-8-[(5-cyclopropylpyrazin-2-yl)oxy]-2-[3-(trifluoromethyl)benzoyl]octahydro-5H-pyrrolo[1,2-a][1,4]diazepin-5-one

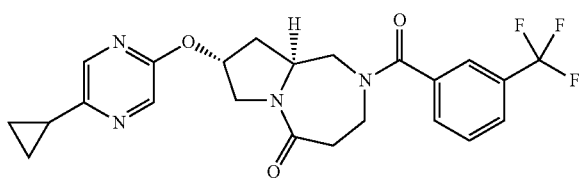 [SMILES: O=C(c1cccc(C(F)(F)F)c1)N1CCC(=O)N2C[C@H](Oc3cnc(C4CC4)cn3)C[C@H]2C1]

The title compound was prepared according to the procedure described in Example 28, Part G, substituting 3-(trifluoromethyl)benzoyl chloride for 3-(trifluoromethyl)benzene-1-sulfonyl chloride. $^1$H NMR (500 MHz, pyridine-d$_5$) δ ppm 8.20-7.87 (m, 3H), 7.86-7.68 (m, 2H), 7.56-7.46 (m, 1H), 5.48 (bs, 1H), 4.41-4.15 (m, 3H), 4.02-3.69 (m, 1H), 3.64-3.55 (m, 1H), 3.11-2.70 (m, 3H), 2.62 (dd, J=13.2, 9.2 Hz, 1H), 2.54-2.40 (m, 1H), 2.11-1.98 (m, 1H), 1.92 (ddd, J=14.2, 10.0, 4.3 Hz, 1H), 1.14-0.99 (m, 2H), 1.01-0.86 (m, 2H); MS (ESI) m/z 461 (M+H)$^+$.

Example 33

Preparation of (8R,9aS)-8-[(5-cyclopropylpyrazin-2-yl)oxy]-2-[4-(trifluoromethyl)benzoyl]octahydro-5H-pyrrolo[1,2-a][1,4]diazepin-5-one

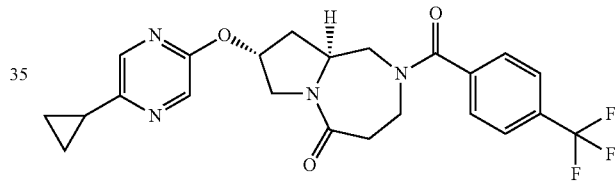

The title compound was prepared according to the procedure described in Example 28, Part G, substituting 4-(trifluoromethyl)benzoyl chloride for 3-(trifluoromethyl)benzene-1-sulfonyl chloride. $^1$H NMR (500 MHz, pyridine-d$_5$) δ ppm 8.19-7.98 (m, 2H), 7.76 (bs, 4H), 5.48 (bs, 1H), 4.60-4.29 (m, 2H), 4.15-3.71 (m, 2H), 3.62 (s, 2H), 3.45-2.64 (m, 3H), 2.52-2.39 (m, 1H), 2.18-1.75 (m, 3H), 1.13-1.04 (m, 2H), 1.01-0.85 (m, 2H); MS (ESI) m/z 461 (M+H)$^+$.

Example 34

Preparation of (8R,9aS)-8-[(5-cyclopropylpyrazin-2-yl)oxy]-2-[2-fluoro-3-(trifluoromethyl)benzoyl]octahydro-5H-pyrrolo[1,2-a][1,4]diazepin-5-one

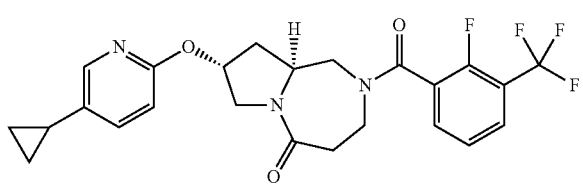 [SMILES: O=C(c1cccc(C(F)(F)F)c1F)N1CCC(=O)N2C[C@H](Oc3ccc(C4CC4)cn3)C[C@H]2C1]

The title compound was prepared according to the procedure described in Example 28, Part G, substituting 2-fluoro- 3-(trifluoromethyl)benzoyl chloride for 3-(trifluoromethyl)benzene-1-sulfonyl chloride. $^1$H NMR (500 MHz, pyridine-$d_5$) δ ppm 8.25-8.14 (m, 0.5H), 8.10 (d, J=6.8, 1H), 8.04-7.99 (m, 0.5H), 7.98-7.75 (m, 1H), 7.72-7.61 (m, 1H), 7.42-7.24 (m, 1H), 5.53-5.41 (m, 1H), 5.19-4.99 (m, 1H), 4.55-4.26 (m, 2H), 3.98-3.69 (m, 2H), 3.50-3.09 (m, 1H), 3.02-2.80 (m, 2H), 2.79-2.69 (m, 1H), 2.54-2.36 (m, 1H), 2.11-1.83 (m, 2H), 1.15-0.99 (m, 2H), 0.99-0.85 (m, 2H); MS (ESI) m/z 479 (M+H)$^+$.

Example 35

Preparation of (8R,9aS)-8-[(5-cyclopropylpyrazin-2-yl)oxy]-2-[3-fluoro-4-(trifluoromethyl)benzoyl]octahydro-5H-pyrrolo[1,2-a][1,4]diazepin-5-one

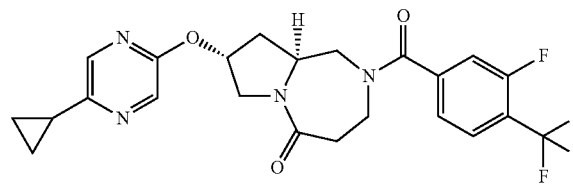

The title compound was prepared according to the procedure described in Example 28, Part G, substituting 3-fluoro-4-(trifluoromethyl)benzoyl chloride for 3-(trifluoromethyl)benzene-1-sulfonyl chloride. $^1$H NMR (500 MHz, pyridine-$d_5$) δ ppm 8.14 (bs, 1H), 7.93 (m, 2H), 7.78-7.63 (m, 2H), 5.52-5.41 (m, 1H), 4.63-4.27 (m, 2H), 4.15-3.77 (m, 2H), 3.56-2.72 (m, 4H), 2.53-2.40 (m, 2H), 2.09-1.87 (m, 2H), 1.19-0.98 (m, 2H), 1.00-0.86 (m, 2H); MS (ESI) m/z 479 (M+H)$^+$.

Example 36

Preparation of (8R,9aS)-8-[(5-cyclopropylpyrazin-2-yl)oxy]-2-[4-fluoro-3-(trifluoromethyl)benzoyl]octahydro-5H-pyrrolo[1,2-a][1,4]diazepin-5-one

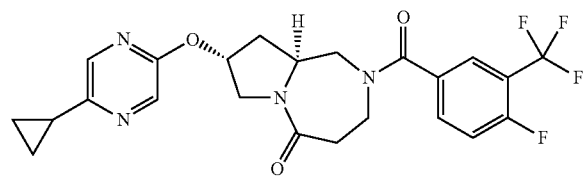 [SMILES: O=C(c1ccc(F)c(C(F)(F)F)c1)N1CCC(=O)N2C[C@H](Oc3cnc(C4CC4)cn3)C[C@H]2C1]

The title compound was prepared according to the procedure described in Example 28, Part G, substituting 4-fluoro-3-(trifluoromethyl)benzoyl chloride for 3-(trifluoromethyl)benzene-1-sulfonyl chloride. $^1$H NMR (500 MHz, pyridine-$d_5$) δ ppm 8.14 (bs, 1H), 8.09-8.02 (m, 2H), 7.89 (bs, 1H), 7.40-7.31 (m, 1H), 5.48 (bs, 1H), 4.42-4.34 (m, 2H), 4.30-3.68 (m, 2H), 3.62-2.67 (m, 4H), 2.52-2.43 (m, 2H), 2.05-1.97 (m, 2H), 1.13-1.05 (m, 2H), 0.96-0.90 (m, 2H); MS (ESI) m/z 479 (M+H)$^+$.

Example 37

Preparation of (8R,9aS)-8-[(5-cyclopropylpyrazin-2-yl)oxy]-2-[3-(trifluoromethoxy)benzoyl]octahydro-5H-pyrrolo[1,2-a][1,4]diazepin-5-one

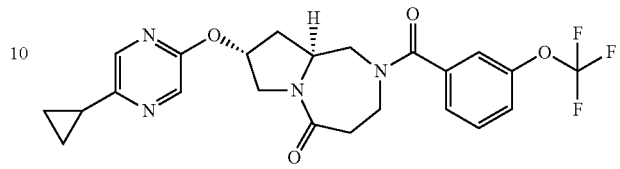

The title compound was prepared according to the procedure described in Example 28, Part G, substituting 3-(trifluoromethoxy)benzoyl chloride for 3-(trifluoromethyl)benzene-1-sulfonyl chloride. $^1$H NMR (500 MHz, pyridine-$d_5$) δ ppm 8.14 (bs, 1H), 8.07 (bs, 1H), 7.66 (m, 1H), 7.49-7.32 (m, 2H), 5.47 (bs, 1H), 4.41-4.34 (m, 2H), 3.88-3.80 (m, 2H), 3.61-2.58 (m, 4H), 2.51-2.34 (m, 2H), 2.16-1.61 (m, 2H), 1.10-1.05 (m, 2H), 0.96-0.89 (m, 2H); MS (ESI) m/z 477 (M+H)$^+$.

Example 38

Preparation of (8R,9aS)-8-[(5-cyclopropylpyrazin-2-yl)oxy]-2-[4-(trifluoromethoxy)benzoyl]octahydro-5H-pyrrolo[1,2-a][1,4]diazepin-5-one

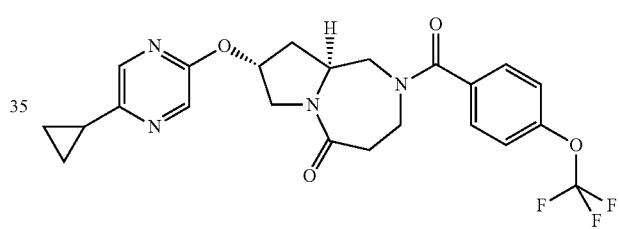

The title compound was prepared according to the procedure described in Example 28, Part G, substituting 4-(trifluoromethoxy)benzoyl chloride for 3-(trifluoromethyl)benzene-1-sulfonyl chloride. $^1$H NMR (400 MHz, pyridine-$d_5$, 90° C.) δ ppm 8.07 (d, J=1.3 Hz, 1H), 7.98 (d, J=1.3 Hz, 1H), 7.66-7.56 (m, 2H), 7.28 (d, J=8.0 Hz, 2H), 5.50-5.43 (m, 1H), 4.50 (d, J=12.3 Hz, 1H), 4.37-4.15 (m, 2H), 3.82 (dd, J=13.6, 4.4 Hz, 2H), 3.24 (ddd, J=14.4, 10.8, 1.9 Hz, 1H), 3.01 (dd, J=14.1, 9.4 Hz, 1H), 2.82 (dd, J=15.2, 2.6 Hz, 1H), 2.79-2.64 (m, 1H), 2.46-2.37 (m, 1H), 2.04-1.88 (m, 2H), 1.30-0.92 (m, 2H), 0.93-0.78 (m, 2H); MS (ESI) m/z 477 (M+H)$^+$.

Example 39

Preparation of (trifluoromethyl)phenyl]acetyl}octahydro-5H-pyrrolo[1,2-a][1,4]diazepin-5-one

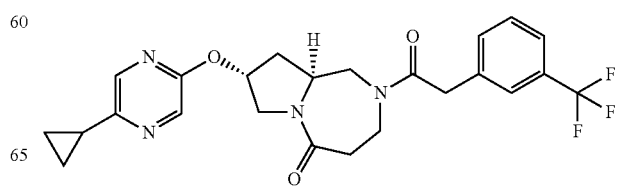

To a solution of the product from Example 28, Part F (95 mg, 0.245 mmol) in anhydrous methanol (3 mL) was added 4 M HCl in 1,4-dioxane (0.611 mL, 2.446 mmol). The resulting mixture was stirred at room temperature for 18 hours, and the solvent was removed in vacuo. The resulting solid was dissolved in dichloromethane (3 mL) and triethylamine (0.112 mL, 0.807 mmol). To the solution was added 2-(3-(trifluoromethyl)phenyl)acetic acid (0.055 g, 0.269 mmol), 1-hydroxybenzotriazole hydrate (0.041 g, 269 mmol) and N-(3-dimethylaminopropyl)-N'-ethylcarbodiimide hydrochloride (0.052 g, 0.269 mmol), and the resulting mixture was stirred at room temperature for 16 hours. The mixture was partitioned between water and dichloromethane. The organic extract was washed with brine, dried over $MgSO_4$, filtered, and concentrated in vacuo. The crude product was purified by column chromatography on silica gel using a solvent gradient of 0-2% methanol in dichloromethane. The resulting oil was triturated with ethyl acetate and hexanes to give a solid that was collected by filtration and dried to give the title compound as a colorless solid (0.085 g, 73%). $^1$H NMR (400 MHz, pyridine-$d_5$, 90° C.) δ ppm 8.06-7.96 (m, 2H), 7.73 (bs, 1H), 7.56 (d, J=1.3 Hz, 1H), 7.49 (d, J=1.3 Hz, 1H), 7.38 (t, J=7.8 Hz, 1H), 5.44 (t, J=4.5 Hz, 1H), 5.14-4.23 (m, 2H), 4.20-4.13 (m, 1H), 4.05 (t, J=7.1 Hz, 1H), 3.94 (bs, 2H), 5.84-3.75 (m, 1H), 3.68-2.67 (m, 3H), 2.68-2.57 (m, 1H), 2.37 (ddt, J=13.9, 6.6, 1.9 Hz, 1H), 2.04-1.86 (m, 2H), 1.07-0.94 (m, 2H), 0.95-0.78 (m, 2H); MS (ESI) m/z 475 (M+H)$^+$.

Example 40

Preparation of (8R,9aS)-8-[(5-cyclopropylpyrazin-2-yl)oxy]-2-{hydroxy[3-(trifluoromethyl)phenyl]acetyl}octahydro-5H-pyrrolo[1,2-a][1,4]diazepin-5-one

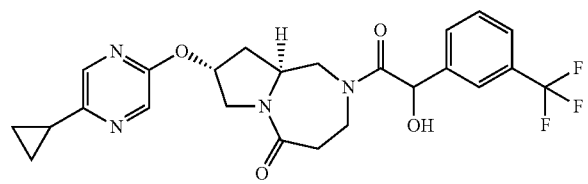 [SMILES: O=C(C(O)c1cccc(C(F)(F)F)c1)N1CCC(=O)N2C[C@H](Oc3cnc(C4CC4)cn3)C[C@H]2C1]

To a solution of the product from Example 28, Part F (90 mg, 0.232 mmol) in anhydrous methanol (3 mL) was added 4 M HCl in 1,4-dioxane (0.579 mL, 2.317 mmol). The resulting mixture was stirred at room temperature for 18 hours, and the volatiles were removed in vacuo. The residue was suspended in N,N-dimethylformamide (3 mL), 2-hydroxy-2-(3-(trifluoromethyl)phenyl)acetic acid (0.056 g, 0.255 mmol), O-(7-azabenzotriazol-1-yl)-N,N,N',N'-tetramethyluronium hexafluorophosphate (HATU, 0.106 g, 0.278 mmol), and N-methyl morpholine (0.117 g, 1.158 mmol) were added, and the resulting solution was stirred at room temperature for 16 hours. The mixture was partitioned between water and ethyl acetate. The organic extract was washed with brine, dried over $MgSO_4$, filtered, and concentrated in vacuo. The crude product was purified by column chromatography on silica gel using a solvent gradient of 0-7% methanol in dichloromethane. The title compound was obtained as a colorless solid (0.065 g, 57% yield). $^1$H NMR (400 MHz, pyridine-$d_5$, 90° C.) δ ppm 8.09-7.99 (m, 2H), 7.98 (d, J=1.4 Hz, 1H), 7.87-7.79 (m, 1H), 7.56 (d, J=1.3 Hz, 1H), 7.43 (t, J=7.8 Hz, 1H), 5.94-5.85 (m, 1H), 5.40 (t, J=4.1 Hz, 1H), 4.90-4.15 (m, 3H), 4.12 (d, J=13.5 Hz, 1H), 3.73 (dd, J=13.5, 4.3 Hz, 1H), 3.50-2.15 (m, 6H), 2.07-1.79 (m, 2H), 1.05-0.93 (m, 2H), 0.95-0.83 (m, 2H).); MS (ESI) m/z 491 (M+H)$^+$.

Example 41

Preparation of (8R,9aS)-8-[(5-cyclopropylpyrazin-2-yl)oxy]-2-{(methylamino)[3-(trifluoromethyl)phenyl]acetyl}octahydro-5H-pyrrolo[1,2-a][1,4]diazepin-5-one

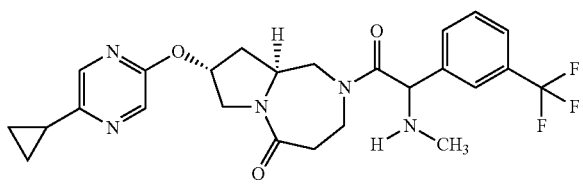 [SMILES: CNC(C(=O)N1CCC(=O)N2C[C@H](Oc3cnc(C4CC4)cn3)C[C@H]2C1)c1cccc(C(F)(F)F)c1]

To a solution of the product from Example 40 (50 mg, 0.102 mmol) in dichloromethane (2 mL), was added methanesulfonyl chloride (0.009 mL, 0.112 mmol) followed by diisopropylethylamine (0.027 mL, 153 mmol), and the resulting mixture was stirred at room temperature for 16 hours. The mixture was partitioned between water and dichloromethane, and the organic extract was washed with brine and dried over $MgSO_4$. The drying agent was removed by filtration, and the filtrate was concentrated in vacuo. The oily residue was dissolved in tetrahydrofuran (2.0 mL), a 2.0 M solution of methylamine in tetrahydrofuran (0.242 mL, 0.484 mmol) was added, and the resulting mixture was stirred at 45° C. for 16 hours. The mixture was concentrated in vacuo, and the residue was partitioned between ethyl acetate and water. The organic extract was washed with brine, dried over $MgSO_4$, filtered, and concentrated in vacuo. The crude product was purified by column chromatography on silica gel using a solvent gradient of 0-10% methanol in dichloromethane. The title compound was obtained as a waxy solid (0.011 g, 23%). $^1$H NMR (501 MHz, pyridine-$d_5$, 90° C.) δ ppm 8.06-7.90 (m, 3H), 7.73 (t, J=6.9 Hz, 1H), 7.55 (d, J=7.5 Hz, 1H), 7.46-7.28 (m, 1H), 5.42 (m, 1H), 4.89 (d, J=24.0 Hz, 1H), 4.14 (d, J=13.8 Hz, 1H), 3.76 (dd, J=13.4, 4.4 Hz, 1H), 3.32-2.44 (m, 4H), 2.39 (d, J=4.9 Hz, 3H), 2.28-1.79 (m, 2H), 1.69-1.10 (m, 5H), 1.07-0.78 (m, 4H); MS (ESI) m/z 504 (M+H)$^+$.

Example 42

Preparation of (8R,9aS)-8-[(5-cyclopropylpyrazin-2-yl)oxy]-2-[3-(trifluoromethyl)benzyl]octahydro-5H-pyrrolo[1,2-a][1,4]diazepin-5-one

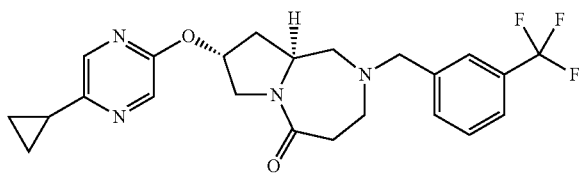 [SMILES: O=C1CCN(Cc2cccc(C(F)(F)F)c2)C[C@@H]2C[C@@H](Oc3cnc(C4CC4)cn3)CN12]

To a solution of the product from Example 28, Part F (65 mg, 0.167 mmol) in anhydrous methanol (3 mL) was added 4 M HCl in 1,4-dioxane (0.418 mL, 1.673 mmol). The resulting mixture was stirred at room temperature for 18 hours, and the volatiles were removed in vacuo. The resulting solid was dissolved in dichloromethane (3 mL) and triethylamine (0.117 mL, 0.837 mmol). To the solution was added 3-(trifluoromethyl)benzaldehyde (29 mg, 0.167 mmol), acetic acid (0.029 mL, 0.507 mmol), and polymer-supported cyanoborohydride (73 mg, 0.753 mmol). The resulting mixture was stirred at room temperature for 18 hours; then the mixture was filtered and concentrated in vacuo. The crude product was purified by column chromatography on silica gel using a solvent gradient of 0-10% methanol in dichloromethane. The title compound was obtained as a waxy solid (0.048 g, 64%). $^1$H NMR (400 MHz, pyridine-$d_5$, 90° C.) δ ppm 8.08 (d, J=1.3 Hz, 1H), 7.98 (d, J=1.4 Hz, 1H), 7.74 (bs, 1H), 7.56 (t, J=7.7 Hz, 2H), 7.42 (t, J=7.7 Hz, 1H), 5.47-5.41 (m, 1H), 4.29-4.17 (m, 2H), 3.75 (dd, J=13.4, 4.4 Hz, 1H), 3.62 (s, 2H), 3.51 (s, 1H), 2.98-2.90 (m, 1H), 2.91-2.75 (m, 2H), 2.59 (dd, J=14.8, 6.8 Hz, 1H), 2.46-2.28 (m, 2H), 2.20 (dd, J=12.7, 9.2 Hz, 1H), 2.03-1.93 (m, 1H), 1.82 (ddd, J=14.1, 9.6, 4.6 Hz, 1H), 1.03-0.93 (m, 2H), 0.94-0.83 (m, 2H); MS (ESI) m/z 447 (M+H)$^+$.

Example 43

Preparation of (8R,9aS)-8-[(5-cyclopropylpyrazin-2-yl)oxy]-2-[3-(trifluoromethoxy)benzyl]octahydro-5H-pyrrolo[1,2-a][1,4]diazepin-5-one

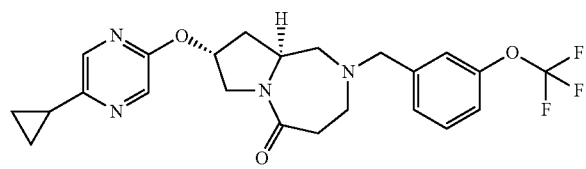 [SMILES: O=C1CCN(Cc2cccc(OC(F)(F)F)c2)C[C@@H]2C[C@@H](Oc3cnc(C4CC4)cn3)CN12]

The title compound was prepared according to the procedure described in Example 42 substituting 3-(trifluoromethoxy)benzaldehyde for 3-(trifluoromethyl)benzaldehyde. $^1$H NMR (400 MHz, pyridine-$d_5$, 90° C.) δ ppm 8.08 (d, J=1.4 Hz, 1H), 7.98 (d, J=1.4 Hz, 1H), 7.44-7.37 (m, 2H), 7.23 (d, J=1.4 Hz, 2H), 5.47-5.41 (m, 1H), 4.27-4.17 (m, 2H), 3.75 (dd, J=13.4, 4.4 Hz, 1H), 3.56 (s, 2H), 2.97-2.89 (m, 1H), 2.91-2.76 (m, 2H), 2.64-2.55 (m, 1H), 2.40 (d, J=12.2 Hz, 1H), 2.37-2.27 (m, 1H), 2.17 (dd, J=12.7, 9.2 Hz, 1H), 2.03-1.93 (m, 1H), 1.82 (ddd, J=14.0, 9.6, 4.5 Hz, 1H), 1.03-0.92 (m, 2H), 0.92-0.84 (m, 2H); MS (ESI) m/z 463 (M+H)$^+$.

Example 44

Preparation of (8R,9aS)-8-[(5-cyclopropylpyrazin-2-yl)oxy]-2-[4-(trifluoromethoxy)benzyl]octahydro-5H-pyrrolo[1,2-a][1,4]diazepin-5-one

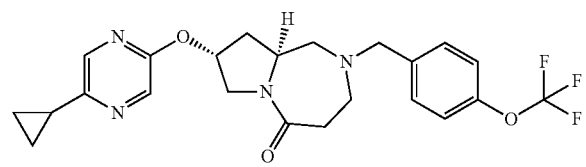 [SMILES: O=C1CCN(Cc2ccc(OC(F)(F)F)cc2)C[C@@H]2C[C@@H](Oc3cnc(C4CC4)cn3)CN12]

The title compound was prepared according to the procedure described in Example 42 substituting 4-(trifluoromethoxy)benzaldehyde for 3-(trifluoromethyl)benzaldehyde. $^1$H NMR (400 MHz, pyridine-$d_5$, 90° C.) δ ppm 8.09 (d, J=1.4 Hz, 1H), 7.98 (d, J=1.4 Hz, 1H), 7.36 (d, J=2.9 Hz, 1H), 7.36-7.27 (m, 2H), 7.17 (d, J=2.9 Hz, 1H), 5.44 (t, J=4.6 Hz, 1H), 4.29-4.17 (m, 2H), 3.75 (dd, J=13.4, 4.3 Hz, 1H), 3.59 (s, 2H), 2.97-2.75 (m, 3H), 2.64-2.55 (m, 1H), 2.45-2.28 (m, 2H), 2.19 (dd, J=12.7, 9.2 Hz, 1H), 2.03-1.93 (m, 1H), 1.82 (ddd, J=14.1, 9.6, 4.5 Hz, 1H), 1.06-0.92 (m, 2H), 0.94-0.78 (m, 2H); MS (ESI) m/z 463 (M+H)$^+$.

Example 45

Preparation of (8R,9aS)-2-[3-(trifluoromethyl)benzyl]-8-{[5-(trifluoromethyl)pyridin-2-yl]oxy}octahydro-5H-pyrrolo[1,2-a][1,4]diazepin-5-one

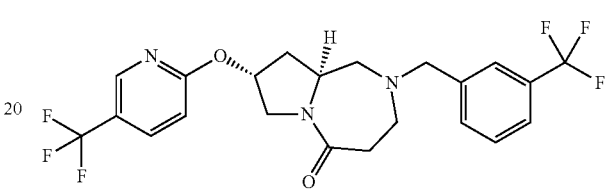

The title compound was prepared according to the procedure described in Example 42 substituting the product from Example 31, Part A for the product from Example 28, Part F. $^1$H NMR (400 MHz, pyridine-$d_5$, 90° C.) δ ppm 8.50-8.45 (m, 1H), 7.81-7.73 (m, 2H), 7.62-7.52 (m, 2H) 7.42 (t, J=7.7 Hz, 1H), 6.79 (d, J=8.7 Hz, 1H), 5.58 (t, J=4.6 Hz, 1H), 4.30-4.18 (m, 2H), 3.78 (dd, J=13.4, 4.3 Hz, 1H), 3.63 (s, 2H), 2.99-2.92 (m, 1H), 2.92-2.75 (m, 2H), 2.65-2.55 (m, 1H), 2.47-2.30 (m, 2H), 2.22 (dd, J=12.7, 9.2 Hz, 1H), 1.85 (ddd, J=14.1, 9.7, 4.6 Hz, 1H); MS (ESI) m/z 474 (M+H)$^+$.

Example 46

Preparation of (8S,9aR)-8-[(5-cyclopropylpyrazin-2-yl)oxy]-2-[5-(trifluoromethyl)pyridin-2-yl]octahydro-5H-pyrrolo[1,2-a][1,4]diazepin-5-one

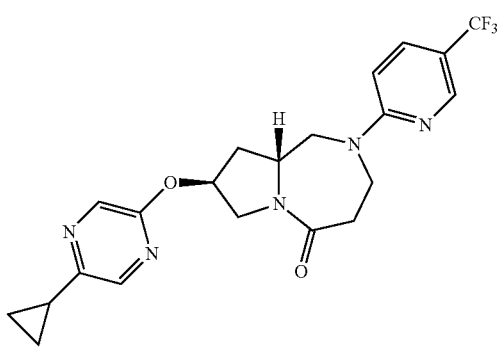 [SMILES: O=C1CCN(c2ccc(C(F)(F)F)cn2)C[C@H]2C[C@H](Oc3cnc(C4CC4)cn3)CN12]

Part A. Preparation of tert-butyl (2R,4R)-4-(benzyloxy)-2-formylpyrrolidine-1-carboxylate and tert-butyl (2S,4R)-4-(benzyloxy)-2-formylpyrrolidine-1-carboxylate To a solution of tert-butyl (2S,4R)-4-(benzyloxy)-2-formylpyrrolidine-1-carboxylate (17 g, 0.055 mol, Example 28, Part B) in tetrahydrofuran (180 mL) was added 1,8-diazabicyclo[5.4.0]undec-7-ene (4.25 g, 0.0276 mol) at 10° C., and the reaction mixture was stirred at 20-25° C. for 16 hours. The reaction mixture was concentrated, diluted with dichloromethane (200 mL) and washed with water (200 mL×2). The organic layer was dried over anhydrous sodium sulfate and concentrated to give a mixture of tert-butyl (2R,4R)-4-(benzyloxy)-2-formylpyrrolidine-1-carboxylate and tert-butyl (2S,4R)-4-(benzyloxy)-2-formylpyrrolidine-1-carboxylate, (17 g, 100%) as pale brown oil which was taken as such for the next step without any purification.

Part B. Preparation of tert-butyl (2R,4R)-2-{[benzyl (3-ethoxy-3-oxopropyl)amino]methyl}-4-(benzyloxy)pyrrolidine-1-carboxylate and tert-butyl (2S, 4R)-2-{[benzyl(3-ethoxy-3-oxopropyl)amino] methyl}-4-(benzyloxy)pyrrolidine-1-carboxylate Sodium triacetoxyborohydride (17.7 g, 0.083 mol) was added to a solution of ethyl 3-(benzylamino)propanoate (11.5 g, 0.055 mol) and Part A (17 g, 0.055 mol) in dichloromethane (200 mL) at 10° C. The resultant mixture was stirred at 25° C. for 30 minutes. The reaction mixture was quenched with saturated sodium bicarbonate solution (150 mL) and extracted with dichloromethane (100 mL). The organic layer was separated, washed with water (100 mL) and brine (50 mL), dried over anhydrous sodium sulfate, filtered and concentrated to supply tert-butyl (2R,4R)-2-{[benzyl(3-ethoxy-3-oxopropyl)amino]methyl}-4-(benzyloxy)pyrrolidine-1-carboxylate and tert-butyl (2S,4R)-2-{[benzyl(3-ethoxy-3-oxopropyl)amino]methyl}-4-(benzyloxy)pyrrolidine-1-carboxylate (20.3 g, 73.8%) as pale yellow oil in a ratio of 2:3 determined by HPLC (column: Agilent ZORBAX® Eclipse XDB C18, 150 mm×4.6 mm, 3.5 µm; gradient: 5-90% acetonitrile in 20 mM ammonium acetate/water over nine minutes with a hold at 90% for an additional seven minutes; flow rate: 1.0 mL/minute; temperature: 25° C.). Retention time for the (2R,4R) isomer was 13.293 minutes and for the (2S,4R) isomer, 13.626 minutes. $^1$H NMR (300 MHz, CDCl$_3$) δ ppm 7.41-7.20 (m, 10 H), 4.45-3.79 (m, 6 H), 3.64-3.28 (m, 3 H), 3.10-1.90 (m, 9 H), 1.56-1.42 (m, 9 H), 1.32-1.20 (m, 3 H).

Part C. Preparation of (8R,9aR)-2-benzyl-8-(benzyloxy)octahydro-5H-pyrrolo[1,2-a][1,4]diazepin-5-one To a 2:3 mixture of tert-butyl (2R,4R)-2-{[benzyl(3-ethoxy-3-oxopropyl)amino]methyl}-4-(benzyloxy)pyrrolidine-1-carboxylate and tert-butyl (2S,4R)-2-{[benzyl(3-ethoxy-3-oxopropyl)amino]methyl}-4-(benzyloxy) pyrrolidine-1-carboxylate (25 g, 0.050 mol, Part B) in methanol (125 mL) was added a solution of 4.0 M HCl/dioxane (125 mL) while maintaining the internal temperature below 5° C. The reaction mixture was allowed to stir at 20-25° C. for 22 hours and was then concentrated. The residue was stirred with toluene (250 mL) and 1 M sodium carbonate solution (250 mL). The organic layer was separated, washed with water (100 mL) and brine (100 mL), dried over anhydrous sodium sulfate and filtered. The toluene filtrate was heated to reflux at 115° C. for four hours and was then concentrated. The isomers were separated by silica gel column chromatography eluted with ethyl acetate/hexane (60:40) to give (8R,9aR)-2-benzyl-8-(benzyloxy)octahydro-5H-pyrrolo[1,2-a][1,4]diazepin-5-one (6.2 g, 35%) as dark brown oil. HPLC (column: Agilent ZORBAX® RX-C8, 150 mm×4.6 mm, 5 µm; gradient: 10-80% acetonitrile in 0.1% phosphoric acid/water over 13 minutes with a hold at 80% for an additional five minutes; flow rate: 1.0 mL/minute; temperature: 30° C.). Retention time for the titled isomer was 7.147 minutes and for the (8R,9aS) isomer, 6.704 minutes. $^1$H NMR (300 MHz, CDCl$_3$) δ ppm 7.41-7.23 (m, 10 H), 4.62-4.47 (m, 2 H), 4.11-3.96 (m, 2 H), 3.83-3.75 (m, 1 H), 3.64-3.56 (m, 3 H), 3.02-2.74 (m, 3 H), 2.61-2.53 (m, 1 H), 2.47-2.36 (m, 3 H), 1.88-1.79 (m, 1 H).

Part D. Preparation of tert-butyl (8R,9aR)-8-hydroxy-5-oxohexahydro-1H-pyrrolo[1,2-a][1,4]diazepine-2(3H)-carboxylate To a solution of (8R,9aR)-2-benzyl-8-(benzyloxy)octahydro-5H-pyrrolo[1,2-a][1,4]diazepin-5-one (6 g, 0.017 mol, Part C) in ethanol (60 mL) was added 20% Pd(OH)$_2$/C (3.5 g) and di-tert-butyl dicarbonate (7.5 g, 0.034 mol) in an autoclave. The reaction mixture was hydrogenated (30 psi) at 50° C. for four hours and then filtered through a bed of diatomaceous earth. The filter bed was washed with ethanol (30 mL), and the combined filtrates were concentrated. The residue was dissolved in water (10 ml) and extracted with dichloromethane (25 mL×3). The combined organic layers were dried over anhydrous sodium sulfate and concentrated. The solid obtained was washed with tert-butyl methyl ether (25 mL) to give the titled compound (3 g, 65%) as white solid. HPLC (column: Agilent ZORBAX® RX-C8, 150 mm×4.6 mm, 5 µm; gradient: 40-80% acetonitrile in 0.1% phosphoric acid/water over 13 minutes with a hold at 80% for an additional five minutes; flow rate: 1.5 mL/minute; temperature: 30° C.). Retention time for the titled isomer was 1.389 minutes. Chiral HPLC (column: Chiral Technologies Chiralpak® IC™, 250 mm×4.6 mm, 5 µm; eluent: 15% (1:1) methanol/ethanol in 0.1% triethylamine/heptane; flow rate: 1.0 mL/minute; temperature: 30° C.). Retention time for the titled isomer was 17.355 minutes. $^1$H NMR (300 MHz, CDCl$_3$) δ ppm 4.36-4.46 (m, 1 H) 4.04-4.26 (m, 2 H) 3.81-3.94 (m, 1 H) 3.56-3.71 (m, 2 H) 3.09 (dd, J=14.1, 10.0 Hz, 1 H) 2.52-2.70 (m, 2 H) 2.35-2.48 (m, 1 H) 1.77-1.89 (m, J=9.8, 3.7 Hz, 1 H) 1.47 (s, 9 H); MS (ESI+) m/z 541.6 (2M+H)$^+$.

Part E. Preparation of tert-butyl (8S,9aR)-8-[(4-nitrobenzoyl)oxy]-5-oxohexahydro-1H-pyrrolo[1,2-a][1,4]diazepine-2(3H)-carboxylate tert-Butyl (8R,9aR)-8-hydroxy-5-oxohexahydro-1H-pyrrolo[1,2-a][1,4]diazepine-2(3H)-carboxylate (50 mg, 0.185 mmol, 1.0 equivalent, Part D), triphenylphosphine (60.6 mg, 0.231 mmol, 1.25 equivalents), and 4-nitrobenzoic acid (46.4 mg, 0.277 mmol, 1.5 equivalents) were dissolved in tetrahydrofuran (1.0 mL), and the resulting solution was cooled to −78° C. Diisopropyl azodicarboxylate (0.043 mL, 0.222 mmol, 1.2 equivalents) was dissolved in tetrahydrofuran (0.5 mL), and the resultant solution was added to the reaction mixture. The reaction mixture was removed from the cooling bath and warmed to room temperature for 0.5 hour. After the addition of 1 drop of saturated sodium bicarbonate, the tetrahydrofuran solution was loaded directly onto 2 sequentially linked 4 g silica gel cartridges, eluted with 50-100% ethyl acetate/heptanes over 20 minutes. The titled compound coeluted with triphenylphosphine oxide and was used without additional purification (225 mg combined material). $^1$H NMR (400 MHz, CDCl$_3$) δ ppm 8.28 (d, J=8.9 Hz, 2H), 8.15 (d, J=8.9 Hz, 2H), 5.52 (t, J=4.0 Hz, 1H), 4.53-3.94 (m, 4H), 3.73 (dd, J=14.1, 4.2 Hz, 1H), 3.02 (br s, 1H), 2.78-2.59 (m, 3H), 2.55 (dt, J=13.7, 7.0 Hz, 1H), 2.03-1.91 (m, 1H), 1.47 (s, 9H); MS (ESI+) m/z 419.8 (M+H)$^+$.

Part F. Preparation of tert-butyl (8S,9aR)-8-hydroxy-5-oxohexahydro-1H-pyrrolo[1,2-a][1,4]diazepine-2(3H)-carboxylate tert-Butyl (8S,9aR)-8-[(4-nitrobenzoyl)oxy]-5-oxohexahydro-1H-pyrrolo[1,2-a][1,4]diazepine-2(3H)-carboxylate (156 mg, 0.372 mmol, 1.0 equivalent, Part E) was dissolved in methanol (3 mL). Potassium carbonate (20 mg, 0.145 mmol, 0.39 equivalent) was added and stirring was continued at room temperature for 30 minutes. The solvent was removed in vacuo, and the crude material was loaded onto a 12-g silica column with dichloromethane and eluted with 0-5% methanol:dichloromethane over 15 minutes, held at 5% methanol:dichloromethane for five minutes, then eluted with 10% methanol:dichloromethane for 10 minutes to afford the titled compound (65 mg, 0.240 mmol, 64.6% yield over two steps) as a white solid. $^1$H NMR (300 MHz, CDCl$_3$) δ ppm 4.44 (t, J=3.7 Hz, 1H), 4.39-3.86 (m, J=79.8 Hz, 2H), 4.06 (dt, J=17.5, 8.9 Hz, 1H), 3.83 (dd, J=13.2, 2.3 Hz, 1H), 3.51 (dd, J=13.2, 3.7 Hz, 1H), 3.35-2.96 (br s, 1H), 2.74-2.46 (m, 3H), 2.24 (dd, J=13.2, 6.0 Hz, 1H), 1.74 (ddd, J=12.0, 9.0, 3.0 Hz, 1H), 1.48 (s, 9H); MS (ESI+) m/z 270.9 (M+H)$^+$.

Part G. Preparation of tert-butyl (8S,9aR)-8-[(5-cyclopropylpyrazin-2-yl)oxy]-5-oxohexahydro-1H-pyrrolo[1,2-a][1,4]diazepine-2(3H)-carboxylate tert-Butyl (8S,9aR)-8-hydroxy-5-oxohexahydro-1H-pyrrolo[1,2-a][1,4]diazepine-2(3H)-carboxylate (55 mg, 0.203 mmol, Part F) was dissolved in tetrahydrofuran (1.2 mL). Potassium tert-butoxide (0.400 mL, 0.400 mmol, 1.0 M in tetrahydrofuran, 2.0 equivalents) was added at room temperature, and the resulting solution was stirred for five minutes. Then 2-bromo-5-cyclopropylpyrazine (81 mg, 0.407 mmol, 2.0 equivalents) was added as a solution in tetrahydrofuran (0.5 mL). The reaction was allowed to stir at room temperature for 16 hours, at which point it was quenched with 3 drops of saturated sodium bicarbonate. The mixture was concentrated in vacuo, and the residue was loaded onto a 12 g silica column eluted with 100:0 to 95:5 dichloromethane:methanol over 20 minutes to give the titled compound (41 mg, 52% yield) as a white solid. $^1$H NMR (300 MHz, CDCl$_3$) δ ppm 8.02 (d, J=1.0 Hz, 1H), 7.93 (d, J=1.4 Hz, 1H), 5.44 (t, J=4.0 Hz, 1H), 4.45-4.17 (br s, 2H), 4.07-3.98 (m, 2H), 3.67 (dd, J=13.8, 4.1 Hz, 1H), 3.00 (br s, 1H), 2.73-2.66 (m, 3H), 2.49 (dd, J=12.0, 7.6 Hz, 1H), 2.01-1.82 (m, 2H), 1.48 (s, 9H), 1.02-0.89 (m, 4H); MS (ESI+) m/z 333.0 (M-tBu+H)$^+$.

Part H. Preparation of (8S,9aR)-8-[(5-cyclopropylpyrazin-2-yl)oxy]-2-[5-(trifluoromethyl)pyridin-2-yl]octahydro-5H-pyrrolo[1,2-a][1,4]diazepin-5-one tert-Butyl (8S,9aR)-8-[(5-cyclopropylpyrazin-2-yl)oxy]-5-oxohexahydro-1H-pyrrolo[1,2-a][1,4]diazepine-2(3H)-carboxylate (40 mg, 0.103 mmol, 1.0 equivalent, Part G) was dissolved in methanol (1.0 mL) in a 20-mL scintillation vial. In a separate 4-mL vial, acetyl chloride (0.073 ml, 1.030 mmol, 10.0 equivalents) was added to methanol (0.5 mL) at 0° C., and the resulting acidic solution was added to the reaction mixture. The reaction vial was capped, and the reaction mixture was heated to 60° C. for 0.5 hour. The reaction mixture was cooled to room temperature and concentrated, and (8S,9aR)-8-[(5-cyclopropylpyrazin-2-yl)oxy]octahydro-5H-pyrrolo[1,2-a][1,4]diazepin-5-one hydrochloride was used without additional purification in the next step.

(8S,9aR)-8-[(5-Cyclopropylpyrazin-2-yl)oxy]octahydro-5H-pyrrolo[1,2-a][1,4]diazepin-5-one hydrochloride was dissolved in dimethyl sulfoxide (1.0 mL). 2-Chloro-5-(trifluoromethyl)pyridine (28.0 mg, 0.154 mmol, 1.5 equivalents) and sodium carbonate (65.5 mg, 0.618 mmol, 6.0 equivalents) were added, and the resulting suspension was heated to 115° C. for 14 hours. The reaction was cooled to room temperature, diluted with ethyl acetate, and washed with water and brine, and then dried over sodium sulfate. The solvent was removed in vacuo, and the residue was purified via silica chromatography on 2 sequentially linked 4 g silica cartridges, eluting with 25:75 to 0:100 heptanes:ethyl acetate to give the titled compound (16 mg, 40% yield) as a white solid. $^1$H NMR (300 MHz, CDCl$_3$) δ ppm 8.42 (s, 1H), 7.96 (dd, J=14.0, 1.2 Hz, 2H), 7.67 (dd, J=9.0, 2.4 Hz, 1H), 6.66 (d, J=9.0 Hz, 1H), 5.48 (t, J=4.0 Hz, 1H), 4.81 (d, J=14.6 Hz, 1H), 4.37-4.32 (m, 1H), 4.19-4.10 (m, 1H), 4.04 (dd, J=13.9, 2.2 Hz, 1H), 3.73 (dd, J=13.8, 4.1 Hz, 1H), 3.54-3.36 (m, 1H), 3.04 (dd, J=14.5, 9.4 Hz, 1H), 2.75 (dd, J=6.6, 3.6 Hz, 2H), 2.55 (dd, J=13.8, 5.1 Hz, 1H), 2.05-1.95 (m, 2H), 0.98-0.91 (m, 4H); $^1$H NMR (400 MHz, pyridine-d$_5$) δ ppm 8.63 (s, 1H), 8.16 (d, J=1.1 Hz, 1H), 8.08 (d, J=1.2 Hz, 1H), 7.79 (dd, J=9.0, 2.4 Hz, 1H), 6.90 (d, J=9.1 Hz, 1H), 5.52 (t, J=4.0 Hz, 1H), 4.82 (d, J=14.5 Hz, 1H), 4.53-4.24 (m, 3H), 3.92 (dd, J=13.6, 4.1 Hz, 1H), 3.40 (ddd, J=14.7, 10.2, 1.9 Hz, 1H), 3.07 (dd, J=14.5, 9.4 Hz, 1H), 2.89-2.72 (m, 2H), 2.65-2.47 (m, 1H), 2.11-1.91 (m, 2H), 1.10-0.97 (m, 2H), 0.97-0.81 (m, 2H); MS (ESI+) m/z 434.1 (M+H)$^+$; [α]$_D^{24.8}$=−3.2 (c=0.41, CH$_3$OH).

Example 47

Preparation of (8R,9aS)-8-[(5-cyclopropylpyrazin-2-yl)oxy]-2-[5-(trifluoromethyl)pyridin-2-yl]octahydro-5H-pyrrolo[1,2-a][1,4]diazepin-5-one

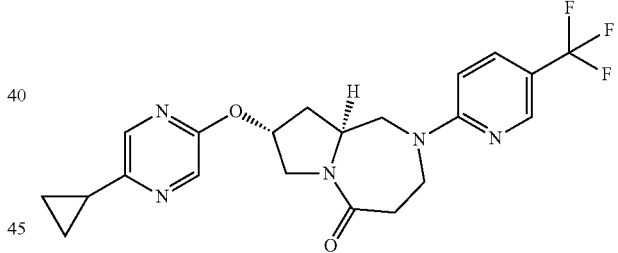

To a solution of the product from Example 28, Part F (60 mg, 0.160 mmol) in anhydrous methanol (2 mL) was added 4 M HCl in 1,4-dioxane (0.386 mL, 1.545 mmol), and the resulting mixture was stirred at room temperature for 18 hours and concentrated in vacuo. The residue was dissolved in dimethyl sulfoxide (1 mL), and sodium carbonate (0.082 g, 0.772 mmol) and 2-chloro-5-(trifluoromethyl)pyridine (0.036 g, 0.201 mmol) were added. The resulting mixture was stirred at 115° C. for 16 hours. The cooled mixture was partitioned between water and ethyl acetate. The organic extract was washed successively with water and brine, dried over MgSO$_4$, filtered, and concentrated in vacuo. The crude product was purified by column chromatography on silica gel using a solvent gradient of 0-2% methanol in dichloromethane to give the title compound as a colorless, crystalline solid (0.033 g, 49%). $^1$H NMR (500 MHz, pyridine-d$_5$, 90° C.) δ ppm 8.65-8.60 (m, 1H), 8.16 (d, J=1.3 Hz, 1H), 8.07 (d, J=1.4 Hz, 1H), 7.79 (dd, J=9.0, 2.5 Hz, 1H), 6.89 (d, J=9.0 Hz, 1H), 5.51 (t, J=4.2 Hz, 1H), 4.85-4.78 (m, 1H), 4.48-4.37 (m, 1H), 4.39-4.27 (m, 1H), 3.91 (dd, J=13.6, 4.2 Hz, 1H), 3.62 (d, J=4.8 Hz, 1H), 3.57-3.35 (m, 1H), 3.06 (dd, J=14.4, 9.4 Hz, 1H), 3.01-2.68 (m, 2H), 2.54 (ddd, J=13.9, 6.4, 2.1 Hz, 1H), 2.18-1.83 (m, 2H), 1.11-0.97 (m, 2H), 0.99-0.80 (m, 2H); MS (ESI) m/z 434 (M+H)+.

Example 48

Preparation of (8R,9aS)-8-[(5-cyclopropylpyrazin-2-yl)oxy]-2-[6-(trifluoromethyl)pyridin-2-yl]octahydro-5H-pyrrolo[1,2-a][1,4]diazepin-5-one

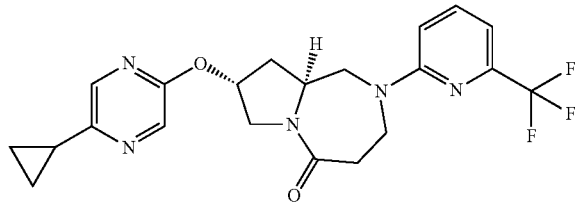 [SMILES: O=C1CCN(c2cccc(C(F)(F)F)n2)C[C@@H]2C[C@@H](Oc3cnc(C4CC4)cn3)CN12]

The title compound was prepared according to the procedure described in Example 47, substituting 2-chloro-6-(trifluoromethyl)pyridine for 2-chloro-5-(trifluoromethyl)pyridine. $^1$H NMR (500 MHz, pyridine-d$_5$, 90° C.) δ ppm 8.19-8.14 (m, 1H), 8.06 (d, J=1.4 Hz, 1H), 7.66-7.59 (m, 1H), 7.08-6.96 (m, 2H), 5.52-5.45 (m, 1H), 4.74-4.62 (m, 1H), 4.47-4.22 (m, 1H), 4.11-3.86 (m, 1H), 3.60 (d, J=12.5 Hz, 1H), 3.39-3.27 (m, 1H), 3.04 (dd, J=14.5, 9.3 Hz, 1H), 2.87-2.58 (m, 2H), 2.50 (s, 1H), 2.19-1.92 (m, 2H), 1.18-0.99 (m, 2H), 0.99-0.83 (m, 2H); MS (ESI) m/z 434 (M+H)+.

Example 49

Preparation of (8R,9aS)-2-[3-chloro-5-(trifluoromethyl)pyridin-2-yl]-8-[(5-cyclopropylpyrazin-2-yl)oxy]octahydro-5H-pyrrolo[1,2-a][1,4]diazepin-5-one

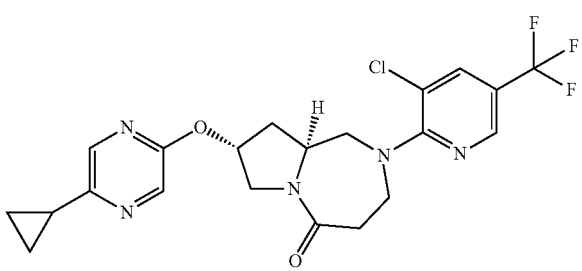 [SMILES: O=C1CCN(c2ncc(C(F)(F)F)cc2F)C[C@@H]2C[C@@H](Oc3cnc(C4CC4)cn3)CN12]

The title compound was prepared according to the procedure described in Example 47, substituting 3-chloro-2-fluoro-5-(trifluoromethyl)pyridine for 2-chloro-5-(trifluoromethyl)pyridine. $^1$H NMR (400 MHz, pyridine-d$_5$, 90° C.) δ ppm 8.43 (d, J=2.0 Hz, 1H), 8.05 (dd, J=37.6, 1.4 Hz, 2H), 7.89 (d, J=2.2 Hz, 1H), 5.52 (t, J=4.6 Hz, 1H), 4.65-4.36 (m, 1H), 4.34-4.18 (m, 3H), 3.51 (s, 1H), 3.29 (ddd, J=14.4, 10.7, 1.5 Hz, 1H), 3.07 (dd, J=14.2, 9.3 Hz, 1H), 2.98 (ddd, J=15.4, 10.6, 2.3 Hz, 1H), 2.83 (ddd, J=15.4, 6.7, 1.5 Hz, 1H), 2.53 (ddt, J=13.9, 6.8, 1.9 Hz, 1H), 2.06-1.94 (m, 2H), 1.04-0.93 (m, 2H), 0.94-0.82 (m, 2H); MS (ESI) m/z 468 (M+H)+.

Example 50

Preparation of (8R,9aS)-8-[(5-cyclopropylpyrazin-2-yl)oxy]-2-[3-fluoro-5-(trifluoromethyl)pyridin-2-yl]octahydro-5H-pyrrolo[1,2-a][1,4]diazepin-5-one

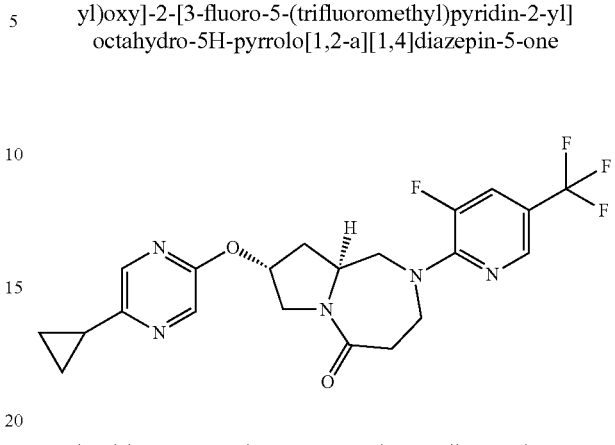

The title compound was prepared according to the procedure described in Example 47, substituting 2,3-difluoro-5-(trifluoromethyl)pyridine for 2-chloro-5-(trifluoromethyl)pyridine. $^1$H NMR (400 MHz, pyridine-d$_5$, 90° C.) δ ppm 8.30 (bs, 1H), 8.04 (dd, J=30.4, 1.4 Hz, 2H), 7.55 (d, J=2.2 Hz, 1H), 5.51 (t, J=4.6 Hz, 1H), 4.57-4.49 (m, 1H), 4.47-4.30 (m, 2H), 4.28-4.20 (m, 1H), 3.51 (s, 1H), 3.41-3.31 (m, 1H), 3.13 (dd, J=14.5, 9.2 Hz, 1H), 2.94-2.76 (m, 2H), 2.51 (ddt, J=13.9, 6.7, 1.9 Hz, 1H), 2.05-1.94 (m, 2H), 1.03-0.92 (m, 2H), 0.93-0.82 (m, 2H); MS (ESI) m/z 452 (M+H)+.

Example 51

Preparation of (8R,9aS)-2-(5-cyclopropylpyrazin-2-yl)-8-{[5-(trifluoromethyl)pyridin-2-yl]oxy}octahydro-5H-pyrrolo[1,2-a][1,4]diazepin-5-one

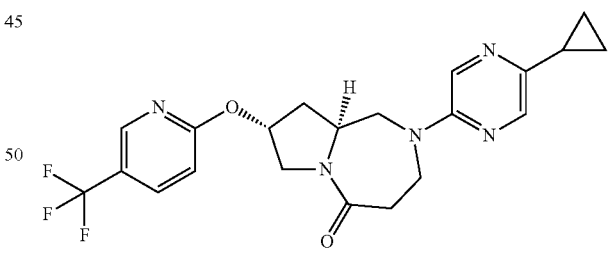

The title compound was prepared according to the procedure described in Example 47 substituting the product from Example 31, Part A for the product from Example 28, Part F, and substituting 2-bromo-5-cyclopropylpyrazine for 2-chloro-5-(trifluoromethyl)pyridine. $^1$H NMR (400 MHz, pyridine-d$_5$, 90° C.) δ ppm 8.49 (s, 1H), 8.13 (dd, J=36.6, 1.5 Hz, 2H), 7.76 (dd, J=8.7, 2.6 Hz, 1H), 6.77 (d, J=8.7 Hz, 1H), 5.62 (t, J=4.6 Hz, 1H), 4.60-4.52 (m, 1H), 4.22-4.32 (m, 1H), 3.96-3.55 (m, 2H), 3.51 (s, 1H), 3.34 (ddd, J=14.7, 9.7, 2.6 Hz, 1H), 3.04 (dd, J=14.4, 9.3 Hz, 1H), 2.84-2.68 (m, 2H), 2.49 (ddt, J=13.9, 6.6, 1.8 Hz, 1H), 2.17-1.93 (m, 2H), 1.14-0.92 (m, 2H), 0.94-0.81 (m, 2H); MS (ESI) m/z 434 (M+H)+.

Example 52

Preparation of (8R,9aS)-2-{[4-(trifluoromethyl)phenyl]sulfonyl}-8-{[5-(trifluoromethyl)pyridin-2-yl]oxy}octahydro-5H-pyrrolo[1,2-a][1,4]diazepin-5-one

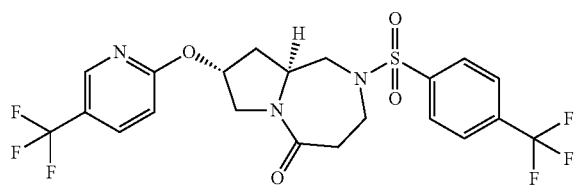 [SMILES: O=C1CCN(S(=O)(=O)c2ccc(C(F)(F)F)cc2)C[C@@H]2C[C@@H](Oc3ccc(C(F)(F)F)cn3)CN12]

The title compound was prepared according to the procedure described in Example 28 substituting 2-chloro-5-(trifluoromethyl)pyridine for 2-bromo-5-cyclopropylpyrazine in Example 28, Part F and substituting 4-(trifluoromethyl)benzene-1-sulfonyl chloride for 3-(trifluoromethyl)benzene-1-sulfonyl chloride in Example 28, Part G. $^1$H NMR (400 MHz, pyridine-$d_5$, 90° C.) δ ppm 8.50-8.45 (m, 1H), 8.10-8.03 (m, 2H), 7.84 (s, 1H), 7.83-7.76 (m, 2H), 6.79 (d, J=8.7 Hz, 1H), 5.58 (t, J=4.6 Hz, 1H), 4.32-4.22 (m, 2H), 4.23-4.19 (m, 2H), 4.20-4.02 (m, 1H), 3.75 (dd, J=13.5, 4.3 Hz, 1H), 2.92-2.61 (m, 3H), 2.48 (ddt, J=14.0, 7.0, 1.9 Hz, 1H), 2.02-1.90 (m, 1H); MS (ESI) m/z 524 (M+H)$^+$.

Example 53

Preparation of (8R,9aS)-2-{[3-(trifluoromethyl)phenyl]sulfonyl}-8-{[6-(trifluoromethyl)pyridin-3-yl]oxy}octahydro-5H-pyrrolo[1,2-a][1,4]diazepin-5-one

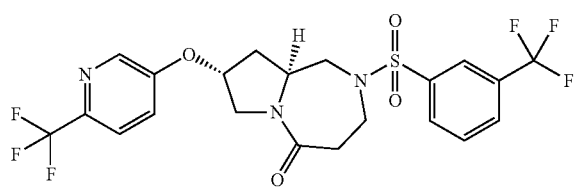 [SMILES: O=C1CCN(S(=O)(=O)c2cccc(C(F)(F)F)c2)C[C@@H]2C[C@@H](Oc3ccc(C(F)(F)F)nc3)CN12]

The title compound was prepared according to the procedure described in Example 28 substituting 5-chloro-2-(trifluoromethyl)pyridine for 2-bromo-5-cyclopropylpyrazine in Example 28, Part F. $^1$H NMR (400 MHz, pyridine-$d_5$, 90° C.) δ ppm 1.94 (ddd, J=14.3, 10.0, 4.4 Hz, 1H), 2.45 (dd, J=14.0, 6.7 Hz, 1H), 2.64-2.99 (m, 4H), 3.71 (dd, J=13.5, 4.1 Hz, 1H), 4.05-4.37 (m, 4H), 4.98 (t, J=4.1 Hz, 1H), 7.34 (dd, J=8.6, 2.7 Hz, 1H), 7.64 (dd, J=18.4, 8.3 Hz, 2H), 7.86 (d, J=7.8 Hz, 1H), 8.13 (d, J=7.9 Hz, 1H), 8.29 (s, 1H), 8.42 (d, J=2.7 Hz, 1H); MS (ESI) m/z 524 (M+H)$^+$.

Example 54

Preparation of (8R,9aS)-2-{[4-(trifluoromethyl)phenyl]sulfonyl}-8-{[6-(trifluoromethyl)pyridin-3-yl]oxy}octahydro-5H-pyrrolo[1,2-a][1,4]diazepin-5-one

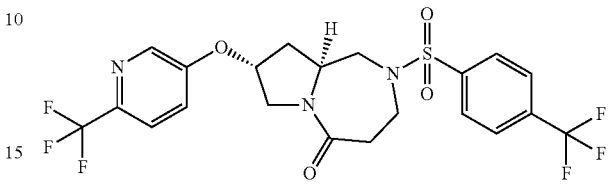

The title compound was prepared according to the procedure described in Example 28 substituting 5-chloro-2-(trifluoromethyl)pyridine for 2-bromo-5-cyclopropylpyrazine in Example 28, Part F and substituting 4-(trifluoromethyl)benzene-1-sulfonyl chloride for 3-(trifluoromethyl)benzene-1-sulfonyl chloride in Example 28, Part G. $^1$H NMR (400 MHz, pyridine-$d_5$, 90° C.) δ ppm 1.96 (ddd, J=14.2, 9.9, 4.4 Hz, 1H), 2.47 (dd, J=14.0, 6.7 Hz, 1H), 2.67-2.94 (m, 4H), 3.72 (dd, J=13.5, 4.1 Hz, 1H), 4.04-4.38 (m, 4H), 5.00 (t, J=4.1 Hz, 1H), 7.35 (dd, J=8.7, 2.8 Hz, 1H), 7.62 (d, J=8.7 Hz, 1H), 7.82 (d, J=8.3 Hz, 2H), 8.06 (d, J=8.2 Hz, 2H), 8.42 (d, J=2.8 Hz, 1H); MS (ESI) m/z 524 (M+H)$^+$.

Example 55

Preparation of (8R,9aR)-8-[(5-cyclopropylpyrazin-2-yl)oxy]-2-[5-(trifluoromethyl)pyridin-2-yl]octahydro-5H-pyrrolo[1,2-a][1,4]diazepin-5-one

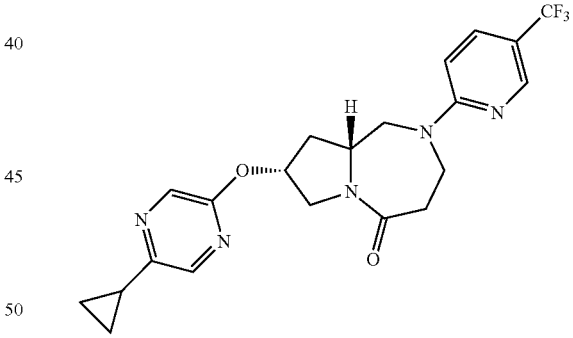

Part A. Preparation of tert-butyl (8R,9aR)-8-[(5-cyclopropylpyrazin-2-yl)oxy]-5-oxohexahydro-1H-pyrrolo[1,2-a][1,4]diazepine-2(3H)-carboxylate tert-Butyl (8R,9aR)-8-hydroxy-5-oxohexahydro-1H-pyrrolo[1,2-a][1,4]diazepine-2(3H)-carboxylate (60 mg, 0.222 mmol, 1.0 equivalent, Example 46, Part D) was dissolved in tetrahydrofuran (1.0 mL). Potassium tert-butoxide (0.311 mL, 0.311 mmol, 1 M in tetrahydrofuran, 1.4 equivalents) was added at room temperature, and the resulting yellow solution was stirred for five minutes. Then 2-bromo-5-cyclopropylpyrazine (57.4 mg, 0.289 mmol, 1.3 equivalents) was added as a solution in tetrahydrofuran (0.5 mL), and the reaction mixture was stirred for 16 hours at the same temperature. The reaction mixture was quenched with 1 drop of saturated sodium bicarbonate, the solvent was removed in vacuo, and the crude material was loaded onto a 12 g silica column with 5% methanol/dichloromethane and eluted with 100:0 to 95:5 dichloromethane:methanol over 20 minutes to give the titled compound (50 mg, 0.129 mmol, 58.0% yield) as a white solid. $^1$H NMR (400 MHz, CDCl$_3$) δ ppm 8.02 (s, 1H), 7.94 (d, J=1.1 Hz, 1H), 5.38 (br s, 1H), 4.23 (br s, 2H), 3.95 (t, J=7.2 Hz, 1H), 3.90-3.73 (m, 2H), 3.00 (br s, 2H), 2.71-2.45 (m, 3H), 2.18-1.86 (m, 2H), 1.47 (s, 9H), 1.05-0.85 (m, 4H); MS (ESI+) m/z 333.0 (M-tBu+H)$^+$.

Part B. Preparation of (8R,9aR)-8-[5-cyclopropy-lpyrazin-2-yl)oxy]-2-[5-(trifluoromethyl)pyridin-2-yl]octahydro-5H-pyrrolo[1,2-a][1,4]diazepin-5-one tert-Butyl (8R,9aR)-8-[(5-cyclopropylpyrazin-2-yl)oxy]-5-oxohexahydro-1H-pyrrolo[1,2-a][1,4]diazepine-2(3H)-carboxylate (50 mg, 0.103 mmol, Part A) was dissolved in methanol (1.0 mL) in a 20-mL scintillation vial. In a separate 4-mL vial, acetyl chloride (0.090 ml, 1.29 mmol) was added to methanol (0.5 mL) at 0° C., and the resulting acidic solution was added to the reaction vial. The vial was capped, and the reaction mixture was heated to 60° C. for 0.5 hour. The reaction mixture was then cooled to room temperature and concentrated to provide (8R,9aR)-8-[(5-cyclopropylpyrazin-2-yl)oxy]octahydro-5H-pyrrolo[1,2-a][1,4]diazepin-5-one hydrochloride that was used in the next step without additional purification.

(8R,9aR)-8-[(5-Cyclopropylpyrazin-2-yl)oxy]octahydro-5H-pyrrolo[1,2-a][1,4]diazepin-5-one hydrochloride was dissolved in dimethyl sulfoxide (1.0 mL). 2-Chloro-5-(trifluoromethyl)pyridine (36.0 mg, 0.198 mmol, 1.9 equivalents) and sodium carbonate (82.0 mg, 0.774 mmol, 7.5 equivalents) were added, and the resulting suspension was heated to 115° C. for 14 hours. The reaction mixture was cooled to room temperature, diluted with ethyl acetate, washed with water and brine, and then dried over sodium sulfate. The solvent was removed in vacuo, and the residue was purified via silica chromatography on 2 sequentially linked 4 g silica cartridges, eluted with 25:75 to 0:100 heptanes:ethyl acetate to give the titled compound (26 mg, 0.055 mmol, 47% yield) as a white solid. $^1$H NMR (400 MHz, CDCl$_3$) δ ppm 8.41 (s, 1H), 8.06 (s, 1H), 7.95 (s, 1H), 7.66 (dd, J=9.0, 2.2 Hz, 1H), 6.65 (d, J=9.0 Hz, 1H), 5.56-5.20 (m, 1H), 4.63 (d, J=14.4 Hz, 1H), 4.34 (d, J=15.2 Hz, 1H), 4.03 (td, J=9.3, 3.7 Hz, 1H), 3.90 (d, J=12.0 Hz, 1H), 3.83 (dd, J=16.0, 8.0 Hz, 1H), 3.56-3.41 (m, 1H), 3.36 (dd, J=14.4, 9.7 Hz, 1H), 2.72 (dd, J=12.1, 7.3 Hz, 2H), 2.66 (ddd, J=14.2, 9.1, 5.1 Hz, 1H), 2.15 (d, J=14.0 Hz, 1H), 2.06-1.91 (m, 1H), 1.04-0.88 (m, 4H); $^1$H NMR (400 MHz, pyridine-d$_5$) δ ppm 8.64 (s, 1H), 8.25 (d, J=1.2 Hz, 1H), 8.09 (d, J=1.2 Hz, 1H), 7.79 (dd, J=9.1, 2.4 Hz, 1H), 6.90 (d, J=9.1 Hz, 1H), 5.53-5.38 (m, 1H), 4.67 (d, J=14.3 Hz, 1H), 4.46 (d, J=15.4 Hz, 1H), 4.14 (d, J=13.2 Hz, 1H), 4.04 (ddd, J=18.1, 11.2, 4.4 Hz, 2H), 3.57-3.40 (m, 2H), 2.96-2.80 (m, 2H), 2.62 (ddd, J=14.1, 9.0, 5.3 Hz, 1H), 2.16 (dd, J=14.0, 3.3 Hz, 1H), 2.04 (td, J=8.2, 4.1 Hz, 1H), 1.15-1.04 (m, 2H), 1.04-0.83 (m, 2H); MS (ESI+) m/z 434.1 (M+H)$^+$; [α]$_D^{24.6}$=+37.3 (c=0.85, CH$_3$OH).

Example 56

Preparation of (8R,9aR)-8-[(5-cyclopropylpyrazin-2-yl)oxy]-2-[4-(trifluoromethoxy)benzyl]octahydro-5H-pyrrolo[1,2-a][1,4]diazepin-5-one

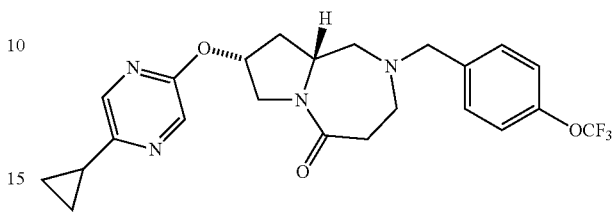

(8R,9aR)-8-[(5-Cyclopropylpyrazin-2-yl)oxy]octahydro-5H-pyrrolo[1,2-a][1,4]diazepin-5-one hydrochloride (60 mg, 0.185 mmol, prepared as described in Example 55, Part B) was suspended in dichloromethane (1.0 mL) in a 4-mL scintillation vial. 4-(Trifluoromethoxy)benzaldehyde (45.7 mg, 0.240 mmol, 1.3 equivalents) was added followed by triethylamine (0.051 mL, 0.369 mmol, 2.0 equiv). After stirring for 10 minutes, sodium triacetoxyborohydride (94 mg, 0.443 mmol, 2.4 equivalents) was added, and the reaction was stirred at room temperature for an additional four hours. The suspension was loaded directly onto a 4 g silica gel column and eluted with ethyl acetate (flow rate=18 mL/minute) over 20 minutes to give the title compound as a light yellow oil (42 mg, 50%). $^1$H NMR (400 MHz, CDCl$_3$) δ ppm 8.03 (d, J=1.2 Hz, 1H), 7.93 (d, J=1.3 Hz, 1H), 7.35 (d, J=8.6 Hz, 2H), 7.17 (d, J=8.0 Hz, 2H), 5.44-5.24 (m, 1H), 4.10 (td, J=9.3, 4.5 Hz, 1H), 3.88 (dd, J=13.2, 5.2 Hz, 1H), 3.74 (dd, J=13.2, 2.0 Hz, 1H), 3.59 (s, 2H), 2.91 (dd, J=12.6, 6.8 Hz, 1H), 2.86-2.71 (m, 2H), 2.71-2.50 (m, 2H), 2.50-2.31 (m, 2H), 2.08-1.82 (m, 2H), 1.00-0.88 (m, 4H); MS (ESI+) m/z 463.1 (M+H)$^+$; [α]$_D^{23.6}$=0.08 (c=0.17, CH$_3$OH).

Example 57

Preparation of (8R,9aR)-8-[(5-cyclopropylpyrazin-2-yl)oxy]-2-[3-(trifluoromethyl)benzoyl]octahydro-5H-pyrrolo[1,2-a][1,4]diazepin-5-one

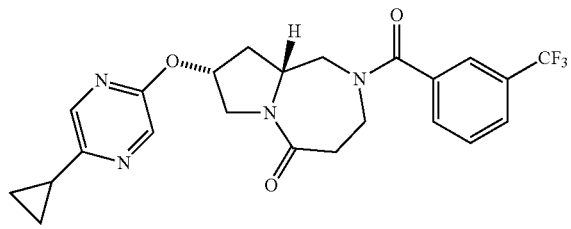

(8R,9aR)-8-[(5-Cyclopropylpyrazin-2-yl)oxy]octahydro-5H-pyrrolo[1,2-a][1,4]diazepin-5-one hydrochloride (27.6 mg, 0.085 mmol, 1 equivalent, prepared as described in Example 55, Part B) was suspended in dichloromethane (1.0 mL) in a 4-mL scintillation vial. 3-(Trifluoromethyl)benzoyl chloride (23.05 mg, 0.111 mmol, 1.3 equivalents) was added as a solution in dichloromethane (0.1 mL) followed by the addition of triethylamine (0.059 mL, 0.425 mmol, 5.0 equiv) and 4-(dimethylamino)pyridine (1.0 mg, 0.0085 mmol, 0.1 equivalent). The resulting solution was stirred at room temperature for an additional 30 minutes. The reaction was loaded directly onto a 4 g silica gel column eluted with 50:50 to 100:0 ethyl acetate:heptanes (flow rate=18 mL/minute) over 20 minutes to give the title compound as a white solid (25 mg, 64%). $^1$H NMR (400 MHz, pyridine-$d_5$, 90° C.) δ ppm 8.06 (s, 1H), 7.97 (d, J=1.3 Hz, 1H), 7.89 (s, 1H), 7.68 (dd, J=18.2, 7.8 Hz, 2H), 7.47 (t, J=7.8 Hz, 1H), 5.40 (dq, J=8.0, 4.0 Hz, 1H), 4.53-4.10 (m, 1H), 4.13 (td, J=8.8, 3.6 Hz, 2H), 3.96 (d, J=4.1 Hz, 2H), 3.41 (dd, J=13.9, 10.0 Hz, 1H), 3.32-3.17 (m, 1H), 2.90-2.67 (m, 2H), 2.55 (ddd, J=14.2, 8.8, 5.5 Hz, 1H), 2.07-1.91 (m, 2H), 1.06-0.97 (m, 2H), 0.92-0.79 (m, 2H); MS (ESI+) m/z 461.1 (M+H)$^+$; $[α]_D^{23.7}$=0.10 (c=0.12, CH$_3$OH).

Example 58

Preparation of (8R,9aR)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one

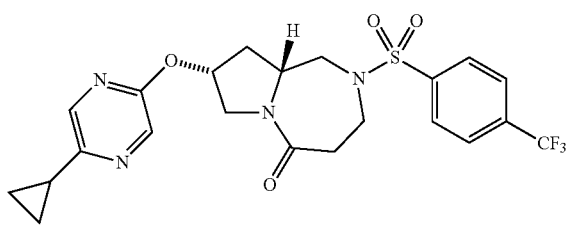

(8R,9aR)-8-[(5-Cyclopropylpyrazin-2-yl)oxy]octahydro-5H-pyrrolo[1,2-a][1,4]diazepin-5-one hydrochloride (27.6 mg, 0.085 mmol, 1.0 equivalent, prepared as described in Example 55, Part B) was suspended in dichloromethane (1.0 mL) in a 4-mL scintillation vial. Triethylamine (43 mg, 0.425 mmol, 5.0 equivalents) was added followed by 4-(trifluoromethyl)benzene-1-sulfonyl chloride (27 mg, 0.11 mmol, 1.3 equivalents) as a solution in dichloromethane (0.1 mL). The reaction was stirred for 15 minutes. The mixture was loaded directly onto a 4 g silica gel column and with 0:100 to 50:50 ethyl acetate:heptanes (flow rate=18 mL/minute) over 20 minutes to give the title compound as a white solid (25 mg, 62%). $^1$H NMR (400 MHz, CDCl$_3$) δ ppm 7.95 (d, J=1.4 Hz, 1H), 7.92 (d, J=1.4 Hz, 1H), 7.89 (d, J=8.4 Hz, 2H), 7.82 (d, J=8.4 Hz, 2H), 5.53-5.25 (m, 1H), 4.17 (td, J=9.4, 3.0 Hz, 1H), 4.12-4.00 (m, 1H), 3.97 (d, J=13.4 Hz, 1H), 3.79 (d, J=3.5 Hz, 2H), 2.99-2.55 (m, 5H), 2.14-1.92 (m, 2H), 0.95 (ddt, J=12.1, 7.0, 2.0 Hz, 4H); MS (ESI+) m/z expected 497.1; found: 497.0 (M+H)$^+$; $[α]_D^{24.1}$=0.19 (c=0.12, CH$_3$OH).

Example 59

Preparation of (8S,9aS)-8-[(5-cyclopropylpyrazin-2-yl)oxy]-2-[4-(trifluoromethoxy)benzyl]octahydro-5H-pyrrolo[1,2-a][1,4]diazepin-5-one

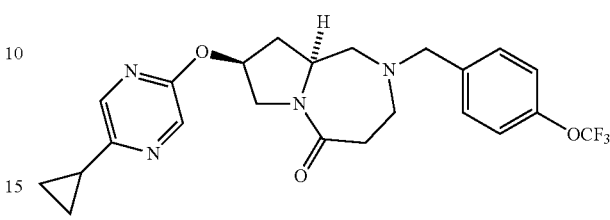

Part A. Preparation of tert-butyl (8S,9aS)-8-[(4-nitrobenzoyl)oxy]-5-oxohexahydro-1H-pyrrolo[1,2-a][1,4]diazepine-2(3H)-carboxylate tert-Butyl (8R,9aS)-8-hydroxy-5-oxohexahydro-1H-pyrrolo[1,2-a][1,4]diazepine-2(3H)-carboxylate (370 mg, 1.369 mmol, prepared as described in Example 28, Part E), triphenylphosphine (449 mg, 1.711 mmol), and 4-nitrobenzoic acid (343 mg, 2.053 mmol) were dissolved in tetrahydrofuran (6.0 mL), and the resulting solution was cooled to −78° C. Diisopropyl azodicarboxylate (332 mg, 1.642 mmol) in tetrahydrofuran (1.5 mL) was added. The mixture was warmed to room temperature, and stirred for two hours. Then one drop of water was added. The mixture was concentrated. The residue was purified by chromatography on silica gel (ethyl acetate/heptanes=1:1 then ethyl acetate) to give 500 mg (87% yield) of the title compound as an oil. $^1$H NMR (500 MHz, CDCl$_3$) δ ppm 1.50 (s, 9H), 2.10 (m, 1H), 2.70 (m, 3H), 3.00 (m, 2H), 3.82 (m, 1H), 3.96-4.40 (m, 4H), 5.52 (t, J=4 Hz, 1H), 8.18 (d, J=8 Hz, 2H), 8.32 (d, J=8 Hz, 2H); MS (ESI) m/z 420.0 (M+H)$^+$.

Part B. Preparation of tert-butyl (8S,9aS)-8-hydroxy-5-oxohexahydro-1H-pyrrolo[1,2-a][1,4]diazepine-2(3H)-carboxylate To tert-butyl (8S,9aS)-8-[(4-nitrobenzoyl)oxy]-5-oxohexahydro-1H-pyrrolo[1,2-a][1,4]diazepine-2(3H)-carboxylate (495 mg, 0.291 mmol, Part A) in methanol (8 ml) was added potassium carbonate (98 mg, 0.708 mmol). The mixture was stirred at room temperature for one hour, and then concentrated. The residue was purified by chromatography on silica gel (ethyl acetate, then ethyl acetate/methanol=10:1) to give 280 mg (88% yield) of the title compound as a solid. $^1$H NMR (400 MHz, DMSO-$d_6$) δ ppm 1.40 (s, 9H), 1.61 (m, 1H), 2.24 (m, 1H), 2.38 (m, 1H), 2.58 (m, 1H), 2.80-3.15 (m, 2H), 3.23 (dd, J=13, 4 Hz, 1H), 3.42 (dd, J=13, 4 Hz, 1H), 3.81 (m, 1H), 3.98 (m, 2H), 4.18 (m, 1H), 5.02 (t, J=4 Hz, 1H); MS (ESI) m/z 271.0 (M+H)$^+$.

Part C. Preparation of tert-butyl (8S,9aS)-8-[(5-cyclopropylpyrazin-2-yl)oxy]-5-oxohexahydro-1H-pyrrolo[1,2-a][1,4]diazepine-2(3H)-carboxylate To tert-butyl (8S,9aS)-8-hydroxy-5-oxohexahydro-1H-pyrrolo[1,2-a][1,4]diazepine-2(3H)-carboxylate (270 mg, 1 mmol, Part B) and 2-bromo-5-cyclopropylpyrazine (299 mg, 1.5 mmol) in tetrahydrofuran (3 mL) and dichloromethane (1 mL) was added potassium t-butoxide (3 mL, 3 mmol, 1 M in tetrahydrofuran). The mixture was stirred at room temperature for three days, and then concentrated. The residue was purified by chromatography on silica gel (ethyl acetate) to give 255 mg (65.6% yield) of the title compound as a solid. $^1$H NMR (400 MHz, CDCl$_3$) δ ppm 0.98 (m, 4H), 1.47 (s, 9H), 2.01 (m, 2H), 2.61 (m, 3H), 3.01 (m, 2H), 3.80-3.98 (m, 3H), 4.22 (m, 2H), 5.40 (m, 1H), 7.95 (d, J=1 Hz, 1H), 8.02 (d, J=1 Hz, 1H); MS (ESI) m/z 389.0 (M+H)$^+$.

Part D. Preparation of (8S,9aS)-8-[(5-cyclopropylpyrazin-2-yl)oxy]octahydro-5H-pyrrolo[1,2-a][1,4]diazepin-5-one hydrochloride To tert-butyl (8S,9aS)-8-[(5-cyclopropylpyrazin-2-yl)oxy]-5-oxohexahydro-1H-pyrrolo[1,2-a][1,4]diazepine-2(3H)-carboxylate (254 mg, 0.654 mmol, Part C) in methanol/dichloromethane (1:1, 1 mL) was added 4 N HCl solution in dioxane (3 mL). The mixture was stirred at room temperature for three hours and then concentrated to give 212 mg (100% yield) of the title compound as a solid which was used without purification. $^1$H NMR (400 MHz, DMSO-d$_6$) δ ppm 0.82 (m, 2H), 0.96 (m, 2H), 2.10 (m, 2H), 2.66 (m, 1H), 3.10 (m, 3H), 3.40 (m, 2H), 3.65 (m, 2H), 4.22 (m, 1H), 4.40 (m, 1H), 5.38 (m, 1H), 8.15 (d, J=1 Hz, 1H), 8.19 (d, J=1 Hz, 1H), 9.38 (br s, 1H), 9.50 (br s, 1H); MS (ESI) m/z 289.0 (M+H)$^+$.

Part E. Preparation of (8S,9aS)-8-[(5-cyclopropylpyrazin-2-yl)oxy]-2-[4-(trifluoromethoxy)benzyl]octahydro-5H-pyrrolo[1,2-a][1,4]diazepin-5-one To (8S,9aS)-8-[(5-cyclopropylpyrazin-2-yl)oxy]octahydro-5H-pyrrolo[1,2-a][1,4]diazepin-5-one hydrochloride (50 mg, 0.154 mmol, Part D) in anhydrous dichloroethane (0.7 mL) was added 4-(trifluoromethoxy)benzaldehyde (38 mg, 0.2 mmol), and N-ethyl-N-isopropylpropan-2-amine (39.8 mg, 0.308 mmol). After 10 minutes, sodium triacetoxyborohydride (75 mg, 0.354 mmol) was added. The mixture was stirred at room temperature overnight and then concentrated. The residue was purified by chromatography on silica gel (ethyl acetate) to give 33 mg (46.4% yield) of the title compound as a solid. $^1$H NMR (400 MHz, DMSO-d$_6$) δ ppm 0.83 (m, 2H), 0.98 (m, 2H), 1.82 (m, 1H), 2.12 (m, 1H), 2.20-2.32 (m, 2H), 2.42 (dd, J=12, 8 Hz, 1H), 2.61 (m, 1H), 2.70-2.90 (m, 3H), 3.50 (br d, J=12 Hz, 1H), 3.57 (br d, J=12 Hz, 1H), 3.62-3.72 (m, 2H), 4.12 (m, 1H), 5.29 (m, 1H), 7.31 (d, J=9 Hz, 2H), 7.43 (d, J=9 Hz, 2H), 8.15 (s, 1H), 8.18 (s, 1H); MS (ESI) m/z 463.0 (M+H)$^+$.

Example 60

Preparation of (8S,9aS)-8-[(5-cyclopropylpyrazin-2-yl)oxy]-2-[3-(trifluoromethyl)benzoyl]octahydro-5H-pyrrolo[1,2-a][1,4]diazepin-5-one

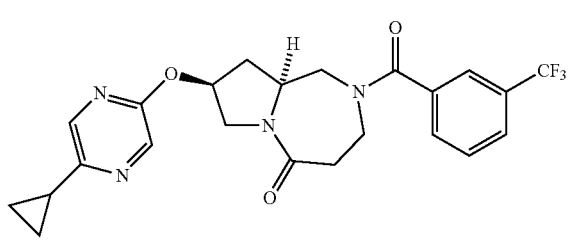 [SMILES: O=C(c1cccc(C(F)(F)F)c1)N1CCC(=O)N2C[C@@H](Oc3cnc(C4CC4)cn3)C[C@H]2C1]

To (8S,9aS)-8-[(5-cyclopropylpyrazin-2-yl)oxy]octahydro-5H-pyrrolo[1,2-a][1,4]diazepin-5-one hydrochloride (50 mg, 0.154 mmol, prepared as described in Example 59, Part D) in dichloromethane (1 mL) was added triethylamine (62.3 mg, 0.616 mmol) followed by 3-(trifluoromethyl)benzoyl chloride (38.5 mg, 0.185 mmol) in dichloromethane (0.5 mL). The mixture was stirred at room temperature for 3 hours and then concentrated. The residue was purified by chromatography on silica gel (ethyl acetate) to give 34 mg (48% yield) of the title compound as a solid. $^1$H NMR (400 MHz, CDCl$_3$) δ ppm 0.87-1.02 (m, 4H), 2.00 (m, 1H), 2.23 (m 1H), 2.60-2.90 (m, 3H), 3.10-3.40 (m, 2H), 3.70-3.96 (m, 3H), 4.09 (m, 1H), 4.80 (m, 1H), 5.42 (m, 1H), 7.60 (m, 2H), 7.70 (br s, 1H), 7.76 (m, 1H), 8.00 (m, 2H); MS (ESI) m/z 461.0 (M+H)$^+$.

Example 61

Preparation of (8S,9aS)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one

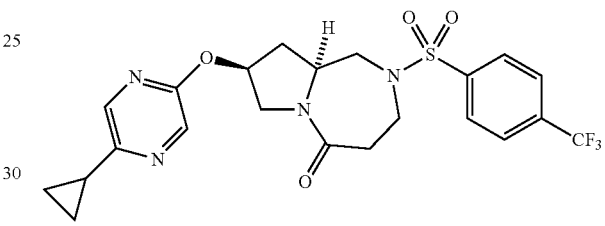

To (8S,9aS)-8-[(5-cyclopropylpyrazin-2-yl)oxy]octahydro-5H-pyrrolo[1,2-a][1,4]diazepin-5-one hydrochloride (50 mg, 0.154 mmol, prepared as described in Example 59, Part D) in dichloromethane (1 mL) was added triethylamine (62.3 mg, 0.616 mmol) followed by 4-(trifluoromethyl)benzene-1-sulfonyl chloride (45.2 mg, 0.185 mmol) in dichloromethane (0.5 mL). The mixture was stirred at room temperature for 18 hours and then concentrated. The residue was purified by chromatography on silica gel (ethyl acetate) to give 37 mg (48.4% yield) of the title compound as a solid. $^1$H NMR (400 MHz, CDCl$_3$) δ ppm 0.86-1.02 (m, 4H), 2.00 (m, 1H), 2.08 (br d, J=14 Hz, 1H), 2.66-2.92 (m, 5H), 3.78 (d, J=4 Hz, 2H), 3.99 (br d, J=12 Hz, 1H), 4.03 (dd, J=12, 8 Hz, 1H), 4.18 (m, 1H), 5.40 (m, 1H), 7.81 (d, J=9 Hz, 2H), 7.87 (m, 4H); MS (ESI) m/z 497.0 (M+H)$^+$.

Example 62

Preparation of (8S,9aR)-8-[(5-cyclopropylpyrazin-2-yl)oxy]-2-[4-(trifluoromethoxy)benzyl]octahydro-5H-pyrrolo[1,2-a][1,4]diazepin-5-one

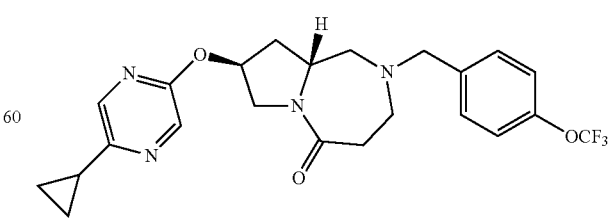

(8S,9aR)-8-[(5-Cyclopropylpyrazin-2-yl)oxy]octahydro-5H-pyrrolo[1,2-a][1,4]diazepin-5-one hydrochloride (45 mg, 0.139 mmol, prepared as described in Example 46, Part H) was suspended in dichloromethane (1.5 mL) in a 4-mL scintillation vial. Triethylamine (28.0 mg, 0.277 mmol) was added followed by the addition of 4-(trifluoromethoxy)benzaldehyde (34.2 mg, 0.180 mmol) as a solution in dichloromethane (0.2 mL). The resulting solution was stirred at room temperature for 15 minutes, at which point sodium triacetoxyborohydride (70.5 mg, 0.333 mmol) was added as a neat solid in one portion, and the resulting suspension was stirred at room temperature for an additional 4 hours. The suspension was loaded directly onto a 4 g silica column and eluted with ethyl acetate (flow rate=18 mL/minute) over 15 minutes to give the title compound as a colorless oil (34 mg, 53%). $^1$H NMR (400 MHz, CDCl$_3$) δ ppm 8.02 (d, J=1.2 Hz, 1H), 7.92 (d, J=1.3 Hz, 1H), 7.35 (d, J=8.6 Hz, 2H), 7.17 (d, J=8.0 Hz, 2H), 5.41 (t, J=3.9 Hz, 1H), 4.18 (dd, J=16.4, 9.4 Hz, 1H), 4.02 (dd, J=13.7, 2.0 Hz, 1H), 3.69-3.45 (m, 3H), 2.94 (d, J=12.5 Hz, 2H), 2.81 (d, J=12.0 Hz, 1H), 2.60 (dd, J=14.8, 6.9 Hz, 1H), 2.50-2.34 (m, 2H), 2.15 (dd, J=12.8, 9.3 Hz, 1H), 1.98 (tt, J=7.9, 5.1 Hz, 1H), 1.86 (ddd, J=14.4, 10.4, 4.4 Hz, 1H), 1.02-0.79 (m, 4H); MS (ESI+) m/z 463.1 (M+H)$^+$; [α]$_D^{24.1}$=−0.04 (c=0.23, CH$_3$OH).

Example 63

Preparation of (8S,9aR)-8-[(5-cyclopropylpyrazin-2-yl)oxy]-2-[3-(trifluoromethyl)benzoyl]octahydro-5H-pyrrolo[1,2-a][1,4]diazepin-5-one

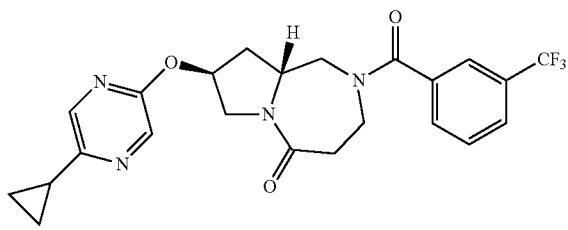 [SMILES: O=C(c1cccc(C(F)(F)F)c1)N1CCC(=O)N2C[C@@H](Oc3cnc(C4CC4)cn3)C[C@@H]2C1]

(8S,9aR)-8-[(5-Cyclopropylpyrazin-2-yl)oxy]octahydro-5H-pyrrolo[1,2-a][1,4]diazepin-5-one hydrochloride (40 mg, 0.123 mmol, 1.0 equivalent, prepared as described in Example 46, Part H) was suspended in dichloromethane (1.0 mL) in a 4-mL scintillation vial, and triethylamine (0.051 mL, 0.37 mmol, 3.0 equivalents) was added. 3-(Trifluoromethyl)benzoyl chloride (33.4 mg, 0.160 mmol, 1.3 equivalents) was added as a solution in 0.1 mL of dichloromethane followed by 4-(dimethylamino)pyridine (1.50 mg, 0.012 mmol, 0.1 equivalent). The reaction was stirred for 30 minutes. The reaction solution was loaded directly onto a 4 g silica column and eluted with 50:50 to 100:0 ethyl acetate:heptanes (flow rate=18 mL/minute) over 20 minutes to give the title compound as a white solid (31 mg, 54%). $^1$H NMR (400 MHz, pyridine-d$_5$, 90° C.) δ ppm 8.07 (d, J=1.3 Hz, 1H), 7.98 (d, J=1.3 Hz, 1H), 7.91 (s, 1H), 7.72 (d, J=7.7 Hz, 1H), 7.66 (d, J=7.8 Hz, 1H), 7.48 (t, J=7.8 Hz, 1H), 5.47 (t, J=4.4 Hz, 1H), 4.51 (s, 1H), 4.34 (dd, J=17.0, 9.1 Hz, 1H), 4.22 (d, J=13.6 Hz, 2H), 3.84-3.75 (m, 1H), 3.26 (dd, J=12.7, 11.1 Hz, 1H), 3.04 (dd, J=14.2, 9.5 Hz, 1H), 2.94-2.77 (m, 1H), 2.71 (dd, J=15.4, 4.9 Hz, 1H), 2.41 (dd, J=14.0, 6.7 Hz, 1H), 2.05-1.82 (m, 2H), 1.00 (dt, J=4.9, 2.9 Hz, 2H), 0.93-0.80 (m, 2H); MS (ESI+) m/z 461.1 (M+H)$^+$; [α]$_D^{23.6}$=−0.09 (c=0.13, CH$_3$OH).

Example 64

Preparation of (8S,9aR)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one

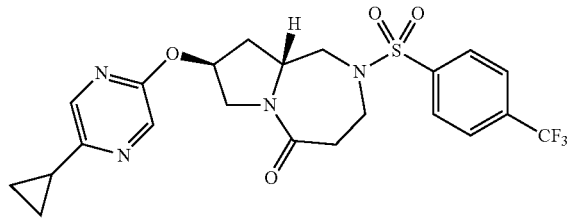 [SMILES: O=C1CCN(S(=O)(=O)c2ccc(C(F)(F)F)cc2)C[C@H]2C[C@H](Oc3cnc(C4CC4)cn3)CN12]

(8S,9aR)-8-[(5-Cyclopropylpyrazin-2-yl)oxy]octahydro-5H-pyrrolo[1,2-a][1,4]diazepin-5-one hydrochloride (35 mg, 0.108 mmol, 1.0 equivalent, prepared as described in Example 46, Part H) was suspended in dichloromethane (1.0 mL) in a 4-mL scintillation vial. Triethylamine (32.7 mg, 0.323 mmol, 3.0 equivalents) was added followed by the addition of 4-(trifluoromethyl)benzene-1-sulfonyl chloride (34.3 mg, 0.140 mmol, 1.3 equivalents). The resulting solution was allowed to stir for 30 minutes at room temperature. The reaction solution was loaded directly onto a 4 g silica gel column and eluted with 0:100 to 50:50 ethyl acetate:heptanes (flow rate=18 mL/minute) over 20 minutes to give the title compound as a white solid (30 mg, 56%). $^1$H NMR (400 MHz, CDCl$_3$) δ ppm 8.03 (d, J=1.3 Hz, 1H), 7.91 (dd, J=9.0, 4.9 Hz, 3H), 7.82 (d, J=8.4 Hz, 2H), 5.43 (t, J=3.9 Hz, 1H), 4.25 (dd, J=16.5, 9.6 Hz, 1H), 4.16-3.95 (m, 3H), 3.57 (dd, J=13.7, 4.0 Hz, 1H), 2.96-2.83 (m, 1H), 2.82-2.64 (m, 2H), 2.65-2.52 (m, 1H), 2.47 (dd, J=13.4, 9.3 Hz, 1H), 2.04-1.84 (m, 2H), 1.08-0.77 (m, 4H); MS (ESI+) m/z 497.0 (M+H)$^+$; [α]$_D^{23.8}$=−0.15 (c=0.13, CH$_3$OH).

Additional examples of compounds of Formula (I) are listed below. Such compounds can be prepared using the general method-of-preparation discussion, specific synthesis examples above, and/or the discussion throughout this application.

Example 65

(8R,9aR)-8-[(5-cyclopropylpyrazin-2-yl)oxy]-2-{[3-(trifluoromethyl)phenyl]sulfonyl}octahydro-1H-pyrrolo[1,2-a][1,4]diazepine Example 66

(8R,9aR)-8-[(5-cyclopropylpyrazin-2-yl)oxy]-2-[{4-(trifluoromethyl)phenyl]sulfonyl}octahydro-1H-pyrrolo[1,2-a][1,4]diazepine Example 67

(8S,9aR)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one Example 68

(8R,9aR)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 69

(8S,9aR)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 70

(8R,9aR)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 71

[(8R,9aR)-8-[(5-cyclopropylpyrazin-2-yl)oxy]hexahydro-1H-pyrrolo[1,2-a][1,4]diazepin-2(3H)-yl][3-(trifluoromethyl)phenyl]methanone

Example 72

[(8R,9aR)-8-[(5-cyclopropylpyrazin-2-yl)oxy]hexahydro-1H-pyrrolo[1,2-a][1,4]diazepin-2(3H)-yl](4-fluorophenyl)methanone

Example 73

[(8R,9aR)-8-[(5-cyclopropylpyrazin-2-yl)oxy]hexahydro-1H-pyrrolo[1,2-a][1,4]diazepin-2(3H)-yl][3-(trifluoromethoxy)phenyl]methanone

Example 74

[(8R,9aR)-8-[(5-cyclopropylpyrazin-2-yl)oxy]hexahydro-1H-pyrrolo[1,2-a][1,4]diazepin-2(3H)-yl][2-fluoro-3-(trifluoromethyl)phenyl]methanone

Example 75

[(8R,9aR)-8-[(5-cyclopropylpyrazin-2-yl)oxy]hexahydro-1H-pyrrolo[1,2-a][1,4]diazepin-2(3H)-yl][5-(trifluoromethyl)pyridin-2-yl]methanone

Example 76

[(8R,9aR)-8-[(5-cyclopropylpyrazin-2-yl)oxy]hexahydro-1H-pyrrolo[1,2-a][1,4]diazepin-2(3H)-yl][6-(trifluoromethyl)pyridin-2-yl]methanone

Example 77

[(8R,9aR)-8-[(5-cyclopropylpyrazin-2-yl)oxy]hexahydro-1H-pyrrolo[1,2-a][1,4]diazepin-2(3H)-yl][4-(trifluoromethyl)phenyl]methanone

Example 78

[(8R,9aR)-8-[(5-cyclopropylpyrazin-2-yl)oxy]hexahydro-1H-pyrrolo[1,2-a][1,4]diazepin-2(3H)-yl][4-fluoro-3-(trifluoromethyl)phenyl]methanone

Example 79

[(8R,9aR)-8-[(5-cyclopropylpyrazin-2-yl)oxy]hexahydro-1H-pyrrolo[1,2-a][1,4]diazepin-2(3H)-yl][3-fluoro-4-(trifluoromethyl)phenyl]methanone

Example 80

(3-chloro-4-fluorophenyl)[(8R,9aR)-8-[(5-cyclopropylpyrazin-2-yl)oxy]hexahydro-1H-pyrrolo[1,2-a][1,4]diazepin-2(3H)-yl]methanone

Example 81

[(8R,9aR)-8-[(5-cyclopropylpyrazin-2-yl)oxy]hexahydro-1H-pyrrolo[1,2-a][1,4]diazepin-2(3H)-yl][2-fluoro-5-(trifluoromethyl)phenyl]methanone

Example 82

[(8R,9aR)-8-[(5-cyclopropylpyrazin-2-yl)oxy]hexahydro-1H-pyrrolo[1,2-a][1,4]diazepin-2(3H)-yl][2-fluoro-4-(trifluoromethyl)phenyl]methanone

Example 83

(8R,9aR)-8-[(5-cyclopropylpyrazin-2-yl)oxy]-2-[5-(trifluoromethyl)pyridin-2-yl]octahydro-1H-pyrrolo[1,2-a][1,4]diazepine

Example 84

(8R,9aR)-8-[(5-cyclopropylpyrazin-2-yl)oxy]-2-[6-(trifluoromethyl)pyridin-2-yl]octahydro-1H-pyrrolo[1,2-a][1,4]diazepine

Example 85

(8R,9aR)-8-[(5-cyclopropylpyrazin-2-yl)oxy]-2-[5-(trifluoromethyl)pyridin-2-yl]octahydro-7H-pyrrolo[1,2-a][1,4]diazepin-7-one

Example 86

(8R,9aR)-8-[(5-cyclopropylpyrazin-2-yl)oxy]-2-[3-(trifluoromethyl)benzyl]octahydro-1H-pyrrolo[1,2-a][1,4]diazepin-1-one

Example 87

(8R,9aR)-8-[(5-cyclopropylpyrazin-2-yl)oxy]-2-[4-(trifluoromethyl)benzyl]octahydro-1H-pyrrolo[1,2-a][1,4]diazepin-1-one

Example 88

(8S,9aR)-8-[(5-cyclopropylpyrazin-2-yl)oxy]-2-[4-(trifluoromethyl)benzyl]octahydro-1H-pyrrolo[1,2-a][1,4]diazepin-1-one

Example 89

(8R,9aR)-8-[(5-cyclopropylpyrazin-2-yl)oxy]-2-[3-fluoro-4-(trifluoromethyl)benzyl]octahydro-1H-pyrrolo[1,2-a][1,4]diazepin-1-one

Example 90

(8R,9aR)-8-[(5-cyclopropylpyrazin-2-yl)oxy]-2-[4-fluoro-3-(trifluoromethyl)benzyl]octahydro-1H-pyrrolo[1,2-a][1,4]diazepin-1-one

Example 91

(8R,9aR)-8-[(5-cyclopropylpyrazin-2-yl)oxy]-2-[3-(trifluoromethyl)phenyl]octahydro-1H-pyrrolo[1,2-a][1,4]diazepin-1-one

Example 92

(8R,9aR)-8-[(5-cyclopropylpyrazin-2-yl)oxy]-2-{[3-(trifluoromethyl)phenyl]sulfonyl}octahydro-5H-pyrrolo[1,2-a][1,4]diazepin-5-one

Example 93

(8R,9aR)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 94

(8R,9aR)-8-[(5-cyclopropylpyrazin-2-yl)oxy]-2-[4-(trifluoromethyl)benzoyl]octahydro-5H-pyrrolo[1,2-a][1,4]diazepin-5-one

Example 95

(8R,9aR)-8-[(5-cyclopropylpyrazin-2-yl)oxy]-2-[2-fluoro-3-(trifluoromethyl)benzoyl]octahydro-5H-pyrrolo[1,2-a][1,4]diazepin-5-one

Example 96

(8R,9aR)-8-[(5-cyclopropylpyrazin-2-yl)oxy]-2-[3-fluoro-4-(trifluoromethyl)benzoyl]octahydro-5H-pyrrolo[1,2-a][1,4]diazepin-5-one

Example 97

(8R,9aR)-8-[(5-cyclopropylpyrazin-2-yl)oxy]-2-[4-fluoro-3-(trifluoromethyl)benzoyl]octahydro-5H-pyrrolo[1,2-a][1,4]diazepin-5-one

Example 98

(8R,9aR)-8-[(5-cyclopropylpyrazin-2-yl)oxy]-2-[3-(trifluoromethoxy)benzoyl]octahydro-5H-pyrrolo[1,2-a][1,4]diazepin-5-one

Example 99

(8R,9aR)-8-[(5-cyclopropylpyrazin-2-yl)oxy]-2-[4-(trifluoromethoxy)benzoyl]octahydro-5H-pyrrolo[1,2-a][1,4]diazepin-5-one

Example 100

(8R,9aR)-8-[(5-cyclopropylpyrazin-2-yl)oxy]-2-{[3-(trifluoromethyl)phenyl]acetyl}octahydro-5H-pyrrolo[1,2-a][1,4]diazepin-5-one

Example 101

(8R,9aR)-8-[(5-cyclopropylpyrazin-2-yl)oxy]-2-{hydroxy[3-(trifluoromethyl)phenyl]acetyl}octahydro-5H-pyrrolo[1,2-a][1,4]diazepin-5-one

Example 102

(8R,9aR)-8-[(5-cyclopropylpyrazin-2-yl)oxy]-2-{(methylamino)[3-(trifluoromethyl)phenyl]acetyl}octahydro-5H-pyrrolo[1,2-a][1,4]diazepin-5-one

Example 103

(8R,9aR)-8-[(5-cyclopropylpyrazin-2-yl)oxy]-2-[3-(trifluoromethyl)benzyl]octahydro-5H-pyrrolo[1,2-a][1,4]diazepin-5-one

Example 104

(8R,9aR)-8-[(5-cyclopropylpyrazin-2-yl)oxy]-2-[3-(trifluoromethoxy)benzyl]octahydro-5H-pyrrolo[1,2-a][1,4]diazepin-5-one

Example 105

(8R,9aR)-2-[3-(trifluoromethyl)benzyl]-8-{[5-(trifluoromethyl)pyridin-2-yl]oxy}octahydro-5H-pyrrolo[1,2-a][1,4]diazepin-5-one

Example 106

(8R,9aR)-8-[(5-cyclopropylpyrazin-2-yl)oxy]-2-[6-(trifluoromethyl)pyridin-2-yl]octahydro-5H-pyrrolo[1,2-a][1,4]diazepin-5-one

Example 107

(8R,9aR)-2-[3-chloro-5-(trifluoromethyl)pyridin-2-yl]-8-[(5-cyclopropylpyrazin-2-yl)oxy]octahydro-5H-pyrrolo[1,2-a][1,4]diazepin-5-one

Example 108

(8R,9aR)-8-[(5-cyclopropylpyrazin-2-yl)oxy]-2-[3-fluoro-5-(trifluoromethyl)pyridin-2-yl]octahydro-5H-pyrrolo[1,2-a][1,4]diazepin-5-one

Example 109

(8R,9aR)-2-(5-cyclopropylpyrazin-2-yl)-8-{[5-(trifluoromethyl)pyridin-2-yl]oxy}octahydro-5H-pyrrolo[1,2-a][1,4]diazepin-5-one

Example 110

(8R,9aR)-2-{[4-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 111

(8R,9aR)-2-{[3-(trifluoromethyl)phenyl]sulfonyl}-8-{[6-(trifluoromethyl)pyridin-3-yl]oxy}octahydro-5H-pyrrolo[1,2-a][1,4]diazepin-5-one

Example 112

(8R,9aR)-2-{[4-(trifluoromethyl)phenyl]sulfonyl}-8-{[6-(trifluoromethyl)pyridin-3-yl]oxy}octahydro-5H-pyrrolo[1,2-a][1,4]diazepin-5-one

Example 113

(8S,9aS)-8-[(5-cyclopropylpyrazin-2-yl)oxy]-2-{[3-(trifluoromethyl)phenyl]sulfonyl}octahydro-1H-pyrrolo[1,2-a][1,4]diazepine

Example 114

(8S,9aS)-8-[(5-cyclopropylpyrazin-2-yl)oxy]-2-{[4-(trifluoromethyl)phenyl]sulfonyl}octahydro-1H-pyrrolo[1,2-a][1,4]diazepine

Example 115

(8R,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 116

(8S,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 117

(8R,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 118

(8S,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 119

[(8S,9aS)-8-[(5-cyclopropylpyrazin-2-yl)oxy]hexahydro-1H-pyrrolo[1,2-a][1,4]diazepin-2(3H)-yl][3-(trifluoromethyl)phenyl]methanone

Example 120

[(8S,9aS)-8-[(5-cyclopropylpyrazin-2-yl)oxy]hexahydro-1H-pyrrolo[1,2-a][1,4]diazepin-2(3H)-yl](4-fluorophenyl)methanone

Example 121

[(8S,9aS)-8-[(5-cyclopropylpyrazin-2-yl)oxy]hexahydro-1H-pyrrolo[1,2-a][1,4]diazepin-2(3H)-yl][3-(trifluoromethoxy)phenyl]methanone

Example 122

[(8S,9aS)-8-[(5-cyclopropylpyrazin-2-yl)oxy]hexahydro-1H-pyrrolo[1,2-a][1,4]diazepin-2(3H)-yl][2-fluoro-3-(trifluoromethyl)phenyl]methanone

Example 123

[(8S,9aS)-8-[(5-cyclopropylpyrazin-2-yl)oxy]hexahydro-1H-pyrrolo[1,2-a][1,4]diazepin-2(3H)-yl][5-(trifluoromethyl)pyridin-2-yl]methanone

Example 124

[(8S,9aS)-8-[(5-cyclopropylpyrazin-2-yl)oxy]hexahydro-1H-pyrrolo[1,2-a][1,4]diazepin-2(3H)-yl][6-(trifluoromethyl)pyridin-2-yl]methanone

Example 125

[(8S,9aS)-8-[(5-cyclopropylpyrazin-2-yl)oxy]hexahydro-1H-pyrrolo[1,2-a][1,4]diazepin-2(3H)-yl][4-(trifluoromethyl)phenyl]methanone

Example 126

[(8S,9aS)-8-[(5-cyclopropylpyrazin-2-yl)oxy]hexahydro-1H-pyrrolo[1,2-a][1,4]diazepin-2(3H)-yl][4-fluoro-3-(trifluoromethyl)phenyl]methanone

Example 127

[(8S,9aS)-8-[(5-cyclopropylpyrazin-2-yl)oxy]hexahydro-1H-pyrrolo[1,2-a][1,4]diazepin-2(3H)-yl][3-fluoro-4-(trifluoromethyl)phenyl]methanone

Example 128

(3-chloro-4-fluorophenyl)[(8S,9aS)-8-[(5-cyclopropylpyrazin-2-yl)oxy]hexahydro-1H-pyrrolo[1,2-a][1,4]diazepin-2(3H)-yl]methanone

Example 129

[(8S,9aS)-8-[(5-cyclopropylpyrazin-2-yl)oxy]hexahydro-1H-pyrrolo[1,2-a][1,4]diazepin-2(3H)-yl][2-fluoro-5-(trifluoromethyl)phenyl]methanone

Example 130

[(8S,9aS)-8-[(5-cyclopropylpyrazin-2-yl)oxy]hexahydro-1H-pyrrolo[1,2-a][1,4]diazepin-2(3H)-yl][2-fluoro-4-(trifluoromethyl)phenyl]methanone

Example 131

(8S,9aS)-8-[(5-cyclopropylpyrazin-2-yl)oxy]-2-[5-(trifluoromethyl)pyridin-2-yl]octahydro-1H-pyrrolo[1,2-a][1,4]diazepine

Example 132

(8S,9aS)-8-[(5-cyclopropylpyrazin-2-yl)oxy]-2-[6-(trifluoromethyl)pyridin-2-yl]octahydro-1H-pyrrolo[1,2-a][1,4]diazepine

Example 133

(8S,9aS)-8-[(5-cyclopropylpyrazin-2-yl)oxy]-2-[5-(trifluoromethyl)pyridin-2-yl]octahydro-7H-pyrrolo[1,2-a][1,4]diazepin-7-one

Example 134

(8S,9aS)-8-[(5-cyclopropylpyrazin-2-yl)oxy]-2-[3-(trifluoromethyl)benzyl]octahydro-1H-pyrrolo[1,2-a][1,4]diazepin-1-one

Example 135

(8S,9aS)-8-[(5-cyclopropylpyrazin-2-yl)oxy]-2-[4-(trifluoromethyl)benzyl]octahydro-1H-pyrrolo[1,2-a][1,4]diazepin-1-one

Example 136

(8R,9aS)-8-[(5-cyclopropylpyrazin-2-yl)oxy]-2-[4-(trifluoromethyl)benzyl]octahydro-1H-pyrrolo[1,2-a][1,4]diazepin-1-one

Example 137

(8S,9aS)-8-[(5-cyclopropylpyrazin-2-yl)oxy]-2-[3-fluoro-4-(trifluoromethyl)benzyl]octahydro-1H-pyrrolo[1,2-a][1,4]diazepin-1-one

Example 138

(8S,9aS)-8-[(5-cyclopropylpyrazin-2-yl)oxy]-2-[4-fluoro-3-(trifluoromethyl)benzyl]octahydro-1H-pyrrolo[1,2-a][1,4]diazepin-1-one

Example 139

(8S,9aS)-8-[(5-cyclopropylpyrazin-2-yl)oxy]-2-[3-(trifluoromethyl)phenyl]octahydro-1H-pyrrolo[1,2-a][1,4]diazepin-1-one

Example 140

(8S,9aS)-8-[(5-cyclopropylpyrazin-2-yl)oxy]-2-{[3-(trifluoromethyl)phenyl]sulfonyl}octahydro-5H-pyrrolo[1,2-a][1,4]diazepin-5-one

Example 141

(8S,9aS)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 142

(8S,9aS)-8-[(5-cyclopropylpyrazin-2-yl)oxy]-2-[4-(trifluoromethyl)benzoyl]octahydro-5H-pyrrolo[1,2-a][1,4]diazepin-5-one

Example 143

(8S,9aS)-8-[(5-cyclopropylpyrazin-2-yl)oxy]-2-[2-fluoro-3-(trifluoromethyl)benzoyl]octahydro-5H-pyrrolo[1,2-a][1,4]diazepin-5-one

Example 144

(8S,9aS)-8-[(5-cyclopropylpyrazin-2-yl)oxy]-2-[3-fluoro-4-(trifluoromethyl)benzoyl]octahydro-5H-pyrrolo[1,2-a][1,4]diazepin-5-one

Example 145

(8S,9aS)-8-[(5-cyclopropylpyrazin-2-yl)oxy]-2-[4-fluoro-3-(trifluoromethyl)benzoyl]octahydro-5H-pyrrolo[1,2-a][1,4]diazepin-5-one

Example 146

(8S,9aS)-8-[(5-cyclopropylpyrazin-2-yl)oxy]-2-[3-(trifluoromethoxy)benzoyl]octahydro-5H-pyrrolo[1,2-a][1,4]diazepin-5-one

Example 147

(8S,9aS)-8-[(5-cyclopropylpyrazin-2-yl)oxy]-2-[4-(trifluoromethoxy)benzoyl]octahydro-5H-pyrrolo[1,2-a][1,4]diazepin-5-one

Example 148

(8S,9aS)-8-[(5-cyclopropylpyrazin-2-yl)oxy]-2-{[3-(trifluoromethyl)phenyl]acetyl}octahydro-5H-pyrrolo[1,2-a][1,4]diazepin-5-one

Example 149

(8S,9aS)-8-[(5-cyclopropylpyrazin-2-yl)oxy]-2-{hydroxy[3-(trifluoromethyl)phenyl]acetyl}octahydro-5H-pyrrolo[1,2-a][1,4]diazepin-5-one

Example 150

(8S,9aS)-8-[(5-cyclopropylpyrazin-2-yl)oxy]-2-{(methylamino)[3-(trifluoromethyl)phenyl]acetyl}octahydro-5H-pyrrolo[1,2-a][1,4]diazepin-5-one

Example 151

(8S,9aS)-8-[(5-cyclopropylpyrazin-2-yl)oxy]-2-[3-(trifluoromethyl)benzyl]octahydro-5H-pyrrolo[1,2-a][1,4]diazepin-5-one

Example 152

(8S,9aS)-8-[(5-cyclopropylpyrazin-2-yl)oxy]-2-[3-(trifluoromethoxy)benzyl]octahydro-5H-pyrrolo[1,2-a][1,4]diazepin-5-one

Example 153

(8S,9aS)-2-[3-(trifluoromethyl)benzyl]-8-{[5-(trifluoromethyl)pyridin-2-yl]oxy}octahydro-5H-pyrrolo[1,2-a][1,4]diazepin-5-one

Example 154

(8S,9aS)-8-[(5-cyclopropylpyrazin-2-yl)oxy]-2-[6-(trifluoromethyl)pyridin-2-yl]octahydro-5H-pyrrolo[1,2-a][1,4]diazepin-5-one

Example 155

(8S,9aS)-2-[3-chloro-5-(trifluoromethyl)pyridin-2-yl]-8-[(5-cyclopropylpyrazin-2-yl)oxy]octahydro-5H-pyrrolo[1,2-a][1,4]diazepin-5-one

Example 156

(8S,9aS)-8-[(5-cyclopropylpyrazin-2-yl)oxy]-2-[3-fluoro-5-(trifluoromethyl)pyridin-2-yl]octahydro-5H-pyrrolo[1,2-a][1,4]diazepin-5-one

Example 157

(8S,9aS)-2-(5-cyclopropylpyrazin-2-yl)-8-{[5-(trifluoromethyl)pyridin-2-yl]oxy}octahydro-5H-pyrrolo[1,2-a][1,4]diazepin-5-one

Example 158

(8S,9aS)-2-{[4-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 159

(8S,9aS)-2-{[3-(trifluoromethyl)phenyl]sulfonyl}-8-{[6-(trifluoromethyl)pyridin-3-yl]oxy}octahydro-5H-pyrrolo[1,2-a][1,4]diazepin-5-one

Example 160

(8S,9aS)-2-{[4-(trifluoromethyl)phenyl]sulfonyl}-8-{[6-(trifluoromethyl)pyridin-3-yl]oxy}octahydro-5H-pyrrolo[1,2-a][1,4]diazepin-5-one

Example 161

(8S,9aR)-8-[(5-cyclopropylpyrazin-2-yl)oxy]-2-{[3-(trifluoromethyl)phenyl]sulfonyl}octahydro-1H-pyrrolo[1,2-a][1,4]diazepine

Example 162

(8S,9aR)-8-[(5-cyclopropylpyrazin-2-yl)oxy]-2-{[4-(trifluoromethyl)phenyl]sulfonyl}octahydro-1H-pyrrolo[1,2-a][1,4]diazepine

Example 163

(8R,9aR)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 164

(8S,9aR)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 165

(8R,9aR)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 166

(8S,9aR)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one

Example 167

[(8S,9aR)-8-[(5-cyclopropylpyrazin-2-yl)oxy]hexahydro-1H-pyrrolo[1,2-a][1,4]diazepin-2(3H)-yl][3-(trifluoromethyl)phenyl]methanone

Example 168

[(8S,9aR)-8-[(5-cyclopropylpyrazin-2-yl)oxy]hexahydro-1H-pyrrolo[1,2-a][1,4]diazepin-2(3H)-yl](4-fluorophenyl)methanone

Example 169

[(8S,9aR)-8-[(5-cyclopropylpyrazin-2-yl)oxy]hexahydro-1H-pyrrolo[1,2-a][1,4]diazepin-2(3H)-yl][3-(trifluoromethoxy)phenyl]methanone

Example 170

[(8S,9aR)-8-[(5-cyclopropylpyrazin-2-yl)oxy]hexahydro-1H-pyrrolo[1,2-a][1,4]diazepin-2(3H)-yl][2-fluoro-3-(trifluoromethyl)phenyl]methanone

Example 171

[(8S,9aR)-8-[(5-cyclopropylpyrazin-2-yl)oxy]hexahydro-1H-pyrrolo[1,2-a][1,4]diazepin-2(3H)-yl][5-(trifluoromethyl)pyridin-2-yl]methanone

Example 172

[(8S,9aR)-8-[(5-cyclopropylpyrazin-2-yl)oxy]hexahydro-1H-pyrrolo[1,2-a][1,4]diazepin-2(3H)-yl][6-(trifluoromethyl)pyridin-2-yl]methanone

Example 173

[(8S,9aR)-8-[(5-cyclopropylpyrazin-2-yl)oxy]hexahydro-1H-pyrrolo[1,2-a][1,4]diazepin-2(3H)-yl][4-(trifluoromethyl)phenyl]methanone

Example 174

[(8S,9aR)-8-[(5-cyclopropylpyrazin-2-yl)oxy]hexahydro-1H-pyrrolo[1,2-a][1,4]diazepin-2(3H)-yl][4-fluoro-3-(trifluoromethyl)phenyl]methanone

Example 175

[(8S,9aR)-8-[(5-cyclopropylpyrazin-2-yl)oxy]hexahydro-1H-pyrrolo[1,2-a][1,4]diazepin-2(3H)-yl][3-fluoro-4-(trifluoromethyl)phenyl]methanone

Example 176

(3-chloro-4-fluorophenyl)[(8S,9aR)-8-[(5-cyclopropylpyrazin-2-yl)oxy]hexahydro-1H-pyrrolo[1,2-a][1,4]diazepin-2(3H)-yl]methanone

Example 177

[(8S,9aR)-8-[(5-cyclopropylpyrazin-2-yl)oxy]hexahydro-1H-pyrrolo[1,2-a][1,4]diazepin-2(3H)-yl][2-fluoro-5-(trifluoromethyl)phenyl]methanone

Example 178

[(8S,9aR)-8-[(5-cyclopropylpyrazin-2-yl)oxy]hexahydro-1H-pyrrolo[1,2-a][1,4]diazepin-2(3H)-yl][2-fluoro-4-(trifluoromethyl)phenyl]methanone

Example 179

(8S,9aR)-8-[(5-cyclopropylpyrazin-2-yl)oxy]-2-[5-(trifluoromethyl)pyridin-2-yl]octahydro-1H-pyrrolo[1,2-a][1,4]diazepine

Example 180

(8S,9aR)-8-[(5-cyclopropylpyrazin-2-yl)oxy]-2-[6-(trifluoromethyl)pyridin-2-yl]octahydro-1H-pyrrolo[1,2-a][1,4]diazepine

Example 181

(8S,9aR)-8-[(5-cyclopropylpyrazin-2-yl)oxy]-2-[5-(trifluoromethyl)pyridin-2-yl]octahydro-7H-pyrrolo[1,2-a][1,4]diazepin-7-one

Example 182

(8S,9aR)-8-[(5-cyclopropylpyrazin-2-yl)oxy]-2-[3-(trifluoromethyl)benzyl]octahydro-1H-pyrrolo[1,2-a][1,4]diazepin-1-one

Example 183

(8S,9aR)-8-[(5-cyclopropylpyrazin-2-yl)oxy]-2-[4-(trifluoromethyl)benzyl]octahydro-1H-pyrrolo[1,2-a][1,4]diazepin-1-one

Example 184

(8S,9aS)-8-[(5-cyclopropylpyrazin-2-yl)oxy]-2-[4-(trifluoromethyl)benzyl]octahydro-1H-pyrrolo[1,2-a][1,4]diazepin-1-one

Example 185

(8S,9aR)-8-[(5-cyclopropylpyrazin-2-yl)oxy]-2-[3-fluoro-4-(trifluoromethyl)benzyl]octahydro-1H-pyrrolo[1,2-a][1,4]diazepin-1-one

Example 186

(8S,9aR)-8-[(5-cyclopropylpyrazin-2-yl)oxy]-2-[4-fluoro-3-(trifluoromethyl)benzyl]octahydro-1H-pyrrolo[1,2-a][1,4]diazepin-1-one

Example 187

(8S,9aR)-8-[(5-cyclopropylpyrazin-2-yl)oxy]-2-[3-(trifluoromethyl)phenyl]octahydro-1H-pyrrolo[1,2-a][1,4]diazepin-1-one

Example 188

(8S,9aR)-8-[(5-cyclopropylpyrazin-2-yl)oxy]-2-{[3-(trifluoromethyl)phenyl]sulfonyl}octahydro-5H-pyrrolo[1,2-a][1,4]diazepin-5-one

Example 189

(8S,9aR)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 190

(8S,9aR)-8-[(5-cyclopropylpyrazin-2-yl)oxy]-2-[4-(trifluoromethyl)benzoyl]octahydro-5H-pyrrolo[1,2-a][1,4]diazepin-5-one

Example 191

(8S,9aR)-8-[(5-cyclopropylpyrazin-2-yl)oxy]-2-[2-fluoro-3-(trifluoromethyl)benzoyl]octahydro-5H-pyrrolo[1,2-a][1,4]diazepin-5-one

Example 192

(8S,9aR)-8-[(5-cyclopropylpyrazin-2-yl)oxy]-2-[3-fluoro-4-(trifluoromethyl)benzoyl]octahydro-5H-pyrrolo[1,2-a][1,4]diazepin-5-one

Example 193

(8S,9aR)-8-[(5-cyclopropylpyrazin-2-yl)oxy]-2-[4-fluoro-3-(trifluoromethyl)benzoyl]octahydro-5H-pyrrolo[1,2-a][1,4]diazepin-5-one

Example 194

(8S,9aR)-8-[(5-cyclopropylpyrazin-2-yl)oxy]-2-[3-(trifluoromethoxy)benzoyl]octahydro-5H-pyrrolo[1,2-a][1,4]diazepin-5-one

Example 195

(8S,9aR)-8-[(5-cyclopropylpyrazin-2-yl)oxy]-2-[4-(trifluoromethoxy)benzoyl]octahydro-5H-pyrrolo[1,2-a][1,4]diazepin-5-one

Example 196

(8S,9aR)-8-[(5-cyclopropylpyrazin-2-yl)oxy]-2-{[3-(trifluoromethyl)phenyl]acetyl}octahydro-5H-pyrrolo[1,2-a][1,4]diazepin-5-one

Example 197

(8S,9aR)-8-[(5-cyclopropylpyrazin-2-yl)oxy]-2-{hydroxy[3-(trifluoromethyl)phenyl]acetyl}octahydro-5H-pyrrolo[1,2-a][1,4]diazepin-5-one

Example 198

(8S,9aR)-8-[(5-cyclopropylpyrazin-2-yl)oxy]-2-{(methylamino)[3-(trifluoromethyl)phenyl]acetyl}octahydro-5H-pyrrolo[1,2-a][1,4]diazepin-5-one

Example 199

(8S,9aR)-8-[(5-cyclopropylpyrazin-2-yl)oxy]-2-[3-(trifluoromethyl)benzyl]octahydro-5H-pyrrolo[1,2-a][1,4]diazepin-5-one

Example 200

(8S,9aR)-8-[(5-cyclopropylpyrazin-2-yl)oxy]-2-[3-(trifluoromethoxy)benzyl]octahydro-5H-pyrrolo[1,2-a][1,4]diazepin-5-one

Example 201

(8S,9aR)-2-[3-(trifluoromethyl)benzyl]-8-{[5-(trifluoromethyl)pyridin-2-yl]oxy}octahydro-5H-pyrrolo[1,2-a][1,4]diazepin-5-one

Example 202

(8S,9aR)-8-[(5-cyclopropylpyrazin-2-yl)oxy]-2-[6-(trifluoromethyl)pyridin-2-yl]octahydro-5H-pyrrolo[1,2-a][1,4]diazepin-5-one

Example 203

(8S,9aR)-2-[3-chloro-5-(trifluoromethyl)pyridin-2-yl]-8-[(5-cyclopropylpyrazin-2-yl)oxy]octahydro-5H-pyrrolo[1,2-a][1,4]diazepin-5-one

Example 204

(8S,9aR)-8-[(5-cyclopropylpyrazin-2-yl)oxy]-2-[3-fluoro-5-(trifluoromethyl)pyridin-2-yl]octahydro-5H-pyrrolo[1,2-a][1,4]diazepin-5-one

Example 205

(8S,9aR)-2-(5-cyclopropylpyrazin-2-yl)-8-{[5-(trifluoromethyl)pyridin-2-yl]oxy}octahydro-5H-pyrrolo[1,2-a][1,4]diazepin-5-one

Example 206

(8S,9aR)-2-{[4-(trifluoromethyl)phenyl]sulfonyl}-8-{[5-(trifluoromethyl)pyridin-2-yl]oxy}octahydro-5H-pyrrolo[1,2-a][1,4]diazepin-5-one

Example 207

(8S,9aR)-2-{[3-(trifluoromethyl)phenyl]sulfonyl}-8-{[6-(trifluoromethyl)pyridin-3-yl]oxy}octahydro-5H-pyrrolo[1,2-a][1,4]diazepin-5-one and

Example 208

(8S,9aR)-2-{[4-(trifluoromethyl)phenyl]sulfonyl}-8-{[6-(trifluoromethyl)pyridin-3-yl]oxy}octahydro-5H-pyrrolo[1,2-a][1,4]diazepin-5-one I. Biological Data Abbreviations which have been used in the descriptions of Biological Data that follow are: EDTA for ethylenediaminetetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; p.o. for per orem (by mouth).

(A) In Vitro Assessment of Calcium Channel Activity

Compounds were tested for effect on calcium flux in cells endogenously expressing human Cav2.2. Specifically, IMR32 cells endogenously expressing human $Ca_v2.2$ were assayed for $Ca^+$ influx using a no-wash calcium indicator dye (Calcium 4 dye: Molecular Probes) and FLIPR technology (Lubin, M L; et al. Assay and Drug Development Technologies, 2006, 4(6), 689-694). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cellbind) at a density of $1-1.2\times10^5$ cells/well and incubated in the maintenance media above for 48 hours at 37° C. Immediately prior to performing the assay the media was removed and cells were loaded for 1.5 hours with 1× Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 60 minute pre-incubation with compounds (full log dilutions from 10 µM to 0.1 nM) in the presence of 1.3 mM $CaCl_2$ and 2 µM nifedipine to block endogenous L-type channels, the external $Ca^{2+}$ concentration was increased to 5 mM $CaCl_2$ and the cells concomitantly depolarized with 80 mM KCl to assay channel activity.

To determine the $IC_{50}$ values, the percent inhibition of the compound at each concentration was determined relative to the activity in the absence of inhibitor, and data was fitted using non-linear regression sigmoidal dose response curve analysis with GraphPad Prism®. Unless otherwise indicated (*), the reported values are average values from at least two runs (i.e., n≥2). Results are reported in Table 3.

TABLE 3

| EXAMPLE | $IC_{50}$ (µM) |
|---|---|
| 1 | 0.32 |
| 2 | 0.20 |
| 3 | 1.25 |
| 4 | 0.88 |
| 5 | 1.76 |
| 6 | 0.91 |
| 7 | 1.66 |
| 8 | 3.04* |
| 9 | 1.35 |
| 10 | 0.92 |
| 11 | 9.27 |
| 12 | 6.22 |
| 13 | 0.88 |
| 14 | 1.45 |
| 15 | 1.33 |
| 16 | 2.30 |
| 17 | 1.58 |
| 18 | 1.19 |
| 19 | 1.21 |
| 20 | 0.75 |
| 21 | 3.47 |
| 22 | 1.72 |
| 23 | 0.98 |
| 24 | 2.94 |
| 25 | 1.19 |
| 26 | 1.10 |
| 27 | 10.0 |
| 28 | 1.83 |
| 29 | 0.49 |
| 30 | 6.34 |
| 31 | 0.60 |
| 32 | 1.72 |
| 33 | 3.73 |
| 34 | 1.01 |
| 35 | 1.03 |
| 36 | 1.78 |
| 37 | 1.14 |
| 38 | 2.81 |
| 39 | 2.08 |
| 40 | 4.70 |
| 41 | 3.45 |
| 42 | 0.92 |

TABLE 3-continued

| EXAMPLE | IC$_{50}$ (μM) |
|---|---|
| 43 | 1.11 |
| 44 | 1.65 |
| 45 | 0.62 |
| 46 | 5.07 |
| 47 | 2.52 |
| 48 | 1.54 |
| 49 | 2.13 |
| 50 | 2.46 |
| 51 | 7.35 |
| 52 | 1.26 |
| 53 | 4.02 |
| 54 | 1.29 |
| 55 | 3.43 |
| 56 | 2.50 |
| 57 | 11.2 |
| 58 | 3.75 |
| 59 | 3.17 |
| 60 | 18.8 |
| 61 | 1.20 |
| 62 | 3.23 |
| 63 | 22.5 |
| 64 | 2.20 |

(B) In Vivo Analgesic Effect (Neuropathic Pain Model)

Test compounds can be evaluated for analgesic effect in an in vivo model of neuropathic pain. Specifically, animals were prepared for testing, by use of a surgical procedure that induces neuropathic pain in one paw. IACUC guidelines for rodent survival surgery were followed. All surgical procedures were conducted on a clean, uncluttered surgical station. The area was wiped with a 70% ethanol solution before and after use. All instruments were sterilized by either autoclave or chemical sterilant (such as 2% glutaraldehyde >10 hours). Surgeons wore sterile gloves (for the initial procedure), clean lab coat or scrubs, hairnet or cap, and a half-mask respirator (when not working under a hood). Surgeons thoroughly washed their hands prior to donning sterile gloves. Gloves were disinfected in-between animals by cleansing with povidone iodine, chlorhexidine or 70% alcohol for at least 30 seconds. If multiple surgeries were performed, the instruments were cleaned and sterilized between procedures with hot glass beads (>10 seconds). To prevent thermal or chemical burns, the instruments were cooled by rinsing in sterile saline before use.

Male, Sprague Dawley® rats, 175-200 g were used for surgeries. To minimize post-operative dehydration/maintain blood volume during the surgery, warmed sterile saline or Lactate Ringers solution at 10-15 mL/kg was administered subcutaneously immediately before or after surgery. This facilitates better renal function and presumably anesthesia product excretion post surgery. For all surgical procedures, anesthesia was induced with 4-5% isoflurane. Anesthesia was maintained during surgery with 1-3% isoflurane. Following induction, the surgical site was carefully shaved and the exposed area was aseptically prepared with povidone-iodine scrub solution and 70% ethanol 2-3 times.

Chronic constriction injury (CCI), a model of neuropathic pain, was produced by following the method of Bennett and Xie (Bennett, G., et al. Pain, 1988, 33, 87-107). After site sterilization and anesthetic procedures outline above were completed, a 1.5 cm incision is made at the mid-thigh level to expose the biceps femoris and gluteous superficialis (right side), which were then separated by blunt dissection. The common sciatic nerve was exposed, isolated, and loosely ligated by four 5-0 chromic gut ligatures with <1 mm spacing between each. The surgical site was closed in layers—muscle is closed with 6.0 absorbable sutures, and the skin closed with wound clips. Animals were allowed to recover on a warming plate and were returned to their home cages when fully ambulatory. Animals were not be used for testing until at least 10 days following surgery.

To measure mechanical sensitivity, tactile allodynia was measured using calibrated von Frey filaments (Stoelting, Wood Dale, Ill.) as described by Chaplan et al. (Chaplan S., et al. J of Neuroscience Methods 1994, 53, 55-63). Filament strengths used were: 0.4, 0.6, 1.0, 2, 4, 6, 8, and 15 g. Rats were placed into inverted individual plastic containers (20× 12.5×20 cm) on top of a suspended wire mesh grid, and acclimated to the test chambers for at least 20 minutes. Filaments were applied perpendicular to the mid-plantar paw surface with enough force to cause slight buckling and held in place for 6-8 seconds. Positive responses included an abrupt withdrawal of the paw from the stimulus or flinching behavior immediately following removal of the stimulus. The maximum force applied was 15 g. The 50% paw withdrawal threshold (PWT) was calculated in grams (g) using the up-down method of Dixon (Dixon W. Ann Rev Pharmacol Toxicol 1980, 20, 441-462). Only rats exhibiting increased mechanical sensitivity were used (threshold responses below 5 g). All compounds were orally administered at 10 mg/kg in 10% dimethyl sulfoxide/polyethylene glycol at a volume of 2.0 mL/kg, and mechanical allodynia was determined 60 minutes following compound administration Results are reported in Table 4. The data are reported as log g values and the percentage of maximum possible effect (% MPE) is calculated using log g values with the Formula:

$$\% \ MPE = \frac{(\log[\text{observed } PWT \text{ in grams}] - \log[\text{mean } PWT \text{ vehicle}])}{(\log[15] - \log[\text{mean } PWT \text{ vehicle}]) * 100}$$

All statistical procedures are run on log g values.

TABLE 4

| EXAMPLE | % MPE |
|---|---|
| 7 | 44 |
| 13 | 40 |
| 19 | 36 |
| 32 | 46 |
| 42 | 27 |
| 44 | 48 |
| 47 | 73 |

The ability of the compounds of the present invention to reduce nociceptive pain can be evaluated using conventional in vivo nociceptive pain models known in the art. Such models include, for example, those described in Pain (1996) 64:493-501; and Pain (2001) 93:69-76.

* * *

The ability of the compounds of the present invention to reduce inflammatory pain can be evaluated using conventional in vivo nociceptive pain models known in the art. Such models include, for example, those described in Pain (1999) 80:67-82.

Although specific embodiments and examples have been described above, these embodiments and examples are only illustrative and do not limit the scope of the invention. Changes and modifications can be made in accordance with ordinary skill in the art without departing from the invention in its broader aspects as defined in the following claims. For example, any embodiment described herein can be combined with any other suitable embodiment described herein to provide additional embodiments.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion or disclaimer of one or more of any of the group members in the claimed invention.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

We claim:
1. A compound or a salt thereof, wherein:
the compound corresponds to Formula (I):

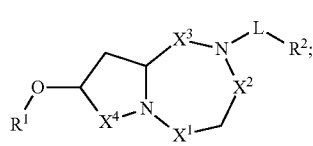

(I)

R¹ is selected from the group consisting of pyridinyl, pyrimidinyl, pyrazinyl, and pyridazinyl, wherein each such substituent is optionally substituted with one, two, or three substituents independently selected from the group consisting of halogen, $C_1$-$C_6$-alkyl, halo-$C_1$-$C_6$-alkyl, and $C_3$-$C_6$-cycloalkyl;

R² is selected from the group consisting of phenyl, pyridinyl, pyrimidinyl, pyrazinyl, and pyridazinyl, wherein each such substituent is optionally substituted with one, two, or three substituents independently selected from the group consisting of halogen, cyano, $C_1$-$C_6$-alkyl, halo-$C_1$-$C_6$-alkyl, $C_1$-$C_6$-alkoxy, halo-$C_1$-$C_6$-alkoxy, and $C_3$-$C_6$-cycloalkyl;

one of $X^1$ and $X^4$ is —C(O)— and the other one of $X^1$ and $X^4$ is —CH$_2$—; $X^2$ is —CH$_2$—; $X^3$ is —CH$_2$—; and L is selected from the group consisting of a bond, —CH$_2$—, —C(O)—, —C(O)C(R$^5$)(H)—, and —S(O)$_2$—;

R³, R⁴, and R⁵ are independently selected from the group consisting of hydrogen, hydroxy, $C_1$-$C_6$-alkyl, $C_1$-$C_6$-alkoxy, and amino, wherein such amino is optionally substituted with one or two independently selected $C_1$-$C_6$-alkyl.

2. The compound or salt of claim 1, wherein the compound corresponds in structure to Formula (I-i):

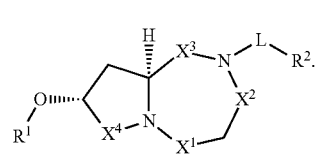

(I-i)

3. The compound or salt of claim 1, wherein the compound corresponds in structure to Formula (I-ii):

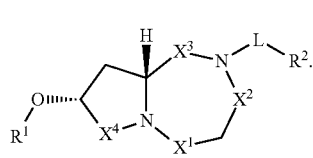

(I-ii)

4. The compound or salt of claim 1, wherein the compound corresponds in structure to Formula (I-iii):

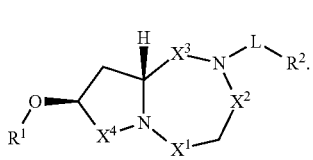

(I-iii)

5. The compound or salt of claim 1, wherein the compound corresponds in structure to Formula (I-iv):

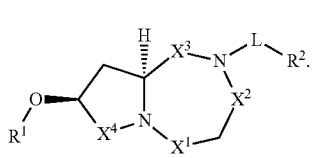

(I-iv)

6. The compound or salt of claim 1, wherein $X^1$—C(O)— and $X^4$ is —CH$_2$.

7. The compound or salt of claim 1, wherein $X^1$ is —CH$_2$— and $X^4$ is —C(O)—.

8. The compound or salt of claim 1, wherein L is —S(O)$_2$—.

9. The compound or salt of claim 1, wherein L is a bond.

10. The compound or salt of claim 1, wherein L is —CH$_2$—.

11. The compound or salt of claim 1, wherein L is —C(O)—.

12. The compound or salt of claim 1, wherein:

R$^1$ is selected from the group consisting of pyridinyl and pyrazinyl, wherein each such substituent is optionally substituted with one or two substituents independently selected from the group consisting of halogen, C$_1$-C$_6$-alkyl, halo-C$_1$-C$_6$-alkyl, and C$_3$-C$_6$-cycloalkyl; and R$^2$ is selected from the group consisting of phenyl and pyridinyl, wherein each such substituent is optionally substituted with one or two substituents independently selected from the group consisting of halogen, cyano, C$_1$-C$_6$-alkyl, halo-C$_1$-C$_6$-alkyl, C$_1$-C$_6$alkoxy, halo-C$_1$-C$_6$-alkoxy, and C$_3$-C$_6$-cycloalkyl.

13. The compound or salt of claim 1, wherein:

R$^1$ is selected from the group consisting of pyridinyl and pyrazinyl, wherein each such substituent is optionally substituted with one substituent selected from the group consisting of halomethyl and cyclopropyl; and R$^2$ is selected from the group consisting of phenyl and pyridinyl, wherein each such substituent is optionally substituted with one or two substituents independently selected from the group consisting of fluoro, trifluoromethyl, and trifluoromethoxy.

14. The compound or salt of claim 1, wherein:

R$^1$ is pyrazinyl, wherein such pyrazinyl is optionally substituted with one or two substituents independently selected from the group consisting of halogen, C$_1$-C$_6$-alkyl, halo-C$_1$-C$_6$-alkyl, and C$_3$-C$_6$-cycloalkyl; and R$^2$ is phenyl, wherein such phenyl is optionally substituted with one or two substituents independently selected from the group consisting of halogen, cyano, C$_1$-C$_6$-alkyl, halo-C$_1$-C$_6$-alkyl, C$_1$-C$_6$-alkoxy, halo-C$_1$-C$_6$-alkoxy, and C$_3$-C$_6$-cycloalkyl.

15. The compound or salt of claim 1, wherein:

R$^1$ is pyrazinyl, wherein such pyrazinyl is optionally substituted with one or two substituents independently selected from the group consisting of halogen, C$_1$-C$_6$-alkyl, halo-C$_1$-C$_6$-alkyl, and C$_3$-C$_6$-cycloalkyl; and R$^2$ is pyridinyl, wherein such pyridinyl is optionally substituted with one or two substituents independently selected from the group consisting of halogen, cyano, C$_1$-C$_6$-alkyl, halo-C$_1$-C$_6$-alkyl, C$_1$-C$_6$-alkoxy, halo-C$_1$-C$_6$-alkoxy, and C$_3$-C$_6$-cycloalkyl.

16. The compound or salt of claim 1, wherein:

R$^1$ is selected from the group consisting of:

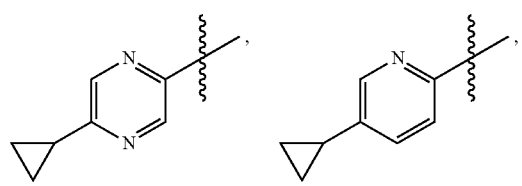

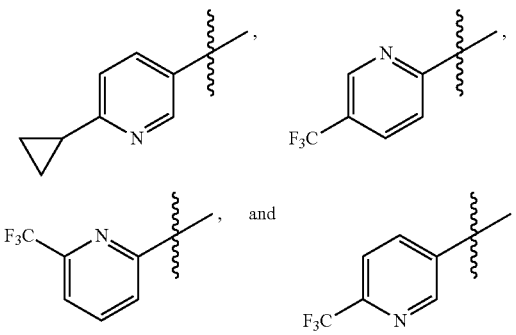

R$^2$ is selected from the group consisting of phenyl and pyridinyl, wherein each such substituent is substituted with one or two substituents independently selected from the group consisting of fluoro, trifluoromethyl, and trifluoromethoxy.

17. The compound or salt of claim 1, wherein:

R$^1$ is selected from the group consisting of pyridinyl and pyrazinyl, wherein each such substituent is substituted with one substituent selected from the group consisting of halomethyl and cyclopropyl; and R$^2$ is selected from the group consisting of:

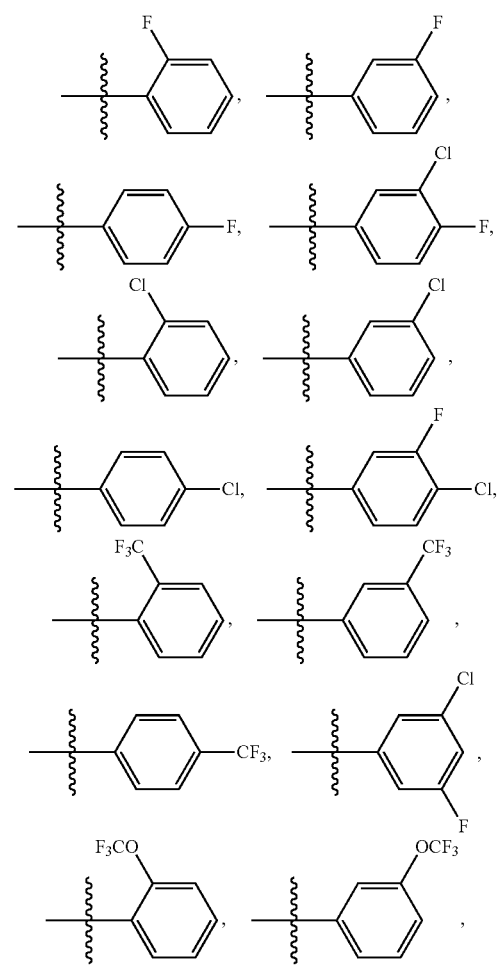

-continued
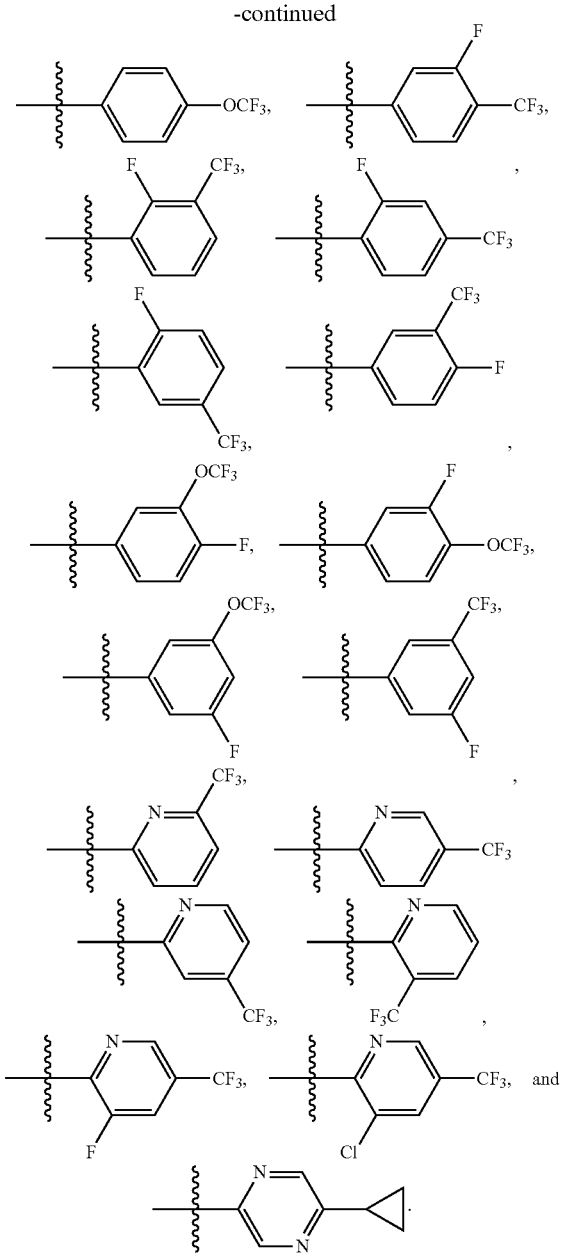
18. The compound or salt of claim 1, wherein:
R¹ is selected from the group consisting of:
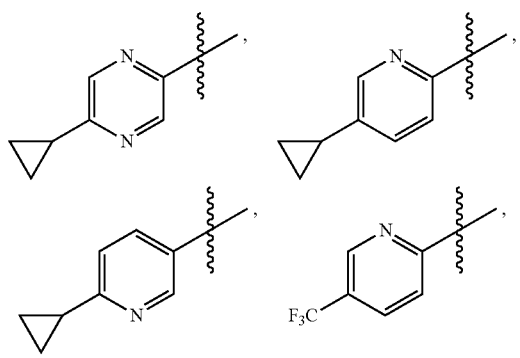
-continued
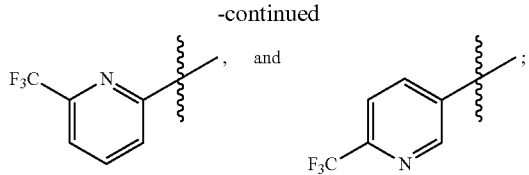
R² is selected from the group consisting of:
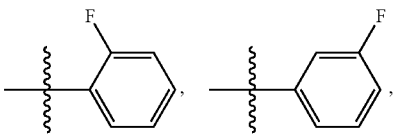
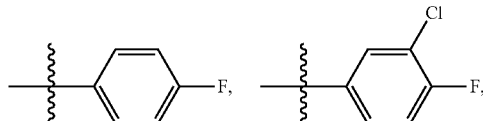
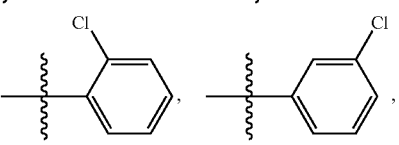
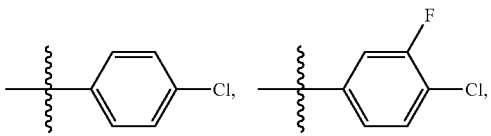
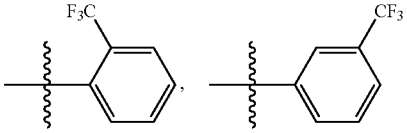
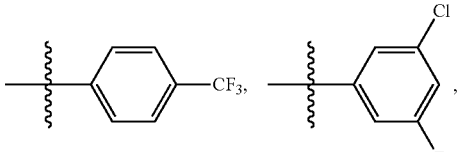
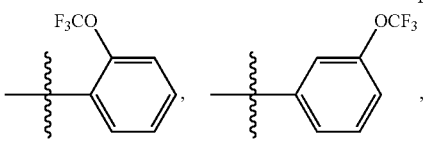
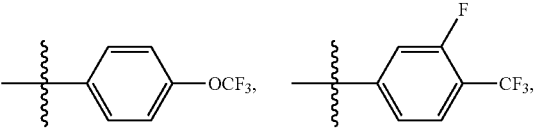
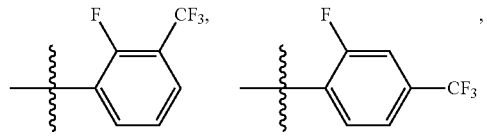
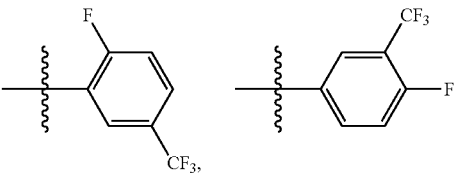

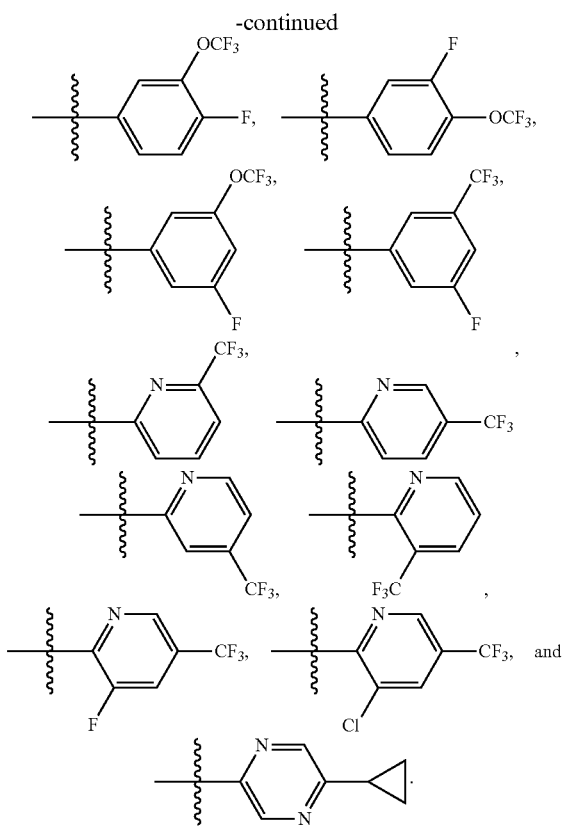

19. The compound or salt of claim 1, wherein:
R¹ is

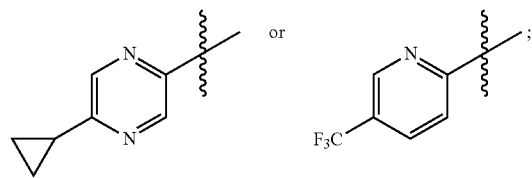 [SMILES: *c1cnc(C2CC2)cn1 ; *c1ccc(C(F)(F)F)cn1]

and

R² is selected from the group consisting of phenyl and pyridinyl, wherein each such substituent is substituted with one or two substituents independently selected from the group consisting of fluoro, trifluoromethyl, and trifluoromethoxy.

20. The compound or salt of claim 1, wherein the compound is selected from the group consisting of:

(8S,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one;

(8R,9aS)-2-{[3-(trifluoromethyl)phenyl]sulfonyl}-8-{[5-(trifluoromethyl)pyridin-2-yl]oxy}octahydro-7H-pyrrolo[1,2-a][1,4]diazepin-7-one;

(8S,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one;

(8R,9aS)-2-{[4-(trifluoromethyl)phenyl]sulfonyl}-8-{[5-(trifluoromethyl)pyridin-2-yl]oxy}octahydro-7H-pyrrolo[1,2-a][1,4]diazepin-7-one;

(8R,9aS)-8-[(5-cyclopropylpyrazin-2-yl)oxy]-2-[5-(trifluoromethyl)pyridin-2-yl]octahydro-7H-pyrrolo[1,2-a][1,4]diazepin-7-one;

(8R,9aS)-8-[(5-cyclopropylpyrazin-2-yl)oxy]-2-{[3-(trifluoromethyl)phenyl]sulfonyl}octahydro-5H-pyrrolo[1,2-a][1,4]diazepin-5-one;

(8R,9aS)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one;

(8S,9aS)-8-[(5-cyclopropylpyrazin-2-yl)oxy]-2-[5-(trifluoromethyl)pyridin-2-yl]octahydro-5H-pyrrolo[1,2-a][1,4]diazepin-5-one;

(8R,9aS)-2-{[3-(trifluoromethyl)phenyl]sulfonyl}-8-{[5-(trifluoromethyl)pyridin-2-yl]oxy}octahydro-5H-pyrrolo[1,2-a][1,4]diazepin-5-one;

(8R,9aS)-8-[(5-cyclopropylpyrazin-2-yl)oxy]-2-[3-(trifluoromethyl)benzoyl]octahydro-5H-pyrrolo[1,2-a][1,4]diazepin-5-one;

(8R,9aS)-8-[(5-cyclopropylpyrazin-2-yl)oxy]-2-[4-(trifluoromethyl)benzoyl]octahydro-5H-pyrrolo[1,2-a][1,4]diazepin-5-one;

(8R,9aS)-8-[(5-cyclopropylpyrazin-2-yl)oxy]-2-[2-fluoro-3-(trifluoromethyl)benzoyl]octahydro-5H-pyrrolo[1,2-a][1,4]diazepin-5-one;

(8R,9aS)-8-[(5-cyclopropylpyrazin-2-yl)oxy]-2-[3-fluoro-4-(trifluoromethyl)benzoyl]octahydro-5H-pyrrolo[1,2-a][1,4]diazepin-5-one;

(8R,9aS)-8-[(5-cyclopropylpyrazin-2-yl)oxy]-2-[4-fluoro-3-(trifluoromethyl)benzoyl]octahydro-5H-pyrrolo[1,2-a][1,4]diazepin-5-one;

(8R,9aS)-8-[(5-cyclopropylpyrazin-2-yl)oxy]-2-[3-(trifluoromethoxy)benzoyl]octahydro-5H-pyrrolo[1,2-a][1,4]diazepin-5-one;

(8R,9aS)-8-[(5-cyclopropylpyrazin-2-yl)oxy]-2-[4-(trifluoromethoxy)benzoyl]octahydro-5H-pyrrolo[1,2-a][1,4]diazepin-5-one;

(8R,9aS)-8-[(5-cyclopropylpyrazin-2-yl)oxy]-2-{[3-(trifluoromethyl)phenyl]acetyl}octahydro-5H-pyrrolo[1,2-a][1,4]diazepin-5-one;

(8R,9aS)-8-[(5-cyclopropylpyrazin-2-yl)oxy]-2-{hydroxy[3-(trifluoromethyl)phenyl]acetyl}octahydro-5H-pyrrolo[1,2-a][1,4]diazepin-5-one;

(8R,9aS)-8-[(5-cyclopropylpyrazin-2-yl)oxy]-2-{(methylamino)[3-(trifluoromethyl)phenyl]acetyl}octahydro-5H-pyrrolo[1,2-a][1,4]diazepin-5-one;

(8R,9aS)-8-[(5-cyclopropylpyrazin-2-yl)oxy]-2-[3-(trifluoromethyl)benzyl]octahydro-5H-pyrrolo[1,2-a][1,4]diazepin-5-one;

(8R,9aS)-8-[(5-cyclopropylpyrazin-2-yl)oxy]-2-[3-(trifluoromethoxy)benzyl]octahydro-5H-pyrrolo[1,2-a][1,4]diazepin-5-one;

(8R,9aS)-8-[(5-cyclopropylpyrazin-2-yl)oxy]-2-[4-(trifluoromethoxy)benzyl]octahydro-5H-pyrrolo[1,2-a][1,4]diazepin-5-one;

(8R,9aS)-2-[3-(trifluoromethyl)benzyl]-8-{[5-(trifluoromethyl)pyridin-2-yl]oxy}octahydro-5H-pyrrolo[1,2-a][1,4]diazepin-5-one;

(8S,9aR)-8-[(5-cyclopropylpyrazin-2-yl)oxy]-2-[5-(trifluoromethyl)pyridin-2-yl]octahydro-5H-pyrrolo[1,2-a][1,4]diazepin-5-one;

(8R,9aS)-8-[(5-cyclopropylpyrazin-2-yl)oxy]-2-[5-(trifluoromethyl)pyridin-2-yl]octahydro-5H-pyrrolo[1,2-a][1,4]diazepin-5-one;

(8R,9aS)-8-[(5-cyclopropylpyrazin-2-yl)oxy]-2-[6-(trifluoromethyl)pyridin-2-yl]octahydro-5H-pyrrolo[1,2-a][1,4]diazepin-5-one;

(8R,9aS)-2-[3-chloro-5-(trifluoromethyl)pyridin-2-yl]-8-[(5-cyclopropylpyrazin-2-yl)oxy]octahydro-5H-pyrrolo[1,2-a][1,4]diazepin-5-one;

(8R,9aS)-8-[(5-cyclopropylpyrazin-2-yl)oxy]-2-[3-fluoro-5-(trifluoromethyl)pyridin-2-yl]octahydro-5H-pyrrolo[1,2-a][1,4]diazepin-5-one;

(8R,9aS)-2-(5-cyclopropylpyrazin-2-yl)-8-{[5-(trifluoromethyl)pyridin-2-yl]oxy}octahydro-5H-pyrrolo[1,2-a][1,4]diazepin-5-one;

(8R,9aS)-2-{[4-(trifluoromethyl)phenyl]sulfonyl}-8-{[5-(trifluoromethyl)pyridin-2-yl]oxy}octahydro-5H-pyrrolo[1,2-a][1,4]diazepin-5-one;

(8R,9aS)-2-{[3-(trifluoromethyl)phenyl]sulfonyl}-8-{[6-(trifluoromethyl)pyridin-3-yl]oxy}octahydro-5H-pyrrolo[1,2-a][1,4]diazepin-5-one;

(8R,9aS)-2-{[4-(trifluoromethyl)phenyl]sulfonyl}-8-{[6-(trifluoromethyl)pyridin-3-yl]oxy}octahydro-5H-pyrrolo[1,2-a][1,4]diazepin-5-one;

(8R,9aR)-8-[(5-cyclopropylpyrazin-2-yl)oxy]-2-[5-(trifluoromethyl)pyridin-2-yl]octahydro-5H-pyrrolo[1,2-a][1,4]diazepin-5-one;

(8R,9aR)-8-[(5-cyclopropylpyrazin-2-yl)oxy]-2-[4-(trifluoromethoxy)benzyl]octahydro-5H-pyrrolo[1,2-a][1,4]diazepin-5-one;

(8R,9aR)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one;

(8R,9aR)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one;

(8S,9aS)-8-[(5-cyclopropylpyrazin-2-yl)oxy]-2-[4-(trifluoromethoxy)benzyl]octahydro-5H-pyrrolo[1,2-a][1,4]diazepin-5-one;

(8S,9aS)-8-[(5-cyclopropylpyrazin-2-yl)oxy]-2-[3-(trifluoromethyl)benzoyl]octahydro-5H-pyrrolo[1,2-a][1,4]diazepin-5-one;

(8S,9aS)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one;

(8S,9aR)-8-[(5-cyclopropylpyrazin-2-yl)oxy]-2-[4-(trifluoromethoxy)benzyl]octahydro-5H-pyrrolo[1,2-a][1,4]diazepin-5-one;

(8S,9aR)-8-[(5-cyclopropylpyrazin-2-yl)oxy]-2-[3-(trifluoromethyl)benzoyl]octahydro-5H-pyrrolo[1,2-a][1,4]diazepin-5-one; and (8S,9aR)-8-[(5-cyclopropylpyrazin-2-yl)oxy]-2-{[4-(trifluoromethyl)phenyl]sulfonyl}octahydro-5H-pyrrolo[1,2-a][1,4]diazepin-5-one.

21. A pharmaceutical composition comprising a therapeutically effective amount of a compound of claim 1, or a pharmaceutically acceptable salt thereof, and a pharmaceutically acceptable carrier.

22. A method for treating pain in a subject in need thereof, wherein the method comprises administering to the subject a therapeutically effective amount of a compound of claim 1 or pharmaceutically acceptable salt thereof.

* * * * *